United States Patent
Jakobi et al.

(10) Patent No.: US 8,975,412 B2
(45) Date of Patent: Mar. 10, 2015

(54) SUBSTITUTED 4-CYANO-3-PHENYL-4-(PYRIDIN-3-YL)BUTANOATES, PROCESSES FOR PREPARATION THEREOF AND USE THEREOF AS HERBICIDES AND PLANT GROWTH REGULATORS

(71) Applicant: Bayer Intellectual Property GmbH, Monheim (DE)

(72) Inventors: Harald Jakobi, Frankfurt (DE); Marc Mosrin, Frankfurt (DE); Hansjörg Dietrich, Liederbach am Taunus (DE); Elmar Gatzweiler, Bad Nauheim (DE); Isolde Häuser-Hahn, Leverkusen (DE); Ines Heinemann, Hofheim (DE); Christopher Hugh Rosinger, Hofheim (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/354,795

(22) PCT Filed: Oct. 29, 2012

(86) PCT No.: PCT/EP2012/071391
§ 371 (c)(1),
(2) Date: Apr. 28, 2014

(87) PCT Pub. No.: WO2013/064462
PCT Pub. Date: May 10, 2013

(65) Prior Publication Data
US 2014/0296073 A1    Oct. 2, 2014

(30) Foreign Application Priority Data
Oct. 31, 2011   (EP) .................................. 11187228

(51) Int. Cl.
*C07D 213/57*    (2006.01)
*A01N 43/40*    (2006.01)
*C07D 213/24*    (2006.01)

(52) U.S. Cl.
CPC ............. *A01N 43/40* (2013.01); *C07D 213/24* (2013.01)
USPC ........................................................ 546/330

(58) Field of Classification Search
USPC ........................................................ 546/330
See application file for complete search history.

(56) References Cited

U.S. PATENT DOCUMENTS 4,224,052 A   9/1980   Szucs

FOREIGN PATENT DOCUMENTS

| EP | 5341 A2 * | 4/1979 | ............... A01N 9/22 |
|----|-----------|--------|--------------------------|
| EP | 0005341 A2 | 11/1979 | |
| EP | 0005341 A3 | 11/1979 | |
| EP | 0266725 A1 | 5/1988 | |
| EP | 0270830 A1 | 6/1988 | |
| JP | 04297454 | 10/1992 | |
| JP | 04297455 | 10/1992 | |
| JP | 05058979 | 3/1993 | |
| WO | 2011003775 A2 | 1/2011 | |
| WO | 2011003776 A2 | 1/2011 | |
| WO | 2011042378 A1 | 4/2011 | |
| WO | 2011073143 A1 | 6/2011 | |
| WO | 2011098417 A1 | 8/2011 | |

OTHER PUBLICATIONS

Dorwald F. A. Side Reactions in Organic Synthesis, 2005, Wiley: VCH, Weinheim p. IX of Preface p. 1-15.*
International Search Report corresponding to PCT/EP2012/071391 mailed on Nov. 14, 2012.

* cited by examiner

*Primary Examiner* — Nizal Chandrakumar
(74) *Attorney, Agent, or Firm* — Miles & Stockbridge PC

(57) ABSTRACT

Compounds of the formula (I) or salts thereof,

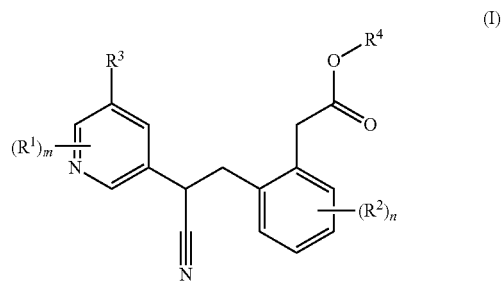

in which $(R^1)_m$, $(R^2)_n$, $R^3$ and $R^4$ as defined in Claim 1 are suitable as herbicides for the control of harmful plants or as plant growth regulators.

The compounds can be prepared by the processes of Claim 7.

12 Claims, No Drawings

SUBSTITUTED 4-CYANO-3-PHENYL-4-(PYRIDIN-3-YL)BUTANOATES, PROCESSES FOR PREPARATION THEREOF AND USE THEREOF AS HERBICIDES AND PLANT GROWTH REGULATORS

CROSS REFERENCE TO RELATED APPLICATIONS

This application is a §371 National Stage Application of PCT/EP2012/071391, filed Oct. 29, 2012, which claims priority to EP 11187228.9, filed Oct. 31, 2011.

BACKGROUND

1. Field of the Invention

The invention relates to the technical field of the herbicides and plant growth regulators, preferably the herbicides for controlling unwanted vegetation or the herbicides for the selective control of broad-leaved weeds and weed grasses in crops of useful plants, or the plant growth regulators which can be used for influencing the growth of crop plants.

2. Description of Related Art

In their application, crop protection agents known to date for the selective control of harmful plants in crops of useful plants or active compounds for controlling unwanted vegetation sometimes have disadvantages, be it (a) that they have no or else insufficient herbicidal activity against particular harmful plants, (b) that the spectrum of harmful plants which can be controlled with an active compound is not wide enough, (c) that their selectivity in crops of useful plants is too low and/or (d) that they have a toxicologically unfavorable profile. Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

The published patent applications EP-A-5341, EP-A-266725, EP-A-270830, JP-04/297454, JP-04/297455, JP-05/058979, WO 2011/003775, WO 2011/003776, WO 2011/042378, WO 2011/073143 and WO2011/098417 disclose herbicidal cyanobutyrates.

EP-A-5341 describes herbicidal esters and amides of 4-cyano-3,4-diarylbutanoic acids. The aryl radicals mentioned are optionally substituted phenyl radicals and unsubstituted pyridyl or thienyl. The specific examples include mainly 4-cyano-3,4-diphenylbutanoic acids and esters. There are two specific examples of compounds containing pyridyl, namely 4-cyano-4-phenyl-4-(pyridin-3-yl)butanoic acid and the corresponding ethyl ester.

According to EP-A-5341, the threo isomers are generally suitable for the non-selective control of harmful plants, whereas the erythro/threo isomer mixtures are suitable for the selective control of harmful plants in some crops of useful plants. Moreover, EP-A-5341 mentions that the 2 enantiomers belonging to the threo form differ in their activities, which was studied in an exemplary manner using the different activities of the enantiomers of the enantiomer pair of 4-cyano-3,4-diphenylbutanoic acid having unsubstituted phenyl radicals.

EP-A-266725 discloses a number of erythro/threo isomer mixtures of 4-cyano-3,4-diphenylbutanoic acids and derivatives thereof which can be used for the selective control of weeds in rice crops.

EP-A-270830 describes that threo isomers and erythro/threo isomer mixtures of 4-cyano-3,4-diarylbutanoic acid (esters) can be used as plant regulators, preventing the development of an infructescence in various harmful grasses. The aryl radicals mentioned are optionally substituted phenyl radicals and unsubstituted pyridyl or halogen-substituted pyridyl. Specific examples relate mainly to (substituted) 4-cyano-3,4-diphenylbutanoic acid (esters). Additionally described are also 4-cyano-3-pyridyl-4-phenylbutanoic acid esters, such as the compound ethyl 4-cyano-3-pyridyl-4-phenylbutanoate, or 4-cyano-3-phenyl-4-pyridylbutanoic acid ester, such as the compound methyl 4-cyano-3-(4-chlorophenyl)-4-(6-fluoropyridin-3-yl)butanoate. JP-04/297455 discloses herbicidal 4-cyano-3-phenyl-4-heteroarylbutanoic acid (esters), where the heterocyclic radicals are selected from the group consisting of 1,2,4-triazolyl, 1-pyrazolyl, 1-imidazolyl, 2- and 3-thienyl, 2- and 3-pyridyl, 1-methylpyrrol-2-yl, 2-quinolinyl, 2-methyl-3-trifluoromethylpyrazol-5-yl and 5-trifluoromethylpyridin-2-yl. Specific compounds from the 3-pyridyl series only comprise unsubstituted pyridin-3-yl radicals, for example the compounds propargyl and allyl 4-cyano-3-phenyl-4-(pyridin-3-yl)butanoate.

WO 2011/003775 discloses specific esters of 4-cyano-3,4-diphenylbutanoic acids which can be used as effective herbicides, preferably also in crops of useful plants. WO 2011/003776, WO 2011/042378, WO 2011/073143 and WO2011/098417 disclose 4-cyano-3,4-diphenylbutanoic acids and esters which have specific substitutions at the phenyl radicals and can be used as effective herbicides, preferably also in crops of useful plants.

The herbicidal activity of the known compounds of the class of substances mentioned, in particular at low application rates, and/or their compatibility with crop plants, remain deserving of improvement.

For the reasons mentioned, there is still a need for alternative, highly active herbicides for the selective application in plant crops or use on non-crop land. It is also desirable to provide alternative chemical active compounds which may be used in an advantageous manner as herbicides or plant growth regulators.

Likewise desirable are compounds having herbicidal activity which are highly effective against economically important harmful plants even at relatively low application rates and can be used selectively in crop plants, preferably with good activity against harmful plants.

SUMMARY

Surprisingly it has now been found that certain heterocyclically substituted cyanobutyrates have particular herbicidal activities and can preferably be employed in some crops selectively for controlling harmful plants.

The present invention provides compounds of the formula (I) or salts thereof

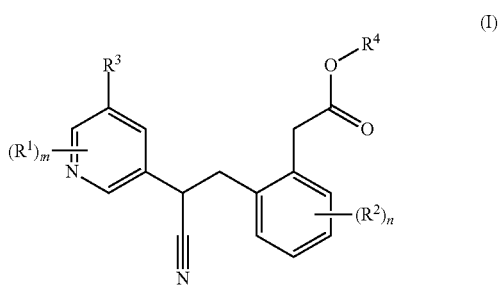

in which ($R^1$)$_m$ represents m substituents $R^1$, where $R^1$, if m=1, or each of the substituents $R^1$, if m is greater than 1, independently of the others represents halogen, cyano, nitro, hydroxy, ($C_1$-$C_8$)-alkyl, ($C_2$-$C_6$)-alkenyl, ($C_2$-$C_6$)-alkynyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-haloalkenyl, ($C_2$-$C_6$)-haloalkynyl, ($C_1$-$C_6$)-alkoxy-($C_1$-$C_4$)-alkyl, ($C_1$-$C_6$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)O$R^5$, C(O)N$R^6R^7$, C(O)-Het$^1$, N$R^8R^9$ or Het$^2$ or where in each case two groups $R^1$ located ortho at the ring or $R^1$ and $R^3$ together represent a group of the formula —$Z^1$-A*-$Z^2$ in which A* represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-A*-$Z^2$ together with the carbon atoms, attached to the group, of the phenyl ring form a fused-on 5- or 6-membered ring, ($R^2$)$_n$ represents n substituents $R^2$, where $R^2$, if n=1, or each of the substituents $R^2$, if n is greater than 1, independently of the others represents halogen, cyano, nitro, hydroxy, ($C_1$-$C_8$)-alkyl, ($C_2$-$C_6$)-alkenyl, ($C_2$-$C_6$)-alkynyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-haloalkenyl, ($C_2$-$C_6$)-haloalkynyl, ($C_1$-$C_6$)-alkoxy-($C_1$-$C_4$)-alkyl, ($C_1$-$C_6$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)O$R^{10}$, C(O)N$R^{11}R^{12}$, C(O)-Het$^3$, N$R^{13}R^{14}$ or Het$^4$ or where in each case two groups $R^2$ located ortho at the ring together are a group of the formula —$Z^3$-A-$Z^4$ in which A represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents a direct bond, O or S and $Z^4$ represents a direct bond, O or S, where the group —$Z^3$-A**-$Z^4$ together with the carbon atoms, attached to the group, of the phenyl ring form a fused-on 5- or 6-membered ring, $R^3$ represents halogen, cyano, nitro, hydroxy, ($C_1$-$C_8$)-alkyl, ($C_2$-$C_6$)-alkenyl, ($C_2$-$C_6$)-alkynyl, ($C_1$-$C_8$)-alkoxy, ($C_1$-$C_8$)-alkylthio, ($C_1$-$C_8$)-alkylsulphinyl, ($C_1$-$C_8$)-alkylsulphonyl, ($C_1$-$C_6$)-haloalkyl, ($C_1$-$C_6$)-haloalkoxy, ($C_1$-$C_6$)-haloalkylthio, ($C_1$-$C_6$)-haloalkylsulphinyl, ($C_1$-$C_6$)-haloalkylsulphonyl, ($C_2$-$C_6$)-haloalkenyl, ($C_2$-$C_6$)-haloalkynyl, ($C_1$-$C_6$)-alkoxy-($C_1$-$C_4$)-alkyl, ($C_1$-$C_6$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)O$R^{15}$, C(O)N$R^{16}R^{17}$, C(O)-Het$^5$, N$R^{18}R^{19}$ or Het$^6$, $R^4$ represents hydrogen or a hydrolyzable radical, preferably $R^4$ represents hydrogen or an optionally substituted hydrocarbon radical or an optionally substituted heterocyclyl radical, where each of the two last-mentioned carbon-containing radicals including substituents has 1 to 30 carbon atoms, preferably 1 to 24 carbon atoms, in particular 1 to 20 carbon atoms, or $R^4$ represents a radical of the formula Si$R^aR^bR^c$, —N$R^aR^b$ or —N=C$R^cR^d$, where in the 3 last-mentioned formulae each of the radicals $R^a$, $R^b$, $R^c$ and $R^d$ independently of the others represents hydrogen or an optionally substituted hydrocarbon radical, where, however, Si$H_3$ for Si$R^aR^bR^c$ is excluded, or $R^a$ and $R^b$ together with the nitrogen atom of the group —N$R^aR^b$ represent a 3- to 9-membered heterocycle which, in addition to the nitrogen atom, may contain one or two further ring heteroatoms from the group consisting of N, O and S and which is unsubstituted or substituted, or $R^c$ and $R^d$ together with the carbon atom of the group —N=C$R^cR^d$ represent a 3- to 9-membered carbocyclic radical or a heterocyclic radical which may contain 1 to 3 ring heteroatoms from the group consisting of N, O and S, where the carbocyclic or heterocyclic radical is unsubstituted or substituted, where each of the radicals $R^a$, $R^b$, $R^c$ and $R^d$ including substituents has up to 30 carbon atoms, preferably up to 24 carbon atoms, in particular up to 20 carbon atoms, or $R^4$ represents a radical of the formula —C(=O)—$R^e$ or —P(=O)($R^f$)$_2$, where $R^e$ and the radicals $R^f$ independently of one another each represent hydrogen, OH, ($C_1$-$C_8$)-alkyl, ($C_1$-$C_4$)-haloalkyl, ($C_2$-$C_8$)-alkenyl, ($C_2$-$C_8$)-alkynyl, ($C_1$-$C_6$)-alkoxy, ($C_1$-$C_6$)-alkoxy-($C_1$-$C_8$)-alkyl, ($C_1$-$C_4$)-haloalkoxy, ($C_1$-$C_4$)-haloalkoxy-($C_1$-$C_8$)-alkyl, ($C_3$-$C_8$)-alkenyloxy, ($C_3$-$C_8$)-alkenyloxy-($C_1$-$C_8$)-alkyl, ($C_3$-$C_8$)-alkynyloxy, ($C_3$-$C_8$)-alkynyloxy-($C_1$-$C_8$)-alkyl, —NR*R**, with R* and R** being defined below, tri-[($C_1$-$C_4$)-alkyl]silyl, tri-[($C_1$-$C_4$)-alkyl]silyl-($C_1$-$C_8$)alkyl, ($C_3$-$C_6$)-cycloalkyl, ($C_3$-$C_6$)-cycloalkyl-($C_1$-$C_8$)-alkyl, ($C_5$-$C_6$)-cycloalkenyl, ($C_5$-$C_6$)-cycloalkenyl-($C_1$-$C_8$)-alkyl, ($C_5$-$C_6$)-cycloalkynyl, ($C_5$-$C_6$)-cycloalkynyl-($C_1$-$C_8$)-alkyl, phenyl, phenyl-($C_1$-$C_8$)-alkyl, phenoxy, phenoxy-($C_1$-$C_8$)-alkyl, phenylamino, phenylamino-($C_1$-$C_8$)-alkyl, a radical Het$^7$, Het$^7$-($C_1$-$C_6$)-alkyl or Het$^7$-O—($C_1$-$C_6$)-alkyl, where each of the 15 last-mentioned radicals is unsubstituted in the acyclic moiety or substituted by one or more identical or different radicals $R^A$ and is unsubstituted in the cyclic moiety or substituted by one or more identical or different radicals $R^B$, $R^5$, $R^{10}$ and $R^{15}$ independently of one another each represent hydrogen, ($C_1$-$C_6$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the group M mentioned below, preferably ($C_1$-$C_4$)-alkyl, $R^6$, $R^7$, $R^8$, $R^9$, $R^{11}$, $R^{12}$, $R^{13}$, $R^{14}$, $R^{16}$, $R^{17}$, $R^{18}$ and $R^{19}$ independently of one another each represent hydrogen, ($C_1$-$C_6$)-alkyl, ($C_2$-$C_6$)-alkenyl or ($C_2$-$C_6$)-alkynyl, where each of the 3 last-mentioned radicals independently of the others is unsubstituted or substituted by one or more radicals from the group consisting of halogen, nitro, cyano and phenyl which is optionally substituted, preferably unsubstituted or substituted by one or more radicals from the group consisting of halogen, nitro, cyano, $(C_1-C_4)$-alkyl and $(C_1-C_4)$-haloalkyl, or $(C_3-C_6)$-cycloalkyl or phenyl, where each of the 2 last-mentioned radicals in each case independently of the other is unsubstituted or substituted by one or more radicals from the group consisting of halogen, nitro, cyano, $(C_1-C_4)$-alkyl, $(C_1-C_4)$-haloalkyl, phenyl and benzyl, where each of the 2 last-mentioned radicals is optionally substituted, preferably unsubstituted or substituted by one or more radicals from the group consisting of halogen, nitro, cyano, $(C_1-C_4)$-alkyl and $(C_1-C_4)$-haloalkyl, Het$^1$, Het$^2$, Het$^3$, Het$^4$, Het$^5$ and Het$^6$ independently of one another each represent a saturated or partially unsaturated radical of a heterocycle having 3 to 9 ring atoms and at least one nitrogen atom as ring heteroatom at position 1 of the ring and optionally 1, 2 or 3 further ring heteroatoms from the group consisting of N, O and S, where the radical of the heterocycle at the nitrogen atom in position 1 of the ring is attached to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl, $(C_1-C_4)$-alkoxy, $(C_1-C_4)$-haloalkoxy, $(C_1-C_4)$-alkylthio and oxo, preferably the radical of a saturated heterocycle of the type mentioned, in particular a morpholino, piperidino or pyrrolidino group, Het$^7$ independently of the others in each case represents a saturated, partially unsaturated or heteroaromatic monocyclic heterocyclyl radical having 3 to 9 ring atoms or a 9- or 10-membered bicyclic heterocycle, each containing 1, 2, 3 or 4 heteroatoms selected from the group consisting of O, N and S, R*, R** independently of one another (and also independently of other radicals NR*R**) each represent H, $(C_1-C_8$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]carbonyl, $[(C_1-C_4)$-alkoxy]carbonyl, $[(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$-alkyl, where each of the 4 last-mentioned radicals is optionally substituted in the cycle by one or more identical or different radicals from the group consisting of halogen, $(C_1-C_4)$-alkyl, $(C_1-C_4)$-haloalkyl, $(C_1-C_4)$-alkoxy and $(C_1-C_4)$-haloalkoxy or, in the case of saturated or partially unsaturated cyclic base groups, also oxo, or R* and R** together with the nitrogen atom represent a 3- to 8-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, R$^A$ represents halogen, cyano, hydroxy or $(C_1-C_6)$-alkoxy, R$^B$ represents halogen, cyano, hydroxy, oxo, nitro, $(C_1-C_8)$-alkyl, $(C_1-C_6)$-haloalkyl, cyano-$(C_1-C_6)$-alkyl, hydroxy-$(C_1-C_6)$-alkyl, nitro-$(C_1-C_6)$-alkyl, $(C_2-C_8)$-alkenyl, $(C_2-C_8)$-haloalkenyl, $(C_2-C_8)$-alkynyl, $(C_2-C_8)$-haloalkynyl, $(C_1-C_8)$-alkoxy, $(C_2-C_8)$-alkenyloxy, $(C_2-C_8)$-alkynyloxy, $(C_1-C_8)$-haloalkoxy, $(C_1-C_6)$-alkoxy-$(C_1-C_6)$-alkyl, $(C_1-C_6)$-alkoxy-$(C_1-C_4)$-alkoxy, $(C_1-C_6)$-haloalkoxy-$(C_1-C_4)$-alkyl, $(C_1-C_6)$-haloalkoxy-$(C_1-C_4)$-alkoxy, $(C_1-C_8)$-alkylthio, $(C_2-C_6)$-alkenylthio, $(C_2-C_6)$-alkynylthio, $(C_1-C_8)$-alkylsulphinyl, $(C_1-C_6)$-haloalkylsulphinyl, $(C_1-C_8)$-alkylsulphonyl, $(C_1-C_6)$-haloalkylsulphonyl, a radical of the formula R$^{aa}$—C(=O)—, R$^{aa}$—C(=O)—$(C_1-C_6)$ alkyl, the radicals R$^{aa}$ being defined below, —NR*R**, R* and R** being defined below, tri-[$(C_1-C_4)$-alkyl]silyl, tri-[$(C_1-C_4)$-alkyl]silyl-$(C_1-C_6)$-alkyl, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, phenyl, phenyl-$(C_1-C_8)$-alkyl, phenoxy, phenoxy-$(C_1-C_8)$-alkyl, phenylamino, phenylamino-$(C_1-C_8)$-alkyl or a 5- or 6-membered monocyclic or 9- or 10-membered bicyclic heterocycle which contains 1, 2, 3 or 4 heteroatoms selected from the group consisting of O, N and S, where each of the 11 last-mentioned radicals is optionally substituted in the cyclic moiety by one or more identical or different radicals R$^{bb}$, R$^{aa}$ independently of one another each represent hydrogen, OH, $(C_1-C_8)$-alkyl, $(C_1-C_6)$-haloalkyl, $(C_2-C_8)$-alkenyl, $(C_2-C_8)$-alkynyl, $(C_1-C_8)$-alkoxy, $(C_1-C_6)$-alkoxy-$(C_1-C_6)$-alkyl, $(C_1-C_6)$-alkoxy-$(C_1-C_6)$-alkyloxy, $(C_1-C_6)$-haloalkoxy, $(C_1-C_6)$-haloalkoxy-$(C_1-C_6)$-alkyl, $(C_1-C_6)$-haloalkoxy-$(C_1-C_6)$-alkoxy, $(C_3-C_8)$-alkenyloxy, $(C_3-C_8)$-alkenyloxy-$(C_1-C_6)$-alkyl, $(C_3-C_8)$-alkenyloxy-$(C_1-C_6)$-alkoxy, $(C_3-C_8)$-alkynyloxy, $(C_3-C_8)$-alkynyloxy-$(C_1-C_6)$-alkyl, $(C_3-C_8)$-alkynyloxy-$(C_1-C_6)$-alkoxy, —NR*R**, where R* and R** are as defined above, tri-[$(C_1-C_4)$alkyl]silyl, tri-[$(C_1-C_4)$alkyl]silyl-$(C_1-C_6)$-alkyl, tri-[$(C_1-C_4)$ alkyl]silyl-$(C_1-C_6)$-alkoxy, $(C_3-C_8)$-cycloalkyl, $(C_3-C_8)$-cycloalkoxy, $(C_3-C_8)$-cycloalkyl-$(C_1-C_8)$-alkyl, $(C_3-C_8)$-cycloalkyl-$(C_1-C_8)$-alkoxy, $(C_5-C_8)$-cycloalkenyl, $(C_5-C_8)$-cycloalkenyl-$(C_1-C_6)$-alkyl, $(C_5-C_8)$-cycloalkenyloxy, $(C_5-C_8)$-cycloalkynyl, $(C_5-C_8)$-cycloalkynyl-$(C_1-C_6)$-alkyl, $(C_5-C_8)$-cycloalkynyl-$(C_1-C_6)$-alkoxy, phenyl, phenyl-$(C_1-C_8)$-alkyl, phenyl-$(C_1-C_8)$-alkoxy, phenoxy, phenoxy-$(C_1-C_8)$-alkyl, phenoxy-$(C_1-C_8)$-alkoxy, phenylamino, phenylamino-$(C_1-C_8)$-alkyl, phenylamino-$(C_1-C_8)$-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the 20 last-mentioned radicals is optionally substituted in the cyclic moiety by one or more identical or different radicals R$^{cc}$, and R$^{bb}$ and R$^{cc}$ independently of one another each represent halogen, $(C_1-C_4)$-alkyl, $(C_1-C_4)$-haloalkyl, $(C_1-C_4)$-alkoxy or $(C_1-C_4)$-haloalkoxy or in the case of saturated or partially unsaturated cyclic base groups also represent oxo and M represents an equivalent of a cation,
preferably a metal ion equivalent, an ammonium ion which is optionally substituted by 1 to 4 identical or different radicals from the group consisting of $(C_1-C_6)$-alkyl, $(C_2-C_6)$-alkenyl, $(C_2-C_6)$-alkynyl, $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_4)$-alkyl, $(C_5-C_6)$-cycloalkenyl-$(C_1-C_4)$-alkyl, phenyl-$(C_1-C_4)$-alkyl, or a tertiary sulphonium ion which is preferably substituted by 3 identical or different radicals from the group consisting of $(C_1-C_6)$-alkyl, $(C_2-C_6)$-alkenyl, $(C_2-C_6)$-alkynyl, $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_4)$-alkyl, $(C_5-C_6)$-cycloalkenyl-$(C_1-C_4)$-alkyl, phenyl-$(C_1-C_4)$-alkyl, in particular $(C_1-C_4)$-alkyl, m represents 0, 1, 2 or 3, preferably 0, 1 or 2, in particular 0 or 1, and n represents 0, 1, 2, 3, 4 or 5, preferably 0, 1, 2 or 3.

DETAILED DESCRIPTION OF A PREFERRED EMBODIMENT

In the formula (I), the formula "$(R^1)_m$" means m radicals $R^1$ which are attached as substituents at the pyridyl ring in question, where the radicals in the case of m greater than 1 may be identical or different and have the meaning mentioned in each case in more detail. In the case m=0, the pyridyl ring in question is not substituted by substituents $R^1$, i.e. all ring carbon atoms of the pyridyl ring in positions 2, 4 and 6 of the pyridin-3-yl radical are attached to a hydrogen atom.

In the formula (I), the formula "$(R^2)_n$" means n radicals $R^2$ which are attached as substituents at the phenyl ring in question, where the radicals in the case of n greater than 1 may be identical or different and have the meaning mentioned in each case in more detail. In the case n=0, the phenyl ring in question is not substituted by substituents $R^2$, i.e. all ring carbon atoms of the phenyl ring in positions 2 to 6 of the phenyl radical are attached to a hydrogen atom.

The compounds of the formula (I) according to the invention include all stereoisomers which can occur on the basis of the centres of asymmetry or double bonds in the molecule whose configuration is not designated specifically in the formula or which are not specified explicitly, and mixtures thereof, including the racemic compounds and the mixtures enriched partly with particular stereoisomers. The invention also includes all tautomers, such as keto and enol tautomers, and their mixtures and salts, if appropriate functional groups are present.

In positions 3 and 4 of the substituted butanoic acid skeleton, the compounds of the formula (I) contain two centres of chirality, and they therefore occur as at least four stereoisomers and mixtures thereof, i.e. 2 enantiomeric erythro isomers and 2 enantiomeric threo isomers. Depending on the substituents $(R^1)_m$ and $(R^2)_n$ $R^3$ and $R^4$, one or more further centres of chirality may be present.

Accordingly, the invention also provides erythro/threo mixtures (diastereomer mixtures) of the compounds of the formula (I).

The invention also provides the racemic erythro isomers or the racemic threo isomers of the compounds of the formula (I).

The invention also provides the optically active (3R, 4S) and (3S, 4R) erythro isomers and mixtures thereof having an excess of one enantiomer.

The invention also provides the optically active (3R, 4R) and (3S, 4S) threo isomers and mixtures thereof having an excess of one enantiomer.

Owing to the two centres of chirality in positions 3 and 4, compounds of the same chemical constitution exist as 4 stereoisomeric configurations, namely two erythro enantiomers having the configurations (3S,4R) [=erythro-1] and (3R,4S) [=erythro-2], respectively, and two threo enantiomers having the configurations (3S,4S) [=threo-1] and (3R, 4R) [=threo-2], respectively; see the scheme below:

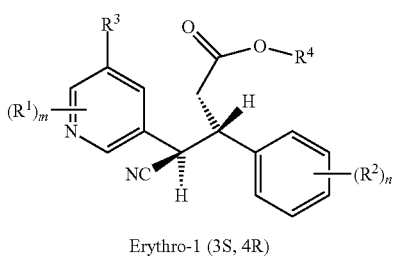

Erythro-1 (3S, 4R)

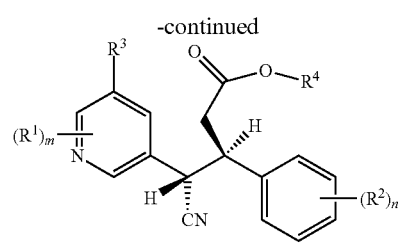

Erythro-2 (3R, 4S)

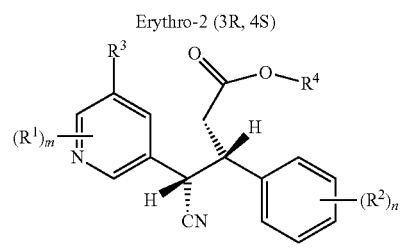

Threo-1 (3S, 4S)

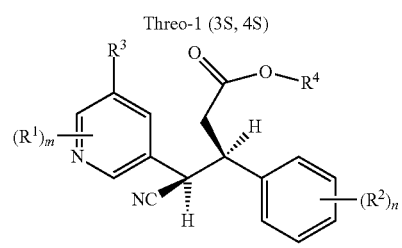

Threo-2 (3R, 4R)

The compounds (I) according to the invention represent diastereomer mixtures of the 4 stereoisomers, but also embrace the separated diastereomeric erythro or threo forms, in each case as a racemic mixture of the erythro enantiomers or threo enantiomers or as pure or stereochemically enriched enantiomers erythro-1, erythro-2, threo-1 or threo-2 mentioned above.

Preference is given to the diastereomer mixtures of the formula (I) (erythro/threo mixtures).

Preference is also given to the racemic erythro mixtures of the formula (I) of the aforementioned enantiomers erythro-1 and erythro-2 in a ratio of 50:50.

Preference is furthermore given to the racemic threo mixtures of the formula (I) of the aforementioned enantiomers threo-1 and threo-2 in a ratio of 50:50.

More preference is given to the (3R,4R) enantiomers threo-2 of the formula (Ia) or salts thereof

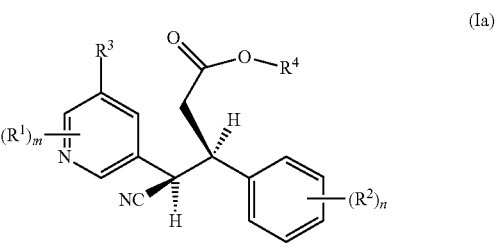

(Ia)

in which $(R^1)_m$ and $(R^2)_n$ are as defined in formula (I), where the stereochemical configuration at the carbon atom in position 3 of the butanoic acid derivative has a stereochemical purity of 60 to 100% (R), preferably 70 to 100% (R), more preferably 80 to 100% (R), in particular 90 to 100% (R), based on the mixture of threo enantiomers present, and the stereochemical configuration at the carbon atom in position 4 of the butanoic acid derivative has a stereochemical purity of 60 to 100% (R), preferably 70 to 100% (R), more preferably 80 to 100% (R), in particular 90 to 100% (R), based on the mixture of threo enantiomers present.

In the case of $R^4$=H or in the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino or else the nitrogen atom in the pyridyl ring, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally usable salts, where the type of salt is generally otherwise immaterial. In general, suitable salts are the salts of those cations or the acid addition salts of those acids whose cations and anions, respectively, have no adverse effect on the herbicidal activity of the compounds (I).

Suitable cations are in particular the ions of the alkali metals, preferably lithium, sodium or potassium, of the alkaline earth metals, preferably calcium or magnesium, and of the transition metals, preferably manganese, copper, zinc or iron. The cation used may also be ammonium or substituted ammonium, where one to four hydrogen atoms may be replaced here by $(C_1-C_4)$-alkyl, hydroxy-$(C_1-C_4)$-alkyl, $(C_1-C_4)$-alkoxy-$(C_1-C_4)$-alkyl, hydroxy-$(C_1-C_4)$-alkoxy-$(C_1-C_4)$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Also suitable are phosphonium ions, sulphonium ions, preferably tri$(C_1-C_4)$ sulphonium, in particular trimethylsulphonium, or sulphoxonium ions, preferably tri$(C_1-C_4)$sulphoxonium, in particular trimethylsulphoxonium.

Anions of useful acid addition salts are primarily chloride, bromide, fluoride, hydrogensulphate, sulphate, dihydrogenphosphate, hydrogenphosphate, nitrate, bicarbonate, carbonate, hexafluorosilicate, hexafluorophosphate, benzoate and also the anions of $(C_1-C_4)$-alkanoic acids, preferably formate, acetate, propionate, butyrate or trifluoroacetate.

In formula (I) and in all subsequent formulae, chemical radicals are referred to by names which are collective terms for the enumeration of individual group members or specifically refer to individual chemical radicals. In general, terms are used which are familiar to the person skilled in the art and/or in particular have the meanings illustrated below.

A hydrolyzable radical (see definition of $R^4$) is a radical which can be hydrolyzed under application conditions, for example a radical which can be hydrolyzed even in the spray liquor or in particular under the physiological conditions in plants, where a compound of the formula (I) having the carboxylic ester group —CO—$OR^4$ ($R^4$ is not hydrogen) is hydrolyzed to the compound of the formula (I) having the carboxylic acid group —CO—OH (i.e. the compound (I) where $R^4$=H). Expressly, the definition of the hydrolyzable radicals also includes radicals where $R^4$=hydrocarbon radical or heterocyclyl radical, the two last-mentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc.; this applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms. The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$-alkyl" is a brief notation for alkyl having from 1 to 4 carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "$(C_1-C_6)$-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbyl radicals such as alkyl, alkenyl and alkynyl radicals, including in composite radicals. Alkyl radicals, including in the combined definitions such as alkoxy, haloalkyl, etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$-cycloalkyl or $(C_5-C_9)$-cycloalkenyl. $(C_3-C_9)$-Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene. $(C_5-C_9)$-Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3- cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$-alkylidene, is the radical of a straight-chain or branched alkane which is bonded via a double bond, the position of the binding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Halogen is, for example, fluorine, chlorine, bromine or iodine. Haloalkyl, -alkenyl and -alkynyl are alkyl, alkenyl and alkynyl, respectively, which are partially or fully substituted by identical or different halogen atoms, preferably from the group consisting of fluorine, chlorine, bromine and iodine, in particular from the group consisting of fluorine, chlorine and bromine, very particularly from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals such as, for example, halocycloalkyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom.

Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

If the heterocyclyl radical or the heterocyclic ring is optionally substituted, it can be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1]octanyl or 1-aza-bicyclo[2.2.1]heptyl.

Optionally substituted heterocyclyl also includes spirocyclic systems, such as, for example, 1-oxa-5-aza-spiro[2.3] hexyl.

It is preferably a radical of a heteroaromatic ring having a heteroatom from the group consisting of N, O and S, for example the radical of a five- or six-membered ring, such as pyridyl, pyrrolyl, thienyl or furyl;
it is furthermore preferably a radical of a corresponding heteroaromatic ring having 2, 3 or 4 heteroatoms, for example pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl. Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms, such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl;
more preference is also given here to heteroaromatic radicals of six-membered heterocycles having 3 nitrogen atoms, such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl;
more preference is also given here to heteroaromatic radicals of five-membered heterocycles
having two nitrogen atoms and one oxygen atom, such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl,
more preference is also given here to heteroaromatic radicals of five-membered heterocycles having two nitrogen atoms and one sulphur atom, such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl;
more preference is also given here to heteroaromatic radicals of five-membered heterocycles having four nitrogen atoms, such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl,
more preference is also given here to heteroaromatic radicals of six-membered heterocycles such as 1,2,4,5-tetrazin-3-yl;
more preference is also given here to heteroaromatic radicals of five-membered heterocycles having three nitrogen atoms and one oxygen or sulphur atom, such as 1,2,3,4-oxatriazol-5-yl; 1,2,3,5-oxatriazol-4-yl; 1,2,3,4-thiatriazol-5-yl; 1,2,3,5-thiatriazol-4-yl;
more preference is also given here to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group consisting of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group consisting of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the hetero-ring atoms which are able to exist in different oxidation states, as in the case of N and S, for example.

Preferred examples of heterocyclyl are a heterocyclic radical having from 3 to 6 ring atoms from the group consisting of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phthalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals. Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group consisting of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulphinyl, alkylsulphonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon radicals mentioned, corresponding unsaturated aliphatic and aromatic radicals, such as optionally substituted alkenyl, alkynyl, alkenyloxy, alkynyloxy, phenyl and phenoxy. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of (followed by the group=list of the substituents)" is, wherever used, meant to be synonymous with "radicals selected from the group consisting of ( . . . )". The term "one or more radicals from the group consisting of (followed by the group=list of the substituents)" is, wherever used, meant to be synonymous with "one or more identical or different radicals selected from the group consisting of ( . . . )".

The substituents given by way of example ("first substituent level") can, if they include hydrocarbon-containing fractions, be further substituted therein if desired ("second substituent level"), by for example one of the substituents as defined for the first substituent level. Corresponding further substituent levels are possible. The term "substituted radical" preferably embraces just one or two substituent levels.

"Parent radical" refers to the respective base structure of a radical to which substituents of a substituent level are attached.

Preferred substituents for the substituent levels are, for example, amino, hydroxyl, halogen, nitro, cyano, mercapto, carboxyl, carbonamide, $SF_5$, aminosulphonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulphinyl, alkylsulphonyl, monoalkylaminosulphonyl, dialkylaminosulphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino. Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably phenyl or phenyl which is unsubstituted or substituted by one or more radicals from the group consisting of halogen, cyano, $(C_1$-$C_4)$-alkyl, $(C_1$-$C_4)$-haloalkyl, $(C_1$-$C_4)$-alkoxy-$(C_1$-$C_4)$alkyl, $(C_1$-$C_4)$-alkoxy, $(C_1$-$C_4)$-haloalkoxy, $(C_1$-$C_4)$-alkoxy-$(C_1$-$C_4)$-alkoxy, $(C_1$-$C_4)$-alkylthio and nitro, in particular phenyl which is optionally substituted by one or more radicals from the group consisting of halogen, $(C_1$-$C_4)$-alkyl, $(C_1$-$C_4)$-haloalkyl and $(C_1$-$C_4)$-alkoxy.

In the case of radicals having carbon atoms, preference is given to those having 1 to 6 carbon atoms, preferably 1 to 4 carbon atoms, especially 1 or 2 carbon atoms. Preference is generally given to substituents from the group consisting of halogen, e.g. fluorine and chlorine, $(C_1$-$C_4)$-alkyl, preferably methyl or ethyl, $(C_1$-$C_4)$-haloalkyl, preferably trifluoromethyl, $(C_1$-$C_4)$-alkoxy, preferably methoxy or ethoxy, $(C_1$-$C_4)$-haloalkoxy, nitro and cyano. Particular preference is given here to the substituents methyl, methoxy, fluorine and chlorine.

Substituted amino, such as mono- or disubstituted amino, is a radical from the group consisting of the substituted amino radicals which are N-substituted, for example, by one or two identical or different radicals from the group consisting of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably $(C_1$-$C_4)$-alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the —CO—R radical of a carboxylic acid HO—CO—R and radicals of acids derived therefrom, such as those of thiocarboxylic acid, optionally N-substituted iminocarboxylic acids or the radical of carbonic monoesters, N-substituted carbamic acid, sulphonic acids, sulphinic acids, N-substituted sulphonamide acids, phosphonic acids or phosphinic acids.

Acyl is, for example, formyl, alkylcarbonyl such as [($C_1$-$C_4$)-alkyl]carbonyl, phenylcarbonyl, alkyloxycarbonyl, phenyloxycarbonyl, benzyloxycarbonyl, alkylsulphonyl, alkylsulphinyl, N-alkyl-1-iminoalkyl and other radicals of organic acids. The radicals may each be substituted further in the alkyl or phenyl moiety, for example in the alkyl moiety by one or more radicals from the group consisting of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$)-alkyl]carbonyl, phenylcarbonyl, alkylsulphonyl, alkylsulphinyl and other radicals of organic acids.

More preferably, acyl is an alkanoyl radical having 1 to 6 carbon atoms, in particular 1 to 4 carbon atoms. Here, ($C_1$-$C_4$)-alkanoyl is the radical of an alkanoic acid having 1 to 4 carbon atoms formed after removal of the OH group of the acid group, i.e. formyl, acetyl, n-propionyl, isopropionyl or n-, i-, sec- or tert-butanoyl.

The "yl position" of a radical denotes the carbon atom having the free bond.

Compounds of the formula (I) according to the invention and compounds of the formula (I) used according to the invention and/or salts thereof are in short also referred to as "compounds (I)".

The invention also provides all stereoisomers which are encompassed by formula (I) and mixtures thereof. Such compounds of the formula (I) contain one or more asymmetric carbon atoms or else double bonds which are not stated separately in the general formulae (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

The compounds of the formula (I) also include all physical forms in which they may be present as a pure substance or, if appropriate, as a mixture with other compounds, in particular also polymorphic crystal forms of the compounds of the formula (I) or salts thereof or solvent adducts (for example hydrates).

Primarily for reasons of higher herbicidal activity, better selectivity, better producibility, better formulatability and/or other relevant properties, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Compounds of the formula (I) according to the invention and their uses according to the invention with the preferred meanings listed below of the symbols or chemical radicals or chemical groups in question are of particular interest, irrespective of the respective other radicals according to the symbols $(R^1)_m$, $(R^2)_n$, $R^3$, $R^4$ and the definitions of m and n in formula (I) and the definitions of the radicals (or chemical groups) according to the symbols $R^5$ to $R^{19}$, $Het^1$ to $Het^7$, M, R* and R**, $R^A$, $R^B$, $R^{aa}$, $R^{bb}$ and $R^{cc}$ in the corresponding sub-meanings of radicals in the formula (I).

Preference is given to compounds (I) in which
$(R^1)_m$ represents m substituents $R^1$,
where $R^1$, if m=1, or each of the substituents $R^1$, if m is greater than 1, independently of the others represents halogen, cyano, nitro, hydroxy, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-haloalkenyl, ($C_2$-$C_4$)-haloalkynyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula $C(O)OR^5$, $C(O)NR^6R^7$, $C(O)$-$Het^1$, $NR^8R^9$ or $Het^2$
or where in each case two groups $R^1$ located ortho at the ring or $R^1$ and $R^3$ together represent a group of the formula —$Z^1$-A*-$Z^2$ in which
A* represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy,
$Z^1$ represents a direct bond, O or S and
$Z^2$ represents a direct bond, O or S,
where the group —$Z^1$-A*-$Z^2$ together with the carbon atoms, attached to the group, of the phenyl ring form a fused-on 5- or 6-membered ring,
$R^5$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the group M mentioned, preferably hydrogen, ($C_1$-$C_4$)-alkyl or the group M mentioned,
$R^6$, $R^7$, $R^8$, $R^9$, $Het^1$ and $Het^2$ have the meanings mentioned, preferably
$R^6$, $R^7$, $R^8$ and $R^9$ independently of one another each represent hydrogen or ($C_1$-$C_4$)-alkyl which is unsubstituted or substituted by one or more radicals from the group consisting of halogen, nitro, cyano and phenyl, or ($C_3$-$C_6$)-cycloalkyl or phenyl, where each of the 2 last-mentioned radicals in each case independently of the other is unsubstituted or substituted by one or more radicals from the group consisting of halogen, ($C_1$-$C_4$)-alkyl, ($C_1$-$C_4$)-haloalkyl, phenyl and benzyl, in particular hydrogen, ($C_1$-$C_4$)-alkyl or ($C_1$-$C_4$)-haloalkyl,
$Het^1$ and $Het^2$ independently of one another each represent a saturated or partially unsaturated radical of a heterocycle having 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, ($C_1$-$C_4$)-alkyl, ($C_1$-$C_4$)-haloalkyl and oxo, preferably the radical of a saturated heterocycle of the type mentioned, in particular a morpholino, piperidino or pyrrolidino group, and
m represents 0, 1, 2 or 3, preferably 0, 1 or 2, in particular 0 or 1.

More preference is given to compounds (I) in which
$(R^1)_m$ represents m substituents $R^1$,
where $R^1$, if m=1, or each of the substituents $R^1$, if m is greater than 1, independently of the others represents halogen, cyano, nitro, hydroxy, ($C_1$-$C_4$)-alkyl, ($C_1$-$C_4$)-alkoxy, ($C_1$-$C_4$)-alkylthio, ($C_1$-$C_4$)-alkylsulphinyl, ($C_1$-$C_4$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_1$-$C_4$)-alkoxy-($C_1$-$C_4$)-alkyl, ($C_3$-$C_6$)-cycloalkyl, or a radical of the formula $C(O)OR^5$, $C(O)NR^6R^7$, $C(O)$-$Het^1$, $NR^8R^9$ or $Het^2$, or where in each case two groups $R^1$ located ortho at the ring or $R^1$ and $R^3$ together represent a group of the formula —$Z^1$-$A^*$-$Z^2$ in which $A^*$ represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^1$ represents a direct bond, O or S and $Z^2$ represents a direct bond, O or S, where the group —$Z^1$-$A^*$-$Z^2$ together with the carbon atoms, attached to the group, of the phenyl ring form a fused-on 5- or 6-membered ring, $R^5$ represents hydrogen, ($C_1$-$C_4$)-alkyl or the group M mentioned, $R^6$, $R^7$, $R^8$ and $R^9$ independently of one another each represent hydrogen, ($C_1$-$C_4$)-alkyl, ($C_1$-$C_4$)-haloalkyl, benzyl, ($C_3$-$C_6$)-cycloalkyl or phenyl, in particular hydrogen, methyl or ethyl, $Het^1$ and $Het^2$ independently of one another each represent a morpholino, piperidino or pyrrolidino group and m represents 0, 1, 2 or 3, preferably 0, 1 or 2, in particular 0 or 1.

Here, more preference is given to compounds (I) in which $(R^1)_m$ represents m substituents $R^1$, where $R^1$, if m=1, or each of the substituents $R^1$, if m is greater than 1, independently of the others represents halogen, cyano, nitro, methyl, ethyl, methoxy, ethoxy, methylthio, ethylthio, ($C_1$-$C_2$)-alkylsulphinyl, ($C_1$-$C_2$)-alkylsulphonyl, ($C_1$-$C_2$)-haloalkyl, ($C_1$-$C_2$)-haloalkoxy, ($C_1$-$C_2$)-haloalkylthio, ($C_1$-$C_2$)-haloalkylsulphinyl, ($C_1$-$C_2$)-haloalkylsulphonyl or ($C_1$-$C_2$)-alkoxy-($C_1$-$C_2$)-alkyl, in particular each of the substituents $R^1$ independently of the others represents halogen, such as fluorine, chlorine, bromine or iodine, or cyano, nitro, methyl, methoxy, methylthio, methylsulphinyl, methylsulphonyl, trifluoromethyl, trifluoromethoxy, difluoromethoxy, trifluoroalkylthio, trifluoromethylsulphinyl or trifluoromethylsulphonyl, in particular cyano or halogen such as fluorine, chlorine or bromine, and m represents 0, 1, 2 or 3, preferably 0, 1 or 2, in particular 0 or 1.

More preference is given to compounds of the formula (I) or salts thereof in which m is 0 (=the number zero, i.e. no substituents $R^1$ are present, i.e. all respective free bonds at the ring are occupied by hydrogen) or preferably $(R^1)_m$ represents 2-bromo, 4-bromo, 6-bromo, 2-chloro, 4-chloro, 6-chloro, 2-fluoro, 4-fluoro, 6-fluoro, 2-cyano, 4-cyano, 6-cyano, 2-methyl, 4-methyl, 6-methyl, 2-ethyl, 4-ethyl, 6-ethyl, 2-$CF_3$, 4-$CF_3$, 6-$CF_3$, 2-methoxy, 4-methoxy, 6-methoxy, 2-ethoxy, 4-ethoxy, 6-ethoxy, 2-trifluoromethoxy, 4-trifluoromethoxy, 6-trifluoromethoxy, 2-difluoromethoxy, 4-difluoromethoxy, 6-difluoromethoxy, 2-methylthio, 4-methylthio, 6-methylthio, 2-methylsulphinyl, 4-methylsulphinyl, 6-methylsulphonyl, 2-methylsulphonyl, 4-methylsulphonyl, 6-methylsulphonyl, 2-nitro, 4-nitro, 6-nitro, 2,4-dimethyl, 2,6-dimethyl, 4,6-dimethyl, 2,4-difluoro, 2,6-difluoro, 4,6-difluoro, 2,4-dichloro, 2,6-dichloro, 4,6-dichloro, (2-Cl-4-F), (2-Cl-6-F), (4-Cl-6-F), (2-F-4-Cl), (2-F-6-Cl), (4-F-6-Cl), 2,4,6-trifluoro or 2,4,6-trichloro, where the numbering of the radical refers to the position of the radical at the pyridin-3-yl radical in which the nitrogen atom is located in position 1 and the carbon atom attached to the butyric acid parent structure is located in position 3 in the ring.

Preference is also given to compounds (I) in which $(R^2)_n$ represents n substituents $R^2$, where $R^2$, if n=1, or each of the substituents $R^2$, if n is greater than 1, independently of the others represents halogen, cyano, nitro, hydroxy, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_6$)-alkylthio, ($C_1$-$C_6$)-alkylsulphinyl, ($C_1$-$C_6$)-alkylsulphonyl, ($C_1$-$C_4$)-haloalkyl, ($C_1$-$C_4$)-haloalkoxy, ($C_1$-$C_4$)-haloalkylthio, ($C_1$-$C_4$)-haloalkylsulphinyl, ($C_1$-$C_4$)-haloalkylsulphonyl, ($C_2$-$C_4$)-haloalkenyl, ($C_2$-$C_4$)-haloalkynyl, ($C_1$-$C_4$)-alkoxy-($C_1$-$C_4$)-alkyl, ($C_1$-$C_4$)-haloalkoxy-($C_1$-$C_4$)-alkyl, ($C_3$-$C_6$)-cycloalkyl which is optionally substituted by one or more radicals from the group consisting of halogen and ($C_1$-$C_4$)-alkyl, ($C_3$-$C_6$)-cycloalkoxy which is optionally substituted by one or more radicals from the group consisting of halogen and ($C_1$-$C_4$)-alkyl, or a radical of the formula C(O)$OR^{10}$, C(O)$NR^{11}R^{12}$, C(O)-$Het^3$, $NR^{13}R^{14}$ or $Het^4$ or where in each case two groups $R^2$ located ortho at the ring together are a group of the formula —$Z^3$-$A^{}$-$Z^4$ in which $A^{}$ represents an alkylene group having 1 to 4 carbon atoms which is optionally substituted by one or more radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy, $Z^3$ represents a direct bond, O or S and $Z^4$ represents a direct bond, O or S, where the group —$Z^3$-$A^{**}$-$Z^4$ together with the carbon atoms, attached to the group, of the phenyl ring form a fused-on 5- or 6-membered ring, $R^{10}$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or the group M mentioned, $R^{11}$, $R^{12}$, $R^{13}$, $R^{14}$, $Het^3$ and $Het^4$ have the meanings mentioned, preferably $R^{11}$, $R^{12}$, $R^{13}$ and $R^{14}$ independently of one another each represent hydrogen or ($C_1$-$C_4$)-alkyl which is unsubstituted or substituted by one or more radicals from the group consisting of halogen, nitro, cyano and phenyl, or ($C_3$-$C_6$)-cycloalkyl or phenyl, where each of the 2 last-mentioned radicals in each case independently of the other is unsubstituted or substituted by one or more radicals from the group consisting of halogen, ($C_1$-$C_4$)-alkyl, ($C_1$-$C_4$)-haloalkyl, phenyl and benzyl, $Het^3$ and $Het^4$ independently of one another each represent a saturated or partially unsaturated radical of a heterocycle having 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, ($C_1$-$C_4$)-alkyl, ($C_1$-$C_4$)-haloalkyl and oxo, preferably the radical of a saturated heterocycle of the type mentioned, in particular a morpholino, piperidino or pyrrolidino group, and n represents 0, 1, 2, 3, 4 or 5, preferably 0, 1, 2 or 3.

Here, more preference is given to compounds (I) in which $(R^2)_n$ represents n substituents $R^2$, where $R^2$, if n=1, or each of the substituents $R^2$, if n is greater than 1, independently of one another represent halogen, cyano, nitro, hydroxy, ($C_1$-$C_4$)-alkyl, ($C_1$-$C_4$)-alkoxy, ($C_1$-$C_4$)-alkylthio, ($C_1$-$C_4$)-alkylsulphinyl, ($C_1$-$C_4$)-alkylsulphonyl, ($C_1$-$C_4$)-haloalkyl, ($C_1$-$C_4$)-haloalkoxy, $(C_1-C_4)$-haloalkylthio, $(C_1-C_4)$-haloalkylsulphinyl, $(C_1-C_4)$-haloalkylsulphonyl, $(C_1-C_4)$-alkoxy-$(C_1-C_4)$-alkyl, $(C_3-C_6)$-cycloalkyl, or a radical of the formula $C(O)OR^{10}$, $C(O)NR^{11}R^{12}$, $C(O)$-Het$^3$, NR$^{13}$R$^{14}$ or Het$^4$ or where in each case two groups $R^2$ located ortho at the ring together are a group of the formula —Z$^3$-A-Z$^4$ in which A represents an alkylene group having 1 to 4 carbon atoms which is optionally substituted by one or more radicals from the group consisting of halogen, $(C_1-C_4)$-alkyl, $(C_1-C_4)$-haloalkyl, $(C_1-C_4)$-alkoxy and $(C_1-C_4)$-haloalkoxy, Z$^3$ represents a direct bond, O or S and Z$^4$ represents a direct bond, O or S, where the group —Z$^3$-A**-Z$^4$ together with the carbon atoms, attached to the group, of the phenyl ring form a fused-on 5- or 6-membered ring, R$^{10}$ represents hydrogen, $(C_1-C_4)$-alkyl or the group M mentioned, R$^{11}$, R$^{12}$, R$^{13}$ and R$^{14}$, Het$^3$ and Het$^4$ have the meanings mentioned, preferably R$^{11}$, R$^{12}$, R$^{13}$ and R$^{14}$ independently of one another each represent hydrogen, $(C_1-C_4)$-alkyl, $(C_1-C_4)$-haloalkyl, benzyl, $(C_3-C_6)$-cycloalkyl or phenyl, Het$^3$ and Het$^4$ independently of one another each represent a morpholino, piperidino or pyrrolidino group and n represents 0, 1, 2, 3, 4 or 5, preferably 0, 1, 2, 3 or 4, in particular 0, 1, 2 or 3.

Here, more preference is given to compounds (I) in which $(R^2)_n$ represents n substituents $R^2$, where $R^2$, if n=1, or each of the substituents $R^2$, if n is greater than 1, independently of the others represents halogen, cyano, nitro, methyl, ethyl, methoxy, ethoxy, methylthio, ethylthio, $(C_1-C_2)$-alkylsulphinyl, $(C_1-C_2)$-alkylsulphonyl, $(C_1-C_2)$-haloalkyl, $(C_1-C_2)$-haloalkoxy, $(C_1-C_2)$-haloalkylthio, $(C_1-C_2)$-haloalkylsulphinyl, $(C_1-C_2)$-haloalkylsulphonyl or $(C_1-C_2)$-alkoxy-$(C_1-C_2)$-alkyl, in particular each of the substituents $R^2$ independently of the others represents halogen, such as fluorine, chlorine, bromine or iodine, or cyano, nitro, methyl, methoxy, methylthio, methylsulphinyl, methylsulphonyl, trifluoromethyl, trifluoromethoxy, difluoromethoxy, trifluoroalkylthio, trifluoromethylsulphinyl or trifluoromethylsulphonyl, in particular cyano, nitro or halogen such as fluorine, chlorine or bromine, and n represents 0, 1, 2, 3, 4 or 5, preferably 0, 1, 2, 3 or 4, in particular 0, 1, 2 or 3.

More preference is given to compounds of the formula (I) or salts thereof in which n represents 0 (=the number zero, i.e. no substituents $R^2$ are present, i.e. all free bonds at the phenyl ring are occupied by hydrogen) or preferably $(R^2)_n$ represents 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-CF$_3$, 3-CF$_3$, 4-CF$_3$, 2-methoxy, 3-methoxy, 4-methoxy, 2-ethoxy, 3-ethoxy, 4-ethoxy, 2-trifluoromethoxy, 3-trifluoromethoxy, 4-trifluoromethoxy, 2-difluoromethoxy, 3-difluoromethoxy, 4-difluoromethoxy, 2-methylthio, 3-methylthio, 4-methylthio, 2-methylsulphinyl, 3-methylsulphinyl, 4-methylsulphinyl, 2-methylsulphonyl, 3-methylsulphonyl, 4-methylsulphonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-NO$_2$-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or else (2,6-difluoro-4-Cl), 2,5-dicyano, 2,6-dicyano, (4-methoxy-3-F), (3-CN-4-F), (3-nitro-4-F), (3-CN-4-Cl), (3-nitro-4-Cl) or (5-CN-2-F), where the numbering of the radicals refers to the position of the radical at the phenyl-1-yl radical in which the carbon atom attached to the 3-position at the butyric acid parent structure has the 1-position in the ring.

More preference is given to compounds of the formula (I) or salts thereof in which $(R^2)_n$ represents 2-cyano, 3-cyano, 4-cyano, 2-bromo, 3-bromo, 4-bromo, 2-chloro, 3-chloro, 4-chloro, 2-fluoro, 3-fluoro, 4-fluoro, 2-nitro, 3-nitro, 4-nitro, 2-methoxy, 3-methoxy, 4-methoxy, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-NO$_2$-3-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or else (2,6-difluoro-4-Cl), 2,5-dicyano, 2,6-dicyano, (4-methoxy-3-F), (3-CN-4-F), (3-nitro-4-F), (3-CN-4-Cl), (3-nitro-4-Cl) or (5-CN-2-F).

More preference is also given to compounds of the formula (I) or salts thereof in which $(R^2)_n$ represents 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, 3,4-dichloro, 3,5-dichloro, (3-Cl-2-F), (3-Cl-4-F), (3-Cl-5-F), (3-Cl-6-F), (4-Cl-2-F), (4-Cl-3-F).

Here, particular preference is given to:

Compounds of the formula (I) or salts thereof in which $(R^2)_n$ represents 3-chloro.

Compounds of the formula (I) or salts thereof in which $(R^2)_n$ represents 4-chloro.

Compounds of the formula (I) or salts thereof in which $(R^2)_n$ represents 2-fluoro.

Compounds of the formula (I) or salts thereof in which $(R^2)_n$ represents 3-fluoro.

Compounds of the formula (I) or salts thereof in which $(R^2)_n$ represents 4-fluoro.

Compounds of the formula (I) or salts thereof in which $(R^2)_n$ represents 2,3-difluoro.

Compounds of the formula (I) or salts thereof in which $(R^2)_n$ represents 2,4-difluoro.

Compounds of the formula (I) or salts thereof in which $(R^2)_n$ represents 2,5-difluoro.

Compounds of the formula (I) or salts thereof in which $(R^2)_n$ represents 2,6-difluoro.

Compounds of the formula (I) or salts thereof in which $(R^2)_n$ represents 3,4-difluoro.

Compounds of the formula (I) or salts thereof in which $(R^2)_n$ represents 3,5-difluoro.

Compounds of the formula (I) or salts thereof in which $(R^2)_n$ represents (3-Cl-2-F).

Compounds of the formula (I) or salts thereof in which $(R^2)_n$ represents (3-Cl-4-F).

Compounds of the formula (I) or salts thereof in which $(R^2)_n$ represents (3-Cl-5-F).

Compounds of the formula (I) or salts thereof in which $(R^2)_n$ represents (3-Cl-6-F).

Compounds of the formula (I) or salts thereof in which $(R^2)_n$ represents (4-Cl-2-F).

Compounds of the formula (I) or salts thereof in which $(R^2)_n$ represents (4-Cl-3-F).

Compounds of the formula (I) or salts thereof in which $(R^2)_n$ represents (2,6-difluoro-4-Cl).

Preference is also given to compounds (I) in which $R^3$ represents halogen, cyano, nitro, hydroxy, $(C_1-C_6)$-alkyl, $(C_2-C_4)$-alkenyl, $(C_2-C_4)$-alkynyl, $(C_1-C_6)$-alkoxy, $(C_1-C_6)$-alkylthio, $(C_1-C_6)$-alkylsulphinyl, $(C_1-C_6)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_2-C_4)$-haloalkenyl, $(C_2-C_4)$-haloalkynyl, $(C_1-C_4)$-alkoxy-$(C_1-C_4)$-alkyl, $(C_1-C_4)$-haloalkoxy-$(C_1-C_4)$-alkyl, $(C_3-C_6)$-cycloalkyl which is optionally substituted by one or more radicals from the group consisting of halogen and $(C_1-C_4)$-alkyl, $(C_3-C_6)$-cycloalkoxy which is optionally substituted by one or more radicals from the group consisting of halogen and $(C_1-C_4)$-alkyl, or a radical of the formula $C(O)OR^{15}$, $C(O)NR^{16}R^{17}$, $C(O)$-Het$^5$, $NR^{18}R^{19}$ or Het$^6$, $R^{15}$ represents hydrogen, $(C_1-C_4)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or the group M mentioned, preferably hydrogen, $(C_1-C_4)$-alkyl or the group M mentioned, $R^{16}$, $R^{17}$, $R^{18}$, $R^{19}$, Het$^5$ and Het$^6$ have the meanings mentioned, preferably $R^{16}$, $R^{17}$, $R^{18}$ and $R^{19}$ independently of one another each represent hydrogen or $(C_1-C_4)$-alkyl which is unsubstituted or substituted by one or more radicals from the group consisting of halogen, nitro, cyano and phenyl, or $(C_3-C_6)$-cycloalkyl or phenyl, where each of the 2 last-mentioned radicals in each case independently of the other is unsubstituted or substituted by one or more radicals from the group consisting of halogen, $(C_1-C_4)$-alkyl, $(C_1-C_4)$-haloalkyl, phenyl and benzyl, in particular hydrogen, $(C_1-C_4)$-alkyl or $(C_1-C_4)$-haloalkyl, Het$^5$ and Het$^6$ independently of one another each represent a saturated or partially unsaturated radical of a heterocycle having 3 to 6 ring atoms and at least one nitrogen atom as ring heteroatoms at position 1 of the ring and optionally 1, 2 or 3 further ring heteroatoms from the group consisting of N, O and S, where the radical of the heterocycle is attached at the nitrogen atom in position 1 of the ring to the remainder of the molecule of the compound of the formula (I) and where the heterocycle is unsubstituted or substituted by one or more radicals from the group consisting of halogen, $(C_1-C_4)$-alkyl, $(C_1-C_4)$-haloalkyl and oxo, preferably the radical of a saturated heterocycle of the type mentioned, in particular a morpholino, piperidino or pyrrolidino group.

More preference is given to compounds (I) in which $R^3$ represents halogen, cyano, nitro, hydroxy, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, $(C_1-C_4)$-haloalkyl, $(C_1-C_4)$-haloalkoxy, $(C_1-C_4)$-haloalkylthio, $(C_1-C_4)$-haloalkylsulphinyl, $(C_1-C_4)$-haloalkylsulphonyl, $(C_1-C_4)$-alkoxy-$(C_1-C_4)$-alkyl, $(C_3-C_6)$-cycloalkyl or a radical of the formula $C(O)OR^{15}$, $C(O)NR^{16}R^{17}$, $C(O)$-Het$^5$, $NR^{18}R^{19}$ or Het$^6$, $R^{15}$ represents hydrogen, $(C_1-C_4)$-alkyl or the group M mentioned, $R^{16}$, $R^{17}$, $R^{18}$ and $R^{19}$ independently of one another each represent hydrogen, $(C_1-C_4)$-alkyl, $(C_1-C_4)$-haloalkyl, benzyl, $(C_3-C_6)$-cycloalkyl or phenyl, in particular hydrogen, methyl or ethyl, Het$^5$ and Het$^6$ independently of one another each represent a morpholino, piperidino or pyrrolidino group.

Here, more preference is given to compounds (I) in which $R^3$ represents halogen, cyano, nitro, methyl, ethyl, methoxy, ethoxy, methylthio, ethylthio, $(C_1-C_2)$-alkylsulphinyl, $(C_1-C_2)$-alkylsulphonyl, $(C_1-C_2)$-haloalkyl, $(C_1-C_2)$-haloalkoxy, $(C_1-C_2)$-haloalkylthio, $(C_1-C_2)$-haloalkylsulphinyl, $(C_1-C_2)$-haloalkylsulphonyl, $(C_1-C_2)$-alkoxy-$(C_1-C_2)$-alkyl or [$(C_1-C_4)$-alkoxy]carbonyl, $R^3$ represents in particular halogen, such as fluorine, chlorine, bromine or iodine, or cyano, nitro, methyl, methoxy, methylthio, methylsulphinyl, methylsulphonyl, trifluoromethyl, trifluoromethoxy, difluoromethoxy, trifluoroalkylthio, trifluoromethylsulphinyl, trifluoromethylsulphonyl, methoxycarbonyl or ethoxycarbonyl, in particular halogen such as fluorine, chlorine or bromine, and m represents 0, 1, 2 or 3, preferably 0, 1 or 2, in particular 0 or 1.

More preference is given to compounds of the formula (I) or salts thereof in which $R^3$ represents bromine, chlorine, fluorine, cyano, methyl, nitro, methoxycarbonyl or ethoxycarbonyl.

More preference is given to compounds of the formula (I) or salts thereof in which $(R^1)_m$ and $R^3$ together represent 5-bromo, 5-chloro, 5-fluoro, 5-cyano, 5-methyl, 5-ethyl, 5-CF$_3$, 5-methoxy, 5-ethoxy, 5-trifluoromethyl, 5-difluoromethoxy, 5-methylthio, 5-methylsulphinyl, 5-methylsulphonyl, 5-nitro, 5-methoxycarbonyl, 5-ethoxycarbonyl, 2,5-difluoro, 4,5-difluoro, 5,6-difluoro, 2,5-dichloro, 4,5-dichloro, 5,6-dichloro, 2,5-dibromo, 4,5-dibromo, 5,6-dibromo, 2,5-dimethyl, 4,5-dimethyl, 5,6-dimethyl, 2,5-dicyano, 4,5-dicyano, 5,6-dicyano, (2-Cl-5-F), (4-Cl-5-F), (6-Cl-5-F), (2-Br-5-F), (4-Br-5-F), (6-Br-5-F), (2-F-5-Cl), (4-F-5-Cl), (6-F-5-Cl), (2-F-5-Br), (4-F-5-Br), (6-F-5-Br), (2-Br-5-Cl), (4-Br-5-Cl), (6-Br-5-Cl), (2-Cl-5-Br), (4-Cl-5-Br), (6-Cl-5-Br), (2-CN-5-F), (4-CN-5-F), (6-CN-5-F), (2-CH$_3$-5-F), (4-CH$_3$-5-F), (6-CH$_3$-5-F), (2-OCH$_3$-5-F), (4-OCH$_3$-5-F), (6-OCH$_3$-5-F), (2-OCHF$_2$-5-F), (4-OCHF$_2$-5-F), (6-OCHF$_2$-5-F), (2-CN-5-Cl), (4-CN-5-Cl), (6-CN-5-Cl), (2-CH$_3$-5-Cl), (4-CH$_3$-5-Cl), (6-CH$_3$-5-Cl), (2-OCH$_3$-5-Cl), (4-OCH$_3$-5-Cl), (6-OCH$_3$-5-Cl), (2-OCHF$_2$-5-Cl), (4-OCHF$_2$-5-Cl), (6-OCHF$_2$-5-Cl),
(2-CN-5-Br), (4-CN-5-Br), (6-CN-5-Br), (2-CH$_3$-5-Br), (4-CH$_3$-5-Br), (6-CH$_3$-5-Br),
(2-OCH$_3$-5-Br), (4-OCH$_3$-5-Br), (6-OCH$_3$-5-Br), (2-OCHF$_2$-5-Br), (4-OCHF$_2$-5-Br), (6-OCHF$_2$-5-Br),
(2-CN-5-CH$_3$), (4-CN-5-CH$_3$), (6-CN-5-CH$_3$), (2-F-5-CH$_3$), (4-F-5-CH$_3$), (6-F-5-CH$_3$), (2-Cl-5-CH$_3$), (4-Cl-5-CH$_3$), (6-Cl-5-CH$_3$), (2-Br-5-CH$_3$), (4-Br-5-CH$_3$), (6-Br-5-CH$_3$), (2-OCH$_3$-5-CH$_3$), (4-OCH$_3$-5-CH$_3$), (6-OCH$_3$-5-CH$_3$), (2-OCHF$_2$-5-CH$_3$), (4-OCHF$_2$-5-CH$_3$), (6-OCHF$_2$-5-CH$_3$), (2-F-5-CN), (4-F-5-CN), (6-F-5-CN), (2-Cl-5-CN), (4-Cl-5-CN), (6-Cl-5-CN), (2-Br-5-CN), (4-Br-5-CN), (6-Br-5-CN), (2-CH$_3$-5-CN), (4-CH$_3$-5-CN), (6-CH$_3$-5-CN), (2-OCH$_3$-5-CN), (4-OCH$_3$-5-CN), (6-OCH$_3$-5-CN), (2-OCHF$_2$-5-CN), (4-OCHF$_2$-5-CN), (6-OCHF$_2$-5-CN), (2-F-5-NO$_2$), (4-F-5-NO$_2$), (6-F-5-NO$_2$), (2-Cl-5-NO$_2$), (4-Cl-5-NO$_2$), (6-Cl-5-NO$_2$), (2-Br-5-NO$_2$), (4-Br-5-NO$_2$), (6-Br-5-NO$_2$), (2-CN-5-NO$_2$), (4-CN-5-NO$_2$), (6-CN-5-NO$_2$), (2-CH$_3$-5-NO$_2$), (4-CH$_3$-5-NO$_2$), (6-CH$_3$-5-NO$_2$), (2-OCH$_3$-5-NO$_2$), (4-OCH$_3$-5-NO$_2$), (6-OCH$_3$-5-NO$_2$), (2-OCHF$_2$-5-NO$_2$), (4-OCHF$_2$-5-NO$_2$), (6-OCHF$_2$-5-NO$_2$), (2-F-5-CO$_2$CH$_3$), (4-F-5-CO$_2$CH$_3$), (6-F-5-CO$_2$CH$_3$), (2-Cl-5-CO$_2$CH$_3$), (4-Cl-5-CO$_2$CH$_3$), (6-Cl-5-CO$_2$CH$_3$), (2-Br-5-CO$_2$CH$_3$), (4-Br-5-CO$_2$CH$_3$), (6-Br-5-CO$_2$CH$_3$), (2-CN-5-CO$_2$CH$_3$), (4-CN-5-CO$_2$CH$_3$), (6-CN-5-CO$_2$CH$_3$), (2-CH$_3$-5-CO$_2$CH$_3$), (4-CH$_3$-5-CO$_2$CH$_3$), (6-CH$_3$-5-CO$_2$CH$_3$), (2-OCH$_3$-5-CO$_2$CH$_3$), (4-OCH$_3$-5-CO$_2$CH$_3$), (6-OCH$_3$-5-CO$_2$CH$_3$), (2-OCHF$_2$-5-CO$_2$CH$_3$), (4-OCHF$_2$-5-CO$_2$CH$_3$) or (6-OCHF$_2$-5-CO$_2$CH$_3$).

More preference is here given to compounds of the formula (I) or salts thereof in which $(R^1)_m$ and $R^3$ together represent 5-bromo, 5-chloro, 5-fluoro, 5-cyano, 5-methyl, 5-ethyl, 5-CF$_3$, 5-methoxy, 5-nitro, 5-methoxycarbonyl, 5-ethoxycarbonyl, 2,5-difluoro, 4,5-difluoro, 5,6-difluoro, 5,6-dichloro, 5,6-dibromo, 5,6-dimethyl, 5,6-dicyano, (6-Cl-5-F), (6-Br-5-F), (2-F-5-Cl), (4-F-5-Cl), (6-F-5-Cl), (2-F-5-Br), (4-F-5-Br), (6-F-5-Br), (6-Br-5-Cl), (6-Cl-5-Br), (6-CN-5-F), (6-CH$_3$-5-F), (6-OCH$_3$-5-F), (6-OCHF$_2$-5-F), (6-CN-5-Cl), (6-CH$_3$-5-Cl), (6-OCH$_3$-5-Cl), (6-OCHF$_2$-5-Cl), (6-CN-5-Br), (6-CH$_3$-5-Br), (6-OCH$_3$-5-Br), (6-OCHF$_2$-5-Br), (6-CN-5-CH$_3$), (2-F-5-CH$_3$), (4-F-5-CH$_3$), (6-F-5-CH$_3$), (6-Cl-5-CH$_3$), (6-Br-5-CH$_3$), (6-OCH$_3$-5-CH$_3$), (6-OCHF$_2$-5-CH$_3$), (2-F-5-CN), (4-F-5-CN), (6-F-5-CN), (6-Cl-5-CN), (6-Br-5-CN), (6-CH$_3$-5-CN), (6-OCH$_3$-5-CN), (6-OCHF$_2$-5-CN), (2-F-5-NO$_2$), (4-F-5-NO$_2$), (6-F-5-NO$_2$), (6-Cl-5-NO$_2$), (6-Br-5-NO$_2$), (6-CN-5-NO$_2$), (6-CH$_3$-5-NO$_2$), (6-OCH$_3$-5-NO$_2$), (6-OCHF$_2$-5-NO$_2$), (2-F-5-CO$_2$CH$_3$), (4-F-5-CO$_2$CH$_3$), (6-F-5-CO$_2$CH$_3$), (6-Cl-5-CO$_2$CH$_3$), (6-Br-5-CO$_2$CH$_3$), (6-CN-5-CO$_2$CH$_3$), (6-CH$_3$-5-CO$_2$CH$_3$), (6-OCH$_3$-5-CO$_2$CH$_3$) or (6-OCHF$_2$-5-CO$_2$CH$_3$).

More preference is given to:
Compounds of the formula (I) or salts thereof in which m=0 and $(R^2)_n$ represents 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F) or else (2,6-difluoro-4-Cl), 3-cyano, 4-cyano, 3-nitro or 4-nitro and $R^3$ represents fluorine, chlorine, bromine, methyl, cyano, nitro or methoxycarbonyl.

Compounds of the formula (I) or salts thereof in which $(R^1)_m$=2-F, 2-Cl, 4-F, 4-Cl, 6-F, 6-Cl, 2-Br, 4-Br, 6-Br, 2-CN, 4-CN, 6-CN, 2-methyl, 4-methyl, 6-methyl, 2-ethyl, 4-ethyl, 6-ethyl, 2-methoxy, 4-methoxy, 6-methoxy, 2-ethoxy, 4-ethoxy, 6-ethoxy, 2-difluoromethoxy, 4-difluoromethoxy, 6-difluoromethoxy, 2-trifluoromethoxy, 4-trifluoromethoxy or 6-trifluoromethoxy and $(R^2)_n$ represents 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F) or else (2,6-difluoro-4-Cl), 3-cyano, 4-cyano, 3-nitro or 4-nitro and $R^3$ represents fluorine, chlorine, bromine, methyl, cyano, nitro, methoxycarbonyl or ethoxycarbonyl.

Compounds of the formula (I) or salts thereof in which $(R^1)_m$=2-F, 2-Cl, 4-F, 4-Cl, 6-F, 6-Cl, 6-Br, 6-CN, 6-methyl, 6-methoxy or 6-difluoromethoxy and $(R^2)_n$ represents 3-chloro, 4-chloro, 2-fluoro, 3-fluoro, 4-fluoro, 2,3-difluoro, 2,4-difluoro, 2,5-difluoro, 2,6-difluoro, 3,4-difluoro, 3,5-difluoro, (3-Cl-2-F), (3-Cl-4-F), (3-Cl-5-F), (3-Cl-6-F), (4-Cl-2-F) or (4-Cl-3-F) or else (2,6-difluoro-4-Cl), 3-cyano, 4-cyano, 3-nitro or 4-nitro and $R^3$ represents fluorine, chlorine, bromine, methyl, cyano, nitro or methoxycarbonyl.

In general, from among the compounds having the above-mentioned meanings for individual groups or combinations of groups $(R^1)_m$, $(R^2)_n$ and $R^3$, preference is given to those in which the remaining groups or combinations of groups in the compounds are defined according to the meanings mentioned as preferred.

Preference is also given to compounds (I) in which

M represents an equivalent of a cation, preferably a metal ion equivalent, an ammonium ion which is optionally substituted by 1 to 4 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl, or a tertiary sulphonium ion which is preferably substituted by 3 identical or different radicals from the group consisting of ($C_1$-$C_4$)-alkyl, ($C_3$-$C_6$)-cycloalkyl, phenyl, ($C_3$-$C_6$)-cycloalkyl-($C_1$-$C_4$)-alkyl and phenyl-($C_1$-$C_4$)-alkyl, in particular ($C_1$-$C_4$)-alkyl.

Preference is given to the compounds of the formula (I) according to the invention, preferably of the formula (Ia), or salts thereof in which $R^4$ represents hydrogen, alkyl, alkenyl or alkynyl, where each of the 3 last-mentioned radicals is unsubstituted or substituted and, including substituents, has up to 30 carbon atoms, preferably up to 24 carbon atoms, in particular up to 20 carbon atoms, or represents cycloalkyl, cycloalkenyl, cycloalkynyl or aryl, where each of the 4 last-mentioned radicals is unsubstituted or substituted and, including substituents, has up to 30 carbon atoms, preferably up to 24 carbon atoms, in particular up to 20 carbon atoms, or represents a heterocyclyl radical having 3 to 9 ring atoms which contains 1 to 4 heteroatoms from the group consisting of N, O and S, which is unsubstituted or substituted and which, including substituents, has 1 to 30 carbon atoms, preferably 1 to 24 carbon atoms, in particular 1 to 20 carbon atoms.

More preference is here also given to compounds (I), preferably of the formula (Ia), or salts thereof in which $R^4$ represents hydrogen.

More preference is here also given to compounds (I), preferably of the formula (Ia), or salts thereof in which $R^4$ represents H, ($C_1$-$C_{18}$)-alkyl, ($C_2$-$C_{18}$)-alkenyl or ($C_2$-$C_{18}$)-alkynyl, where each of the 3 last-mentioned radicals is unsubstituted or substituted and, including substituents, has up to 30 carbon atoms, preferably up to 24 carbon atoms, in particular up to 20 carbon atoms, or represents ($C_3$-$C_9$)-cycloalkyl, ($C_5$-$C_9$)-cycloalkenyl, ($C_5$-$C_9$)-cycloalkynyl or phenyl, where each of the 4 last-mentioned radicals is unsubstituted or substituted and, including substituents, has up to 30 carbon atoms, preferably up to 24 carbon atoms, in particular up to 20 carbon atoms.

More preference is here also given to compounds (I), preferably of the formula (Ia), or salts thereof in which $R^4$ represents hydrogen, ($C_1$-$C_{18}$)-alkyl, ($C_2$-$C_{18}$)-alkenyl or ($C_2$-$C_{18}$)-alkynyl, where each of the 3 last-mentioned radicals is unsubstituted or substituted by one or more radicals from the group consisting of the radicals [subgroups (a)-(d)]

(a) halogen, cyano, thio, nitro, hydroxy, carboxy, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio, ($C_1$-$C_8$)-haloalkylthio, ($C_2$-$C_8$)-haloalkenylthio, ($C_2$-$C_8$)-haloalkynylthio, ($C_1$-$C_8$)-alkylsulphinyl, ($C_2$-$C_8$)-alkenylsulphinyl, ($C_2$-$C_8$)-alkynylsulphinyl, ($C_1$-$C_8$)-haloalkylsulphinyl, ($C_2$-$C_8$)-haloalkenylsulphinyl, ($C_2$-$C_8$)-haloalkynylsulphinyl, ($C_1$-$C_8$)-alkylsulphonyl, ($C_2$-$C_8$)-alkenylsulphonyl, ($C_2$-$C_8$)-alkynylsulphonyl, ($C_1$-$C_8$)-haloalkylsulphonyl, ($C_2$-$C_8$)-haloalkenylsulphonyl, ($C_2$-$C_8$)-haloalkynylsulphonyl, radicals of the formula —NR*R**, where R* and R** are defined as above or below, and $(C_3-C_8)$-cycloalkyl, $(C_5-C_8)$-cycloalkenyl, $(C_5-C_8)$-cycloalkynyl, $(C_3-C_8)$-cycloalkyl-$(C_1-C_6)$-alkoxy, $(C_3-C_8)$-cycloalkyl-$(C_1-C_6)$-alkyl-$S(O)_p$—, $(C_5-C_8)$-cycloalkenyl-$(C_1-C_6)$-alkoxy, $(C_5-C_8)$-cycloalkenyl-$(C_1-C_6)$-alkyl-$S(O)_p$—, $(C_5-C_8)$-cycloalkynyl-$(C_1-C_6)$-alkoxy, $(C_5-C_8)$-cycloalkynyl-$(C_1-C_6)$-alkyl-$S(O)_p$—, $(C_3-C_8)$-cycloalkoxy, $(C_3-C_8)$-cycloalkyl-$S(O)_p$—, $(C_5-C_8)$-cycloalkenyloxy, $(C_5-C_8)$-cycloalkenyl-$S(O)_p$—, $(C_5-C_8)$cycloalkynyloxy, $(C_5-C_8)$-cycloalkynyl-$S(O)_p$—, $(C_3-C_8)$-cycloalkoxy-$(C_1-C_6)$-alkoxy, $(C_3-C_8)$-cycloalkoxy-$(C_1-C_6)$-alkyl-$S(O)_p$—, phenyl, phenyl-$(C_1-C_6)$-alkoxy, phenoxy, phenyl-$S(O)_p$—, phenyl-$(C_1-C_6)$-alkyl-$S(O)_p$—, phenoxy-$(C_1-C_6)$-alkoxy, phenoxy-$(C_1-C_6)$-alkyl-$S(O)_p$—, a radical $Het^7$, $Het^7$-$S(O)_p$—, $Het^7$-$(C_1-C_6)$-alkoxy, $Het^7$-O—, $Het^7$-O-$(C_1-C_6)$-alkoxy, where the heterocyclic radical $Het^7$ is defined as above or below, where each of the 29 last-mentioned radicals is unsubstituted in the acyclic moiety or substituted by one or more identical or different radicals $R^A$ and is unsubstituted in the cyclic moiety or substituted by one or more identical or different radicals $R^B$ and p independently of the others in each case represents 0, 1 or 2, and preferably the radicals (a)

halogen, cyano, nitro, hydroxy, carboxy, $(C_1-C_6)$-alkoxy, $(C_1-C_8)$-haloalkoxy, $(C_1-C_4)$-alkoxy-$(C_1-C_4)$-alkoxy, $(C_1-C_6)$-alkylthio, $(C_1-C_6)$-haloalkylthio, $(C_1-C_6)$-alkylsulphinyl, $(C_1-C_6)$-haloalkylsulphinyl, $(C_1-C_6)$-alkylsulphonyl, $(C_1-C_8)$-haloalkylsulphonyl, $(C_3-C_8)$-cycloalkyl, $(C_5-C_8)$-cycloalkenyl, $(C_5-C_8)$-cycloalkynyl, $(C_3-C_8)$-cycloalkyl-$(C_1-C_6)$-alkoxy, $(C_5-C_8)$-cycloalkenyl-$(C_1-C_6)$-alkoxy, $(C_5-C_8)$-cycloalkynyl-$(C_1-C_6)$-alkoxy, $(C_3-C_8)$-cycloalkoxy, $(C_3-C_8)$-cycloalkylthio, $(C_3-C_8)$-cycloalkylsulphinyl, $(C_3-C_8)$-cycloalkylsulphonyl, $(C_3-C_8)$-cycloalkoxy-$(C_1-C_6)$-alkoxy, phenyl, phenoxy, phenylthio, phenylsulphinyl, phenylsulphonyl, phenyl-$(C_1-C_6)$-alkoxy, phenyl-$(C_1-C_6)$-alkylthio, phenyl-$(C_1-C_6)$-alkylsulphinyl, phenyl-$(C_1-C_6)$-alkylsulphonyl, phenoxy-$(C_1-C_6)$-alkoxy, phenoxy-$(C_1-C_6)$-alkylthio, phenoxy-$(C_1-C_6)$-alkylsulphinyl and phenoxy-$(C_1-C_6)$-alkylsulphyl, where each of the radicals mentioned with cyclic moieties is unsubstituted in the acyclic moiety or substituted by one or more identical or different radicals $R^A$ and is unsubstituted in the cyclic moiety or substituted by one or more identical or different radicals $R^B$, (b) radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$), preferably a radical of the formula —C(=O)—$R^C$, —C(=O)—O—$R^C$, —O—C(=O)—$R^c$ or —O—C(=O)—O—$R^C$, in particular a radical of the formula —C(=O)—O—$R^C$, —O—C(=O)—$R^c$ or —O—C(=O)—O—$R^C$, where R*, R**, $R^C$ and $R^D$ are as defined below, preferably the radicals (b1)

[($C_1-C_8$)-alkoxy]carbonyl, [($C_1-C_8$)-alkoxy]thiocarbonyl, [($C_2-C_8$)-alkenyloxy]carbonyl, [($C_2-C_8$)-alkynyloxy]carbonyl, [($C_1-C_8$)-alkylthio]carbonyl, [($C_2-C_8$)-alkenylthio]carbonyl, [($C_2-C_8$)-alkynylthio]carbonyl, ($C_1-C_8$)-alkanoyl, [($C_2-C_8$)-alkenyl]carbonyl, [($C_2-C_8$)-alkynyl]carbonyl, [($C_1-C_8$)-alkyl]carbonylamino, [($C_2-C_8$)-alkenyl]carbonylamino, [($C_2-C_8$)-alkynyl]carbonylamino, [($C_1-C_6$)-alkoxy]carbonylamino, [($C_2-C_8$)-alkenyloxy]carbonylamino, [($C_2-C_8$)-alkynyloxy]carbonylamino, [($C_1-C_8$)-alkylamino]carbonylamino, [($C_1-C_6$)-alkyl]carbonyloxy, [($C_2-C_6$)-alkenyl]carbonyloxy, [($C_2-C_6$)-alkynyl]carbonyloxy, [($C_1-C_8$)-alkoxy]carbonyloxy, [($C_2-C_8$)-alkenyloxy]carbonyloxy and [($C_2-C_8$)-alkynyloxy]carbonyloxy, where each of the 23 last-mentioned radicals is unsubstituted or substituted by one or more radicals from the group consisting of halogen, $NO_2$, ($C_1-C_4$)-alkoxy and optionally halogen-, CN, $NO_2$—, ($C_1-C_4$)-alkyl-, ($C_1-C_4$)-alkoxy- and ($C_1-C_4$)-alkylthio-substituted phenyl, and preferably the radicals (b2)

($C_3-C_8$)-cycloalkylcarbonyl, ($C_3-C_8$)-cycloalkyl-[($C_1-C_6$)-alkyl]carbonyl, ($C_3-C_8$)-cycloalkyl-[($C_1-C_6$)-alkoxy]carbonyl, ($C_3-C_8$)-cycloalkoxycarbonyl, ($C_3-C_8$)-cycloalkoxy-[($C_1-C_6$)-alkyl]carbonyl, ($C_3-C_8$)-cycloalkoxy-[($C_1-C_6$)-alkoxy]carbonyl, ($C_3-C_8$)-cycloalkylcarbonyloxy, ($C_3-C_8$)-cycloalkyl-[($C_1-C_6$)-alkyl]carbonyloxy, ($C_5-C_8$)-cycloalkenyl-[($C_1-C_6$)-alkyl]carbonyloxy, ($C_5-C_8$)-cycloalkynyl-[($C_1-C_6$)-alkyl]carbonyloxy, ($C_3-C_8$)-cycloalkyl-[($C_1-C_6$)-alkoxy]carbonyloxy, ($C_5-C_8$)-cycloalkenyl-[($C_1-C_6$)-alkoxy]carbonyloxy, ($C_5-C_8$)-cycloalkynyl-[($C_1-C_6$)-alkoxy]carbonyloxy, ($C_3-C_8$)-cycloalkoxycarbonyloxy, ($C_3-C_8$)-cycloalkoxy-[($C_1-C_6$)-alkyl]carbonyloxy, ($C_3-C_8$)-cycloalkoxy-[($C_1-C_6$)-alkoxy]carbonyloxy, ($C_3-C_8$)-cycloalkylcarbonylamino, ($C_3-C_8$)-cycloalkyl-[($C_1-C_6$)-alkyl]carbonylamino, ($C_5-C_8$)-cycloalkenyl-[($C_1-C_6$)-alkyl]carbonylamino, ($C_5-C_8$)-cycloalkynyl-[($C_1-C_6$)-alkyl]carbonylamino, ($C_3-C_8$)-cycloalkyl-[($C_1-C_6$)-alkoxy]carbonylamino, ($C_3-C_8$)-cycloalkoxycarbonylamino, ($C_3-C_8$)-cycloalkoxy-[($C_1-C_6$)-alkyl]carbonylamino and ($C_3-C_8$)-cycloalkoxy-[($C_1-C_6$)-alkoxy]carbonylamino, phenylcarbonyl, phenyl-[($C_1-C_6$)-alkyl]carbonyl, phenyl-[($C_1-C_6$)-alkoxy]carbonyl, phenoxycarbonyl, phenoxy-[($C_1-C_6$)-alkyl]carbonyl, phenoxy-[($C_1-C_6$)-alkoxy]carbonyl, phenylcarbonyloxy, phenyl-[($C_1-C_6$)-alkyl]carbonyloxy, phenyl-[($C_1-C_6$)-alkoxy]carbonyloxy, phenoxycarbonyloxy, phenoxy-[($C_1-C_6$)-alkyl]carbonyloxy, phenoxy-[($C_1-C_6$)-alkoxy]carbonyloxy, phenylcarbonylamino, phenyl-[($C_1-C_6$)-alkyl]carbonylamino, phenyl-[($C_1-C_6$)-alkoxy]carbonylamino, phenoxycarbonylamino,
phenoxy-[($C_1$-$C_6$)-alkyl]carbonylamino,
phenoxy-[($C_1$-$C_6$)-alkoxy]carbonylamino,
 where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzofused, and unsubstituted at the ring or at the polycyclic system or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro, and (c) radicals of the formulae —SiR'$_3$, —O—SiR'$_3$, (R')$_3$Si—($C_1$-$C_6$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OR)$_2$, in which each of the radicals R' independently of the others represents H, ($C_1$-$C_4$)-alkyl or phenyl, which is unsubstituted or substituted by one or more radicals from the group consisting of halogen, ($C_1$-$C_4$)-alkyl, ($C_1$-$C_4$)-alkoxy, ($C_1$-$C_4$)-haloalkyl, ($C_1$-$C_4$)-haloalkoxy and nitro or at two adjacent positions by a ($C_2$-$C_6$)-alkylene bridge, and q represents an integer from 0 to 6, and (d) radicals of the formula R"O—CHR'"CH(OR")—($C_1$-$C_6$)-alkoxy,
 in which each of the radicals R" independently of the others represents H or ($C_1$-$C_4$)-alkyl or together the radicals represent a ($C_1$-$C_6$)-alkylene group and R'" represents H or ($C_1$-$C_4$)-alkyl, or $R^4$ represents ($C_3$-$C_9$)-cycloalkyl, ($C_5$-$C_9$)-cycloalkenyl, ($C_5$-$C_9$)-cycloalkynyl or phenyl,
 where each of the 4 last-mentioned radicals is unsubstituted or substituted by one or more radicals from the group consisting of the radicals [subgroups (a')-(e')]

(a') halogen, cyano, thio, nitro, hydroxy, carboxy, ($C_1$-$C_8$)-alkyl, ($C_1$-$C_8$)-haloalkyl, ($C_1$-$C_4$)-alkoxy-($C_1$-$C_4$)-alkyl, ($C_2$-$C_8$)-alkenyl, ($C_2$-$C_8$)-haloalkenyl, ($C_2$-$C_8$)-alkynyl, ($C_2$-$C_8$)-haloalkynyl, ($C_1$-$C_8$)-alkoxy, ($C_2$-$C_8$)-alkenyloxy, ($C_2$-$C_8$)-alkynyloxy, ($C_1$-$C_8$)-haloalkoxy, ($C_1$-$C_4$)-alkoxy-($C_1$-$C_4$)-alkoxy, ($C_1$-$C_8$)-alkylthio, ($C_2$-$C_8$)-alkenylthio, ($C_2$-$C_8$)-alkynylthio and radicals of the formulae —NR*R**, where the radicals R* and R** are defined below, (b') radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) and —O—P(=O)(O$R^C$)(O$R^D$),
 preferably a radical of the formula —C(=O)—$R^C$, —C(=O)—O—$R^C$, —O—C(=O)—$R^c$ or —O—C(=O)—O—$R^C$, in particular a radical of the formula —C(=O)—O—$R^C$, —O—C(=O)—$R^c$ or —O—C(=O)—O—$R^C$,
 where R*, R**, $R^C$ and $R^D$ are as defined below,
and preferably the radicals (b1')
[($C_1$-$C_8$)-alkoxy]carbonyl, [($C_1$-$C_8$)-alkoxy]thiocarbonyl, [($C_2$-$C_8$)-alkenyloxy]carbonyl, [($C_2$-$C_8$)-alkynyloxy]carbonyl, [($C_1$-$C_8$)-alkylthio]carbonyl, [($C_2$-$C_8$)-alkenylthio]carbonyl, [($C_2$-$C_8$)-alkynylthio]carbonyl, ($C_1$-$C_8$)-alkanoyl, [($C_2$-$C_8$)-alkenyl]carbonyl, [($C_2$-$C_8$)-alkynyl]carbonyl, ($C_1$-$C_4$)-alkylimino, ($C_1$-$C_4$)-alkoxyimino, [($C_1$-$C_8$)-alkyl]carbonylamino, [($C_2$-$C_8$)-alkenyl]carbonylamino, [($C_2$-$C_8$)-alkynyl]carbonylamino, [($C_1$-$C_8$)-alkoxy]carbonylamino, [($C_2$-$C_8$)-alkenyloxy]carbonylamino, [($C_2$-$C_8$)-alkynyloxy]carbonylamino, [($C_1$-$C_8$)-alkylamino]carbonylamino, [($C_1$-$C_6$)-alkyl]carbonyloxy, [($C_2$-$C_6$)-alkenyl]carbonyloxy, [($C_2$-$C_6$)-alkynyl]carbonyloxy, [($C_1$-$C_8$)-alkoxy]carbonyloxy, [($C_2$-$C_8$)-alkenyloxy]carbonyloxy, [($C_2$-$C_8$)-alkynyloxy]carbonyloxy, ($C_1$-$C_8$)-alkylsulphinyl and ($C_1$-$C_8$)-alkylsulphonyl, where each of the 27 last-mentioned radicals is unsubstituted or substituted by one or more radicals from the group consisting of halogen, NO$_2$, ($C_1$-$C_4$)-alkoxy and optionally substituted phenyl, and preferably the radicals (b2')
($C_3$-$C_8$)-cycloalkylcarbonyl,
($C_3$-$C_8$)-cycloalkyl-[($C_1$-$C_6$)-alkyl]carbonyl,
($C_3$-$C_8$)-cycloalkyl-[($C_1$-$C_6$)-alkoxy]carbonyl,
($C_3$-$C_8$)-cycloalkoxycarbonyl,
($C_3$-$C_8$)-cycloalkoxy-[($C_1$-$C_6$)-alkyl]carbonyl,
($C_3$-$C_8$)-cycloalkoxy-[($C_1$-$C_6$)-alkoxy]carbonyl,
($C_3$-$C_8$)-cycloalkylcarbonyloxy,
($C_3$-$C_8$)-cycloalkyl-[($C_1$-$C_6$)-alkyl]carbonyloxy,
($C_5$-$C_8$)-cycloalkenyl-[($C_1$-$C_6$)-alkyl]carbonyloxy,
($C_5$-$C_8$)-cycloalkynyl-[($C_1$-$C_6$)-alkyl]carbonyloxy,
($C_3$-$C_8$)-cycloalkyl-[($C_1$-$C_6$)-alkoxy]carbonyloxy,
($C_5$-$C_8$)-cycloalkenyl-[($C_1$-$C_6$)-alkoxy]carbonyloxy,
($C_5$-$C_8$)-cycloalkynyl-[($C_1$-$C_6$)-alkoxy]carbonyloxy,
($C_3$-$C_8$)-cycloalkoxycarbonyloxy,
($C_3$-$C_8$)-cycloalkoxy-[($C_1$-$C_6$)-alkyl]carbonyloxy,
($C_3$-$C_8$)-cycloalkoxy-[($C_1$-$C_6$)-alkoxy]carbonyloxy,
($C_3$-$C_8$)-cycloalkylcarbonylamino,
($C_3$-$C_8$)-cycloalkyl-[($C_1$-$C_6$)-alkyl]carbonylamino,
($C_5$-$C_8$)-cycloalkenyl-[($C_1$-$C_6$)-alkyl]carbonylamino,
($C_5$-$C_8$)-cycloalkynyl-[($C_1$-$C_6$)-alkyl]carbonylamino,
($C_3$-$C_8$)-cycloalkyl-[($C_1$-$C_6$)-alkoxy]carbonylamino,
($C_3$-$C_8$)-cycloalkoxycarbonylamino,
($C_3$-$C_8$)-cycloalkoxy-[($C_1$-$C_6$)-alkyl]carbonylamino and
($C_3$-$C_8$)-cycloalkoxy-[($C_1$-$C_6$)-alkoxy]carbonylamino,
phenylcarbonyl,
phenyl-[($C_1$-$C_6$)-alkyl]carbonyl,
phenyl-[($C_1$-$C_6$)-alkoxy]carbonyl,
phenoxycarbonyl,
phenoxy-[($C_1$-$C_6$)-alkyl]carbonyl,
phenoxy-[($C_1$-$C_6$)-alkoxy]carbonyl,
phenylcarbonyloxy,
phenyl-[($C_1$-$C_6$)-alkyl]carbonyloxy,
phenyl-[($C_1$-$C_6$)-alkoxy]carbonyloxy,
phenoxycarbonyloxy,
phenoxy-[($C_1$-$C_6$)-alkyl]carbonyloxy,
phenoxy-[($C_1$-$C_6$)-alkoxy]carbonyloxy,
phenylcarbonylamino,
phenyl-[($C_1$-$C_6$)-alkyl]carbonylamino,
phenyl-[($C_1$-$C_6$)-alkoxy]carbonylamino,
phenoxycarbonylamino,
phenoxy-[($C_1$-$C_6$)-alkyl]carbonylamino,
phenoxy-[($C_1$-$C_6$)-alkoxy]carbonylamino,
 where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzofused, and unsubstituted at the ring or at the polycyclic system or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and (c') radicals of the formulae —SiR'$_3$, —O—SiR'$_3$, (R')$_3$Si—$(C_1-C_6)$-alkoxy, —CO—O—NR'$_2$, —O—N=CR'$_2$, —N=CR'$_2$, —O—NR'$_2$, —CH(OR')$_2$ and —O—(CH$_2$)q-CH(OR')$_2$, in which each of the radicals R' independently of the others represents H, $(C_1-C_4)$-alkyl or phenyl, which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or at two adjacent positions by a $(C_2-C_6)$-alkylene bridge, and q represents an integer from 0 to 6, and (d') radicals of the formula R"O—CHR'"CH(OR")—$(C_1-C_6)$-alkoxy, in which each of the radicals R" independently of the others is H or $(C_1-C_4)$-alkyl or together the radicals are a $(C_1-C_6)$-alkylene group and R'" is H or $(C_1-C_4)$-alkyl, and (e') a radical of the formula Het$^7$ which is unsubstituted or substituted by one or more identical or different radicals R$^B$, or R$^4$ represents a polycyclic radical based on $(C_3-C_9)$-cycloalkyl, $(C_5-C_9)$-cycloalkenyl, $(C_5-C_9)$-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals R$^B$, preferably unsubstituted or substituted by one or more radicals from the group consisting of halogen, cyano, nitro, hydroxy, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, $[(C_1-C_8)$-alkoxy]carbonyl, $[(C_1-C_6)$-haloalkoxy]carbonyl and oxo, or R$^4$ represents a heterocyclic radical Het$^7$ which is unsubstituted in the ring or in the polycyclic system or substituted by one or more identical or different radicals R$^B$, preferably unsubstituted or substituted by one or more radicals from the group consisting of halogen, cyano, thio, nitro, hydroxy, carboxy, $(C_1-C_6)$-alkyl, $(C_1-C_6)$-haloalkyl, $(C_1-C_4)$-alkoxy-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkoxy, $(C_1-C_6)$-alkylthio, $(C_2-C_6)$-alkenylthio, $(C_2-C_6)$-alkynylthio, $(C_3-C_6)$-cycloalkyl, $(C_3-C_6)$-cycloalkoxy, $[(C_1-C_8)$-alkoxy]carbonyl, $[(C_1-C_6)$-haloalkoxy]carbonyl and oxo, where in the radicals mentioned above and in the radicals below Het$^7$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, R*, R** independently of one another (i.e. also of other groups NR*R**) each represent H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]carbonyl, $[(C_1-C_4)$-alkoxy]carbonyl, $[(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$-alkyl, where each of the 4 last-mentioned radicals is optionally substituted in the cycle by one or more identical or different radicals R$^{bb}$, or R* and R** together with the nitrogen atom represent a 3- to 8-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, R$^A$ represents halogen, cyano, hydroxy or $(C_1-C_6)$-alkoxy, R$^B$ represents halogen, cyano, hydroxy, oxo, nitro, $(C_1-C_6)$-alkyl, $(C_1-C_4)$-haloalkyl, cyano-$(C_1-C_4)$-alkyl, hydroxy-$(C_1-C_4)$-alkyl, nitro-$(C_1-C_4)$-alkyl, $(C_2-C_6)$-alkenyl, $(C_2-C_6)$-haloalkenyl, $(C_2-C_6)$-alkynyl, $(C_2-C_6)$-haloalkynyl, $(C_1-C_6)$-alkoxy, $(C_2-C_6)$-alkenyloxy, $(C_2-C_6)$-alkynyloxy, $(C_1-C_6)$-haloalkoxy, $(C_1-C_4)$-alkoxy-$(C_1-C_4)$-alkyl, $(C_1-C_4)$-alkoxy-$(C_1-C_4)$-alkoxy, $(C_1-C_4)$-haloalkoxy-$(C_1-C_4)$-alkyl, $(C_1-C_4)$-haloalkoxy-$(C_1-C_4)$-alkoxy, $(C_1-C_6)$-alkylthio, $(C_2-C_6)$-alkenylthio, $(C_2-C_6)$-alkynylthio, $(C_1-C_6)$-alkylsulphinyl, $(C_1-C_6)$-haloalkylsulphinyl, $(C_1-C_6)$-alkylsulphonyl, $(C_1-C_6)$-haloalkylsulphonyl, a radical of the formula R$^{aa}$—C(=O)— or R$^{aa}$—C(=O)—$(C_1-C_6)$ alkyl, the radicals R$^{aa}$ being defined below, —NR*R**, R* and R** being defined below, tri-$[(C_1-C_4)$-alkyl]silyl, tri-$[(C_1-C_4)$-alkyl]silyl-$(C_1-C_6)$-alkyl, $(C_3-C_6)$-cycloalkyl, $(C_3-C_6)$-cycloalkoxy, $(C_3-C_6)$-cycloalkyl-$(C_1-C_4)$-alkyl, $(C_3-C_6)$-cycloalkyl-$(C_1-C_8)$-alkoxy, phenyl, phenyl-$(C_1-C_6)$-alkyl, phenoxy, phenoxy-$(C_1-C_6)$-alkyl, phenylamino, phenylamino-$(C_1-C_6)$-alkyl or a 5- or 6-membered monocyclic or 9- or 10-membered bicyclic heterocycle which contains 1, 2, 3 or 4 heteroatoms selected from the group consisting of O, N and S, where each of the 11 last-mentioned radicals is optionally substituted in the cyclic moiety by one or more identical or different radicals R$^{bb}$, R$^C$, R$^D$ are each independently of one another (also independently of radicals R$^C$, R$^D$ in other groups)

hydrogen, $(C_1-C_8)$-alkyl, $(C_2-C_8)$-alkenyl or $(C_2-C_8)$-alkynyl, where each of the 3 last-mentioned radicals is unsubstituted or substituted by one or more radicals from the group consisting of halogen, cyano, nitro, hydroxy, $(C_1-C_6)$-alkoxy, $(C_2-C_6)$-alkenyloxy, $(C_2-C_6)$-alkynyloxy, $(C_1-C_8)$-haloalkoxy, $(C_1-C_4)$-alkoxy-$(C_1-C_4)$-alkoxy, $(C_1-C_8)$-alkylthio, $(C_1-C_8)$-haloalkylthio, $(C_1-C_8)$-alkylsulphinyl, $(C_1-C_8)$-haloalkylsulphinyl, $(C_1-C_8)$-alkylsulphonyl, $(C_1-C_8)$-haloalkylsulphonyl and tri-$[(C_1-C_4)$-alkyl]silyl, or $(C_3-C_8)$-cycloalkyl, $(C_5-C_8)$-cycloalkenyl, $(C_5-C_8)$-cycloalkynyl, phenyl, $(C_3-C_8)$-cycloalkyl-$(C_1-C_6)$-alkyl, $(C_5-C_8)$-cycloalkenyl-$(C_1-C_6)$-alkyl, $(C_5-C_8)$-cycloalkynyl-$(C_1-C_6)$-alkyl, phenyl-$(C_1-C_6)$-alkyl, $(C_3-C_8)$-cycloalkyloxy-$(C_1-C_6)$-alkyl, $(C_3-C_8)$-cycloalkyl-S(O)$_p$—$(C_1-C_6)$-alkyl, $(C_5-C_8)$-cycloalkenyloxy-$(C_1-C_6)$-alkyl, $(C_5-C_8)$-cycloalkynyloxy-$(C_1-C_6)$-alkyl, phenoxy-$(C_1-C_6)$-alkyl, phenyl-S(O)$_p$—$(C_1-C_6)$-alkyl, ($C_3$-$C_8$)-cycloalkylamino-($C_1$-$C_6$)-alkyl, ($C_5$-$C_8$)-cycloalkenylamino-($C_1$-$C_6$)-alkyl, ($C_5$-$C_8$)-cycloalkynylamino-($C_1$-$C_6$)-alkyl, phenylamino-($C_1$-$C_6$)-alkyl, $Het^7$, $Het^7$-($C_1$-$C_6$)-alkyl, $Het^7$-O—($C_1$-$C_6$)-alkyl or $Het^7$-S(O)$_p$—($C_1$-$C_6$)-alkyl, where $Het^7$ has the meaning mentioned, where each of the 22 last-mentioned radicals is unsubstituted in the acyclic moiety or substituted by one or more identical or different radicals $R^A$ and is unsubstituted in the cyclic moiety or substituted by one or more identical or different radicals $R^B$ and p independently of the others in each case represents 0, 1 or 2, $R^{aa}$ independently of one another each represent hydrogen, OH, ($C_1$-$C_6$)-alkyl, ($C_1$-$C_4$)-haloalkyl, ($C_2$-$C_6$)-alkenyl, ($C_2$-$C_6$)-alkynyl, ($C_1$-$C_6$)-alkoxy, ($C_1$-$C_6$)-alkoxy-($C_1$-$C_6$)-alkyl, ($C_1$-$C_6$)-alkoxy-($C_1$-$C_6$)-alkyloxy, ($C_1$-$C_4$)-haloalkoxy, ($C_1$-$C_4$)-haloalkoxy-($C_1$-$C_6$)-alkyl, ($C_1$-$C_4$)-haloalkoxy-($C_1$-$C_6$)-alkoxy, ($C_3$-$C_6$)-alkenyloxy, ($C_3$-$C_6$)-alkenyloxy-($C_1$-$C_6$)-alkyl, ($C_3$-$C_6$)-alkenyloxy-($C_1$-$C_6$)-alkoxy, ($C_3$-$C_6$)-alkynyloxy, ($C_3$-$C_6$)-alkynyloxy-($C_1$-$C_6$)-alkyl, ($C_3$-$C_6$)-alkynyloxy-($C_1$-$C_6$)-alkoxy, —NR*R*, where R* and R** are as defined above, tri-[($C_1$-$C_4$)alkyl]silyl, tri-[($C_1$-$C_4$)alkyl]silyl-($C_1$-$C_6$)-alkyl, tri-[($C_1$-$C_4$)alkyl]silyl-($C_1$-$C_6$)-alkoxy, ($C_3$-$C_6$)-cycloalkyl, ($C_3$-$C_6$)-cycloalkoxy, ($C_3$-$C_6$)-cycloalkyl-($C_1$-$C_8$)-alkyl, ($C_3$-$C_6$)-cycloalkyl-($C_1$-$C_6$)-alkoxy, ($C_5$-$C_6$)-cycloalkenyl, ($C_5$-$C_6$)-cycloalkenyl-($C_1$-$C_6$)-alkyl, ($C_5$-$C_6$)-cycloalkenyloxy, ($C_5$-$C_6$)-cycloalkynyl, ($C_5$-$C_6$)-cycloalkynyl-($C_1$-$C_6$)-alkyl, ($C_5$-$C_6$)-cycloalkynyl-($C_1$-$C_6$)-alkoxy, phenyl, phenyl-($C_1$-$C_6$)-alkyl, phenyl-($C_1$-$C_6$)-alkoxy, phenoxy, phenoxy-($C_1$-$C_6$)-alkyl, phenoxy-($C_1$-$C_6$)-alkoxy, phenylthio, phenyl-S(O)$_p$—($C_1$-$C_6$)-alkyl, phenyl-S(O)$_p$—($C_1$-$C_6$)-alkoxy, where p independently of the others in each case represents 0, 1 or 2, phenylamino, phenylamino-($C_1$-$C_1$)-alkyl, phenylamino-($C_1$-$C_6$)-alkoxy or a 5- or 6-membered monocyclic or 9- or 10-membered bicyclic heterocycle which is optionally attached via an alkylene group or an alkoxy group and contains 1, 2, 3 or 4 heteroatoms selected from the group consisting of O, N and S, where each of the 20 last-mentioned radicals is optionally substituted in the cyclic moiety by one or more identical or different radicals $R^{cc}$, and $R^{bb}$ and $R^{cc}$ independently of one another each represent halogen, ($C_1$-$C_4$)-alkyl, ($C_1$-$C_4$)-haloalkyl, ($C_1$-$C_4$)-alkoxy or ($C_1$-$C_4$)-haloalkoxy.

More preference is here also given to compounds (I), preferably of the formula (Ia), or salts thereof in which $R^4$ represents hydrogen, ($C_1$-$C_{18}$)-alkyl, ($C_2$-$C_{18}$)-alkenyl or ($C_2$-$C_{18}$)-alkynyl, preferably H, ($C_1$-$C_{12}$)-alkyl, ($C_2$-$C_{12}$)-alkenyl or ($C_2$-$C_{12}$)-alkynyl, in particular H, ($C_1$-$C_8$)-alkyl, ($C_2$-$C_8$)-alkenyl or ($C_2$-$C_8$)-alkynyl, more preferably H or ($C_1$-$C_6$)-alkyl, ($C_2$-$C_6$)-alkenyl or ($C_2$-$C_6$)-alkynyl, more preferably ($C_1$-$C_4$)-alkyl, where each of the 13 last-mentioned radicals containing carbon atoms is unsubstituted or substituted by one or more radicals from the group consisting of the radicals [subgroups (a)-(d)]

(a) halogen, cyano, thio, nitro, hydroxy, carboxy, ($C_1$-$C_6$)-alkoxy, ($C_2$-$C_6$)-alkenyloxy, ($C_2$-$C_6$)-alkynyloxy, ($C_1$-$C_6$)-haloalkoxy, ($C_1$-$C_4$)-alkoxy-($C_1$-$C_4$)-alkoxy, ($C_1$-$C_6$)-alkylthio, ($C_2$-$C_6$)-alkenylthio, ($C_2$-$C_6$)-alkynylthio, ($C_1$-$C_6$)-haloalkylthio, ($C_2$-$C_6$)-haloalkenylthio, ($C_2$-$C_6$)-haloalkynylthio, ($C_1$-$C_6$)-alkylsulphinyl, ($C_2$-$C_6$)-alkenylsulphinyl, ($C_2$-$C_6$)-alkynylsulphinyl, ($C_1$-$C_6$)-haloalkylsulphinyl, ($C_2$-$C_6$)-haloalkenylsulphinyl, ($C_2$-$C_6$)-haloalkynylsulphinyl, ($C_1$-$C_6$)-alkylsulphonyl, ($C_2$-$C_6$)-alkenylsulphonyl, ($C_2$-$C_6$)-alkynylsulphonyl, ($C_1$-$C_6$)-haloalkylsulphonyl, ($C_2$-$C_6$)-haloalkenylsulphonyl, ($C_2$-$C_6$)-haloalkynylsulphonyl, radicals of the formula —NR*R**, where R* and R** are defined below, and ($C_3$-$C_6$)-cycloalkyl, ($C_5$-$C_6$)-cycloalkenyl, ($C_5$-$C_6$)-cycloalkynyl, ($C_3$-$C_6$)-cycloalkyl-($C_1$-$C_4$)-alkoxy, ($C_5$-$C_6$)-cycloalkenyl-($C_1$-$C_4$)-alkoxy, ($C_5$-$C_6$)-cycloalkynyl-($C_1$-$C_4$)-alkoxy, ($C_3$-$C_6$)-cycloalkoxy, ($C_5$-$C_6$)-cycloalkenyloxy, ($C_5$-$C_6$)-cycloalkynyloxy, ($C_3$-$C_6$)-cycloalkoxy-($C_1$-$C_4$)-alkoxy, phenyl, phenyl-($C_1$-$C_6$)-alkoxy, phenoxy, phenoxy-($C_1$-$C_4$)-alkoxy, phenyl-S(O)$_p$—, phenyl-($C_1$-$C_6$)-alkyl-S(O)$_p$—, phenyloxy-($C_1$-$C_6$)-alkyl-S(O)$_p$—, a radical $Het^7$, $Het^7$-($C_1$-$C_6$)-alkoxy, $Het^7$-O—, $Het^7$-O—($C_1$-$C_4$)-alkoxy, $Het^7$-($C_1$-$C_6$)-alkoxy, $Het^7$-S(O)$_p$—, $Het^7$-O—($C_1$-$C_4$)-alkyl-S(O)$_p$—, where the heterocyclic radical $Het^7$ is defined as above or below, where each of the 24 last-mentioned radicals is unsubstituted in the acyclic moiety or substituted by one or more identical or different radicals $R^A$ and is unsubstituted in the cyclic moiety or substituted by one or more identical or different radicals $R^B$ and p independently of the others in each case represents 0, 1 or 2, and preferably the radicals (a1)

halogen, cyano, nitro, hydroxy, carboxy, ($C_1$-$C_6$)-alkoxy, ($C_1$-$C_6$)-haloalkoxy, ($C_1$-$C_4$)-alkoxy-($C_1$-$C_4$)-alkoxy, ($C_1$-$C_6$)-alkylthio, ($C_1$-$C_6$)-haloalkylthio, ($C_1$-$C_6$)-alkylsulphinyl, ($C_1$-$C_6$)-haloalkylsulphinyl, ($C_3$-$C_6$)-cycloalkyl, ($C_5$-$C_6$)-cycloalkenyl, ($C_5$-$C_6$)-cycloalkynyl, ($C_3$-$C_6$)-cycloalkyl-($C_1$-$C_4$)-alkoxy, ($C_5$-$C_4$)-cycloalkenyl-($C_1$-$C_4$)-alkoxy, ($C_5$-$C_4$)-cycloalkynyl-($C_1$-$C_4$)-alkoxy, ($C_3$-$C_4$)-cycloalkoxy, ($C_3$-$C_4$)-cycloalkoxy-($C_1$-$C_4$)-alkoxy, phenyl, phenyl-($C_1$-$C_4$)-alkoxy, phenoxy and phenoxy-($C_1$-$C_4$)-alkoxy, phenylthio, phenylsulphinyl, phenylsulphonyl, where each of the radicals (a1) is unsubstituted in the acyclic moiety or substituted by one or more identical or different radicals $R^A$ and is unsubstituted in the cyclic moiety or substituted by one or more identical or different radicals $R^B$, (b) radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^c$)($R^D$), —P(=O)(O$R^c$)(O$R^D$) and —O—P(=O)(O$R^c$)(O$R^D$), preferably a radical of the formula —C(=O)—$R^C$, —C(=O)—O—$R^C$, —O—C(=O)—$R^c$ or —O—C(=O)—O—$R^C$, in particular a radical of the formula —C(=O)—O—$R^C$, —O—C(=O)—$R^c$ or —O—C(=O)—O—$R^C$, where R*, R**, $R^C$ and $R^D$ are as defined below, preferably the radicals (b1)

[($C_1$-$C_6$)-alkoxy]carbonyl, [($C_1$-$C_6$)-alkoxy]thiocarbonyl, [($C_2$-$C_6$)-alkenyloxy]carbonyl, [($C_2$-$C_8$)-alkynyloxy]carbonyl, [($C_1$-$C_6$)-alkylthio]carbonyl, [($C_2$-$C_6$)-alkenylthio]carbonyl, [($C_2$-$C_6$)-alkynylthio]carbonyl, ($C_1$-$C_6$)-alkanoyl, [($C_2$-$C_6$)-alkenyl]carbonyl, [($C_2$-$C_6$)-alkynyl]carbonyl, [($C_1$-$C_6$)-alkyl]carbonylamino, [($C_2$-$C_6$)-alkenyl]carbonylamino, [($C_2$-$C_6$)-alkynyl]carbonylamino, [($C_1$-$C_6$)-alkoxy]carbonylamino, [($C_2$-$C_6$)-alkenyloxy]carbonylamino, [($C_2$-$C_6$)-alkynyloxy]carbonylamino, [($C_1$-$C_6$)-alkylamino]carbonylamino, [($C_1$-$C_6$)-alkyl]carbonyloxy, [($C_2$-$C_6$)-alkenyl]carbonyloxy, [($C_2$-

C$_6$)-alkynyl]carbonyloxy, [(C$_1$-C$_6$)-alkoxy]carbonyloxy, [(C$_2$-C$_6$)-alkenyloxy]carbonyloxy and [(C$_2$-C$_6$)-alkynyloxy]carbonyloxy, where each of the 23 last-mentioned radicals is unsubstituted or substituted by one or more radicals from the group consisting of halogen, NO$_2$, (C$_1$-C$_4$)-alkoxy and optionally halogen-, CN, NO$_2$, (C$_1$-C$_4$)-alkyl-, (C$_1$-C$_4$)-alkoxy- and (C$_1$-C$_4$)-alkylthio-substituted phenyl, and preferably the radicals (b2)

(C$_3$-C$_6$)-cycloalkylcarbonyl,
(C$_3$-C$_6$)-cycloalkyl-[(C$_1$-C$_4$)-alkyl]carbonyl,
(C$_3$-C$_6$)-cycloalkyl-[(C$_1$-C$_4$)-alkoxy]carbonyl,
(C$_3$-C$_6$)-cycloalkoxycarbonyl,
(C$_3$-C$_6$)-cycloalkoxy-[(C$_1$-C$_4$)-alkyl]carbonyl,
(C$_3$-C$_6$)-cycloalkoxy-[(C$_1$-C$_4$)-alkoxy]carbonyl,
(C$_3$-C$_6$)-cycloalkylcarbonyloxy,
(C$_3$-C$_6$)-cycloalkyl-[(C$_1$-C$_4$)-alkyl]carbonyloxy,
(C$_5$-C$_6$)-cycloalkenyl-[(C$_1$-C$_4$)-alkyl]carbonyloxy,
(C$_5$-C$_6$)-cycloalkynyl-[(C$_1$-C$_4$)-alkyl]carbonyloxy,
(C$_3$-C$_6$)-cycloalkyl-[(C$_1$-C$_4$)-alkoxy]carbonyloxy,
(C$_5$-C$_6$)-cycloalkenyl-[(C$_1$-C$_4$)-alkoxy]carbonyloxy,
(C$_5$-C$_6$)-cycloalkynyl-[(C$_1$-C$_4$)-alkoxy]carbonyloxy,
(C$_3$-C$_6$)-cycloalkoxycarbonyloxy,
(C$_3$-C$_6$)-cycloalkoxy-[(C$_1$-C$_4$)-alkyl]carbonyloxy,
(C$_3$-C$_6$)-cycloalkoxy-[(C$_1$-C$_4$)-alkoxy]carbonyloxy,
(C$_3$-C$_6$)-cycloalkylcarbonylamino,
(C$_3$-C$_6$)-cycloalkyl-[(C$_1$-C$_4$)-alkyl]carbonylamino,
(C$_5$-C$_6$)-cycloalkenyl-[(C$_1$-C$_4$)-alkyl]carbonylamino,
(C$_5$-C$_6$)-cycloalkynyl-[(C$_1$-C$_4$)-alkyl]carbonylamino,
(C$_3$-C$_6$)-cycloalkyl-[(C$_1$-C$_4$)-alkoxy]carbonylamino,
(C$_3$-C$_6$)-cycloalkoxycarbonylamino,
(C$_3$-C$_6$)-cycloalkoxy-[(C$_1$-C$_4$)-alkyl]carbonylamino and
(C$_3$-C$_6$)-cycloalkoxy-[(C$_1$-C$_4$)-alkoxy]carbonylamino,
phenylcarbonyl,
phenyl-[(C$_1$-C$_4$)-alkyl]carbonyl,
phenyl-[(C$_1$-C$_4$)-alkoxy]carbonyl,
phenoxycarbonyl,
phenoxy-[(C$_1$-C$_4$)-alkyl]carbonyl,
phenoxy-[(C$_1$-C$_4$)-alkoxy]carbonyl,
phenylcarbonyloxy,
phenyl-[(C$_1$-C$_4$)-alkyl]carbonyloxy,
phenyl-[(C$_1$-C$_4$)-alkoxy]carbonyloxy,
phenoxycarbonyloxy,
phenoxy-[(C$_1$-C$_4$)-alkyl]carbonyloxy,
phenoxy-[(C$_1$-C$_4$)-alkoxy]carbonyloxy,
phenylcarbonylamino,
phenyl-[(C$_1$-C$_4$)-alkyl]carbonylamino,
phenyl-[(C$_1$-C$_4$)-alkoxy]carbonylamino,
phenoxycarbonylamino,
phenoxy-[(C$_1$-C$_4$)-alkyl]carbonylamino,
phenoxy-[(C$_1$-C$_4$)-alkoxy]carbonylamino, where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro, and (c) radicals of the formulae —SiR'$_3$, —O—SiR'$_3$, (R')$_3$Si—(C$_1$-C$_4$)-alkoxy, —CO—O—NR'$_2$, —O—N=CR'$_2$, —N=CR'$_2$, —O—NR'$_2$, —CH(OR')$_2$ and —O—(CH$_2$)$_q$—CH(OH)$_2$, in which each of the radicals R' independently of the others represents H, (C$_1$-C$_4$)-alkyl or phenyl, which is unsubstituted or substituted by one or more radicals from the group consisting of halogen, (C$_1$-C$_4$)-alkyl, (C$_1$-C$_4$)-alkoxy, (C$_1$-C$_4$)-haloalkyl, (C$_1$-C$_4$)-haloalkoxy and nitro or at two adjacent positions by a (C$_2$-C$_6$)-alkylene bridge, and q represents an integer from 0 to 6, and (d) radicals of the formula R"O—CHR"'CH(OR")—(C$_1$-C$_6$)-alkoxy, in which each of the radicals R" independently of the others represents H or (C$_1$-C$_4$)-alkyl or together the radicals represent a (C$_1$-C$_6$)-alkylene group and R"' represents H or (C$_1$-C$_4$)-alkyl, or R$^4$ represents (C$_3$-C$_6$)-cycloalkyl, (C$_5$-C$_6$)-cycloalkenyl, (C$_5$-C$_6$)-cycloalkynyl or phenyl, where each of the 4 last-mentioned radicals is unsubstituted or substituted by one or more radicals from the group consisting of the radicals [subgroups (a')-(e')]

(a') halogen, cyano, thio, nitro, hydroxy, carboxy, (C$_1$-C$_6$)-alkyl, (C$_1$-C$_6$)-haloalkyl, (C$_1$-C$_4$)-alkoxy-(C$_1$-C$_4$)-alkyl, (C$_2$-C$_6$)-alkenyl, (C$_2$-C$_6$)-haloalkenyl, (C$_2$-C$_6$)-alkynyl, (C$_2$-C$_6$)-haloalkynyl, (C$_1$-C$_6$)-alkoxy, (C$_2$-C$_6$)-alkenyloxy, (C$_2$-C$_6$)-alkynyloxy, (C$_1$-C$_6$)-haloalkoxy, (C$_1$-C$_4$)-alkoxy-(C$_1$-C$_4$)-alkoxy, (C$_1$-C$_6$)-alkylthio, (C$_2$-C$_6$)-alkenylthio, (C$_2$-C$_6$)-alkynylthio and radicals of the formulae —NR*R**, where the radicals R* and R** are as defined above or below, (b') radicals of the formulae —C(=O)—R$^C$, —C(=O)—O—R$^C$, —O—C(=O)—R$^C$, —O—C(=O)—O—R$^C$, —C(=O)—S—R$^C$, —C(=S)—S—R$^C$, —C(=S)—S—R$^C$, —C(=O)—NR*R**, —C(=O)—O—NR*R**, —O—C(=O)—NR*R**, —N(R*)—C(=O)—R$^C$, —N(R*)—C(=O)—NR*R**, —N(R*)—C(=O)—O—R$^C$, —P(=O)(R$^C$)(R$^D$), —P(=O)(OR$^c$)(R$^D$), —P(=O)(OR$^c$)(OR$^D$) and —O—P(=O)(OR$^c$)(OR$^D$), preferably a radical of the formula —C(=O)—R$^C$, —C(=O)—O—R$^C$, —O—C(=O)—R$^c$ or —O—C(=O)—O—R$^C$, in particular a radical of the formula —C(=O)—O—R$^C$, —O—C(=O)—R$^c$ or —O—C(=O)—O—R$^C$, where R*, R**, R$^C$ and R$^D$ are as defined below, and preferably the radicals (b1')

[(C$_1$-C$_6$)-alkoxy]carbonyl, [(C$_1$-C$_6$)-alkoxy]thiocarbonyl, [(C$_2$-C$_6$)-alkenyloxy]carbonyl, [(C$_2$-C$_6$)-alkynyloxy]carbonyl, [(C$_1$-C$_6$)-alkylthio]carbonyl, [(C$_2$-C$_6$)-alkenylthio]carbonyl, [(C$_2$-C$_6$)-alkynylthio]carbonyl, (C$_1$-C$_8$)-alkanoyl, [(C$_2$-C$_6$)-alkenyl]carbonyl, [(C$_2$-C$_6$)-alkynyl]carbonyl, (C$_1$-C$_4$)-alkylimino, (C$_1$-C$_4$)-alkoxyimino, [(C$_1$-C$_6$)-alkyl]carbonylamino, [(C$_2$-C$_6$)-alkenyl]carbonylamino, [(C$_2$-C$_6$)-alkynyl]carbonylamino, [(C$_1$-C$_6$)-alkoxy]carbonylamino, [(C$_2$-C$_6$)-alkenyloxy]carbonylamino, [(C$_2$-C$_6$)-alkynyloxy]carbonylamino, [(C$_1$-C$_6$)-alkylamino]carbonylamino, [(C$_1$-C$_4$)-alkyl]carbonyloxy, [(C$_2$-C$_4$)-alkenyl]carbonyloxy, [(C$_2$-C$_4$)-alkynyl]carbonyloxy, [(C$_1$-C$_6$)-alkoxy]carbonyloxy, [(C$_2$-C$_6$)-alkenyloxy]carbonyloxy, [(C$_2$-C$_6$)-alkynyloxy]carbonyloxy, (C$_1$-C$_6$)-alkylsulphinyl and (C$_1$-C$_6$)-alkylsulphonyl, where each of the 27 last-mentioned radicals is unsubstituted or substituted by one or more radicals from the group consisting of halogen, NO$_2$, (C$_1$-C$_4$)-alkoxy and optionally substituted phenyl, and preferably the radicals (b2')

(C$_3$-C$_6$)-cycloalkylcarbonyl,
(C$_3$-C$_6$)-cycloalkyl-[(C$_1$-C$_4$)-alkyl]carbonyl,
(C$_3$-C$_6$)-cycloalkyl-[(C$_1$-C$_4$)-alkoxy]carbonyl, $(C_3-C_6)$-cycloalkoxycarbonyl,
$(C_3-C_6)$-cycloalkoxy-[$(C_1-C_4)$-alkyl]carbonyl,
$(C_3-C_6)$-cycloalkoxy-[$(C_1-C_4)$-alkoxy]carbonyl,
$(C_3-C_6)$-cycloalkylcarbonyloxy,
$(C_3-C_6)$-cycloalkyl-[$(C_1-C_4)$-alkyl]carbonyloxy,
$(C_5-C_6)$-cycloalkenyl-[$(C_1-C_4)$-alkyl]carbonyloxy,
$(C_5-C_6)$-cycloalkynyl-[$(C_1-C_4)$-alkyl]carbonyloxy,
$(C_3-C_6)$-cycloalkyl-[$(C_1-C_4)$-alkoxy]carbonyloxy,
$(C_5-C_6)$-cycloalkenyl-[$(C_1-C_4)$-alkoxy]carbonyloxy,
$(C_5-C_6)$-cycloalkynyl-[$(C_1-C_4)$-alkoxy]carbonyloxy,
$(C_3-C_6)$-cycloalkoxycarbonyloxy,
$(C_3-C_6)$-cycloalkoxy-[$(C_1-C_4)$-alkyl]carbonyloxy,
$(C_3-C_6)$-cycloalkoxy-[$(C_1-C_4)$-alkoxy]carbonyloxy,
$(C_3-C_6)$-cycloalkylcarbonylamino,
$(C_3-C_6)$-cycloalkyl-[$(C_1-C_4)$-alkyl]carbonylamino,
$(C_5-C_6)$-cycloalkenyl-[$(C_1-C_4)$-alkyl]carbonylamino,
$(C_5-C_6)$-cycloalkynyl-[$(C_1-C_4)$-alkyl]carbonylamino,
$(C_3-C_6)$-cycloalkyl-[$(C_1-C_4)$-alkoxy]carbonylamino,
$(C_3-C_6)$-cycloalkoxycarbonylamino,
$(C_3-C_6)$-cycloalkoxy-[$(C_1-C_4)$-alkyl]carbonylamino and
$(C_3-C_6)$-cycloalkoxy-[$(C_1-C_4)$-alkoxy]carbonylamino,
phenylcarbonyl,
phenyl-[$(C_1-C_4)$-alkyl]carbonyl,
phenyl-[$(C_1-C_4)$-alkoxy]carbonyl,
phenoxycarbonyl,
phenoxy-[$(C_1-C_4)$-alkyl]carbonyl,
phenoxy-[$(C_1-C_4)$-alkoxy]carbonyl,
phenylcarbonyloxy,
phenyl-[$(C_1-C_4)$-alkyl]carbonyloxy,
phenyl-[$(C_1-C_4)$-alkoxy]carbonyloxy,
phenoxycarbonyloxy,
phenoxy-[$(C_1-C_4)$-alkyl]carbonyloxy,
phenoxy-[$(C_1-C_4)$-alkoxy]carbonyloxy,
phenylcarbonylamino,
phenyl-[$(C_1-C_4)$-alkyl]carbonylamino,
phenyl-[$(C_1-C_4)$-alkoxy]carbonylamino,
phenoxycarbonylamino,
phenoxy-[$(C_1-C_4)$-alkyl]carbonylamino,
phenoxy-[$(C_1-C_4)$-alkoxy]carbonylamino,
where each of the 42 last-mentioned radicals is optionally fused in the cyclic moiety with a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably benzo-fused, and unsubstituted at the ring or at the polycyclic system or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro, and (c') radicals of the formulae —$SiR'_3$, —O—$SiR'_3$, $(R')_3Si$—$(C_1-C_6)$-alkoxy, —CO—O—$NR'_2$, —O—N=$CR'_2$, —N=$CR'_2$, —O—$NR'_2$, —$CH(OR')_2$ and —O—$(CH_2)_q$—$CH(OH)_2$, in which each of the radicals R' independently of the others represents H, $(C_1-C_4)$-alkyl or phenyl, which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or at two adjacent positions by a $(C_2-C_6)$-alkylene bridge, and q represents an integer from 0 to 6, and (d') radicals of the formula R"O—CHR'"CH(OR")—$(C_1-C_6)$-alkoxy, in which each of the radicals R" independently of the others is H or $(C_1-C_4)$-alkyl or together the radicals are a $(C_1-C_6)$-alkylene group and R'" is H or $(C_1-C_4)$-alkyl, and (e') a radical of the formula $Het^7$ which is unsubstituted or substituted by one or more identical or different radicals $R^B$, or $R^4$ represents a polycyclic radical based on $(C_3-C_6)$-cycloalkyl, $(C_5-C_6)$-cycloalkenyl, $(C_5-C_6)$-cycloalkynyl or phenyl, where the base ring is fused with a carbocyclic or heterocyclic ring, preferably a 5- or 6-membered ring having 0 or 1 to 3 ring heteroatoms from the group consisting of N, O and S, preferably benzo-fused, and where the base ring or the polycyclic system is unsubstituted or substituted by one or more identical or different radicals $R^B$, preferably unsubstituted or substituted by one or more radicals from the group consisting of halogen, cyano, nitro, hydroxy, carboxy, $(C_1-C_4)$-alkyl, $(C_1-C_4)$-haloalkyl, $(C_1-C_4)$-alkoxy-$(C_1-C_4)$-alkyl, $(C_2-C_4)$-alkenyl, $(C_2-C_4)$-haloalkenyl, $(C_2-C_4)$-alkynyl, $(C_2-C_4)$-haloalkynyl, $(C_1-C_4)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkoxy, $(C_1-C_4)$-alkylthio, $(C_2-C_4)$-alkenylthio, $(C_2-C_4)$-alkynylthio, $(C_3-C_6)$-cycloalkyl, $(C_3-C_6)$-cycloalkoxy, [$(C_1-C_4)$-alkoxy]carbonyl, [$(C_1-C_4)$-haloalkoxy]carbonyl and oxo, or $R^4$ represents a heterocyclic radical $Het^7$ which is unsubstituted in the ring or in the polycyclic system or substituted by one or more identical or different radicals $R^B$, preferably unsubstituted or substituted by one or more radicals from the group consisting of halogen, cyano, thio, nitro, hydroxy, carboxy, $(C_1-C_4)$-alkyl, $(C_1-C6)$-haloalkyl, $(C_1-C_4)$-alkoxy-$(C_1-C_4)$-alkyl, $(C_2-C_4)$-alkenyl, $(C_2-C_4)$-haloalkenyl, $(C_2-C_4)$-alkynyl, $(C_2-C_4)$-haloalkynyl, $(C_1-C_6)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkoxy, $(C_1-C_4)$-alkylthio, $(C_2-C_4)$-alkenylthio, $(C_2-C_4)$-alkynylthio, $(C_3-C_4)$-cycloalkyl, $(C_3-C_6)$-cycloalkoxy, [$(C_1-C_4)$-alkoxy]carbonyl, [$(C_1-C_6)$-haloalkoxy]carbonyl and oxo, where $Het^7$, $R^*$, $R^{**}$, $R^A$, $R^B$, $R^C$, $R^D$, $R^{aa}$, $R^{bb}$ and $R^{cc}$ have the meanings already mentioned above, preferably $Het^7$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle which contains 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, $R^*$, $R^{**}$ independently of one another (i.e. also of other groups $NR^*R^{**}$) each represent H, $(C_1-C_6)$-alkyl, $(C_2-C_6)$-alkenyl, $(C_2-C_6)$-alkynyl, $(C_1-C_4)$-alkoxy-$(C_1-C_4)$-alkyl, $(C_1-C_6)$-alkanoyl, [$(C_1-C_4)$-haloalkyl]carbonyl, [$(C_1-C_4)$-alkoxy]carbonyl, [$(C_1-C_4)$-haloalkoxy]carbonyl, $(C_3-C_6)$-cycloalkyl, $(C_3-C_6)$-cycloalkyl-$(C_1-C_4)$-alkyl, phenyl, phenyl-$(C_1-C_4)$-alkyl, where each of the 4 last-mentioned radicals is optionally substituted in the cycle by one or more identical or different radicals $R^{bb}$, or preferably H, $(C_1-C_4)$-alkyl, allyl, propargyl, $(C_1-C_4)$-alkoxy-$(C_1-C_4)$-alkyl, formyl, acetyl, n-propanoyl, isopropanoyl, trifluoroacetyl, trichloroacetyl, methoxycarbonyl, ethoxycarbonyl, n- or i-propoxycarbonyl, n-, i-, sec-, t-Butoxycarbonyl, [$(C_1-C_4)$-haloalkoxy]-carbonyl, cyclopropyl, cyclobutyl, cyclopentyl, cyclohexyl, cyclopropylmethyl, phenyl, benzyl, 1- or 2-phenylethyl, R* and R** together with the nitrogen atom represent a preferably saturated 5- to 6-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, preferably a 1-piperidine, 1-piperazine, 1-pyrrolidine, 1-pyrazolidine, 1-piperazolidine or 1-morpholine radical, $R^A$ represents halogen, cyano, hydroxy or $(C_1-C_6)$-alkoxy, $R^B$ represents halogen, cyano, hydroxy, oxo, nitro, $(C_1-C_4)$-alkyl, $(C_1-C_4)$-haloalkyl, cyano-$(C_1-C_4)$-alkyl, hydroxy-$(C_1-C_4)$-alkyl, nitro-$(C_1-C_4)$-alkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkyl, $(C_1-C_4)$-alkoxy-$(C_1-C_4)$-alkoxy, $(C_1-C_4)$-alkylthio, $(C_1-C_4)$-alkylsulphonyl, $(C_1-C_4)$-haloalkylsulphonyl, a radical of the formula $R^{aa}$—C(=O)— or $R^{aa}$—C(=O)—$(C_1-C_6)$-alkyl, where the radicals $R^{aa}$ are defined below, —NR*R**, where R* and R** are defined below, cyclopropyl, cyclopropylmethyl, phenyl, benzyl, 1- or 2-phenylethyl, phenoxy, 2-phenoxyethyl or a 5- or 6-membered monocyclic or 9- or 10-membered bicyclic heterocycle which contains 1, 2, 3 or 4 heteroatoms selected from the group consisting of O, N and S, where each of the 9 last-mentioned radicals is optionally substituted in the cyclic moiety by one or more identical or different radicals $R^{bb}$, $R^C$, $R^D$ are each independently of one another (also independently of radicals $R^C$, $R^D$ in other groups)

hydrogen, $(C_1-C_6)$-alkyl, $(C_2-C_6)$-alkenyl or $(C_2-C_6)$-alkynyl, where each of the 3 last-mentioned radicals is unsubstituted or substituted by one or more radicals from the group consisting of halogen, cyano, nitro, hydroxy, $(C_1-C_4)$-alkoxy, $(C_2-C_4)$-alkenyloxy, $(C_2-C_4)$-alkynyloxy, $(C_1-C_4)$-haloalkoxy, $(C_1-C_4)$-alkoxy-$(C_1-C_4)$-alkoxy, $(C_1-C_4)$-alkylthio, $(C_1-C_6)$-alkylsulphonyl and $(C_1-C_8)$-haloalkylsulphonyl, or $(C_3-C_6)$-cycloalkyl, $(C_5-C_6)$-cycloalkenyl, $(C_5-C_6)$-cycloalkynyl, phenyl, $(C_3-C_6)$-cycloalkyl-$(C_1-C_6)$-alkyl, phenyl-$(C_1-C_6)$-alkyl, phenoxy-$(C_1-C_4)$-alkyl or phenylamino-$(C_1-C_6)$-alkyl, radicals $Het^7$, $Het^7$-$(C_1-C_6)$-alkyl, $Het^7$-O—$(C_1-C_6)$-Alkyl, where $Het^7$ has the meaning mentioned, where each of the 12 last-mentioned radicals is unsubstituted in the acyclic moiety or substituted by one or more identical or different radicals $R^A$ and is unsubstituted in the cyclic moiety or substituted by one or more identical or different radicals $R^B$, $R^{aa}$ independently of one another each represent hydrogen, OH, $(C_1-C_6)$-alkyl, $(C_1-C_4)$-haloalkyl, $(C_2-C_4)$-alkenyl, $(C_2-C_4)$-alkynyl, $(C_1-C_6)$-alkoxy, $(C_1-C_4)$-alkoxy-$(C_1-C_4)$-alkyl, $(C_1-C_4)$-alkoxy-$(C_1-C_4)$-alkyloxy, $(C_1-C_4)$-haloalkoxy, $(C_1-C_4)$-haloalkoxy-$(C_1-C_4)$-alkyl, $(C_1-C_4)$-haloalkoxy-$(C_1-C_4)$-alkoxy, —NR*R**, where R* and R** are as defined above, $(C_3-C_6)$-cycloalkyl, $(C_3-C_6)$-cycloalkoxy, $(C_3-C_6)$-cycloalkyl-$(C_1-C_6)$-alkyl, $(C_3-C_6)$-cycloalkyl-$(C_1-C_6)$-alkoxy, phenyl, phenyl-$(C_1-C_4)$-alkyl, phenyl-$(C_1-C_4)$-alkoxy, phenoxy, phenoxy-$(C_1-C_4)$-alkyl, phenoxy-$(C_1-C_4)$-alkoxy, phenylamino, phenylamino-$(C_1-C_4)$-alkyl, phenylamino-$(C_1-C_4)$-alkoxy or 5- or 6-membered monocyclic or 9- or 10-membered bicyclic heterocycle which is optionally attached via a $(C_1-C_4)$-alkylene group or a $(C_1-C_4)$-alkoxy group and contains 1, 2, 3 or 4 heteroatoms selected from the group consisting of O, N and S, where each of the 14 last-mentioned radicals is optionally substituted in the cyclic moiety by one or more identical or different radicals $R^{cc}$, $R^{bb}$ independently of one another each represent halogen, $(C_1-C_4)$-alkyl, $(C_1-C_4)$-haloalkyl, $(C_1-C_4)$-alkoxy or $(C_1-C_4)$-haloalkoxy, preferably halogen, methyl, $CF_3$, $CCl_3$, methoxy, ethoxy, $OCH_2F$, $OCF_2H$ or $OCF_3$ and $R^{cc}$ independently of one another each represent halogen, $(C_1-C_4)$-alkyl, $(C_1-C_4)$-haloalkyl, $(C_1-C_4)$-alkoxy or $(C_1-C_4)$-haloalkoxy, preferably halogen, methyl, $CF_3$, $CCl_3$, methoxy, ethoxy, $OCH_2F$, $OCF_2H$ or $OCF_3$.

More preference is here also given to compounds (I), preferably of the formula (Ia), or salts thereof in which $R^4$ represents H, $(C_1-C_6)$-alkyl, $(C_2-C_6)$-alkenyl, $(C_2-C_6)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, alkylsulphinyl, alkylsulphonyl, $(C_3-C_6)$-cycloalkyl which is unsubstituted or substituted by one or more radicals from the group consisting of halogen and $(C_1-C_4)$-alkyl, and phenyl, phenoxy, phenylthio, phenylsulphinyl, phenylsulphonyl, where the phenyl ring in the 5 last-mentioned radicals is in each case unsubstituted or substituted by one or more radicals from the group consisting of halogen, $(C_1-C_4)$-alkyl, $(C_1-C_4)$-alkoxy and $(C_1-C_4)$-haloalkyl, and a radical $Het^7$, preferably a saturated or partially unsaturated monocyclic heterocyclyl radical which has 5 or 6 ring atoms and contains 1, 2 or 3 heteroatoms selected from the group consisting of O, N and S and is unsubstituted or substituted by one or more radicals selected from the group consisting of halogen, $(C_1-C_4)$-alkyl, $(C_1-C_4)$-alkoxy and $(C_1-C_4)$-haloalkyl, or $R^4$ represents $(C_3-C_6)$-cycloalkyl which is unsubstituted or substituted by one or more radials from the group consisting of $(C_1-C_4)$-alkyl, $(C_1-C_4)$-alkoxy and $(C_1-C_4)$-haloalkyl, or $R^4$ represents phenyl which is unsubstituted or substituted by one or more radials from the group consisting of halogen, $(C_1-C_4)$-alkyl, $(C_1-C_4)$-alkoxy and $(C_1-C_4)$-haloalkyl.

Particular preference is here also given to compounds (I), preferably of the formula (Ia), or salts thereof in which $R^4$ represents H, $(C_1-C_4)$-alkyl, $(C_2-C_4)$-alkenyl or $(C_2-C_4)$-alkynyl, where each of the 3 last-mentioned radicals is unsubstituted or substituted by one or more radicals from the group consisting of halogen, $(C_1-C_4)$-alkoxy, $(C_1-C_4)$-alkylthio, cyclopropyl, cyclobutyl, where each of the two last-mentioned radicals is unsubstituted or substituted by one or more radicals from the group consisting of halogen and $(C_1-C_4)$-alkyl, and phenyl, phenylthio (=phenylsulphanyl), phenylsulphinyl, phenylsulphonyl, where each of the 4 last-mentioned radicals is unsubstituted or substituted by one or more radicals from the group consisting of halogen, $(C_1-C_4)$-alkyl, $(C_1-C_4)$-alkoxy and $(C_1-C_4)$-haloalkyl.

More preferably $R^4$ also represents a polycyclic radical based on $(C_3-C_9)$-cycloalkyl, $(C_5-C_9)$-cycloalkenyl, $(C_5-C_9)$-cycloalkynyl or phenyl, where the base ring is condensed, preferably benzo-fused, with a carbocyclic or heterocyclic ring, preferably a 5- or 6-membered ring having 0 or 1 to 3 ring heteroatoms from the group consisting of N, O and S, and where the base ring or the polycyclic system is unsubstituted or substituted by one or more radicals from the group consisting of halogen, cyano, nitro, $(C_1$-$C_6)$-alkyl, $(C_1$-$C_6)$-haloalkyl, $(C_1$-$C_4)$-alkoxy-$(C_1$-$C_4)$-alkyl, $(C_2$-$C_4)$-alkenyl, $(C_2$-$C_4)$-alkynyl, $(C_1$-$C_4)$-alkoxy, $(C_1$-$C_4)$-haloalkoxy, $(C_1$-$C_4)$-alkoxy-$(C_1$-$C_4)$-alkoxy, $(C_1$-$C_4)$-alkylthio, $(C_3$-$C_6)$-cycloalkyl, $(C_3$-$C_6)$-cycloalkoxy, [$(C_1$-$C_4)$-alkoxy]carbonyl and [$(C_1$-$C_4)$-haloalkoxy]carbonyl.

Preference is also given to compounds (I), preferably of the formula (Ia), or salts thereof in which $R^4$ represents a saturated, partially unsaturated or heteroaromatic heterocyclyl radical which has 3 to 9 ring atoms, preferably 5 or 6 ring atoms, which has 1 to 4 heteroatoms, preferably 1 to 3 ring heteroatoms from the group consisting of N, O and S and which is unsubstituted or substituted by one or more identical or different radicals from the group consisting of halogen, cyano, thio, nitro, hydroxy, $(C_1$-$C_6)$-alkyl, $(C_1$-$C_6)$-haloalkyl, $(C_1$-$C_6)$-alkoxy-$(C_1$-$C_4)$-alkyl, $(C_2$-$C_4)$-alkenyl, $(C_2$-$C_6)$-haloalkenyl, $(C_2$-$C_6)$-alkynyl, $(C_2$-$C_6)$-haloalkynyl, $(C_1$-$C_6)$-alkoxy, $(C_2$-$C_6)$-alkenyloxy, $(C_2$-$C_6)$-alkynyloxy, $(C_1$-$C_6)$-haloalkoxy, $(C_1$-$C_6)$-alkoxy-$(C_1$-$C_4)$-alkoxy, $(C_1$-$C_4)$-alkylthio, $(C_2$-$C_6)$-alkenylthio, $(C_2$-$C_6)$-alkynylthio, $(C_3$-$C_6)$-cycloalkyl, $(C_3$-$C_6)$-cycloalkoxy, [$(C_1$-$C_8)$-alkoxy]carbonyl, [$(C_1$-$C_6)$-haloalkoxy]carbonyl and oxo.

Preference is also given to compounds (I), preferably of the formula (Ia), or salts thereof in which $R^4$ represents a radical of the formula $SiR^aR^bR^c$, —$NR^aR^b$ or —$N=CR^cR^d$, preferably of the formula —$NR^aR^b$ or —$N=CR^cR^d$, where in the 5 last-mentioned formulae each of the radicals $R^a$, $R^b$, $R^c$ and $R^d$ independently of the others represents hydrogen, $(C_1$-$C_4)$-alkyl, $(C_2$-$C_4)$-alkenyl, $(C_2$-$C_4)$-alkynyl, benzyl, substituted benzyl, phenyl or substituted phenyl, but where $SiH_3$ for $SiR^aR^bR^c$ is excluded, or $R^a$ and $R^b$ together with the nitrogen atom represent a 3- to 8-membered heterocycle which, in addition to the nitrogen atom, may contain one or two further ring heteroatoms from the group consisting of N, O and S and which is unsubstituted or substituted by one or more radicals from the group consisting of $(C_1$-$C_4)$-alkyl and $(C_1$-$C_4)$-haloalkyl, or $R^c$ and $R^d$ together with the carbon atom represent a 3- to 8-membered carbocyclic radical or heterocyclic radical which may contain 1 to 3 ring heteroatoms from the group consisting of N, O and S, where the carbocyclic or heterocyclic radical is unsubstituted or substituted by one or more radicals from the group consisting of $(C_1$-$C_4)$-alkyl and $(C_1$-$C_4)$-haloalkyl.

Particular preference is also given to compounds (I), preferably of the formula (Ia), or salts thereof in which $R^4$ represents H, methyl, ethyl, n-propyl, i-propyl, n-butyl, s-butyl, i-butyl, t-butyl, allyl, ethynyl, propargyl (prop-2-yn-1-yl), prop-1-yn-1-yl, but-2-yn-1-yl, but-3-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, phenyl, 2-carboxyphenyl, 2-chlorophenyl, 3-chlorophenyl, 4-chlorophenyl, 2-fluorophenyl, 3-fluorophenyl, 4-fluorophenyl, 3-methoxyphenyl, 4-methoxyphenyl, 2-methoxyphenyl, 3-methoxyphenyl, 4-methoxyphenyl, benzyl, 2-fluorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenylethyl, 1-phenylethyl, (4-chlorophenyl)methyl [i.e. =$CH_2$(4-Cl-Ph)=4-chlorobenzyl], (4-fluorophenyl)methyl [d. h. =$CH_2$(4-F-Ph)], (4-methoxyphenyl)methyl [i.e. =$CH_2$(4-OMe-Ph)], 2-phenoxyethyl, 2-phenylthioethyl [=2-(phenylsulphanyl)ethyl], 2-phenylsulphinylethyl, 2-phenylsulphonylethyl, trifluoromethyl, difluoromethyl, fluoromethyl, trichloromethyl, dichloromethyl, chloromethyl, methoxymethyl, 2-methoxyethyl, 2,2,2-trifluoroethyl, 1,1,1-trifluoroprop-2-yl, 2,2-difluoroethyl, 1,3-difluoroprop-2-yl, 2,3-dimethoxypropyl, 2,3-dimethoxyprop-2-yl, 2,2-dimethoxyeth-2-yl, 2-(2,2,2-trifluoroethoxy)ethyl, 2-fluoroethyl, 2-chloroethyl, 2-bromoethyl, 2-iodoethyl, 2,2,3,3,3-pentafluoropropyl, 1-hydroxyprop-2-yl, 2-hydroxyprop-2-yl, 2-hydroxyprop-1-yl, 3-hydroxypropyl, 3-hydroxyprop-2-yl, (2-methoxyethoxy)methyl; 2-(2-methoxyethoxy)ethyl; (2-ethoxyethoxy)methyl; 2-(2-ethoxyethoxy)ethyl, (acetoxy)methyl, (propanoyloxy)methyl, (2-methylpropanoyloxy)methyl, (2,2-dimethylpropanoyloxy)methyl, 1-(acetoxy)ethyl, 2-(acetoxy)ethyl, 2-(propanoyloxy)ethyl, 1-(propanoyloxy)ethyl, 1-(2-methylpropanoyloxy)eth-1-yl, 2-(2-methylpropanoyloxy)eth-1-yl, 2-(2,2-dimethylpropanoyloxy)ethyl [i.e. 1-(t-butylcarbonyloxy)ethyl], 2-(2,2-dimethylpropanoyloxy)ethyl;

1-(2,2-dimethylpropanoyloxy)-2-methylprop-1-yl, 1-(t-butylcarbonyloxy)-2-methylprop-1-yl, (methoxycarbonyl)methyl, (ethoxycarbonyl)methyl, (n-propoxycarbonyl)methyl, (1-propoxycarbonyl)methyl, (n-butoxycarbonyl)methyl, (s-butoxycarbonyl)methyl, (1-butoxycarbonyl)methyl, (t-butoxycarbonyl)methyl, 1-(methoxycarbonyl)ethyl, 2-(methoxycarbonyl)ethyl, 1-(ethoxycarbonyl)ethyl, 2-(ethoxycarbonyl)ethyl, 1-(n-propoxycarbonyl)ethyl, 2-(n-propoxycarbonyl)ethyl, 1-(1-propoxycarbonyl)ethyl, 2-(1-propoxycarbonyl)ethyl, 1-(n-butoxycarbonyl)ethyl, 2-(n-butoxycarbonyl)ethyl, 1-(s-butoxycarbonyl)ethyl, 2-(s-butoxycarbonyl)ethyl, 1-(1-butoxycarbonyl)ethyl, 2-(1-butoxycarbonyl)ethyl, 1-(t-butoxycarbonyl)ethyl, 2-(t-butoxycarbonyl)ethyl, (methoxycarbonyloxy)methyl, (ethoxycarbonyloxy)methyl, (n-propoxycarbonyloxy)methyl, (1-propoxycarbonyloxy)methyl, (n-butoxycarbonyloxy)methyl, (s-butoxycarbonyloxy)methyl, (1-butoxycarbonyloxy)methyl, (t-butoxycarbonyloxy)methyl, 1-(methoxycarbonyloxy)ethyl, 2-(methoxycarbonyloxy)ethyl, 1-(ethoxycarbonyloxy)ethyl, 2-(ethoxycarbonyloxy)ethyl, 1-(n-propoxycarbonyloxy)ethyl, 2-(n-propoxycarbonyloxy)ethyl, 1-(1-propoxycarbonyloxy)ethyl, 2-(1-propoxycarbonyloxy)ethyl, 1-(n-butoxycarbonyloxy)ethyl, 2-(n-butoxycarbonyloxy)ethyl, 1-(s-butoxycarbonyloxy)ethyl, 2-(s-butoxycarbonyloxy)ethyl, 1-(1-butoxycarbonyloxy)ethyl, 2-(1-butoxycarbonyloxy)ethyl, 1-(t-butoxycarbonyloxy)ethyl, 2-(t-butoxycarbonyloxy)ethyl, (cyclohexoxycarbonyloxy)methyl, 1-(cyclohexoxycarbonyloxy)eth-1-yl, 2-(cyclohexoxycarbonyloxy)eth-1-yl, (acetyl)methyl, 1-(acetyl)ethyl, 2-(acetyl)ethyl, 1-(acetyl)propyl, 2-(acetyl)propyl, 3-(acetyl)propyl, (propanoyl)methyl, 1-(propanoyl)ethyl, 2-(propanoyl)ethyl, 1-(propanoyl)propyl, 2-(propanoyl)propyl, 3-(propanoyl)propyl, 1-(propanoyl)-2-methylpropyl,
2-ethylthioethyl [=2-(ethylsulphanyl)ethyl], 2-(ethylsulphinyl)ethyl, 2-(ethylsulphonyl)ethyl,
2-(ethylideneaminooxy)ethyl, 2-(prop-2-ylideneaminooxy)ethyl, 2-(but-2-ylideneaminooxy)ethyl, 2-(pent-3-ylideneaminooxy)ethyl,
(N,N-dimethylamino)methyl, 2-(N,N-dimethylamino)eth-1-yl, 1-(N,N-dimethylamino)eth-1-yl, 2-(N,N-diethylamino)eth-1-yl, 1-(N,N-diethylamino)eth-1-yl, (N,N-diethylamino)methyl,
(N,N-dimethylaminocarbonyl)methyl, 1-(N,N-dimethylaminocarbonyl)ethyl, 2-(N,N-dimethylaminocarbonyl)ethyl, (N,N-diethylaminocarbonyl)methyl, 1-(N,N-diethylaminocarbonyl)ethyl, 2-(N,N-diethylaminocarbonyl)ethyl, 1-(dimethylamino)prop-2-yl [i.e. 2-(dimethylamino)-1-methylethyl], 1-(diethylamino)prop-2-yl,
trimethylsilylmethyl, 1-(trimethylsilyl)ethyl, 2-(trimethylsilyl)ethyl, triethylsilylmethyl, 1-(triethylsilyl)ethyl, 2-(triethylsilyl)ethyl,
cyclopropyl, cyclopropylmethyl, 1-cyclopropylethyl, 2-cyclopropylethyl, (1-methylcyclopropyl)methyl, 1-(1-methylcyclopropyl)ethyl, 2-(1-methylcyclopropyl)ethyl, (2,2-dichlorcyclopropyl)methyl, 1-(2,2-dichlorcyclopropyl)ethyl, 2-(2,2-dichlorcyclopropyl)ethyl, (2,2-dimethylcyclopropyl)methyl, 1-(2,2-dimethylcyclopropyl)ethyl, 2-(2,2-dimethylcyclopropyl)ethyl, cyclobutylmethyl, cyclopentylmethyl, cyclohexylmethyl or
pyrid-2-yl, pyrid-3-yl, pyrid-4-yl, 2-chloropyrid-3-yl, 3-chloropyrid-2-yl, thien-2-yl, thien-3-yl, 2-chlorothien-3-yl, 3-chlorothien-2-yl, 4-chlorothien-2-yl, thietan-3-yl,
(1-ethyl-5-methyl-1H-pyrazol-4-yl)methyl, 1-(1-ethyl-5-methyl-1H-pyrazol-4-yl)ethyl, 2-(1-ethyl-5-methyl-1H-pyrazol-4-yl)ethyl,
(1-ethyl-3-methyl-1H-pyrazol-4-yl)methyl, 1-(1-ethyl-3-methyl-1H-pyrazol-4-yl)ethyl, 2-(1-ethyl-3-methyl-1H-pyrazol-4-yl)ethyl,
tetrahydrofuran-2-yl, tetrahydrofuran-3-yl, tetrahydrofuran-2-ylmethyl, tetrahydrofuran-3-ylmethyl, (5-methyl-2-oxo-1,3-dioxol-4-yl)methyl;
oxetan-3-yl, (oxetan-3-yl)methyl, (oxetan-2-yl)methyl, (1,3-dioxolan-2-yl)methyl, (1,3-dioxolan-4-yl)methyl, 5-methyl-2-oxo-1,3-dioxolan-4-yl)methyl, (morpholin-4-yl)methyl; 1-(morpholin-4-yl)ethyl, 2-(morpholin-4-yl)ethyl, 2,3-dihydro-1H-inden-2-yl, dihydro-1H-inden-3-yl, dihydro-1H-inden-4-yl, dihydro-1H-inden-5-yl, 1H-inden-2-yl, 1H-inden-3-yl, 1H-inden-4-yl, 1H-inden-5-yl, 1H-inden-6-yl or 1H-inden-7-yl.

Here, very particular preference is given to compounds (I), preferably of the formula (Ia), and salts thereof in which
$R^4$ represents H, methyl, ethyl, n-propyl, isopropyl, n-butyl, s-butyl, isobutyl, t-butyl, phenyl, benzyl, $CH_2$(4-Cl-Ph), i.e. (4-chlorophenyl)methyl, $CH_2$(4-F-Ph), i.e. (4-fluorophenyl)methyl, $CH_2$(4-OMe-Ph), i.e. (4-methoxyphenyl)methyl, 2-fluorobenzyl, 2-fluorobenzyl, 3-fluorobenzyl, 4-fluorobenzyl, 2,3-difluorobenzyl, 2,4-difluorobenzyl, 2,5-difluorobenzyl, 2,6-difluorobenzyl, 3,4-difluorobenzyl, 3,5-difluorobenzyl, 2-phenoxyethyl, 2-ethylthioethyl, 2-ethylsulphinylethyl, 2-ethylsulphonylethyl, 2-phenylthioethyl, 2-phenylsulphinylethyl, 2-phenylsulphonylethyl, methoxymethyl, 2-methoxyethyl, tetrahydrofuran-2-ylmethyl, 2-(dimethylamino)ethyl, oxetan-3-yl, (3-methyloxetan-3-yl)methyl, thietan-3-yl, trifluoromethyl, difluoromethyl, 2,2,2-trifluoroethyl, 2,2-difluoroethyl, 2-fluoroethyl, 2,2,3,3,3-pentafluoropropyl, cyclopropylmethyl, 1-cyclopropylethyl, (1-methylcyclopropyl)methyl, (2,2-dichlorocyclopropyl)methyl, (2,2-dimethylcyclopropyl)methyl, tetrahydrofuran-2-ylmethyl, allyl, ethynyl, propargyl (=prop-2-yn-1-yl), prop-1-yn-1-yl, 2-chloroprop-2-en-1-yl, 3-phenylprop-2-yn-1-yl, 3,3-dichloroprop-2-en-1-yl, 3,3-dichloro-2-fluoroprop-2-en-1-yl, methylprop-2-yn-1-yl, 2-methylprop-2-en-1-yl, but-2-en-1-yl, but-3-en-1-yl, but-2-yn-1-yl, but-3-yn-1-yl, 4-chlorobut-2-yn-1-yl, 3-methylbut-2-en-1-yl, 3-methylbut-1-en-1-yl, 1-(2E)-1-methylbut-2-en-1-yl, (E)-pent-3-en-2-yl or (Z)-pent-3-en-2-yl, cyclobutylmethyl, cyclopentylmethyl, cyclohexylmethyl or 1-ethyl-5-methyl-1H-pyrazol-4-methyl, i.e. (1-ethyl-5-methyl-1H-pyrazol-4-yl)methyl.

Here, very particular preference is given to compounds (I), preferably of the formula (Ia), and salts thereof in which
$R^4$ represents H, methyl, ethyl, n-butyl, s-butyl, isobutyl, t-butyl, allyl and propargyl, in particular methyl or ethyl.

The invention also includes all tautomers, such as keto and enol tautomers, and their mixtures and salts, if appropriate functional groups are present.

The present invention also provides processes for preparing the compounds of the general formula (I) or (Ia) and/or their salts. This includes processes which can be carried out analogously to known methods.

To prepare the compounds (I) according to the invention, it is possible to use initially the corresponding diastereomer mixtures in the form of their racemic mixtures. The preparation of the diastereomer mixtures of the cyanobutyrates is known in principle; see, for example, EP-A 5341, EP-A 266725, EP-A270 830, JP 04/297454, JP 04/297455, JP 05/058979, WO 2011/003776, WO 2011/003775, WO 2011/042378, WO 2011/073143, WO 2011/098417.

Analogously to the synthesis routes described in the publications cited, the compounds can be prepared by standard processes of organic chemistry.

Diastereomer mixtures of the compounds of the formula (I) comprising the compound (I) to be prepared are obtained, for example, characterized in that
(a) compounds of the formula (II) ("cyanomethylpyridines"/"pyridylacetonitriles")

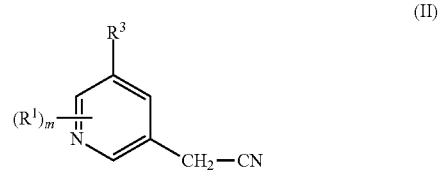

are reacted with compounds of the formula (III) (cinnamic acid derivatives) or salts thereof

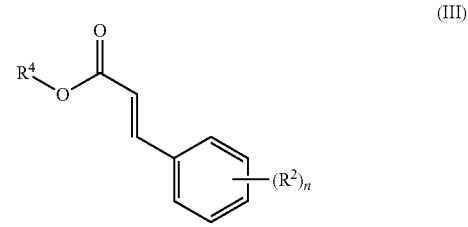

to give compounds of the formula (I) (diastereomers/racemic)

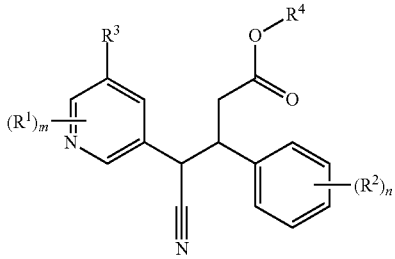

where R$^1$, R$^2$, R$^3$, R$^4$, m and n in the compounds (II) and (III) are as defined in the respective compound of the formula (I) to be prepared.

In the process mentioned above and in the processes below, in some cases solvents are employed. In this context, "inert solvents" refers in each case to solvents which are inert under the particular reaction conditions, but which do not have to be inert under all reaction conditions.

The process described in each case can be carried out in apparatuses customary in the laboratory, in pilot plants and in plants for preparing commercial amounts and industrial processes, or alternatively also in a microwave oven.

The starting materials (III) required for preparing the compounds (I) are known from the literature cited above or can be prepared analogously to the literature cited.

The starting materials (II) required for preparing the compounds (I) are commercially available, described in the literature or can be prepared analogously to processes described in the literature.

The reaction according to variant (a) can be carried out, for example, according to methods and under conditions like those known for Michael additions. The reaction is carried out, for example, at temperatures of from −100° C. to 150° C., preferably from −78° C. to 100° C., in an organic or inorganic solvent, generally in the presence of a base or a catalyst or both [cf. J. Chem. Soc. (1945), p. 438].

Suitable solvents are, for example, organic solvents such as:
  aliphatic hydrocarbons such as pentane, hexane, cyclohexane or petroleum ether;
  aromatic hydrocarbons such as toluene, o-, m- or p-xylene,
  halogenated hydrocarbons such as methylene chloride, chloroform or chlorobenzene,
  ethers, such as diethyl ether, diisopropyl ether, tert-butyl methyl ether, dioxane, anisole and tetrahydrofuran (THF),
  nitriles such as acetonitrile or propionitrile,
  ketones such as acetone, methyl ethyl ketone, diethyl ketone and tert-butyl methyl ketone,
  alcohols such as methanol, ethanol, n-propanol, isopropanol, n-butanol and tert-butanol, and also
  dimethyl sulphoxide, dimethylformamide, dimethylacetamide, sulpholane,
  mixtures of the organic solvents mentioned.

In individual cases, it is also appropriate to use inorganic solvents such as water or mixtures of organic solvents with water.

Preferred solvents are THF, toluene and methanol, and mixtures thereof with other organic solvents.

The reaction by preparation variant (a) is preferably carried out in the presence of a base, for example from the group consisting of the inorganic compounds such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group consisting of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7ene (DBU). Preferred bases are, for example, potassium tert-butoxide, lithium bis(trimethylsilyl)amide, DBU or 7-methyl-1,5,7-triazabicyclo[4.4.0]-dec-5-ene.

The amount of base may generally be varied within wide limits. For example, it may be expedient to employ the base in catalytic amounts, in substoichiometric amounts, in equimolar amounts or in excess. A preferably liquid organic base may optionally also be used as solvent.

Suitable catalysts for the Michael addition according to variant (a) are acidic catalysts, for example from the group consisting of the inorganic acids, for example Broensted acids, such as hydrofluoric acid, hydrochloric acid, hydrobromic acid, sulphuric acid or perchloric acid, or Lewis acids, such as boron trifluoride, aluminium trichloride, iron(III) chloride, tin(IV) chloride, titanium(IV) chloride, scandium (III) triflate or zinc(II) chloride, and also organic acids, for example formic acid, acetic acid, propionic acid, oxalic acid, toluenesulphonic acid, benzenesulphonic acid, camphorsulphonic acid, citric acid or trifluoroacetic acid.

The amount of acidic catalyst may generally be varied within wide limits. For example, it may be expedient to employ the acid in catalytic amounts, in substoichiometric amounts, in equimolar amounts or in excess. A preferably liquid acid may optionally also be used as solvent.

Variant (a1) for the preparation of intermediates of the formula (II):

Compounds of the formula (II) and salts thereof in which R$^1$, R$^3$ and m are defined as in the respective compound of the formula (I) to be prepared are also obtained, for example, according to process [variant (a1)], characterized in that a pyridinecarboxylic acid of the formula (IV) or its ester of the formula (V),

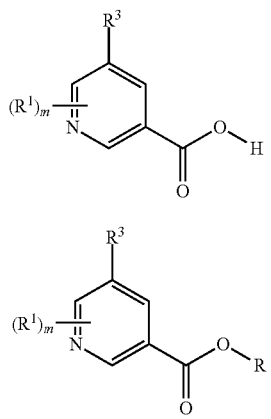

(IV)

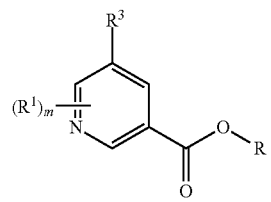

(V)

where the radical R in the formula (V) represents a hydrocarbon radical, preferably $(C_1-C_6)$-alkyl, $(C_1-C_6)$-haloalkyl or $(C_1-C_4)$-alkoxy-$(C_1-C_4)$-alkyl, in particular methyl or ethyl, is reduced to give the compound of the formula (VI) (=reduction at the acid or ester group),

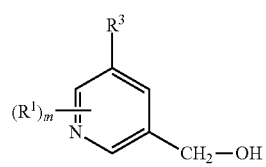

(VI)

and the compound (VI) is converted into the compound (VII),

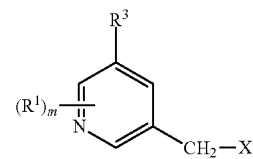

(VII)

where X represents a leaving group, for example halogen, such as chlorine, bromine or iodine, obtained by a halogenation reaction such as, for example, substitution by halide, or sulphonates of the formula —O—SO$_2$—R(R=$(C_1-C_6)$-alkyl, $(C_1-C_6)$-haloalkyl, phenyl, which is optionally substituted, for example by halogen, nitro or alkyl), for example mesylate (R=methyl), triflate (R=CF$_3$), tosylate (R=p-tolyl), bromylate (R=p-bromophenyl), nosylate (R=p-nitrophenyl), obtained by esterification of an appropriate sulphonyl chloride with compounds of the formula (VI),
and the compound (VII) is converted by substitution with cyanide into the compound (II),

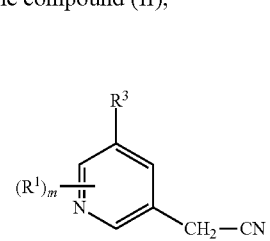

(II)

where $R^1$, $R^3$ and m in the formulae (IV), (V), (VI) and (VII) are as defined in formula (II) or formula (I).

The individual synthesis steps according to variant (a1) are known in principle to the person skilled in the art and described, for example, in Acta Pharm. Suecica 1972, 9, 411-418; J. Org. Chem. 1999, 64 (23), 8576-8581; Synthesis 1998, 9, 1335-1338; J. Med. Chem. 2000, 43 (18) 3386-3399; U.S. Pat. No. 5,225,423 (Shell Research Limited 1993), U.S. Pat. No. 4,966,902 (Hoechst AG, 1990); WO2007/045989 (Pfizer Limited, 2007); US2004/242572 (Boehringer Ingelheim International GmbH, 2004) and the literature cited therein.

Diastereomer mixtures or racemic diastereomers of the compounds of the formula (I) can be obtained according to variant (b) by transesterification, characterized in that
(b) compounds of the formula (I*)

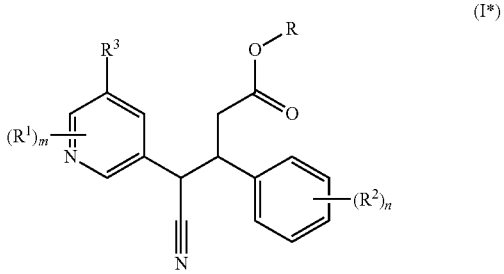

(I*)

in which R is a radical from the group consisting of the radicals possible for $R^4$ but different from the radical $R^4$ in the compound (I) to be prepared, is reacted with a compound of the formula $R^4$—OH in which $R^4$ is defined as in formula (I), to give compound (I), where $R^1$, $R^2$, $R^3$, m and n in the compound (I*) are as defined in the compound of the formula (I) to be prepared in each case.

In a particular embodiment, according to variant (b1) it is also possible to obtain, as compounds (I), stereochemically enriched compounds of the formula (Ia), characterized in that
(b1) stereochemically enriched compounds of the formula (Ia*), which correspond stereochemically [i.e. are at least as enriched as in the desired compound (Ia)]

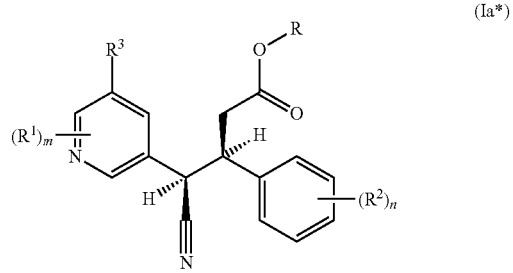

(Ia*)

in which R is a radical from the group consisting of the radicals possible for $R^4$, but different from the radical $R^4$ in the compound (Ia) to be prepared, is reacted with a compound of the formula $R^4$—OH in which $R^4$ is defined as in the compound of the formula (Ia) to be prepared.

The transesterifications (b) and (b1) can be carried out, for example, using a suitable alcohol $R^4$—OH in the presence of a catalyst, optionally in the presence of an aprotic solvent. Furthermore, in general, those conditions are advantageous where the chemical equilibrium is shifted to the side of the desired product, for example using a large excess of the alcohol R⁴—OH under virtually anhydrous conditions, for example in the presence of a molecular sieve.

The reactions (transesterifications) can generally be carried out at temperatures of from 0° C. to 180° C., preferably from 20° C. to 100° C., in the presence of a Lewis or Broenstedt acid or an enzyme [cf. J. Org. Chem. 2002, 67, 431].

Suitable solvents are, for example, organic aprotic solvents such as:
- aliphatic hydrocarbons such as pentane, hexane, cyclohexane or petroleum ether;
- aromatic hydrocarbons such as toluene, o-, m- or p-xylene,
- halogenated hydrocarbons such as methylene chloride (dichloromethane), chloroform or chlorobenzene,
- ethers, such as diethyl ether, diisopropyl ether, tert-butyl methyl ether, dioxane, anisole or tetrahydrofuran (THF),
- nitriles such as acetonitrile or propionitrile,
- ketones such as acetone, methyl ethyl ketone, diethyl ketone and tert-butyl methyl ketone,
- dimethyl sulphoxide, dimethylformamide, dimethylacetamide or sulpholane or
- mixtures of the organic solvents mentioned.

The preferred solvent is the alcohol R⁴—OH, which is at the same time used as reaction partner for the transesterification, optionally in combination with one of the aprotic organic solvents mentioned.

Alternatively, it is also possible to obtain the desired ester from another ester in two steps by acidic or basic hydrolysis of the other esters to the free acid, i.e. to compounds (1*) or (Ia*), in which R is in each case H, and subsequent esterification with an alcohol R⁴—OH.

Variants (c) and (c1):

The preparation of diastereomer mixtures or racemic diastereomers of the formula (I) according to variant (c) or optically active compounds (Ia) according to variant (c1) is therefore characterized in that a compound of the abovementioned formula (I*) or the formula (Ia*) in which the radicals R are each hydrogen (free carboxylic acids) is esterified with an alcohol of the formula R⁴—OH by customary methods, if appropriate combined with a previous preparation (c-1) or (c1-1) of the free acid from another ester of the formula (I*) or the formula (Ia*) in which the radicals R are each not hydrogen.

The esterification from the free acid of the formula (I*)/ R=H or (Ia*)/R=H can be carried out, for example, analogously to customary methods, for example at temperatures of from 0° C. to 120° C., preferably from 20° C. to 50° C., optionally in the presence of a catalyst, in a substantially anhydrous medium or under conditions where the water including the water formed during the esterification is bound or otherwise removed. Suitable catalysts are anhydrous acids and bases, preferably organic acids or bases; see handbooks for chemical processes for esterifying carboxylic acids; see also, for example, J. Am. Chem. Soc. 2007, 129 (43), 13321; J. Org. Chem. 1984, 49 (22), 4287.

Suitable solvents for the esterification are the aprotic organic solvents mentioned above for process variants (b) and (b1), including the alcohol R⁴—OH which is at the same time used as a reaction partner for the esterification, optionally in combination with one of the aprotic organic solvents mentioned.

Suitable catalysts for the esterification are the bases or acidic or basic catalysts mentioned for mentioned process variant (a) (Michael addition), in anhydrous form or with a water content which is as low as possible. Preferred catalysts are the bases lithium hydroxide, potassium carbonate or organic amines such as pyridines, substituted pyridines and DBU.

Any hydrolysis carried out before the esterification [process variants (c-1) and (c1-1)] of other esters of the formula (I*) or the formula (Ia*), where R is in each case not H, can be carried out analogously to customary methods, for example at temperatures of from 0° C. to 120° C., preferably from 20° C. to 50° C., if appropriate in the presence of a catalyst, in a water-containing medium/solvent; see handbooks on chemical processes for hydrolysing carboxylic esters; see also, for example, J. Am. Chem. Soc. 2007, 129 (43), 13321; J. Org. Chem. 1984, 49 (22), 4287.

A suitable solvent for the hydrolysis [process variants (c-1) and (c1-1)] is water or a water-containing organic solvent, for example the organic solvent mentioned based on process variant (a) mentioned (Michael addition), preferably water or polar organic solvents containing water, such as THF.

Suitable catalysts for the hydrolysis are the acids, bases or acidic or basic catalysts mentioned for process variant (a) (Michael addition), in each case containing water. Preferred catalysts are aqueous acids and bases, in particular bases such as lithium hydroxide, sodium hydroxide, potassium carbonate, pyridines, substituted pyridines and DBU in the presence of organic solvents.

The catalysts for the esterification or the hydrolysis can generally be employed in catalytic amounts. In general, it is also possible to use relatively large amounts including equimolar amounts or in molar excess. Frequently, a use as solvent is also possible.

The reaction mixtures are worked up in a customary manner, for example by mixing with water, separating the phases and, if appropriate, chromatographic purification of the crude products. Some of the intermediates and end products are obtained in the form of colourless or slightly brownish viscous oils which are purified or freed from volatile components under reduced pressure and at moderately elevated temperature.

If the intermediates and end products are obtained as solids, the purification can also be carried out by recrystallization or digestion. If individual compounds (I) or (Ia) cannot be obtained by the routes described above, they can be prepared by derivatization of other compounds (I) or (Ia).

To prepare the erythro compounds, threo compounds or optically active erythro or threo compounds according to the invention, preferably the threo compounds (Ia), from the diastereomer mixtures of the compounds (I), it is necessary to enrich the respective diastereomer, for example the threo isomer or the stereoisomer (enantiomer) erythro-1, erythro-2, threo-1 or threo-2, preferably threo-2, from the mixture of the stereoisomers in an appropriate manner. Accordingly, an expedient process comprises the initial isolation of the erythro-1 and erythro-2 or threo isomers threo-1 and threo-2 from the diastereomer mixture of the compounds of the formula (I) which still comprises the other isomers, and optionally the subsequent optical resolution with isolation or enrichment of the enantiomer from the mixture with the other enantiomers.

The isolation of the diastereomers as a racemic mixture can be carried out analogously to the customary separation and purification processes mentioned above (diastereomer separation).

Suitable for the subsequent preparation of compounds of the optically active compounds (I), preferably for the formula (Ia), are methods for optical resolution generally known to the person skilled in the art from analogous cases (cf. handbooks of stereochemistry), for example following processes for separating mixtures into diastereomers, for example by physical processes, such as crystallization, chromatographic processes, in particular column chromatography and high-pressure liquid chromatography, distillation, if appropriate under reduced pressure, extraction and other processes, it is possible to separate remaining mixtures of enantiomers, generally by chromatographic separation on chiral solid phases. Suitable for preparative amounts or on an industrial scale are processes such as the crystallization of diastereomeric salts which can be obtained from the diastereomer mixtures using optically active acids and, if appropriate, provided that acidic groups are present, using optically active bases.

Optically active acids which are suitable for optical resolution by crystallization of diastereomeric salts are, for example, camphorsulphonic acid, camphoric acid, bromocamphorsulphonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystals, by acidification or using a base.

Accordingly, the invention also provides the process for preparing the optically active compounds (I) [variant (d)], preferably (Ia), characterized in that
(d) an optical resolution is carried out with compounds (I), preferably the erythro compounds or in particular the threo compounds of the formula (I), and the desired enantiomer, preferably the compound (Ia), is isolated in a stereochemical purity of from 60 to 100%, preferably from 70 to 100%, more preferably from 80 to 100%, in particular from 90 to 100%, based on the mixture of the erythro and threo enantiomers present.

As an alternative to the optical resolution methods mentioned, enantioselective processes starting with stereochemically pure starting materials are in principle also suitable for preparing the optically active enantiomers, preferably the threo-2 enantiomers (Ia).

The following acids are generally suitable for preparing the acid addition salts of the compounds of the formula (I): hydrohalic acids, such as hydrochloric acid or hydrobromic acid, furthermore phosphoric acid, nitric acid, sulphuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulphonic acids, such as p-toluenesulphonic acid and 1,5-naphthalenedisulphonic acid. The acid addition compounds of the formula (I) can be obtained in a simple manner by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

The base addition salts of the compounds of the formula (I) are preferably prepared in inert polar solvents, such as, for example, water, methanol or acetone, at temperatures of from 0 to 100° C. Examples of bases which are suitable for the preparation of the salts according to the invention are alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide of the formula [NRR'R''R''']$^+$ OH$^-$.

Collections of compounds of the formula (I) which can be synthesized by the aforementioned process can also be prepared in a parallel manner, it being possible for this to take place in a manual, partly automated or completely automated manner. In this connection, it is possible to automate the reaction procedure, the work-up or the purification of the products and/or intermediates. Overall, this is understood as meaning a procedure as described, for example, by S. H. DeWitt in "Annual Reports in Combinatorial Chemistry and Molecular Diversity: Automated Synthesis", Volume 1, Verlag Escom, 1997, pages 69 to 77.

For the parallelized reaction procedure and workup it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleißheim, Germany. For the parallel purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described here, the preparation of compounds of the formula (I) can take place completely or partially by solid-phase supported methods. For this purpose, individual intermediates or all intermediates in the synthesis or a synthesis adapted for the corresponding procedure are bound to a synthesis resin. Solid-phase-supported synthesis methods are described extensively in the specialist literature, for example Barry A. Bunin in "The Combinatorial Index", Academic Press, 1998.

The use of solid-phase-supported synthesis methods permits a number of protocols, which are known from the literature and which for their part may be performed manually or in an automated manner, to be carried out. For example, the "teabag method" (Houghten, U.S. Pat. No. 4,631,211; Houghten et al., Proc. Natl. Acad. Sci, 1985, 82, 5131-5135) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The compounds of the formula (I) according to the invention (and/or their salts), above and hereinbelow also referred to together as "compounds according to the invention", "compounds (I) according to the invention" or in short as "compounds (I)", have excellent herbicidal efficacy against a broad spectrum of economically important monocotyledonous and dicotyledonous annual harmful plants. The active compounds also have good control over perennial harmful plants which are difficult to control and produce shoots from rhizomes, root stocks or other perennial organs.

The present invention therefore also relates to a method for controlling unwanted plants or for regulating the growth of plants, preferably in crops of plants, where one or more compound(s) according to the invention is/are applied to the plants (for example harmful plants such as monocotyledonous or dicotyledonous weeds or undesired crop plants), to the seed (for example grains, seeds or vegetative propagules such as tubers or shoot parts with buds), to the soil in or on which the plants grow (for example the soil of cropland or non-cropland) or to the area on which the plants grow (for example the area under cultivation). In this context, the compounds according to the invention can be applied for example in pre-sowing (if appropriate also by incorporation into the soil), pre-emergence or post-emergence. Specific examples may be mentioned of some representatives of the monocotyledonous and dicotyledonous weed flora which can be controlled by the compounds according to the invention, without the enumeration being restricted to certain species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die completely.

If the active ingredients are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants. Inhibiting the vegetative growth plays an important role in many monocotyledonous and dicotyledonous crops since for example lodging can be reduced, or prevented completely, hereby.

By virtue of their herbicidal and plant growth-regulating properties, the active compounds can also be used for control of harmful plants in crops of genetically modified plants or plants modified by conventional mutagenesis. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition.

It is preferred with a view to trangenic crops to use the compounds according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant-growth-regulatory properties, the active compounds can also be employed for controlling harmful plants in crops of known genetically modified plants or genetically modified plants still to be developed. In general, the transgenic plants are distinguished by especially advantageous properties, for example by resistances to certain pesticides, mainly certain herbicides, resistances to plant diseases or causative organisms of plant diseases, such as certain insects or microorganisms such as fungi, bacteria or viruses. Other specific characteristics relate, for example, to the harvested material with regard to quantity, quality, storability, composition and specific constituents. Thus, transgenic plants are known whose starch content is increased, or whose starch quality is altered, or those where the harvested material has a different fatty acid composition. Other particular properties may be tolerance or resistance to abiotic stressors, for example heat, low temperatures, drought, salinity and ultraviolet radication.

It is preferred to use the compounds of the formula (I) according to the invention or salts thereof in economically important transgenic crops of useful plants and ornamental plants, for example of cereals such as wheat, barley, rye, oats, millet, rice, cassava and corn or else crops of sugar beet, cotton, soybean, oilseed rape, potato, tomato, peas and other vegetables.

It is preferred to employ the compounds of the formula (I) according to the invention as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP-A-0221044, EP-A-0131624). For example, the following have been described in several cases:

- recombinant modifications of crop plants for the purpose of modifying the starch synthesized in the plants (for example WO 92/11376, WO 92/14827, WO 91/19806).
- transgenic crop plants which are resistant to particular herbicides of the glufosinate type (cf., for example, EP-A-0242236, EP-A-242246) or glyphosate type (WO 92/00377) or the sulphonylureas (EP-A-0257993, U.S. Pat. No. 5,013,659),
- transgenic crop plants, for example cotton, which is capable of producing Bacillus thuringiensis toxins (Bt toxins), which make the plants resistant to certain pests (EP-A-0142924, EP-A-0193259),
- transgenic crop plants with a modified fatty acid composition (WO 91/13972),
- genetically modified crop plants with novel constituents or secondary metabolites, for example novel phytoalexins, which bring about an increased disease resistance (EPA 309862, EPA0464461),
- genetically modified plants with reduced photorespiration which feature higher yields and higher stress tolerance (EPA 0305398),
- transgenic crop plants which produce pharmaceutically or diagnostically important proteins ("molecular pharming"),
- transgenic crop plants which are distinguished by higher yields or better quality,
- transgenic crop plants which are distinguished by a combination, for example of the abovementioned novel properties ("gene stacking").

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg. or Christou, "Trends in Plant Science" 1 (1996) 423-431.

For such recombinant manipulations, nucleic acid molecules which allow mutagenesis or a sequence change by recombination of DNA sequences can be introduced into plasmids. For example, base substitutions can be carried out, part-sequences can be removed, or natural or synthetic sequences may be added with the aid of standard methods. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product. For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. both monocotyledonous and dicotyledonous plants.

Thus, it is possible to obtain transgenic plants whose properties are altered by overexpression, suppression or inhibition of homologous (=natural) genes or gene sequences, or expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group consisting of the sulphonylureas, glyphosate, glufosinate or benzoylisoxazoles and analogous active compounds.

On employment of the inventive active ingredients in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants. Preference is given to the use by the pre- or post-emergence method in cereals such as wheat, barley, rye, oats, millet and rice, in particular in wheat by the post-emergence method.

Preference is also given to the use by the pre- or post-emergence method in corn, in particular by the pre-emergence method in corn.

Preference is also given to the use by the pre- or post-emergence method in soybeans, in particular by the post-emergence method in soybeans.

The use according to the invention for the control of harmful plants or for growth regulation of plants also includes the case in which the active compound of the formula (I) or its salt is not formed from a precursor substance ("prodrug") until after application on the plant, in the plant or in the soil.

The invention also provides the method (application method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation aids, such as inert materials, surfactants, solvents and further additives are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie", volume 7, C. Hanser Verlag Munich, 4th ed. 1986.

Wettable powders are preparations which can be dispersed uniformly in water and, as well as the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulphates, alkanesulphonates, alkylbenzenesulphonates, sodium lignosulphonate, sodium 2,2'-dinaphthylmethane-6,6'-disulphonate, sodium dibutylnaphthalenesulphonate or else sodium oleoylmethyltaurinate. To prepare the wettable powders, the herbicidally active compounds are ground finely, for example in customary apparatus such as hammer mills, blower mills and air-jet mills, and simultaneously or subsequently mixed with the formulation assistants.

Emulsifiable concentrates are produced by dissolving the active compound in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). The emulsifiers used may, for example, be: alkylarylsulphonic calcium salts, such as calcium dodecylbenzenesulphonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, such as, for example, sorbitan fatty acid esters, or polyoxyethylene sorbitan esters, such as, for example, polyoxyethylene sorbitan fatty acid esters.

Dusting products are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, e.g. oil-in-water emulsions (EW), can be prepared, for example, by means of stirrers, colloid mills and/or static mixers using aqueous organic solvents and if appropriate surfactants, as have for example already been listed above in connection with the other types of formulation.

Granules can be produced either by spraying the active compound onto adsorptive granulated inert material or by applying active compound concentrates by means of adhesives, for example polyvinyl alcohol, sodium polyacrylate or mineral oils, to the surface of carrier substances, such as sand, kaolinites or of granulated inert material. Suitable active compounds can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations comprise generally from 0.1 to 99% by weight, in particular from 0.1 to 95% by weight, of active compound of the formula (I) and/or salts thereof.

In wettable powders, the active compound concentration is, for example, about 10 to 90% by weight; the remainder to 100% by weight consists of the customary formulation constituents. In emulsifiable concentrates, the active ingredient concentration may be about 1 to 90% and preferably 5 to 80% by weight. Dust-type formulations contain from 1 to 30% by weight of active compound, preferably usually from 5 to 20% by weight of active compound; sprayable solutions contain from about 0.05 to 80% by weight, preferably from 2 to 50% by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described, inter alia, in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active compounds to be combined.

Combination partners for the compounds according to the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoen desaturase, photosystem I, photosystem II, protoporphyrinogen oxidase, as are described in, for example, Weed Research 26 (1986) 441-445 or "The Pesticide Manual", 15th edition, The British Crop Protection Council and the Royal Soc. of Chemistry, 2006 and the literature cited therein. Known herbicides or plant growth regulators which can be combined with the compounds according to the invention are, for example, the following active compounds (the compounds are either designated by the common name according to the International Organization for Standardization (ISO) or by the chemical name, or by the code number) and always comprise all use forms such as acids, salts, esters and isomers such as stereoisomers and optical isomers. In this case, one or else, in some cases, more than one use form is mentioned by way of example: acetochlor, acibenzolar, acibenzolar-5-methyl, acifluorfen, acifluorfen-sodium, aclonifen, alachlor, allidochlor, alloxydim, alloxydim-sodium, ametryne, amicarbazone, amidochlor, amidosulphuron, aminocyclopyrachlor, aminocyclopyrachlor-potassium, aminocyclopyrachlor-methyl, aminopyralid, amitrole, ammonium sulphamate, ancymidol, anilofos, asulam, atrazine, azafenidin, azimsulphuron, aziprotryne, beflubutamid, benazolin, benazolin-ethyl, bencarbazone, benfluralin, benfuresate, bensulide, bensulphuron, bensulphuron-methyl, bentazone, benzfendizone, benzobicyclon, benzofenap, benzofluor, benzoylprop, bicyclopyrone, bifenox, bilanafos, bilanafos-sodium, bispyribac, bispyribac-sodium, bromacil, bromobutide, bromofenoxim, bromoxynil, bromuron, buminafos, busoxinone, butachlor, butafenacil, butamifos, butenachlor, butralin, butroxydim, butylate, cafenstrole, carbetamide, carfentrazone, carfentrazone-ethyl, chlomethoxyfen, chloramben, chlorazifop, chlorazifop-butyl, chlorbromuron, chlorbufam, chlorfenac, chlorfenac-sodium, chlorfenprop, chlorflurenol, chlorflurenol-methyl, chloridazon, chlorimuron, chlorimuron-ethyl, chlormequat-chloride, chlornitrofen, chlorophthalim, chlorthal-dimethyl, chlortoluron, chlorsulphuron, cinidon, cinidon-ethyl, cinmethylin, cinosulphuron, clethodim, clodinafop, clodinafop-propargyl, clofencet, clofencet-potassium, clomazone, clomeprop, cloprop, clopyralid, cloransulam, cloransulam-methyl, cumyluron, cyanamide, cyanazine, cyclanilide, cycloate, cyclosulphamuron, cycloxydim, cycluron, cyhalofop, cyhalofop-butyl, cyperquat, cyprazine, cyprazole, 2,4-D, 2,4-DB, daimuron/dymron, dalapon, daminozide, dazomet, n-decanol, desmedipham, desmetryn, detosyl-pyrazolate (DTP), diallate, dicamba, dichlobenil, dichlorprop, dichlorprop-P, diclofop, diclofop-methyl, diclofop-P-methyl, diclosulam, diethatyl, diethatyl-ethyl, difenoxuron, difenzoquat, diflufenican, diflufenzopyr, diflufenzopyr-sodium, dikegulac-sodium, dimefuron, dimepiperate, dimethachlor, dimethametryn, dimethenamid, dimethenamid-P, dimethipin, dimetrasulphuron, dinitramine, dinoseb, dinoterb, diphenamid, dipropetryn, diquat, diquat-dibromide, dithiopyr, diuron, DNOC, eglinazine-ethyl, endothal, EPTC, esprocarb, ethalfluralin, ethametsulphuron, ethametsulphuron-methyl, ethephon, ethidimuron, ethiozin, ethofumesate, ethoxyfen, ethoxyfen-ethyl, ethoxysulphuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulphonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoprop, fenoxaprop, fenoxaprop-P, fenoxaprop-ethyl, fenoxaprop-P-ethyl, fenoxasulphone, fentrazamide, fenuron, flamprop, flamprop-M-isopropyl, flamprop-M-methyl, flazasulphuron, florasulam, fluazifop, fluazifop-P, fluazifop-butyl, fluazifop-P-butyl, fluazolate, flucarbazone, flucarbazone-sodium, flucetosulphuron, fluchloralin, flufenacet (thiafluamide), flufenpyr, flufenpyr-ethyl, flumetralin, flumetsulam, flumiclorac, flumiclorac-pentyl, flumioxazin, flumipropyn, fluometuron, fluorodifen, fluoroglycofen, fluoroglycofen-ethyl, flupoxam, flupropacil, flupropanate, flupyrsulphuron, flupyrsulphuron-methyl-sodium, flurenol, flurenol-butyl, fluridone, fluorochloridone, fluoroxypyr, fluoroxypyr-meptyl, flurprimidol, flurtamone, fluthiacet, fluthiacet-methyl, fluthiamide, fomesafen, foramsulphuron, forchlorfenuron, fosamine, furyloxyfen, gibberellic acid, glufosinate, glufosinate-ammonium, glufosinate-P, glufosinate-P-ammonium, glufosinate-P-sodium, glyphosate, glyphosate-isopropylammonium, H-9201, i.e. O-(2,4-dimethyl-6-nitrophenyl) O-ethyl isopropylphosphoramidothioate, halosafen, halosulphuron, halosulphuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapyr, imazapyr-isopropylammonium, imazaquin, imazaquin-ammonium, imazethapyr, imazethapyr-ammonium, imazosulphuron, inabenfide, indanofan, indaziflam, indoleacetic acid (IAA), 4-indol-3-ylbutyric acid (IBA), iodosulphuron, iodosulphuron-methyl-sodium, iofensulphuron, iofensulphuron-sodium, ioxynil, ipfencarbazone, isocarbamid, isopropalin, isoproturon, isouron, isoxaben, isoxachlortole, isoxaflutole, isoxapyrifop, KUH-043, i.e. 3-({[5-(difluoromethyl)-1-methyl-3-(trifluoromethyl)-1H-pyrazol-4-yl]methyl}sulphonyl)-5,5-dimethyl-4,5-dihydro-1,2-oxazole, karbutilate, ketospiradox, lactofen, lenacil, linuron, maleic hydrazide, MCPA, MCPB, MCPB-methyl, -ethyl and -sodium, mecoprop, mecoprop-sodium, mecoprop-butotyl, mecoprop-P-butotyl, mecoprop-P-dimethylammonium, mecoprop-P-2-ethylhexyl, mecoprop-P-potassium, mefenacet, mefluidide, mepiquat-chloride, mesosulphuron, mesosulphuron-methyl, mesotrione, methabenzthiazuron, metam, metamifop, metamitron, metazachlor, metazasulphuron, methazole, methiopyrsulphuron, methiozolin, methoxyphenone, methyldymron, 1-methylcyclopropene, methyl isothiocyanate, metobenzuron, metobromuron, metolachlor, S-metolachlor, metosulam, metoxuron, metribuzin, metsulphuron, metsulphuron-methyl, molinate, monalide, monocarbamide, monocarbamide dihydrogensulphate, monolinuron, monosulphuron, monosulphuron ester, monuron, MT-128, i.e. 6-chloro-N-[(2E)-3-chloroprop-2-en-1-yl]-5-methyl-N-phenylpyridazine-3-amine, MT-5950, i.e. N-[3-chloro-4-(1-methylethyl)phenyl]-2-methylpentanamide, NGGC-011, naproanilide, napropamide, naptalam, NC-310, i.e. 4-(2,4-dichlorobenzoyl)-1-methyl-5-benzyloxypyrazole, neburon, nicosulphuron, nipyraclofen, nitralin, nitrofen, nitrophenolate-sodium (isomer mixture), nitrofluorfen, nonanoic acid, norflurazon, orbencarb, orthosulphamuron, oryzalin, oxadiargyl, oxadiazon, oxasulphuron, oxaziclomefone, oxyfluorfen, paclobutrazole, paraquat, paraquat dichloride, pelargonic acid (nonanoic acid), pendimethalin, pendralin, penoxsulam, pentanochlor, pentoxazone, perfluidone, pethoxamid, phenisopham, phenmedipham, phenmediphamethyl, picloram, picolinafen, pinoxaden, piperophos, pirifenop, pirifenop-butyl, pretilachlor, primisulphuron, primisulphuron-methyl, probenazole, profluazole, procyazine, prodiamine, prifluraline, profoxydim, prohexadione, prohexadione-calcium, prohydrojasmone, prometon, prometryn, propachlor, propanil, propaquizafop, propazine, propham, propisochlor, propoxycarbazone, propoxycarbazone-sodium, propyrisulphuron, propyzamide, prosulphalin, prosulphocarb, prosulphuron, prynachlor, pyraclonil, pyraflufen, pyraflufen-ethyl, pyrasulphotole, pyrazolynate (pyrazolate), pyrazosulphuron, pyrazosulphuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulphan, pyrithiobac, pyrithiobac-sodium, pyroxasulphone, pyroxsulam, quinclorac, quinmerac, quinoclamine, quizalofop, quizalofop-ethyl, quizalofop-P, quizalofop-P-ethyl, quizalofop-P-tefuryl, rimsulphuron, saflufenacil, secbumeton, sethoxydim, siduron, simazine, simetryn, SN-106279, i.e. methyl (2R)-2-({7-[2-chloro-4-(trifluoromethyl)phenoxy]-2-naphthyl}oxy)propanoate, sulcotrione, sulphallate (CDEC), sulphentrazone, sulphometuron, sulphometuronmethyl, sulphosate (glyphosate-trimesium), sulphosulphuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, tebutam, tebuthiuron, tecnazene, tefuryltrione, tembotrione, tepraloxydim, terbacil, terbucarb, terbuchlor, terbumeton, terbuthylazine, terbutryne, thenylchlor, thiafluamide, thiazafluoron, thiazopyr, thidiazimin, thidiazuron, thiencarbazone, thiencarbazone-methyl, thifensulphuron, thifensulphuron-methyl, thiobencarb, tiocarbazil, topramezone, tralkoxydim, triafamone, triallate, triasulphuron, triaziflam, triazofenamide, tribenuron, tribenuron-methyl, trichloroacetic acid (TCA), triclopyr, tridiphane, trietazine, trifloxysulphuron, trifloxysulphuron-sodium, trifluralin, triflusulphuron, triflusulphuron-methyl, trimeturon, trinexapac, trinexapac-ethyl, tritosulphuron, tsitodef, uniconazole, uniconazole-P, vernolate, ZJ-0862, i.e. 3,4-dichloro-N-{2-[(4,6-dimethoxypyrimidin-2-yl)oxy]benzyl}aniline, and the following compounds:

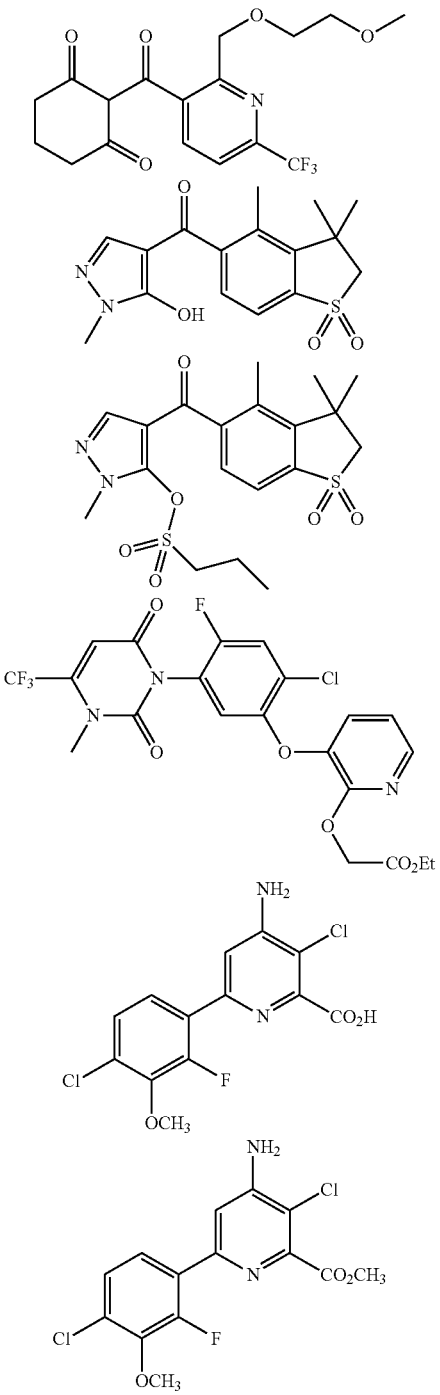

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugar beet, sugar cane, oilseed rape, cotton and soybeans, preferably cereals. The following groups of compounds are suitable, for example, as safeners for the compounds (I) and their combinations with further pesticides:

A) compounds of the formula (S-I)

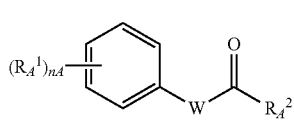
(S-I)

where the symbols and indices have the following meanings:

$n_A$ is a natural number from 0 to 5, preferably from 0 to 3;

$R_A^1$ is halogen, $(C_1-C_4)$-alkyl, $(C_1-C_4)$-alkoxy, nitro or $(C_1-C_4)$-haloalkyl;

$W_A$ is an unsubstituted or substituted divalent heterocyclic radical from the group consisting of the partially unsaturated or aromatic five-membered heterocycles having 1 to 3 ring heteroatoms of the N or O type, where at least one nitrogen atom and at most one oxygen atom is present in the ring, preferably a radical from the group consisting of $(W_A^1)$ to $(W_A^4)$,

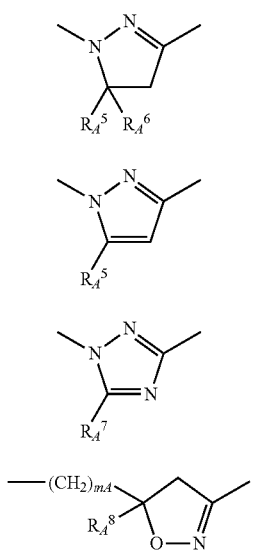

$m_A$ is 0 or 1;

$R_A^2$ is $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S-1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ is hydrogen or an unsubstituted or substituted aliphatic hydrocarbyl radical preferably having a total of 1 to 18 carbon atoms;

$R_A^4$ is hydrogen, $(C_1-C_6)$-alkyl, $(C_1-C_6)$-alkoxy or substituted or unsubstituted phenyl;

$R_A^5$ is H, $(C_1-C_8)$-alkyl, $(C_1-C_8)$-haloalkyl, $(C_1-C_4)$-alkoxy $(C_1-C_8)$-alkyl, cyano or $COOR_A^9$ in which $R_A^9$ is hydrogen, $(C_1-C_8)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and are hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the type of the dichlorophenylpyrazoline-3-carboxylic acid, preferably compounds such as ethyl 1-2,4-dichlorophenyl)-5-(ethoxycarbonyl)-5-methyl-2-pyrazoline-3-carboxylate (S1-1) ("mefenpyr-diethyl", see Pestic. Man.), and related compounds as described in WO 91/07874;

b) derivatives of dichlorophenylpyrazolecarboxylic acid, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl) pyrazole-3-carboxylate (S1-4), ethyl 1-(2,4-dichlorophenyl)-5-phenylpyrazole-3-carboxylate (S1-5) and related compounds as described in EP-A-333 131 and EP-A-269 806;

c) compounds of the triazolecarboxylic acid type, preferably compounds such as fenchlorazole(-ethyl), i.e. ethyl 1-(2,4-dichlorophenyl)-5-trichloromethyl-(1H)-1,2,4-triazole-3-carboxylate (S1-6), and related compounds as described in EP-A-174 562 and EP-A-346 620;

d) compounds of the type of the 5-benzyl- or 5-phenyl-2-isoxazoline-3-carboxylic acid or the 5,5-diphenyl-2-isoxazoline-3-carboxylic acid, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds, as described in WO 91/08202, or ethyl 5,5-diphenyl-2-isoxazolinecarboxylate (S1-9) ("isoxadifen-ethyl") or n-propyl 5,5-diphenyl-2-isoxazolinecarboxylate (S1-10) or ethyl 5-(4-fluorophenyl)-5-phenyl-2-isoxazoline-3-carboxylate (S1-11), as described in the patent application WO-A-95/07897.

B) Quinoline derivatives of the formula (S-II)

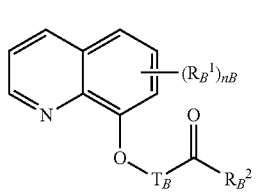
(S-II)

where the symbols and indices have the following meanings:

$R_B^1$ is halogen, $(C_1-C_4)$-alkyl, $(C_1-C_4)$-alkoxy, nitro or $(C_1-C_4)$-haloalkyl;

$n_B$ is a natural number from 0 to 5, preferably from 0 to 3;

$R_B^2$ is $OR_B^5$, $SR_B^3$ or $NR_B^3R_B^4$ or a saturated or unsaturated 3- to 7-membered heterocycle having at least one nitrogen atom and up to 3 heteroatoms, preferably from the group consisting of O and S, which is joined to the carbonyl group in (S-II) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_B^3$, NH $R^e$ or $N(CH_3)_2$, especially of the formula $OR_B^3$;

$R_B^3$ is hydrogen or an unsubstituted or substituted aliphatic hydrocarbyl radical preferably having a total of 1 to 18 carbon atoms;

$R_B^4$ is hydrogen, $(C_1-C_6)$-alkyl, $(C_1-C_6)$-alkoxy or substituted or unsubstituted phenyl;

$T_B$ is a $(C_1$ or $C_2)$-alkanediyl chain which is unsubstituted or substituted by one or two $(C_1-C_4)$-alkyl radicals or by $[(C_1-C_3)$-alkoxy]carbonyl;

preferably:

a) compounds of the 8-quinolinoxyacetic acid type (S2), preferably
  1-methylhexyl 5-chloro-8-quinolinoxyacetate (common name "cloquintocet-mexyl" (S2-1) (see Pestic. Man.),
  1,3-dimethylbut-1-yl 5-chloro-8-quinolinoxyacetate (S2-2),
  4-allyloxybutyl 5-chloro-8-quinolinoxyacetate (S2-3),
  1-allyloxyprop-2-yl 5-chloro-8-quinolinoxyacetate (S2-4),
  ethyl 5-chloro-8-quinolinoxyacetate (S2-5),
  methyl 5-chloro-8-quinolinoxyacetate (S2-6),
  allyl 5-chloro-8-quinolinoxyacetate (S2-7),
  2-(2-propylideneiminoxy)-1-ethyl 5-chloro-8-quinolinoxyacetate (S2-8), 2-oxoprop-1-yl 5-chloro-8-quinolinoxyacetate (S2-9) and related compounds as described in EP-A-86 750, EP-A-94 349 and EP-A-191 736 or EP-A-0 492 366, and also their hydrates and salts as described in WO-A-2002/034048.

b) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

C) Compounds of the formula (S-III)

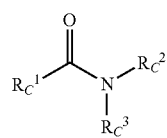

(S-III)

where the symbols and indices have the following meanings:

$R_C^1$ is $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2, R_C^3$ are identical or different and are hydrogen, $(C_1-C_4)$-alkyl, $(C_2-C_4)$-alkenyl, $(C_2-C_4)$-alkynyl, $(C_1-C_4)$-haloalkyl, $(C_2-C_4)$-haloalkenyl, $(C_1-C_4)$-alkylcarbamoyl-$(C_1-C_4)$-alkyl, $(C_2-C_4)$-alkenylcarbamoyl-$(C_1-C_4)$-alkyl, $(C_1-C_4)$-alkoxy-$(C_1-C_4)$-alkyl, dioxolanyl-$(C_1-C_4)$-alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type which are frequently used as pre-emergence safeners (soil-active safeners), such as, for example, "dichlormid" (see Pestic. Man.) (=N,N-diallyl-2,2-dichloroacetamide),
"R-29148" (=3-dichloroacetyl-2,2,5-trimethyl-1,3-oxazolidine from Stauffer),
"R-28725" (=3-dichloroacetyl-2,2,-dimethyl-1,3-oxazolidine from Stauffer), "benoxacor" (see Pestic. Man.) (=4-dichloroacetyl-3,4-dihydro-3-methyl-2H-1,4-benzoxazine),
"PPG-1292" (=N-allyl-N-[(1,3-dioxolan-2-yl)methyl] dichloroacetamide from PPG Industries),
"DKA-24" (=N-allyl-N—[(allylaminocarbonyl)methyl] dichloroacetamide from Sagro-Chem),
"AD-67" or "MON 4660" (=3-dichloroacetyl-1-oxa-3-azaspiro[4,5]decane from Nitrokemia or Monsanto),
"TI-35" (=1-dichloroacetylazepane from TRI-Chemical RT)
"diclonon" (dicyclonon) or "BAS145138" or "LAB145138" (=3-dichloroacetyl-2,5,5-trimethyl-1,3-diazabicyclo[4.3.0]nonane from BASF) and
"furilazole" or "MON 13900" (see Pestic. Man.) (=(RS)-3-dichloroacetyl-5-(2-furyl)-2,2-dimethyloxazolidine)

D) N-Acylsulphonamides of the formula (S-IV) and their salts

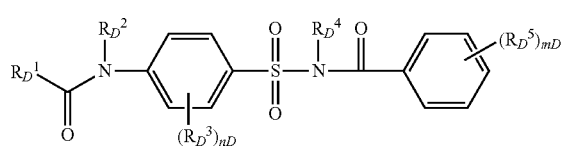

(S-IV)

in which $R_D^1$ is hydrogen, a hydrocarbon radical, a hydrocarbonoxy radical, a hydrocarbonthio radical or a heterocyclyl radical which is preferably attached via a carbon atom, where each of the 4 last-mentioned radicals is unsubstituted or substituted by one or more identical or different radicals from the group consisting of halogen, cyano, nitro, amino, hydroxy, carboxy, formyl, carboxamide, sulphonamide and radicals of the formula $—Z^a—R^a$,
  where each hydrocarbon moiety has preferaby 1 to 20 carbon atoms and a carbon-containing radical $R_D^1$ including substituents has preferably 1 to 30 carbon atoms;

$R_D^2$ is hydrogen or $(C_1-C_4)$-alkyl, preferably hydrogen, or $R_D^1$ and $R_D^2$ together with the group of the formula —CO—N— are the radical of a 3- to 8-membered saturated or unsaturated ring;

$R_D^3$ are identical or different and are halogen, cyano, nitro, amino, hydroxy, carboxy, formyl, $CON H_2$, $SO_2NH_2$ or a radical of the formula $—Z^b—R^b$;

$R_D^4$ is hydrogen or $(C_1-C_4)$-alkyl, preferably H;

$R_D^5$ are identical or different and are halogen, cyano, nitro, amino, hydroxy, carboxy, CHO, $CON H_2$, $SO_2NH_2$ or a radical of the formula $—Z^c—R^c$;

$R^a$ is a hydrocarbon radical or a heterocyclyl radical, where each of the two last-mentioned radicals is unsubstituted or substituted by one or more identical or different radicals from the group consisting of halogen, cyano, nitro, amino, hydroxyl, mono- and di-$[(C_1-C_4)$-alkyl]amino, or an alkyl radical in which a plurality, preferably 2 or 3, non-adjacent $CH_2$ groups are in each case replaced by an oxygen atom;

$R^b$, $R^c$ are identical or different and are a hydrocarbon radical or a heterocyclyl radical, where each of the two last-mentioned radicals is unsubstituted or substituted by one or more identical or different radicals from the group consisting of halogen, cyano, nitro, amino, hydroxy, phosphoryl, halo-$(C_1-C_4)$-alkoxy, mono- and di-$[(C_1-C_4)$-alkyl]amino, or an alkyl radical in which a plurality, preferably 2 or 3, non-adjacent $CH_2$ groups are in each case replaced by an oxygen atom;

$Z^a$ is a divalent group of the formula —O—, —S—, —CO—, —CS—, —CO—O—, —CO—S—, —O—CO—, —S—CO—, —SO—, —SO$_2$—, —NR*—, —CO—NR*—, —NR*—CO—, —SO$_2$—NR*— or —NR*—SO$_2$—, where the bond indicated on the right-hand side of the divalent group in question is the bond to the radical $R^a$ and where the R* in the 5 last-mentioned radicals independently of one another are each H, ($C_1$-$C_4$)-alkyl or halo-($C_1$-$C_4$)-alkyl;

$Z^b$, $Z^c$ are independently of one another a direct bond or a divalent group of the formula —O—, -S-, —CO—, —CS—, —CO—O—, —CO—S—, —O—CO—, —S—CO—, —SO—, —SO$_2$—, —NR*—, —SO$_2$—NR*—, —NR*—SO$_2$—, —CO—NR*— or —NR*—CO—, where the bond indicated at the right-hand side of the divalent group in question is the bond to the radical $R^b$ or $R^c$ and where the R* in the 5 last-mentioned radicals independently of one another are each H, ($C_1$-$C_4$)-alkyl or halo-($C_1$-$C_4$)-alkyl;

$n_D$ is an integer from 0 to 4, preferably 0, 1 or 2, particularly preferably 0 or 1, and $m_D$ is an integer from 0 to 5, preferably 0, 1, 2 or 3, in particular 0, 1 or 2;

E) acylsulphamoylbenzamides of the formula (S-V), if appropriate also in salt form,

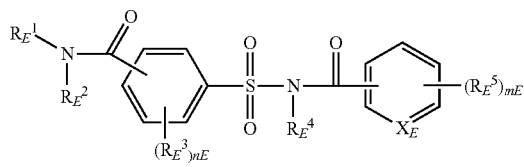

(S-V)

in which $X_E$ is CH or N, $R_E^1$ is hydrogen, heterocyclyl or a hydrocarbon radical, where the two last-mentioned radicals are optionally substituted by one or more identical or different radicals from the group consisting of halogen, cyano, nitro, amino, hydroxy, carboxy, CHO, $CONH_2$, $SO_2NH_2$ and $Z^a$—$R^a$;

$R_E^2$ is hydrogen, hydroxy, ($C_1$-$C_6$)-alkyl, ($C_2$-$C_6$)-alkenyl, ($C_2$-$C_6$)-alkynyl, ($C_1$-$C_6$)-alkoxy, ($C_2$-$C_6$)-alkenyloxy, where the five last-mentioned radicals are optionally substituted by one or more identical or different radicals from the group consisting of halogen, hydroxy, ($C_1$-$C_4$)-alkyl, ($C_1$-$C_4$)-alkoxy and ($C_1$-$C_4$)-alkylthio, or $R_E^1$ and $R_E^2$ together with the nitrogen atom that carries them are a 3- to 8-membered saturated or unsaturated ring;

$R_E^3$ is halogen, cyano, nitro, amino, hydroxy, carboxy, CHO, $CONH_2$, $SO_2NH_2$ or $Z^b$—$R^{13}$, $R_E^4$ is hydrogen, ($C_1$-$C_4$)-alkyl, ($C_2$-$C_4$)-alkenyl or ($C_2$-$C_4$)-alkynyl;

$R_E^5$ is halogen, cyano, nitro, amino, hydroxy, carboxy, phosphoryl, CHO, $CONH_2$, $SO_2NH_2$ or $Z^c$—$R^c$;

$R^a$ is a ($C_2$-$C_{20}$)-alkyl radical whose carbon chain is interrupted once or more than once by
  oxygen atoms, is heterocyclyl or a hydrocarbon radical, where the two last-mentioned radicals are optionally substituted by one or more identical or different radicals from the group consisting of halogen, cyano, nitro, amino, hydroxyl, mono- and di-[($C_1$-$C_4$)-alkyl]-amino;

$R^b$, $R^c$ are identical or different and are a ($C_2$-$C_{20}$)-alkyl radical whose carbon chain is interrupted once or more than once by oxygen atoms, are heterocyclyl or a hydrocarbon radical, where the two last-mentioned radicals are optionally substituted by one or more identical or different radicals from the group consisting of halogen, cyano, nitro, amino, hydroxyl, phosphoryl, ($C_1$-$C_4$)-haloalkoxy, mono- and di-[($C_1$-$C_4$)-alkyl]amino;

$Z^a$ is a divalent unit from the group consisting of O, S, CO, CS, C(O)O, C(O)S, SO, $SO_2$, $NR^d$, $C(O)NR^d$ and $SO_2NR^d$;

$Z^b$, $Z^c$ are identical or different and are a direct bond or divalent unit from the group consisting of O, S, CO, CS, C(O)O, C(O)S, SO, $SO_2$, $NR^d$, $SO_2NR^d$ and $C(O)NR^d$;

$R^d$ is hydrogen, ($C_1$-$C_4$)-alkyl or ($C_1$-$C_4$)-haloalkyl;

$n_E$ is an integer from 0 to 4, and $m_E$ if X is CH, is an integer from 0 to 5, and, if X is N, is an integer from 0 to 4;

from among these, preference is given to compounds (also in the form of their salts) of the type of the acylsulphamoylbenzamides, for example of the formula (S-VI) below, which are known, for example, from WO 99/16744,

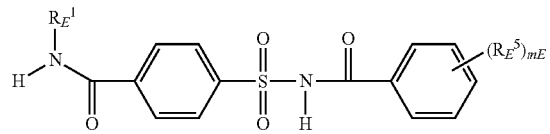

(S-VI)

for example those in which $R_E^1$=cyclopropyl and $R_E^5$=2-OMe ("cyprosulphamide", S3-1), $R_E^1$=cyclopropyl and $R_E^5$=5-Cl-2-OMe (S3-2), $R_E^1$=ethyl and $R_E^5$=2-OMe (S3-3), $R_E^1$=isopropyl and $R_E^5$=5-Cl-2-OMe (S3-4) and $R_E^1$=isopropyl and $R_E^5$=2-OMe (S3-5);

F) compounds of the type of the N-acylsulphamoylphenylureas of the formula (S-VII), which are known, for example, from EP-A-365484

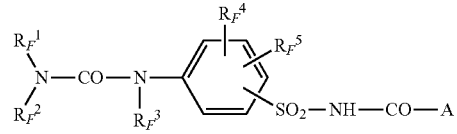

(S-VII)

in which

A is a radical from the group consisting of

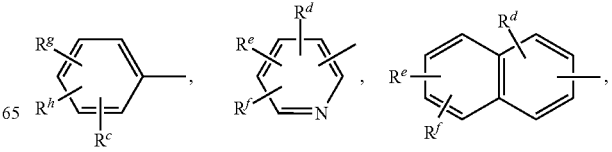

-continued

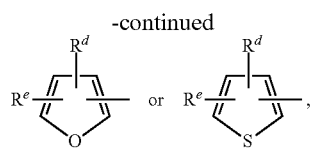

$R_F^1$ and $R_F^2$ independently of one another are hydrogen, $(C_1-C_8)$-alkyl, $(C_3-C_8)$-cycloalkyl, $(C_3-C_6)$-alkenyl, $(C_3-C_6)$-alkynyl,

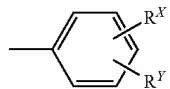

or $(C_1-C_4)$Alkoxy substituted by

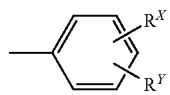

or $(C_1-C_4)$Alkoxy, or
$R_F^1$ and $R_F^2$ together are a $(C_4-C_6)$-alkylene bridge and a $(C_4-C_6)$-alkylene bridge interrupted by oxygen, sulphur, SO, SO$_2$, NH or —N(C$_1$-C$_4$-alkyl)-,
$R_F^3$ is hydrogen or $(C_1-C_4)$-alkyl,
$R_F^4$ and $R_F^5$ independently of one another are hydrogen, halogen, cyano, nitro, trifluoromethyl, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, —COOR$^j$, —CONR$^k$R$^m$, —COR$^n$, —SO$_2$NR$^k$R$^m$ or —OSO$_2$—C$_1$-C$_4$-alkyl, or R$^a$ and R$^b$ together are a $(C_3-C_4)$-alkylene bridge which may be substituted by halogen or $C_1$-$C_4$-alkyl, or a $(C_3-C_4)$-alkenylene bridge which may be substituted by halogen or $(C_1-C_4)$-alkyl, or a $C_4$-alkadienylene bridge which may be substituted by halogen or $(C_1-C_4)$-alkyl, and
R$^g$ and R$^h$ independently of one another are hydrogen, halogen, $C_1$-$C_4$-alkyl, trifluoromethyl, methoxy, methylthio or —COOR$^j$, where
R$^c$ is hydrogen, halogen, $(C_1-C_4)$-alkyl or methoxy,
R$^d$ is hydrogen, halogen, nitro, $(C_1-C_4)$-alkyl, $(C_1-C_4)$-alkoxy, $(C_1-C_4)$-alkylthio, $(C_1-C_4)$-alkylsulphinyl, $(C_1-C_4)$-alkylsulphonyl, —COOR$^j$ or —CONR$^k$R$^m$,
R$^e$ is hydrogen, halogen, $C_1$-$C_4$-alkyl, —COOR$^j$, trifluoromethyl or methoxy, or R$^d$ and R$^e$ together are a $(C_3-C_4)$-alkylene bridge,
R$^f$ is hydrogen, halogen or $(C_1-C_4)$-alkyl,
R$^X$ and R$^Y$ independently of one another are hydrogen, halogen, $(C_1-C_4)$-alkyl, $(C_1-C_4)$-alkoxy, $(C_1-C_4)$-alkylthio, —COOR$^4$, trifluoromethyl, nitro or cyano,
R$^j$, R$^k$ and R$^m$ independently of one another are hydrogen or $(C_1-C_4)$-alkyl,
R$^k$ and R$^m$ together are a $(C_4-C_6)$-alkylene bridge and a $(C_4-C_6)$-alkylene bridge interrupted by oxygen, NH or —N(C$_1$-C$_4$-alkyl)-, and
R$^n$ is $(C_1-C_4)$-alkyl, phenyl or phenyl substituted by halogen, $(C_1-C_4)$-alkyl, methoxy, nitro or trifluoromethyl,
from among these, preference is given to:
1-[4-(N-2-methoxybenzoylsulphamoyl)phenyl]-3-methylurea,
1-[4-(N-2-methoxybenzoylsulphamoyl)phenyl]-3,3-dimethylurea,
1-[4-(N-4,5-dimethylbenzoylsulphamoyl)phenyl]-3-methylurea,
1-[4-(N-naphthoylsulphamoyl)phenyl]-3,3-dimethylurea,
including the stereoisomers and agriculturally customary salts, G) active compounds from the class of the hydroxyaromatics and the aromatic-aliphatic carboxylic acid derivatives, for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 1,2-dihydro-2-oxo-6-trifluoromethylpyridine-3-carboxamide, 2-hydroxycinnamic acid, 2,4-dichlorocinnamic acid, as described in WO 2004084631, WO 2005015994, WO 2006007981, WO 2005016001;

H) active compounds from the class of the 1,2-dihydroquinoxalin-2-ones, for example
1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulphonylaminoethyl)-3-(2-thienyl)-1,2-dihydroquinoxalin-2-one, as described in WO 2005112630, I) active compounds which, in addition to herbicidal action against harmful plants, also have safener action on crop plants such as rice, for example "dimepiperate" or "MY-93" (see Pestic. Man.) (=S-1-methyl-1-phenylethyl piperidine-1-thiocarboxylate), which is known as safener for rice against damage caused by the herbicide molinate,
"daimuron" or "SK 23" (see Pestic. Man.) (=1-(1-methyl-1-phenylethyl)-3-p-tolylurea), which is known as safener for rice against imazosulfuron herbicide damage,
"cumyluron"="JC-940" (3-(2-chlorophenylmethyl)-1-(1-methyl-1-phenylethyl)urea, see JP-A-60087254), which is known as a safener for rice against damage by some herbicides,
"methoxyphenone" or "NK 049" (=3,3'-dimethyl-4-methoxybenzophenone), which is known as safener for rice against damage by some herbicides,
"CSB" (=1-bromo-4-(chloromethylsulphonyl)benzene) (CAS Reg. No. 54091-06-4 from Kumiai), which is known as safener for rice against damage by some herbicides, K) compounds of the formula (S-IX), as described in WO-A-1998/38856,

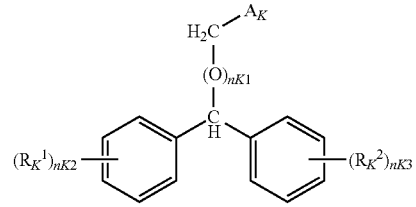

(S-IX)

where the symbols and indices have the following meanings:
$R_K^1$, $R_K^2$ independently of one another are halogen, $(C_1-C_4)$-alkyl, $(C_1-C_4)$-alkoxy, $(C_1-C_4)$-haloalkyl, $(C_1-C_4)$-alkylamino, di$(C_1-C_4)$-alkylamino, nitro;
$A_K$ is COOR$_K^3$ or COOR$_K^4$
$R_K^3$, $R_K^4$ independently of one another are hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium, $n_K^1$ is 0 or 1 and $n_K^2$, $n_K^3$ independently of one another are 0, 1 or 2;

preferably:

methyl (diphenylmethoxy)acetate (CAS reg no: 41858-19-9),

L) compounds of the formula (S-X)
  as described in WO A-98/27049

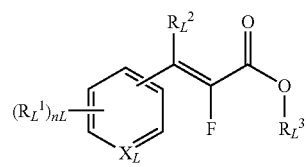

where the symbols and indices have the following meanings:

$X_L$ is CH or N, $n_L$ if X=N, is an integer from 0 to 4 and
  if X=CH, is an integer from 0 to 5, $R_L^1$ is halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulphonyl, $(C_1-C_4)$-alkoxycarbonyl, optionally substituted phenyl, optionally substituted phenoxy, $R_L^2$ is hydrogen or $(C_1-C_4)$-alkyl $R_L^3$ is hydrogen, $(C_1-C_8)$-alkyl, $(C_1-C_4)$-alkenyl, $(C_1-C_4)$-alkynyl, or aryl, where each of the aforementioned carbon-containing radicals is unsubstituted or substituted by one or more, preferably up to three identical or different radicals from the group consisting of halogen and alkoxy; or salts thereof.

M) Active compounds from the class of the 3-(5-tetrazolylcarbonyl)-2-quinolones, for example
  1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolylcarbonyl)-2-quinolone (CAS Reg. No.: 95855-00-8), as described in WO-A-1999000020, N) compounds of the formula (S-XI) or (S-XII)
  as described in WO-A-2007023719 and WO-A-2007023764

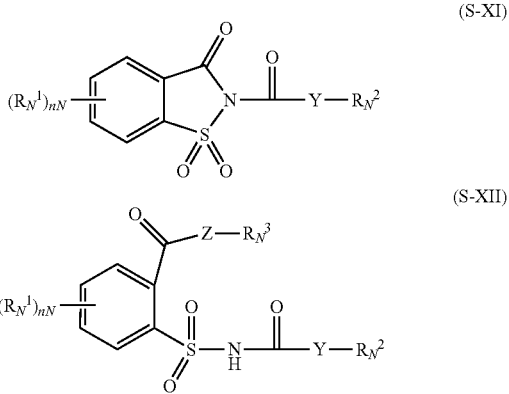

in which $R_N^1$ is halogen, $(C_1-C_4)$-alkyl, methoxy, nitro, cyano, $CF_3$, $OCF_3$, Y, Z independently of one another are O or S, $n_N$ is an integer from 0 to 4, $R_N^2$ is $(C_1-C_{16})$-alkyl, $(C_2-C_6)$-alkenyl, $(C_3-C_6)$-cycloalkyl, aryl; benzyl, halobenzyl, $R_N^3$ is hydrogen, $(C_1-C_6)$-alkyl;

O) one or more compounds from the group consisting of:
  1,8-naphthalic anhydride,
  O,O-diethyl S-2-ethylthioethyl phosphorodithioate (disulfoton),
  4-chlorophenyl methylcarbamate (mephenate),
  O,O-diethyl O-phenyl phosphorothioate (dietholate),
  4-carboxy-3,4-dihydro-2H-1-benzopyran-4-acetic acid (CL-304415, CAS Reg. No.: 31541-57-8),
  2-propenyl 1-oxa-4-azaspiro[4.5]decane-4-carbodithioate (MG-838, CAS Reg. No.: 133993-74-5),
  methyl [(3-oxo-1H-2-benzothiopyran-4(3H)-ylidene) methoxy]acetate (from WOA98/13361; CAS Reg. No.: 205121-04-6),
  cyanomethoxyimino(phenyl)acetonitrile (cyometrinil)
  1,3-dioxolan-2-ylmethoxyimino(phenyl)acetonitrile (oxabetrinil),
  4'-chloro-2,2,2-trifluoroacetophenone 0-1,3-dioxolan-2-ylmethyloxime (fluxofenim),
  4,6-dichloro-2-phenylpyrimidine (fenclorim),
  benzyl 2-chloro-4-trifluoromethyl-1,3-thiazole-5-carboxylate (flurazole),
  2-dichloromethyl-2-methyl-1,3-dioxolane (MG-191),
  including the stereoisomers possible in each case, and the salts customary in agriculture.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tankmix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Preparations in the form of dusts, granules for soil application or granules for broadcasting and sprayable solutions are usually not diluted further with other inert substances prior to application.

The required application rate of the compounds of the formula (I) and/or their salts varies according to the external conditions such as, inter alia, temperature, humidity and the type of herbicide used. It can vary within wide limits. For the application as herbicide for controlling harmful plants, it is, for example, in the range of from 0.001 to 10.0 kg/ha or more of active substance, preferably in the range of from 0.005 to 5 kg/ha, in particular in the range of from 0.01 to 1 kg/ha, of active substance. This applies both to the pre-emergence and the post-emergence application.

When used as plant growth regulator, for example as culm stabilizer for crop plants like those mentioned above, preferably cereal plants, such as wheat, barley, rye, triticale, millet, rice or corn, the application rate is, for example, in the range of from 0.001 to 2 kg/ha or more of active substance, preferably in the range of from 0.005 to 1 kg/ha, in particular in the range of from 10 to 500 g/ha of active substance, very particularly from 20 to 250 g/ha of active substance. This applies both to application by the pre-emergence method and the post-emergence method, the post-emergence treatment generally being preferred.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

In an exemplary manner, some synthesis examples of compounds of the general formula (I) are described below. In the examples, the amounts (including percentages) refer to the weight, unless especially stated otherwise.

The symbols ">" and "<" mean "greater than" and "smaller than", respectively. The symbol "≥" means "greater than or equal to", the symbol "≤" means "smaller than or equal to".

If, in the context of the description and the examples, the terms "R" and "S" are given for the absolute configuration on a center of chirality of the stereoisomers of the formula (I), this RS nomenclature follows, unless defined differently, the Cahn-Ingold-Prelog rule.

(A) Synthesis Examples

Example A1 erythro- and threo-Methyl 4-cyano-4-(5-bromopyridin-3-yl)-3-(4-chlorophenyl)butanoate (Table 2, Examples erythro-Ibb1082 and threo-Ibb1082)

Under protective gas (Ar), 0.055 g (1.015 mmol) of potassium tert-butoxide was added to 1.048 g (5.329 mmol) of methyl 3-(4-chlorophenyl)acrylate and 1.000 g (5.075 mmol) of (5-bromopyridin-3-yl)acetonitrile in 8.0 ml of toluene. 3 ml of dimethylformamide were added, and the mixture was stirred at 80° C. for 8 h. The solvent was removed under reduced pressure and the residue was taken up in dichloromethane and washed twice with in each case 25 ml of water. The combined organic phases were washed successively with 1N aqueous hydrochloric acid and with saturated aqueous sodium chloride solution and dried over sodium sulphate. The solvent was removed under reduced pressure. Chromatography of the residue on silica gel (gradient: starting with ethyl acetate/heptane=5:95 over the course of 20 minutes increased to ethyl acetate/heptane=30:70) gave, successively, 0.578 g (29% of theory) of threo-methyl 4-cyano-4-(5-bromopyridin-3-yl)-3-(4-chlorophenyl)butanoate and 0.800 g (40% of theory) of erythro-methyl 4-cyano-4-(5-bromopyridin-3-yl)-3-(4-chlorophenyl)butanoate. The configuration was assigned by comparison of the chemical shifts of the respective CHCN doublets at 4.12 ppm and 4.49 ppm, respectively, in the $^1$H-NMR (CDCl$_3$). The lower-field signal was assigned to the erythro-diastereomer, analogously to the literature. $^1$H-NMR in CDCl$_3$ see Table 2.

Example A2

Methyl (3S,4S)-4-cyano-4-(5-bromopyridin-3-yl)-3-(4-chlorophenyl)butanoate (Table 2, Example threo-1-Ibb1082)

Preparative chromatography [(80 ml/min of n-heptane/2-propanol (70:30)] of the mixture, obtained in Example A1, of the racemic threo-methyl 4-cyano-4-(5-bromopyridin-3-yl)-3-(4-chlorophenyl)butanoate on a chiral solid phase [Chiralpak IC, 20 μm, (250×50)-mm column] gave 232.0 mg of methyl (3S,4S)-4-cyano-4-(5-bromopyridin-3-yl)-3-(4-chlorophenyl)butanoate [chemical purity>95% (NMR), isomeric purity>99% (chiral HPLC)], which was the first of the two stereoisomers to elute (retention time=12.17 min). Specific rotation [α]: +61°. For $^1$H-NMR in CDCl$_3$ and retention time in analytical HPLC: see Table 2.

Example A3

Methyl (3R,4R)-4-cyano-4-(5-bromopyridin-3-yl)-3-(4-chlorophenyl)butanoate (Table 2, Example threo-2-Ibb1082)

Preparative chromatography [(80 ml/min of n-heptane/2-propanol (70:30)] of the mixture, obtained in Example A1, of the racemic threo-methyl 4-cyano-4-(5-bromopyridin-3-yl)-3-(4-chlorophenyl)butanoate on a chiral solid phase [Chiralpak IC, 20 μm, (250×50)-mm column] gave 73.0 mg of methyl (3R,4R)-4-cyano-4-(5-bromopyridin-3-yl)-3-(4-chlorophenyl)butanoate [chemical purity>95% (NMR), isomeric purity>99% (chiral HPLC)], which was the last of the two stereoisomers to elute (retention time=20.01 min). Specific rotation [α]: −61°. For $^1$H-NMR in CDCl$_3$ and retention time in analytical HPLC: see Table 2.

The compounds, described in tables below, of the absolute configuration (3R,4R) are obtained according to or analogously to the examples described above.

Example A4

4-Cyano-4-(5-bromopyridin-3-yl)-3-(4-chlorophenyl)butanoic acid (Table 2, Examples Iba1082)

Under protective gas (Ar), 3.0 ml of 2 molar aqueous sodium hydroxide solution were added to 0.630 g (1.600 mmol) of methyl 4-cyano-3-(2,6-difluorophenyl)-4-(3,4-difluorophenyl)butanoate (Example A1) in 160 ml of methanol, and the mixture was stirred at 25° C. for 2 h. The methanol was removed under reduced pressure. The residue was acidified with 2N aqueous hydrochloric acid (pH=3). Filtration and drying of the residue under high vacuum at 40° C. gave 0.593 g (99.8% of theory) of the title compound as a colourless solid [(erythro:threo=35:65, comparison of the doublets in the $^1$H-NMR in CDCl$_3$ at 4.14 (threo) and 4.50 ppm (erythro)]. $^1$H-NMR in CDCl$_3$ see Table 2.

Example A5

Ethyl 4-cyano-4-(5-bromopyridin-3-yl)-3-(4-chlorophenyl)butanoate (Table 2, Examples Ibc1082)

Under protective gas (Ar), 0.121 g (0.632 mmol) of N'-(3-dimethylaminopropyl)-N-ethylcarbodiimide (EDC), a spatula tip of 4-dimethylaminopyridine (DMAP) and 0.061 g (1.317 mmol) of ethanol were added to 0.200 g (0.527 mmol) of 4-cyano-4-(5-bromopyridin-3-yl)-3-(4-chlorophenyl)butanoic acid (Example A4) in 4 ml of dichloromethane, and the mixture was stirred at 25° C. for 8 h. The solvent was removed under reduced pressure and the residue was taken up in dichloromethane and washed twice with in each case 15 ml of water. The combined organic phases were dried over sodium sulphate and the solvent was removed under reduced pressure. Chromatography of the residue on silica gel (gradient: starting with ethyl acetate/heptane=5:95 over the course of 20 minutes increased to ethyl acetate/heptane=20:80) gave 0.143 g (67% of theory) of the title compound (erythro:threo=58:42). $^1$H-NMR in CDCl$_3$ see Table 2.

The compounds described in the tables below are obtained according to or analogously to the examples described above.

In the tables:
Ex.=Example number
H=hydrogen (atom)
Me=methyl
Et=ethyl
n-Pr=n-propyl
i-Pr=isopropyl
rt=retention time
F, Cl, Br, I=fluorine, chlorine, bromine and iodine, respectively, in accordance with the conventional chemical atom symbol
CN=cyano
$NO_2$=nitro
MeO or OMe=methoxy
$CF_3$=trifluoromethyl
$OCF_3$=trifluoromethoxy
$OCF_2H$=difluoromethoxy
$CO_2Me$=methoxycarbonyl ("methylester group")

The position of a substituent at the phenyl ring, for example in position 2, is stated as a prefix to the symbol or the abbreviation of the radical, for example
2-Cl=2-chloro
2-F=2-fluoro Numerations of the substituent positions for di- or trisubstituted substitution patterns are analogously stated as a prefix, for example
3,4-$Me_2$=3,4-dimethyl (e.g. as substitution at the phenyl ring)
3,5-$F_2$=3,5-difluoro (e.g. as substitution at the phenyl ring)
3,4-$F_2$=3,4-difluoro (e.g. as substitution at the phenyl ring)

Other abbreviations are to be understood analogously to the examples stated above.
"$(R^1)_m$="H"=no substituent other than $R^3$ present (m=0)
"$(R^2)_n$="H"=unsubstituted cycle (n=0)

In addition, the customary chemical symbols and formulae apply, such as, for example, $CH_2$ for methylene or $CF_3$ for trifluoromethyl or OH for hydroxyl. Correspondingly, composite meanings are defined as composed of the abbreviations mentioned.

The retention times ("rt") given for the compounds of Tables 2a-2f were obtained by analytical HPLC of the compounds (I) on a chiral solid phase. At a concentration of 1 mg/ml, the compounds of the formula (I) were dissolved in dichloromethane p.a. and directly subjected to HPLC. The chromatographically purified compounds (I) have a stereochemical purity of ≥90%.

TABLE 1

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1 | H | 4-F | F |
| 2 | H | 4-Cl | F |
| 3 | H | 4-Br | F |
| 4 | H | H | F |
| 5 | H | 4-Me | F |
| 6 | H | 4-CN | F |
| 7 | H | 4-$NO_2$ | F |
| 8 | H | 4-OMe | F |
| 9 | H | 3-F | F |
| 10 | H | 3-Cl | F |
| 11 | H | 3-Br | F |
| 12 | H | 3-Me | F |
| 13 | H | 3-CN | F |
| 14 | H | 3-$NO_2$ | F |
| 15 | H | 3-OMe | F |
| 16 | H | 2-F | F |
| 17 | H | 2-Cl | F |
| 18 | H | 2-Br | F |
| 19 | H | 2-Me | F |
| 20 | H | 2-CN | F |
| 21 | H | 2-$NO_2$ | F |
| 22 | H | 2-OMe | F |
| 23 | H | 2,3-$F_2$ | F |
| 24 | H | 2,4-$F_2$ | F |
| 25 | H | 2,5-$F_2$ | F |
| 26 | H | 2,6-$F_2$ | F |
| 27 | H | 3,4-$F_2$ | F |
| 28 | H | 3,5-$F_2$ | F |
| 29 | H | 2,3-$Cl_2$ | F |
| 30 | H | 2,4-$Cl_2$ | F |
| 31 | H | 2,5-$Cl_2$ | F |
| 32 | H | 2,6-$Cl_2$ | F |
| 33 | H | 3,4-$Cl_2$ | F |
| 34 | H | 3,5-$Cl_2$ | F |
| 35 | H | 2-F, 3-Cl | F |
| 36 | H | 2-F, 4-Cl | F |
| 37 | H | 2-F, 5-Cl | F |
| 38 | H | 2-F, 6-Cl | F |
| 39 | H | 2,6-$F_2$, 4-Cl | F |
| 40 | H | 3-F, 4-Cl | F |
| 41 | H | 3-Cl, 5-F | F |
| 42 | H | 2-Cl, 5-F | F |
| 43 | H | 3-CN, 4-Cl | F |
| 44 | H | 3-$NO_2$, 4-Cl | F |
| 45 | H | 2-F, 4-Br | F |
| 46 | 6-F | 4-F | F |
| 47 | 6-F | 4-Cl | F |
| 48 | 6-F | 4-Br | F |
| 49 | 6-F | H | F |
| 50 | 6-F | 4-Me | F |
| 51 | 6-F | 4-CN | F |
| 52 | 6-F | 4-$NO_2$ | F |
| 53 | 6-F | 4-OMe | F |
| 54 | 6-F | 3-F | F |
| 55 | 6-F | 3-Cl | F |
| 56 | 6-F | 3-Br | F |
| 57 | 6-F | 3-Me | F |
| 58 | 6-F | 3-CN | F |
| 59 | 6-F | 3-$NO_2$ | F |
| 60 | 6-F | 3-OMe | F |
| 61 | 6-F | 2-F | F |
| 62 | 6-F | 2-Cl | F |
| 63 | 6-F | 2-Br | F |
| 64 | 6-F | 2-Me | F |
| 65 | 6-F | 2-CN | F |
| 66 | 6-F | 2-$NO_2$ | F |
| 67 | 6-F | 2-OMe | F |
| 68 | 6-F | 2,3-$F_2$ | F |
| 69 | 6-F | 2,4-$F_2$ | F |
| 70 | 6-F | 2,5-$F_2$ | F |
| 71 | 6-F | 2,6-$F_2$ | F |
| 72 | 6-F | 3,4-$F_2$ | F |
| 73 | 6-F | 3,5-$F_2$ | F |
| 74 | 6-F | 2,3-$Cl_2$ | F |
| 75 | 6-F | 2,4-$Cl_2$ | F |
| 76 | 6-F | 2,5-$Cl_2$ | F |
| 77 | 6-F | 2,6-$Cl_2$ | F |
| 78 | 6-F | 3,4-$Cl_2$ | F |
| 79 | 6-F | 3,5-$Cl_2$ | F |
| 80 | 6-F | 2-F, 3-Cl | F |
| 81 | 6-F | 2-F, 4-Cl | F |
| 82 | 6-F | 2-F, 5-Cl | F |
| 83 | 6-F | 2-F, 6-Cl | F |
| 84 | 6-F | 2,6-$F_2$, 4-Cl | F |
| 85 | 6-F | 3-F, 4-Cl | F |
| 86 | 6-F | 3-Cl, 5-F | F |
| 87 | 6-F | 2-Cl, 5-F | F |
| 88 | 6-F | 3-CN, 4-Cl | F |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 89 | 6-F | 3-$NO_2$, 4-Cl | F |
| 90 | 6-F | 2-F, 4-Br | F |
| 91 | 6-Cl | 4-F | F |
| 92 | 6-Cl | 4-Cl | F |
| 93 | 6-Cl | 4-Br | F |
| 94 | 6-Cl | H | F |
| 95 | 6-Cl | 4-Me | F |
| 96 | 6-Cl | 4-CN | F |
| 97 | 6-Cl | 4-$NO_2$ | F |
| 98 | 6-Cl | 4-OMe | F |
| 99 | 6-Cl | 3-F | F |
| 100 | 6-Cl | 3-Cl | F |
| 101 | 6-Cl | 3-Br | F |
| 102 | 6-Cl | 3-Me | F |
| 103 | 6-Cl | 3-CN | F |
| 104 | 6-Cl | 3-$NO_2$ | F |
| 105 | 6-Cl | 3-OMe | F |
| 106 | 6-Cl | 2-F | F |
| 107 | 6-Cl | 2-Cl | F |
| 108 | 6-Cl | 2-Br | F |
| 109 | 6-Cl | 2-Me | F |
| 110 | 6-Cl | 2-CN | F |
| 111 | 6-Cl | 2-$NO_2$ | F |
| 112 | 6-Cl | 2-OMe | F |
| 113 | 6-Cl | 2,3-$F_2$ | F |
| 114 | 6-Cl | 2,4-$F_2$ | F |
| 115 | 6-Cl | 2,5-$F_2$ | F |
| 116 | 6-Cl | 2,6-$F_2$ | F |
| 117 | 6-Cl | 3,4-$F_2$ | F |
| 118 | 6-Cl | 3,5-$F_2$ | F |
| 119 | 6-Cl | 2,3-$Cl_2$ | F |
| 120 | 6-Cl | 2,4-$Cl_2$ | F |
| 121 | 6-Cl | 2,5-$Cl_2$ | F |
| 122 | 6-Cl | 2,6-$Cl_2$ | F |
| 123 | 6-Cl | 3,4-$Cl_2$ | F |
| 124 | 6-Cl | 3,5-$Cl_2$ | F |
| 125 | 6-Cl | 2-F, 3-Cl | F |
| 126 | 6-Cl | 2-F, 4-Cl | F |
| 127 | 6-Cl | 2-F, 5-Cl | F |
| 128 | 6-Cl | 2-F, 6-Cl | F |
| 129 | 6-Cl | 2,6-$F_2$, 4-Cl | F |
| 130 | 6-Cl | 3-F, 4-Cl | F |
| 131 | 6-Cl | 3-Cl, 5-F | F |
| 132 | 6-Cl | 2-Cl, 5-F | F |
| 133 | 6-Cl | 3-CN, 4-Cl | F |
| 134 | 6-Cl | 3-$NO_2$, 4-Cl | F |
| 135 | 6-Cl | 2-F, 4-Br | F |
| 136 | 6-Br | 4-F | F |
| 137 | 6-Br | 4-Cl | F |
| 138 | 6-Br | 4-Br | F |
| 139 | 6-Br | H | F |
| 140 | 6-Br | 4-Me | F |
| 141 | 6-Br | 4-CN | F |
| 142 | 6-Br | 4-$NO_2$ | F |
| 143 | 6-Br | 4-OMe | F |
| 144 | 6-Br | 3-F | F |
| 145 | 6-Br | 3-Cl | F |
| 146 | 6-Br | 3-Br | F |
| 147 | 6-Br | 3-Me | F |
| 148 | 6-Br | 3-CN | F |
| 149 | 6-Br | 3-$NO_2$ | F |
| 150 | 6-Br | 3-OMe | F |
| 151 | 6-Br | 2-F | F |
| 152 | 6-Br | 2-Cl | F |
| 153 | 6-Br | 2-Br | F |
| 154 | 6-Br | 2-Me | F |
| 155 | 6-Br | 2-CN | F |
| 156 | 6-Br | 2-$NO_2$ | F |
| 157 | 6-Br | 2-OMe | F |
| 158 | 6-Br | 2,3-$F_2$ | F |
| 159 | 6-Br | 2,4-$F_2$ | F |
| 160 | 6-Br | 2,5-$F_2$ | F |
| 161 | 6-Br | 2,6-$F_2$ | F |
| 162 | 6-Br | 3,4-$F_2$ | F |
| 163 | 6-Br | 3,5-$F_2$ | F |
| 164 | 6-Br | 2,3-$Cl_2$ | F |
| 165 | 6-Br | 2,4-$Cl_2$ | F |
| 166 | 6-Br | 2,5-$Cl_2$ | F |
| 167 | 6-Br | 2,6-$Cl_2$ | F |
| 168 | 6-Br | 3,4-$Cl_2$ | F |
| 169 | 6-Br | 3,5-$Cl_2$ | F |
| 170 | 6-Br | 2-F, 3-Cl | F |
| 171 | 6-Br | 2-F, 4-Cl | F |
| 172 | 6-Br | 2-F, 5-Cl | F |
| 173 | 6-Br | 2-F, 6-Cl | F |
| 174 | 6-Br | 2,6-$F_2$, 4-Cl | F |
| 175 | 6-Br | 3-F, 4-Cl | F |
| 176 | 6-Br | 3-Cl, 5-F | F |
| 177 | 6-Br | 2-Cl, 5-F | F |
| 178 | 6-Br | 3-CN, 4-Cl | F |
| 179 | 6-Br | 3-$NO_2$, 4-Cl | F |
| 180 | 6-Br | 2-F, 4-Br | F |
| 181 | 6-CN | 4-F | F |
| 182 | 6-CN | 4-Cl | F |
| 183 | 6-CN | 4-Br | F |
| 184 | 6-CN | H | F |
| 185 | 6-CN | 4-Me | F |
| 186 | 6-CN | 4-CN | F |
| 187 | 6-CN | 4-$NO_2$ | F |
| 188 | 6-CN | 4-OMe | F |
| 189 | 6-CN | 3-F | F |
| 190 | 6-CN | 3-Cl | F |
| 191 | 6-CN | 3-Br | F |
| 192 | 6-CN | 3-Me | F |
| 193 | 6-CN | 3-CN | F |
| 194 | 6-CN | 3-$NO_2$ | F |
| 195 | 6-CN | 3-OMe | F |
| 196 | 6-CN | 2-F | F |
| 197 | 6-CN | 2-Cl | F |
| 198 | 6-CN | 2-Br | F |
| 199 | 6-CN | 2-Me | F |
| 200 | 6-CN | 2-CN | F |
| 201 | 6-CN | 2-$NO_2$ | F |
| 202 | 6-CN | 2-OMe | F |
| 203 | 6-CN | 2,3-$F_2$ | F |
| 204 | 6-CN | 2,4-$F_2$ | F |
| 205 | 6-CN | 2,5-$F_2$ | F |
| 206 | 6-CN | 2,6-$F_2$ | F |
| 207 | 6-CN | 3,4-$F_2$ | F |
| 208 | 6-CN | 3,5-$F_2$ | F |
| 209 | 6-CN | 2,3-$Cl_2$ | F |
| 210 | 6-CN | 2,4-$Cl_2$ | F |
| 211 | 6-CN | 2,5-$Cl_2$ | F |
| 212 | 6-CN | 2,6-$Cl_2$ | F |
| 213 | 6-CN | 3,4-$Cl_2$ | F |
| 214 | 6-CN | 3,5-$Cl_2$ | F |
| 215 | 6-CN | 2-F, 3-Cl | F |
| 216 | 6-CN | 2-F, 4-Cl | F |
| 217 | 6-CN | 2-F, 5-Cl | F |
| 218 | 6-CN | 2-F, 6-Cl | F |
| 219 | 6-CN | 2,6-$F_2$, 4-Cl | F |
| 220 | 6-CN | 3-F, 4-Cl | F |
| 221 | 6-CN | 3-Cl, 5-F | F |
| 222 | 6-CN | 2-Cl, 5-F | F |
| 223 | 6-CN | 3-CN, 4-Cl | F |
| 224 | 6-CN | 3-$NO_2$, 4-Cl | F |
| 225 | 6-CN | 2-F, 4-Br | F |
| 226 | 6-Me | 4-F | F |
| 227 | 6-Me | 4-Cl | F |
| 228 | 6-Me | 4-Br | F |
| 229 | 6-Me | H | F |
| 230 | 6-Me | 4-Me | F |
| 231 | 6-Me | 4-CN | F |
| 232 | 6-Me | 4-$NO_2$ | F |
| 233 | 6-Me | 4-OMe | F |
| 234 | 6-Me | 3-F | F |
| 235 | 6-Me | 3-Cl | F |
| 236 | 6-Me | 3-Br | F |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 237 | 6-Me | 3-Me | F |
| 238 | 6-Me | 3-CN | F |
| 239 | 6-Me | 3-NO$_2$ | F |
| 240 | 6-Me | 3-OMe | F |
| 241 | 6-Me | 2-F | F |
| 242 | 6-Me | 2-Cl | F |
| 243 | 6-Me | 2-Br | F |
| 244 | 6-Me | 2-Me | F |
| 245 | 6-Me | 2-CN | F |
| 246 | 6-Me | 2-NO$_2$ | F |
| 247 | 6-Me | 2-OMe | F |
| 248 | 6-Me | 2,3-F$_2$ | F |
| 249 | 6-Me | 2,4-F$_2$ | F |
| 250 | 6-Me | 2,5-F$_2$ | F |
| 251 | 6-Me | 2,6-F$_2$ | F |
| 252 | 6-Me | 3,4-F$_2$ | F |
| 253 | 6-Me | 3,5-F$_2$ | F |
| 254 | 6-Me | 2,3-Cl$_2$ | F |
| 255 | 6-Me | 2,4-Cl$_2$ | F |
| 256 | 6-Me | 2,5-Cl$_2$ | F |
| 257 | 6-Me | 2,6-Cl$_2$ | F |
| 258 | 6-Me | 3,4-Cl$_2$ | F |
| 259 | 6-Me | 3,5-Cl$_2$ | F |
| 260 | 6-Me | 2-F, 3-Cl | F |
| 261 | 6-Me | 2-F, 4-Cl | F |
| 262 | 6-Me | 2-F, 5-Cl | F |
| 263 | 6-Me | 2-F, 6-Cl | F |
| 264 | 6-Me | 2,6-F$_2$, 4-Cl | F |
| 265 | 6-Me | 3-F, 4-Cl | F |
| 266 | 6-Me | 3-Cl, 5-F | F |
| 267 | 6-Me | 2-Cl, 5-F | F |
| 268 | 6-Me | 3-CN, 4-Cl | F |
| 269 | 6-Me | 3-NO$_2$, 4-Cl | F |
| 270 | 6-Me | 2-F, 4-Br | F |
| 271 | 6-OMe | 4-F | F |
| 272 | 6-OMe | 4-Cl | F |
| 273 | 6-OMe | 4-Br | F |
| 274 | 6-OMe | H | F |
| 275 | 6-OMe | 4-Me | F |
| 276 | 6-OMe | 4-CN | F |
| 277 | 6-OMe | 4-NO$_2$ | F |
| 278 | 6-OMe | 4-OMe | F |
| 279 | 6-OMe | 3-F | F |
| 280 | 6-OMe | 3-Cl | F |
| 281 | 6-OMe | 3-Br | F |
| 282 | 6-OMe | 3-Me | F |
| 283 | 6-OMe | 3-CN | F |
| 284 | 6-OMe | 3-NO$_2$ | F |
| 285 | 6-OMe | 3-OMe | F |
| 286 | 6-OMe | 2-F | F |
| 287 | 6-OMe | 2-Cl | F |
| 288 | 6-OMe | 2-Br | F |
| 289 | 6-OMe | 2-Me | F |
| 290 | 6-OMe | 2-CN | F |
| 291 | 6-OMe | 2-NO$_2$ | F |
| 292 | 6-OMe | 2-OMe | F |
| 293 | 6-OMe | 2,3-F$_2$ | F |
| 294 | 6-OMe | 2,4-F$_2$ | F |
| 295 | 6-OMe | 2,5-F$_2$ | F |
| 296 | 6-OMe | 2,6-F$_2$ | F |
| 297 | 6-OMe | 3,4-F$_2$ | F |
| 298 | 6-OMe | 3,5-F$_2$ | F |
| 299 | 6-OMe | 2,3-Cl$_2$ | F |
| 300 | 6-OMe | 2,4-Cl$_2$ | F |
| 301 | 6-OMe | 2,5-Cl$_2$ | F |
| 302 | 6-OMe | 2,6-Cl$_2$ | F |
| 303 | 6-OMe | 3,4-Cl$_2$ | F |
| 304 | 6-OMe | 3,5-Cl$_2$ | F |
| 305 | 6-OMe | 2-F, 3-Cl | F |
| 306 | 6-OMe | 2-F, 4-Cl | F |
| 307 | 6-OMe | 2-F, 5-Cl | F |
| 308 | 6-OMe | 2-F, 6-Cl | F |
| 309 | 6-OMe | 2,6-F$_2$, 4-Cl | F |
| 310 | 6-OMe | 3-F, 4-Cl | F |
| 311 | 6-OMe | 3-Cl, 5-F | F |
| 312 | 6-OMe | 2-Cl, 5-F | F |
| 313 | 6-OMe | 3-CN, 4-Cl | F |
| 314 | 6-OMe | 3-NO$_2$, 4-Cl | F |
| 315 | 6-OMe | 2-F, 4-Br | F |
| 316 | 2-F | 4-F | F |
| 317 | 2-F | 4-Cl | F |
| 318 | 2-F | 4-Br | F |
| 319 | 2-F | H | F |
| 320 | 2-F | 4-Me | F |
| 321 | 2-F | 4-CN | F |
| 322 | 2-F | 4-NO$_2$ | F |
| 323 | 2-F | 4-OMe | F |
| 324 | 2-F | 3-F | F |
| 325 | 2-F | 3-Cl | F |
| 326 | 2-F | 3-Br | F |
| 327 | 2-F | 3-Me | F |
| 328 | 2-F | 3-CN | F |
| 329 | 2-F | 3-NO$_2$ | F |
| 330 | 2-F | 3-OMe | F |
| 331 | 2-F | 2-F | F |
| 332 | 2-F | 2-Cl | F |
| 333 | 2-F | 2-Br | F |
| 334 | 2-F | 2-Me | F |
| 335 | 2-F | 2-CN | F |
| 336 | 2-F | 2-NO$_2$ | F |
| 337 | 2-F | 2-OMe | F |
| 338 | 2-F | 2,3-F$_2$ | F |
| 339 | 2-F | 2,4-F$_2$ | F |
| 340 | 2-F | 2,5-F$_2$ | F |
| 341 | 2-F | 2,6-F$_2$ | F |
| 342 | 2-F | 3,4-F$_2$ | F |
| 343 | 2-F | 3,5-F$_2$ | F |
| 344 | 2-F | 2,3-Cl$_2$ | F |
| 345 | 2-F | 2,4-Cl$_2$ | F |
| 346 | 2-F | 2,5-Cl$_2$ | F |
| 347 | 2-F | 2,6-Cl$_2$ | F |
| 348 | 2-F | 3,4-Cl$_2$ | F |
| 349 | 2-F | 3,5-Cl$_2$ | F |
| 350 | 2-F | 2-F, 3-Cl | F |
| 351 | 2-F | 2-F, 4-Cl | F |
| 352 | 2-F | 2-F, 5-Cl | F |
| 353 | 2-F | 2-F, 6-Cl | F |
| 354 | 2-F | 2,6-F$_2$, 4-Cl | F |
| 355 | 2-F | 3-F, 4-Cl | F |
| 356 | 2-F | 3-Cl, 5-F | F |
| 357 | 2-F | 2-Cl, 5-F | F |
| 358 | 2-F | 3-CN, 4-Cl | F |
| 359 | 2-F | 3-NO$_2$, 4-Cl | F |
| 360 | 2-F | 2-F, 4-Br | F |
| 361 | 4-F | 4-F | F |
| 362 | 4-F | 4-Cl | F |
| 363 | 4-F | 4-Br | F |
| 364 | 4-F | H | F |
| 365 | 4-F | 4-Me | F |
| 366 | 4-F | 4-CN | F |
| 367 | 4-F | 4-NO$_2$ | F |
| 368 | 4-F | 4-OMe | F |
| 369 | 4-F | 3-F | F |
| 370 | 4-F | 3-Cl | F |
| 371 | 4-F | 3-Br | F |
| 372 | 4-F | 3-Me | F |
| 373 | 4-F | 3-CN | F |
| 374 | 4-F | 3-NO$_2$ | F |
| 375 | 4-F | 3-OMe | F |
| 376 | 4-F | 2-F | F |
| 377 | 4-F | 2-Cl | F |
| 378 | 4-F | 2-Br | F |
| 379 | 4-F | 2-Me | F |
| 380 | 4-F | 2-CN | F |
| 381 | 4-F | 2-NO$_2$ | F |
| 382 | 4-F | 2-OMe | F |
| 383 | 4-F | 2,3-F$_2$ | F |
| 384 | 4-F | 2,4-F$_2$ | F |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 385 | 4-F | 2,5-F$_2$ | F |
| 386 | 4-F | 2,6-F$_2$ | F |
| 387 | 4-F | 3,4-F$_2$ | F |
| 388 | 4-F | 3,5-F$_2$ | F |
| 389 | 4-F | 2,3-Cl$_2$ | F |
| 390 | 4-F | 2,4-Cl$_2$ | F |
| 391 | 4-F | 2,5-Cl$_2$ | F |
| 392 | 4-F | 2,6-Cl$_2$ | F |
| 393 | 4-F | 3,4-Cl$_2$ | F |
| 394 | 4-F | 3,5-Cl$_2$ | F |
| 395 | 4-F | 2-F, 3-Cl | F |
| 396 | 4-F | 2-F, 4-Cl | F |
| 397 | 4-F | 2-F, 5-Cl | F |
| 398 | 4-F | 2-F, 6-Cl | F |
| 399 | 4-F | 2,6-F$_2$, 4-Cl | F |
| 400 | 4-F | 3-F, 4-Cl | F |
| 401 | 4-F | 3-Cl, 5-F | F |
| 402 | 4-F | 2-Cl, 5-F | F |
| 403 | 4-F | 3-CN, 4-Cl | F |
| 404 | 4-F | 3-NO$_2$, 4-Cl | F |
| 405 | 4-F | 2-F, 4-Br | F |
| 406 | 2-Cl | 4-F | F |
| 407 | 2-Cl | 4-Cl | F |
| 408 | 2-Cl | 4-Br | F |
| 409 | 2-Cl | H | F |
| 410 | 2-Cl | 4-Me | F |
| 411 | 2-Cl | 4-CN | F |
| 412 | 2-Cl | 4-NO$_2$ | F |
| 413 | 2-Cl | 4-OMe | F |
| 414 | 2-Cl | 3-F | F |
| 415 | 2-Cl | 3-Cl | F |
| 416 | 2-Cl | 3-Br | F |
| 417 | 2-Cl | 3-Me | F |
| 418 | 2-Cl | 3-CN | F |
| 419 | 2-Cl | 3-NO$_2$ | F |
| 420 | 2-Cl | 3-OMe | F |
| 421 | 2-Cl | 2-F | F |
| 422 | 2-Cl | 2-Cl | F |
| 423 | 2-Cl | 2-Br | F |
| 424 | 2-Cl | 2-Me | F |
| 425 | 2-Cl | 2-CN | F |
| 426 | 2-Cl | 2-NO$_2$ | F |
| 427 | 2-Cl | 2-OMe | F |
| 428 | 2-Cl | 2,3-F$_2$ | F |
| 429 | 2-Cl | 2,4-F$_2$ | F |
| 430 | 2-Cl | 2,5-F$_2$ | F |
| 431 | 2-Cl | 2,6-F$_2$ | F |
| 432 | 2-Cl | 3,4-F$_2$ | F |
| 433 | 2-Cl | 3,5-F$_2$ | F |
| 434 | 2-Cl | 2,3-Cl$_2$ | F |
| 435 | 2-Cl | 2,4-Cl$_2$ | F |
| 436 | 2-Cl | 2,5-Cl$_2$ | F |
| 437 | 2-Cl | 2,6-Cl$_2$ | F |
| 438 | 2-Cl | 3,4-Cl$_2$ | F |
| 439 | 2-Cl | 3,5-Cl$_2$ | F |
| 440 | 2-Cl | 2-F, 3-Cl | F |
| 441 | 2-Cl | 2-F, 4-Cl | F |
| 442 | 2-Cl | 2-F, 5-Cl | F |
| 443 | 2-Cl | 2-F, 6-Cl | F |
| 444 | 2-Cl | 2,6-F$_2$, 4-Cl | F |
| 445 | 2-Cl | 3-F, 4-Cl | F |
| 446 | 2-Cl | 3-Cl, 5-F | F |
| 447 | 2-Cl | 2-Cl, 5-F | F |
| 448 | 2-Cl | 3-CN, 4-Cl | F |
| 449 | 2-Cl | 3-NO$_2$, 4-Cl | F |
| 450 | 2-Cl | 2-F, 4-Br | F |
| 451 | 4-Cl | 4-F | F |
| 452 | 4-Cl | 4-Cl | F |
| 453 | 4-Cl | 4-Br | F |
| 454 | 4-Cl | H | F |
| 455 | 4-Cl | 4-Me | F |
| 456 | 4-Cl | 4-CN | F |
| 457 | 4-Cl | 4-NO$_2$ | F |
| 458 | 4-Cl | 4-OMe | F |
| 459 | 4-Cl | 3-F | F |
| 460 | 4-Cl | 3-Cl | F |
| 461 | 4-Cl | 3-Br | F |
| 462 | 4-Cl | 3-Me | F |
| 463 | 4-Cl | 3-CN | F |
| 464 | 4-Cl | 3-NO$_2$ | F |
| 465 | 4-Cl | 3-OMe | F |
| 466 | 4-Cl | 2-F | F |
| 467 | 4-Cl | 2-Cl | F |
| 468 | 4-Cl | 2-Br | F |
| 469 | 4-Cl | 2-Me | F |
| 470 | 4-Cl | 2-CN | F |
| 471 | 4-Cl | 2-NO$_2$ | F |
| 472 | 4-Cl | 2-OMe | F |
| 473 | 4-Cl | 2,3-F$_2$ | F |
| 474 | 4-Cl | 2,4-F$_2$ | F |
| 475 | 4-Cl | 2,5-F$_2$ | F |
| 476 | 4-Cl | 2,6-F$_2$ | F |
| 477 | 4-Cl | 3,4-F$_2$ | F |
| 478 | 4-Cl | 3,5-F$_2$ | F |
| 479 | 4-Cl | 2,3-Cl$_2$ | F |
| 480 | 4-Cl | 2,4-Cl$_2$ | F |
| 481 | 4-Cl | 2,5-Cl$_2$ | F |
| 482 | 4-Cl | 2,6-Cl$_2$ | F |
| 483 | 4-Cl | 3,4-Cl$_2$ | F |
| 484 | 4-Cl | 3,5-Cl$_2$ | F |
| 485 | 4-Cl | 2-F, 3-Cl | F |
| 486 | 4-Cl | 2-F, 4-Cl | F |
| 487 | 4-Cl | 2-F, 5-Cl | F |
| 488 | 4-Cl | 2-F, 6-Cl | F |
| 489 | 4-Cl | 2,6-F$_2$, 4-Cl | F |
| 490 | 4-Cl | 3-F, 4-Cl | F |
| 491 | 4-Cl | 3-Cl, 5-F | F |
| 492 | 4-Cl | 2-Cl, 5-F | F |
| 493 | 4-Cl | 3-CN, 4-Cl | F |
| 494 | 4-Cl | 3-NO$_2$, 4-Cl | F |
| 495 | 4-Cl | 2-F, 4-Br | F |
| 496 | 6-OCF$_2$H | 4-F | F |
| 497 | 6-OCF$_2$H | 4-Cl | F |
| 498 | 6-OCF$_2$H | 4-Br | F |
| 499 | 6-OCF$_2$H | H | F |
| 500 | 6-OCF$_2$H | 4-Me | F |
| 501 | 6-OCF$_2$H | 4-CN | F |
| 502 | 6-OCF$_2$H | 4-NO$_2$ | F |
| 503 | 6-OCF$_2$H | 4-OMe | F |
| 504 | 6-OCF$_2$H | 3-F | F |
| 505 | 6-OCF$_2$H | 3-Cl | F |
| 506 | 6-OCF$_2$H | 3-Br | F |
| 507 | 6-OCF$_2$H | 3-Me | F |
| 508 | 6-OCF$_2$H | 3-CN | F |
| 509 | 6-OCF$_2$H | 3-NO$_2$ | F |
| 510 | 6-OCF$_2$H | 3-OMe | F |
| 511 | 6-OCF$_2$H | 2-F | F |
| 512 | 6-OCF$_2$H | 2-Cl | F |
| 513 | 6-OCF$_2$H | 2-Br | F |
| 514 | 6-OCF$_2$H | 2-Me | F |
| 515 | 6-OCF$_2$H | 2-CN | F |
| 516 | 6-OCF$_2$H | 2-NO$_2$ | F |
| 517 | 6-OCF$_2$H | 2-OMe | F |
| 518 | 6-OCF$_2$H | 2,3-F$_2$ | F |
| 519 | 6-OCF$_2$H | 2,4-F$_2$ | F |
| 520 | 6-OCF$_2$H | 2,5-F$_2$ | F |
| 521 | 6-OCF$_2$H | 2,6-F$_2$ | F |
| 522 | 6-OCF$_2$H | 3,4-F$_2$ | F |
| 523 | 6-OCF$_2$H | 3,5-F$_2$ | F |
| 524 | 6-OCF$_2$H | 2,3-Cl$_2$ | F |
| 525 | 6-OCF$_2$H | 2,4-Cl$_2$ | F |
| 526 | 6-OCF$_2$H | 2,5-Cl$_2$ | F |
| 527 | 6-OCF$_2$H | 2,6-Cl$_2$ | F |
| 528 | 6-OCF$_2$H | 3,4-Cl$_2$ | F |
| 529 | 6-OCF$_2$H | 3,5-Cl$_2$ | F |
| 530 | 6-OCF$_2$H | 2-F, 3-Cl | F |
| 531 | 6-OCF$_2$H | 2-F, 4-Cl | F |
| 532 | 6-OCF$_2$H | 2-F, 5-Cl | F |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 533 | 6-OCF$_2$H | 2-F, 6-Cl | F |
| 534 | 6-OCF$_2$H | 2,6-F$_2$, 4-Cl | F |
| 535 | 6-OCF$_2$H | 3-F, 4-Cl | F |
| 536 | 6-OCF$_2$H | 3-Cl, 5-F | F |
| 537 | 6-OCF$_2$H | 2-Cl, 5-F | F |
| 538 | 6-OCF$_2$H | 3-CN, 4-Cl | F |
| 539 | 6-OCF$_2$H | 3-NO$_2$, 4-Cl | F |
| 540 | 6-OCF$_2$H | 2-F, 4-Br | F |
| 541 | H | 4-F | Cl |
| 542 | H | 4-Cl | Cl |
| 543 | H | 4-Br | Cl |
| 544 | H | H | Cl |
| 545 | H | 4-Me | Cl |
| 546 | H | 4-CN | Cl |
| 547 | H | 4-NO$_2$ | Cl |
| 548 | H | 4-OMe | Cl |
| 549 | H | 3-F | Cl |
| 550 | H | 3-Cl | Cl |
| 551 | H | 3-Br | Cl |
| 552 | H | 3-Me | Cl |
| 553 | H | 3-CN | Cl |
| 554 | H | 3-NO$_2$ | Cl |
| 555 | H | 3-OMe | Cl |
| 556 | H | 2-F | Cl |
| 557 | H | 2-Cl | Cl |
| 558 | H | 2-Br | Cl |
| 559 | H | 2-Me | Cl |
| 560 | H | 2-CN | Cl |
| 561 | H | 2-NO$_2$ | Cl |
| 562 | H | 2-OMe | Cl |
| 563 | H | 2,3-F$_2$ | Cl |
| 564 | H | 2,4-F$_2$ | Cl |
| 565 | H | 2,5-F$_2$ | Cl |
| 566 | H | 2,6-F$_2$ | Cl |
| 567 | H | 3,4-F$_2$ | Cl |
| 568 | H | 3,5-F$_2$ | Cl |
| 569 | H | 2,3-Cl$_2$ | Cl |
| 570 | H | 2,4-Cl$_2$ | Cl |
| 571 | H | 2,5-Cl$_2$ | Cl |
| 572 | H | 2,6-Cl$_2$ | Cl |
| 573 | H | 3,4-Cl$_2$ | Cl |
| 574 | H | 3,5-Cl$_2$ | Cl |
| 575 | H | 2-F, 3-Cl | Cl |
| 576 | H | 2-F, 4-Cl | Cl |
| 577 | H | 2-F, 5-Cl | Cl |
| 578 | H | 2-F, 6-Cl | Cl |
| 579 | H | 2,6-F$_2$, 4-Cl | Cl |
| 580 | H | 3-F, 4-Cl | Cl |
| 581 | H | 3-Cl, 5-F | Cl |
| 582 | H | 2-Cl, 5-F | Cl |
| 583 | H | 3-CN, 4-Cl | Cl |
| 584 | H | 3-NO$_2$, 4-Cl | Cl |
| 585 | H | 2-F, 4-Br | Cl |
| 586 | 6-F | 4-F | Cl |
| 587 | 6-F | 4-Cl | Cl |
| 588 | 6-F | 4-Br | Cl |
| 589 | 6-F | H | Cl |
| 590 | 6-F | 4-Me | Cl |
| 591 | 6-F | 4-CN | Cl |
| 592 | 6-F | 4-NO$_2$ | Cl |
| 593 | 6-F | 4-OMe | Cl |
| 594 | 6-F | 3-F | Cl |
| 595 | 6-F | 3-Cl | Cl |
| 596 | 6-F | 3-Br | Cl |
| 597 | 6-F | 3-Me | Cl |
| 598 | 6-F | 3-CN | Cl |
| 599 | 6-F | 3-NO$_2$ | Cl |
| 600 | 6-F | 3-OMe | Cl |
| 601 | 6-F | 2-F | Cl |
| 602 | 6-F | 2-Cl | Cl |
| 603 | 6-F | 2-Br | Cl |
| 604 | 6-F | 2-Me | Cl |
| 605 | 6-F | 2-CN | Cl |
| 606 | 6-F | 2-NO$_2$ | Cl |
| 607 | 6-F | 2-OMe | Cl |
| 608 | 6-F | 2,3-F$_2$ | Cl |
| 609 | 6-F | 2,4-F$_2$ | Cl |
| 610 | 6-F | 2,5-F$_2$ | Cl |
| 611 | 6-F | 2,6-F$_2$ | Cl |
| 612 | 6-F | 3,4-F$_2$ | Cl |
| 613 | 6-F | 3,5-F$_2$ | Cl |
| 614 | 6-F | 2,3-Cl$_2$ | Cl |
| 615 | 6-F | 2,4-Cl$_2$ | Cl |
| 616 | 6-F | 2,5-Cl$_2$ | Cl |
| 617 | 6-F | 2,6-Cl$_2$ | Cl |
| 618 | 6-F | 3,4-Cl$_2$ | Cl |
| 619 | 6-F | 3,5-Cl$_2$ | Cl |
| 620 | 6-F | 2-F, 3-Cl | Cl |
| 621 | 6-F | 2-F, 4-Cl | Cl |
| 622 | 6-F | 2-F, 5-Cl | Cl |
| 623 | 6-F | 2-F, 6-Cl | Cl |
| 624 | 6-F | 2,6-F$_2$, 4-Cl | Cl |
| 625 | 6-F | 3-F, 4-Cl | Cl |
| 626 | 6-F | 3-Cl, 5-F | Cl |
| 627 | 6-F | 2-Cl, 5-F | Cl |
| 628 | 6-F | 3-CN, 4-Cl | Cl |
| 629 | 6-F | 3-NO$_2$, 4-Cl | Cl |
| 630 | 6-F | 2-F, 4-Br | Cl |
| 631 | 6-Cl | 4-F | Cl |
| 632 | 6-Cl | 4-Cl | Cl |
| 633 | 6-Cl | 4-Br | Cl |
| 634 | 6-Cl | H | Cl |
| 635 | 6-Cl | 4-Me | Cl |
| 636 | 6-Cl | 4-CN | Cl |
| 637 | 6-Cl | 4-NO$_2$ | Cl |
| 638 | 6-Cl | 4-OMe | Cl |
| 639 | 6-Cl | 3-F | Cl |
| 640 | 6-Cl | 3-Cl | Cl |
| 641 | 6-Cl | 3-Br | Cl |
| 642 | 6-Cl | 3-Me | Cl |
| 643 | 6-Cl | 3-CN | Cl |
| 644 | 6-Cl | 3-NO$_2$ | Cl |
| 645 | 6-Cl | 3-OMe | Cl |
| 646 | 6-Cl | 2-F | Cl |
| 647 | 6-Cl | 2-Cl | Cl |
| 648 | 6-Cl | 2-Br | Cl |
| 649 | 6-Cl | 2-Me | Cl |
| 650 | 6-Cl | 2-CN | Cl |
| 651 | 6-Cl | 2-NO$_2$ | Cl |
| 652 | 6-Cl | 2-OMe | Cl |
| 653 | 6-Cl | 2,3-F$_2$ | Cl |
| 654 | 6-Cl | 2,4-F$_2$ | Cl |
| 655 | 6-Cl | 2,5-F$_2$ | Cl |
| 656 | 6-Cl | 2,6-F$_2$ | Cl |
| 657 | 6-Cl | 3,4-F$_2$ | Cl |
| 658 | 6-Cl | 3,5-F$_2$ | Cl |
| 659 | 6-Cl | 2,3-Cl$_2$ | Cl |
| 660 | 6-Cl | 2,4-Cl$_2$ | Cl |
| 661 | 6-Cl | 2,5-Cl$_2$ | Cl |
| 662 | 6-Cl | 2,6-Cl$_2$ | Cl |
| 663 | 6-Cl | 3,4-Cl$_2$ | Cl |
| 664 | 6-Cl | 3,5-Cl$_2$ | Cl |
| 665 | 6-Cl | 2-F, 3-Cl | Cl |
| 666 | 6-Cl | 2-F, 4-Cl | Cl |
| 667 | 6-Cl | 2-F, 5-Cl | Cl |
| 668 | 6-Cl | 2-F, 6-Cl | Cl |
| 669 | 6-Cl | 2,6-F$_2$, 4-Cl | Cl |
| 670 | 6-Cl | 3-F, 4-Cl | Cl |
| 671 | 6-Cl | 3-Cl, 5-F | Cl |
| 672 | 6-Cl | 2-Cl, 5-F | Cl |
| 673 | 6-Cl | 3-CN, 4-Cl | Cl |
| 674 | 6-Cl | 3-NO$_2$, 4-Cl | Cl |
| 675 | 6-Cl | 2-F, 4-Br | Cl |
| 676 | 6-Br | 4-F | Cl |
| 677 | 6-Br | 4-Cl | Cl |
| 678 | 6-Br | 4-Br | Cl |
| 679 | 6-Br | H | Cl |
| 680 | 6-Br | 4-Me | Cl |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 681 | 6-Br | 4-CN | Cl |
| 682 | 6-Br | 4-NO$_2$ | Cl |
| 683 | 6-Br | 4-OMe | Cl |
| 684 | 6-Br | 3-F | Cl |
| 685 | 6-Br | 3-Cl | Cl |
| 686 | 6-Br | 3-Br | Cl |
| 687 | 6-Br | 3-Me | Cl |
| 688 | 6-Br | 3-CN | Cl |
| 689 | 6-Br | 3-NO$_2$ | Cl |
| 690 | 6-Br | 3-OMe | Cl |
| 691 | 6-Br | 2-F | Cl |
| 692 | 6-Br | 2-Cl | Cl |
| 693 | 6-Br | 2-Br | Cl |
| 694 | 6-Br | 2-Me | Cl |
| 695 | 6-Br | 2-CN | Cl |
| 696 | 6-Br | 2-NO$_2$ | Cl |
| 697 | 6-Br | 2-OMe | Cl |
| 698 | 6-Br | 2,3-F$_2$ | Cl |
| 699 | 6-Br | 2,4-F$_2$ | Cl |
| 700 | 6-Br | 2,5-F$_2$ | Cl |
| 701 | 6-Br | 2,6-F$_2$ | Cl |
| 702 | 6-Br | 3,4-F$_2$ | Cl |
| 703 | 6-Br | 3,5-F$_2$ | Cl |
| 704 | 6-Br | 2,3-Cl$_2$ | Cl |
| 705 | 6-Br | 2,4-Cl$_2$ | Cl |
| 706 | 6-Br | 2,5-Cl$_2$ | Cl |
| 707 | 6-Br | 2,6-Cl$_2$ | Cl |
| 708 | 6-Br | 3,4-Cl$_2$ | Cl |
| 709 | 6-Br | 3,5-Cl$_2$ | Cl |
| 710 | 6-Br | 2-F, 3-Cl | Cl |
| 711 | 6-Br | 2-F, 4-Cl | Cl |
| 712 | 6-Br | 2-F, 5-Cl | Cl |
| 713 | 6-Br | 2-F, 6-Cl | Cl |
| 714 | 6-Br | 2,6-F$_2$, 4-Cl | Cl |
| 715 | 6-Br | 3-F, 4-Cl | Cl |
| 716 | 6-Br | 3-Cl, 5-F | Cl |
| 717 | 6-Br | 2-Cl, 5-F | Cl |
| 718 | 6-Br | 3-CN, 4-Cl | Cl |
| 719 | 6-Br | 3-NO$_2$, 4-Cl | Cl |
| 720 | 6-Br | 2-F, 4-Br | Cl |
| 721 | 6-CN | 4-F | Cl |
| 722 | 6-CN | 4-Cl | Cl |
| 723 | 6-CN | 4-Br | Cl |
| 724 | 6-CN | H | Cl |
| 725 | 6-CN | 4-Me | Cl |
| 726 | 6-CN | 4-CN | Cl |
| 727 | 6-CN | 4-NO$_2$ | Cl |
| 728 | 6-CN | 4-OMe | Cl |
| 729 | 6-CN | 3-F | Cl |
| 730 | 6-CN | 3-Cl | Cl |
| 731 | 6-CN | 3-Br | Cl |
| 732 | 6-CN | 3-Me | Cl |
| 733 | 6-CN | 3-CN | Cl |
| 734 | 6-CN | 3-NO$_2$ | Cl |
| 735 | 6-CN | 3-OMe | Cl |
| 736 | 6-CN | 2-F | Cl |
| 737 | 6-CN | 2-Cl | Cl |
| 738 | 6-CN | 2-Br | Cl |
| 739 | 6-CN | 2-Me | Cl |
| 740 | 6-CN | 2-CN | Cl |
| 741 | 6-CN | 2-NO$_2$ | Cl |
| 742 | 6-CN | 2-OMe | Cl |
| 743 | 6-CN | 2,3-F$_2$ | Cl |
| 744 | 6-CN | 2,4-F$_2$ | Cl |
| 745 | 6-CN | 2,5-F$_2$ | Cl |
| 746 | 6-CN | 2,6-F$_2$ | Cl |
| 747 | 6-CN | 3,4-F$_2$ | Cl |
| 748 | 6-CN | 3,5-F$_2$ | Cl |
| 749 | 6-CN | 2,3-Cl$_2$ | Cl |
| 750 | 6-CN | 2,4-Cl$_2$ | Cl |
| 751 | 6-CN | 2,5-Cl$_2$ | Cl |
| 752 | 6-CN | 2,6-Cl$_2$ | Cl |
| 753 | 6-CN | 3,4-Cl$_2$ | Cl |
| 754 | 6-CN | 3,5-Cl$_2$ | Cl |
| 755 | 6-CN | 2-F, 3-Cl | Cl |
| 756 | 6-CN | 2-F, 4-Cl | Cl |
| 757 | 6-CN | 2-F, 5-Cl | Cl |
| 758 | 6-CN | 2-F, 6-Cl | Cl |
| 759 | 6-CN | 2,6-F$_2$, 4-Cl | Cl |
| 760 | 6-CN | 3-F, 4-Cl | Cl |
| 761 | 6-CN | 3-Cl, 5-F | Cl |
| 762 | 6-CN | 2-Cl, 5-F | Cl |
| 763 | 6-CN | 3-CN, 4-Cl | Cl |
| 764 | 6-CN | 3-NO$_2$, 4-Cl | Cl |
| 765 | 6-CN | 2-F, 4-Br | Cl |
| 766 | 6-Me | 4-F | Cl |
| 767 | 6-Me | 4-Cl | Cl |
| 768 | 6-Me | 4-Br | Cl |
| 769 | 6-Me | H | Cl |
| 770 | 6-Me | 4-Me | Cl |
| 771 | 6-Me | 4-CN | Cl |
| 772 | 6-Me | 4-NO$_2$ | Cl |
| 773 | 6-Me | 4-OMe | Cl |
| 774 | 6-Me | 3-F | Cl |
| 775 | 6-Me | 3-Cl | Cl |
| 776 | 6-Me | 3-Br | Cl |
| 777 | 6-Me | 3-Me | Cl |
| 778 | 6-Me | 3-CN | Cl |
| 779 | 6-Me | 3-NO$_2$ | Cl |
| 780 | 6-Me | 3-OMe | Cl |
| 781 | 6-Me | 2-F | Cl |
| 782 | 6-Me | 2-Cl | Cl |
| 783 | 6-Me | 2-Br | Cl |
| 784 | 6-Me | 2-Me | Cl |
| 785 | 6-Me | 2-CN | Cl |
| 786 | 6-Me | 2-NO$_2$ | Cl |
| 787 | 6-Me | 2-OMe | Cl |
| 788 | 6-Me | 2,3-F$_2$ | Cl |
| 789 | 6-Me | 2,4-F$_2$ | Cl |
| 790 | 6-Me | 2,5-F$_2$ | Cl |
| 791 | 6-Me | 2,6-F$_2$ | Cl |
| 792 | 6-Me | 3,4-F$_2$ | Cl |
| 793 | 6-Me | 3,5-F$_2$ | Cl |
| 794 | 6-Me | 2,3-Cl$_2$ | Cl |
| 795 | 6-Me | 2,4-Cl$_2$ | Cl |
| 796 | 6-Me | 2,5-Cl$_2$ | Cl |
| 797 | 6-Me | 2,6-Cl$_2$ | Cl |
| 798 | 6-Me | 3,4-Cl$_2$ | Cl |
| 799 | 6-Me | 3,5-Cl$_2$ | Cl |
| 800 | 6-Me | 2-F, 3-Cl | Cl |
| 801 | 6-Me | 2-F, 4-Cl | Cl |
| 802 | 6-Me | 2-F, 5-Cl | Cl |
| 803 | 6-Me | 2-F, 6-Cl | Cl |
| 804 | 6-Me | 2,6-F$_2$, 4-Cl | Cl |
| 805 | 6-Me | 3-F, 4-Cl | Cl |
| 806 | 6-Me | 3-Cl, 5-F | Cl |
| 807 | 6-Me | 2-Cl, 5-F | Cl |
| 808 | 6-Me | 3-CN, 4-Cl | Cl |
| 809 | 6-Me | 3-NO$_2$, 4-Cl | Cl |
| 810 | 6-Me | 2-F, 4-Br | Cl |
| 811 | 6-OMe | 4-F | Cl |
| 812 | 6-OMe | 4-Cl | Cl |
| 813 | 6-OMe | 4-Br | Cl |
| 814 | 6-OMe | H | Cl |
| 815 | 6-OMe | 4-Me | Cl |
| 816 | 6-OMe | 4-CN | Cl |
| 817 | 6-OMe | 4-NO$_2$ | Cl |
| 818 | 6-OMe | 4-OMe | Cl |
| 819 | 6-OMe | 3-F | Cl |
| 820 | 6-OMe | 3-Cl | Cl |
| 821 | 6-OMe | 3-Br | Cl |
| 822 | 6-OMe | 3-Me | Cl |
| 823 | 6-OMe | 3-CN | Cl |
| 824 | 6-OMe | 3-NO$_2$ | Cl |
| 825 | 6-OMe | 3-OMe | Cl |
| 826 | 6-OMe | 2-F | Cl |
| 827 | 6-OMe | 2-Cl | Cl |
| 828 | 6-OMe | 2-Br | Cl |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 829 | 6-OMe | 2-Me | Cl |
| 830 | 6-OMe | 2-CN | Cl |
| 831 | 6-OMe | 2-NO$_2$ | Cl |
| 832 | 6-OMe | 2-OMe | Cl |
| 833 | 6-OMe | 2,3-F$_2$ | Cl |
| 834 | 6-OMe | 2,4-F$_2$ | Cl |
| 835 | 6-OMe | 2,5-F$_2$ | Cl |
| 836 | 6-OMe | 2,6-F$_2$ | Cl |
| 837 | 6-OMe | 3,4-F$_2$ | Cl |
| 838 | 6-OMe | 3,5-F$_2$ | Cl |
| 839 | 6-OMe | 2,3-Cl$_2$ | Cl |
| 840 | 6-OMe | 2,4-Cl$_2$ | Cl |
| 841 | 6-OMe | 2,5-Cl$_2$ | Cl |
| 842 | 6-OMe | 2,6-Cl$_2$ | Cl |
| 843 | 6-OMe | 3,4-Cl$_2$ | Cl |
| 844 | 6-OMe | 3,5-Cl$_2$ | Cl |
| 845 | 6-OMe | 2-F, 3-Cl | Cl |
| 846 | 6-OMe | 2-F, 4-Cl | Cl |
| 847 | 6-OMe | 2-F, 5-Cl | Cl |
| 848 | 6-OMe | 2-F, 6-Cl | Cl |
| 849 | 6-OMe | 2,6-F$_2$, 4-Cl | Cl |
| 850 | 6-OMe | 3-F, 4-Cl | Cl |
| 851 | 6-OMe | 3-Cl, 5-F | Cl |
| 852 | 6-OMe | 2-Cl, 5-F | Cl |
| 853 | 6-OMe | 3-CN, 4-Cl | Cl |
| 854 | 6-OMe | 3-NO$_2$, 4-Cl | Cl |
| 855 | 6-OMe | 2-F, 4-Br | Cl |
| 856 | 2-F | 4-F | Cl |
| 857 | 2-F | 4-Cl | Cl |
| 858 | 2-F | 4-Br | Cl |
| 859 | 2-F | H | Cl |
| 860 | 2-F | 4-Me | Cl |
| 861 | 2-F | 4-CN | Cl |
| 862 | 2-F | 4-NO$_2$ | Cl |
| 863 | 2-F | 4-OMe | Cl |
| 864 | 2-F | 3-F | Cl |
| 865 | 2-F | 3-Cl | Cl |
| 866 | 2-F | 3-Br | Cl |
| 867 | 2-F | 3-Me | Cl |
| 868 | 2-F | 3-CN | Cl |
| 869 | 2-F | 3-NO$_2$ | Cl |
| 870 | 2-F | 3-OMe | Cl |
| 871 | 2-F | 2-F | Cl |
| 872 | 2-F | 2-Cl | Cl |
| 873 | 2-F | 2-Br | Cl |
| 874 | 2-F | 2-Me | Cl |
| 875 | 2-F | 2-CN | Cl |
| 876 | 2-F | 2-NO$_2$ | Cl |
| 877 | 2-F | 2-OMe | Cl |
| 878 | 2-F | 2,3-F$_2$ | Cl |
| 879 | 2-F | 2,4-F$_2$ | Cl |
| 880 | 2-F | 2,5-F$_2$ | Cl |
| 881 | 2-F | 2,6-F$_2$ | Cl |
| 882 | 2-F | 3,4-F$_2$ | Cl |
| 883 | 2-F | 3,5-F$_2$ | Cl |
| 884 | 2-F | 2,3-Cl$_2$ | Cl |
| 885 | 2-F | 2,4-Cl$_2$ | Cl |
| 886 | 2-F | 2,5-Cl$_2$ | Cl |
| 887 | 2-F | 2,6-Cl$_2$ | Cl |
| 888 | 2-F | 3,4-Cl$_2$ | Cl |
| 889 | 2-F | 3,5-Cl$_2$ | Cl |
| 890 | 2-F | 2-F, 3-Cl | Cl |
| 891 | 2-F | 2-F, 4-Cl | Cl |
| 892 | 2-F | 2-F, 5-Cl | Cl |
| 893 | 2-F | 2-F, 6-Cl | Cl |
| 894 | 2-F | 2,6-F$_2$, 4-Cl | Cl |
| 895 | 2-F | 3-F, 4-Cl | Cl |
| 896 | 2-F | 3-Cl, 5-F | Cl |
| 897 | 2-F | 2-Cl, 5-F | Cl |
| 898 | 2-F | 3-CN, 4-Cl | Cl |
| 899 | 2-F | 3-NO$_2$, 4-Cl | Cl |
| 900 | 2-F | 2-F, 4-Br | Cl |
| 901 | 4-F | 4-F | Cl |
| 902 | 4-F | 4-Cl | Cl |
| 903 | 4-F | 4-Br | Cl |
| 904 | 4-F | H | Cl |
| 905 | 4-F | 4-Me | Cl |
| 906 | 4-F | 4-CN | Cl |
| 907 | 4-F | 4-NO$_2$ | Cl |
| 908 | 4-F | 4-OMe | Cl |
| 909 | 4-F | 3-F | Cl |
| 910 | 4-F | 3-Cl | Cl |
| 911 | 4-F | 3-Br | Cl |
| 912 | 4-F | 3-Me | Cl |
| 913 | 4-F | 3-CN | Cl |
| 914 | 4-F | 3-NO$_2$ | Cl |
| 915 | 4-F | 3-OMe | Cl |
| 916 | 4-F | 2-F | Cl |
| 917 | 4-F | 2-Cl | Cl |
| 918 | 4-F | 2-Br | Cl |
| 919 | 4-F | 2-Me | Cl |
| 920 | 4-F | 2-CN | Cl |
| 921 | 4-F | 2-NO$_2$ | Cl |
| 922 | 4-F | 2-OMe | Cl |
| 923 | 4-F | 2,3-F$_2$ | Cl |
| 924 | 4-F | 2,4-F$_2$ | Cl |
| 925 | 4-F | 2,5-F$_2$ | Cl |
| 926 | 4-F | 2,6-F$_2$ | Cl |
| 927 | 4-F | 3,4-F$_2$ | Cl |
| 928 | 4-F | 3,5-F$_2$ | Cl |
| 929 | 4-F | 2,3-Cl$_2$ | Cl |
| 930 | 4-F | 2,4-Cl$_2$ | Cl |
| 931 | 4-F | 2,5-Cl$_2$ | Cl |
| 932 | 4-F | 2,6-Cl$_2$ | Cl |
| 933 | 4-F | 3,4-Cl$_2$ | Cl |
| 934 | 4-F | 3,5-Cl$_2$ | Cl |
| 935 | 4-F | 2-F, 3-Cl | Cl |
| 936 | 4-F | 2-F, 4-Cl | Cl |
| 937 | 4-F | 2-F, 5-Cl | Cl |
| 938 | 4-F | 2-F, 6-Cl | Cl |
| 939 | 4-F | 2,6-F$_2$, 4-Cl | Cl |
| 940 | 4-F | 3-F, 4-Cl | Cl |
| 941 | 4-F | 3-Cl, 5-F | Cl |
| 942 | 4-F | 2-Cl, 5-F | Cl |
| 943 | 4-F | 3-CN, 4-Cl | Cl |
| 944 | 4-F | 3-NO$_2$, 4-Cl | Cl |
| 945 | 4-F | 2-F, 4-Br | Cl |
| 946 | 2-Cl | 4-F | Cl |
| 947 | 2-Cl | 4-Cl | Cl |
| 948 | 2-Cl | 4-Br | Cl |
| 949 | 2-Cl | H | Cl |
| 950 | 2-Cl | 4-Me | Cl |
| 951 | 2-Cl | 4-CN | Cl |
| 952 | 2-Cl | 4-NO$_2$ | Cl |
| 953 | 2-Cl | 4-OMe | Cl |
| 954 | 2-Cl | 3-F | Cl |
| 955 | 2-Cl | 3-Cl | Cl |
| 956 | 2-Cl | 3-Br | Cl |
| 957 | 2-Cl | 3-Me | Cl |
| 958 | 2-Cl | 3-CN | Cl |
| 959 | 2-Cl | 3-NO$_2$ | Cl |
| 960 | 2-Cl | 3-OMe | Cl |
| 961 | 2-Cl | 2-F | Cl |
| 962 | 2-Cl | 2-Cl | Cl |
| 963 | 2-Cl | 2-Br | Cl |
| 964 | 2-Cl | 2-Me | Cl |
| 965 | 2-Cl | 2-CN | Cl |
| 966 | 2-Cl | 2-NO$_2$ | Cl |
| 967 | 2-Cl | 2-OMe | Cl |
| 968 | 2-Cl | 2,3-F$_2$ | Cl |
| 969 | 2-Cl | 2,4-F$_2$ | Cl |
| 970 | 2-Cl | 2,5-F$_2$ | Cl |
| 971 | 2-Cl | 2,6-F$_2$ | Cl |
| 972 | 2-Cl | 3,4-F$_2$ | Cl |
| 973 | 2-Cl | 3,5-F$_2$ | Cl |
| 974 | 2-Cl | 2,3-Cl$_2$ | Cl |
| 975 | 2-Cl | 2,4-Cl$_2$ | Cl |
| 976 | 2-Cl | 2,5-Cl$_2$ | Cl |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 977 | 2-Cl | 2,6-Cl$_2$ | Cl |
| 978 | 2-Cl | 3,4-Cl$_2$ | Cl |
| 979 | 2-Cl | 3,5-Cl$_2$ | Cl |
| 980 | 2-Cl | 2-F, 3-Cl | Cl |
| 981 | 2-Cl | 2-F, 4-Cl | Cl |
| 982 | 2-Cl | 2-F, 5-Cl | Cl |
| 983 | 2-Cl | 2-F, 6-Cl | Cl |
| 984 | 2-Cl | 2,6-F$_2$, 4-Cl | Cl |
| 985 | 2-Cl | 3-F, 4-Cl | Cl |
| 986 | 2-Cl | 3-Cl, 5-F | Cl |
| 987 | 2-Cl | 2-Cl, 5-F | Cl |
| 988 | 2-Cl | 3-CN, 4-Cl | Cl |
| 989 | 2-Cl | 3-NO$_2$, 4-Cl | Cl |
| 990 | 2-Cl | 2-F, 4-Br | Cl |
| 991 | 4-Cl | 4-F | Cl |
| 992 | 4-Cl | 4-Cl | Cl |
| 993 | 4-Cl | 4-Br | Cl |
| 994 | 4-Cl | H | Cl |
| 995 | 4-Cl | 4-Me | Cl |
| 996 | 4-Cl | 4-CN | Cl |
| 997 | 4-Cl | 4-NO$_2$ | Cl |
| 998 | 4-Cl | 4-OMe | Cl |
| 999 | 4-Cl | 3-F | Cl |
| 1000 | 4-Cl | 3-Cl | Cl |
| 1001 | 4-Cl | 3-Br | Cl |
| 1002 | 4-Cl | 3-Me | Cl |
| 1003 | 4-Cl | 3-CN | Cl |
| 1004 | 4-Cl | 3-NO$_2$ | Cl |
| 1005 | 4-Cl | 3-OMe | Cl |
| 1006 | 4-Cl | 2-F | Cl |
| 1007 | 4-Cl | 2-Cl | Cl |
| 1008 | 4-Cl | 2-Br | Cl |
| 1009 | 4-Cl | 2-Me | Cl |
| 1010 | 4-Cl | 2-CN | Cl |
| 1011 | 4-Cl | 2-NO$_2$ | Cl |
| 1012 | 4-Cl | 2-OMe | Cl |
| 1013 | 4-Cl | 2,3-F$_2$ | Cl |
| 1014 | 4-Cl | 2,4-F$_2$ | Cl |
| 1015 | 4-Cl | 2,5-F$_2$ | Cl |
| 1016 | 4-Cl | 2,6-F$_2$ | Cl |
| 1017 | 4-Cl | 3,4-F$_2$ | Cl |
| 1018 | 4-Cl | 3,5-F$_2$ | Cl |
| 1019 | 4-Cl | 2,3-Cl$_2$ | Cl |
| 1020 | 4-Cl | 2,4-Cl$_2$ | Cl |
| 1021 | 4-Cl | 2,5-Cl$_2$ | Cl |
| 1022 | 4-Cl | 2,6-Cl$_2$ | Cl |
| 1023 | 4-Cl | 3,4-Cl$_2$ | Cl |
| 1024 | 4-Cl | 3,5-Cl$_2$ | Cl |
| 1025 | 4-Cl | 2-F, 3-Cl | Cl |
| 1026 | 4-Cl | 2-F, 4-Cl | Cl |
| 1027 | 4-Cl | 2-F, 5-Cl | Cl |
| 1028 | 4-Cl | 2-F, 6-Cl | Cl |
| 1029 | 4-Cl | 2,6-F$_2$, 4-Cl | Cl |
| 1030 | 4-Cl | 3-F, 4-Cl | Cl |
| 1031 | 4-Cl | 3-Cl, 5-F | Cl |
| 1032 | 4-Cl | 2-Cl, 5-F | Cl |
| 1033 | 4-Cl | 3-CN, 4-Cl | Cl |
| 1034 | 4-Cl | 3-NO$_2$, 4-Cl | Cl |
| 1035 | 4-Cl | 2-F, 4-Br | Cl |
| 1036 | 6-OCF$_2$H | 4-F | Cl |
| 1037 | 6-OCF$_2$H | 4-Cl | Cl |
| 1038 | 6-OCF$_2$H | 4-Br | Cl |
| 1039 | 6-OCF$_2$H | H | Cl |
| 1040 | 6-OCF$_2$H | 4-Me | Cl |
| 1041 | 6-OCF$_2$H | 4-CN | Cl |
| 1042 | 6-OCF$_2$H | 4-NO$_2$ | Cl |
| 1043 | 6-OCF$_2$H | 4-OMe | Cl |
| 1044 | 6-OCF$_2$H | 3-F | Cl |
| 1045 | 6-OCF$_2$H | 3-Cl | Cl |
| 1046 | 6-OCF$_2$H | 3-Br | Cl |
| 1047 | 6-OCF$_2$H | 3-Me | Cl |
| 1048 | 6-OCF$_2$H | 3-CN | Cl |
| 1049 | 6-OCF$_2$H | 3-NO$_2$ | Cl |
| 1050 | 6-OCF$_2$H | 3-OMe | Cl |
| 1051 | 6-OCF$_2$H | 2-F | Cl |
| 1052 | 6-OCF$_2$H | 2-Cl | Cl |
| 1053 | 6-OCF$_2$H | 2-Br | Cl |
| 1054 | 6-OCF$_2$H | 2-Me | Cl |
| 1055 | 6-OCF$_2$H | 2-CN | Cl |
| 1056 | 6-OCF$_2$H | 2-NO$_2$ | Cl |
| 1057 | 6-OCF$_2$H | 2-OMe | Cl |
| 1058 | 6-OCF$_2$H | 2,3-F$_2$ | Cl |
| 1059 | 6-OCF$_2$H | 2,4-F$_2$ | Cl |
| 1060 | 6-OCF$_2$H | 2,5-F$_2$ | Cl |
| 1061 | 6-OCF$_2$H | 2,6-F$_2$ | Cl |
| 1062 | 6-OCF$_2$H | 3,4-F$_2$ | Cl |
| 1063 | 6-OCF$_2$H | 3,5-F$_2$ | Cl |
| 1064 | 6-OCF$_2$H | 2,3-Cl$_2$ | Cl |
| 1065 | 6-OCF$_2$H | 2,4-Cl$_2$ | Cl |
| 1066 | 6-OCF$_2$H | 2,5-Cl$_2$ | Cl |
| 1067 | 6-OCF$_2$H | 2,6-Cl$_2$ | Cl |
| 1068 | 6-OCF$_2$H | 3,4-Cl$_2$ | Cl |
| 1069 | 6-OCF$_2$H | 3,5-Cl$_2$ | Cl |
| 1070 | 6-OCF$_2$H | 2-F, 3-Cl | Cl |
| 1071 | 6-OCF$_2$H | 2-F, 4-Cl | Cl |
| 1072 | 6-OCF$_2$H | 2-F, 5-Cl | Cl |
| 1073 | 6-OCF$_2$H | 2-F, 6-Cl | Cl |
| 1074 | 6-OCF$_2$H | 2,6-F$_2$, 4-Cl | Cl |
| 1075 | 6-OCF$_2$H | 3-F, 4-Cl | Cl |
| 1076 | 6-OCF$_2$H | 3-Cl, 5-F | Cl |
| 1077 | 6-OCF$_2$H | 2-Cl, 5-F | Cl |
| 1078 | 6-OCF$_2$H | 3-CN, 4-Cl | Cl |
| 1079 | 6-OCF$_2$H | 3-NO$_2$, 4-Cl | Cl |
| 1080 | 6-OCF$_2$H | 2-F, 4-Br | Cl |
| 1081 | H | 4-F | Br |
| 1082 | H | 4-Cl | Br |
| 1083 | H | 4-Br | Br |
| 1084 | H | H | Br |
| 1085 | H | 4-Me | Br |
| 1086 | H | 4-CN | Br |
| 1087 | H | 4-NO$_2$ | Br |
| 1088 | H | 4-OMe | Br |
| 1089 | H | 3-F | Br |
| 1090 | H | 3-Cl | Br |
| 1091 | H | 3-Br | Br |
| 1092 | H | 3-Me | Br |
| 1093 | H | 3-CN | Br |
| 1094 | H | 3-NO$_2$ | Br |
| 1095 | H | 3-OMe | Br |
| 1096 | H | 2-F | Br |
| 1097 | H | 2-Cl | Br |
| 1098 | H | 2-Br | Br |
| 1099 | H | 2-Me | Br |
| 1100 | H | 2-CN | Br |
| 1101 | H | 2-NO$_2$ | Br |
| 1102 | H | 2-OMe | Br |
| 1103 | H | 2,3-F$_2$ | Br |
| 1104 | H | 2,4-F$_2$ | Br |
| 1105 | H | 2,5-F$_2$ | Br |
| 1106 | H | 2,6-F$_2$ | Br |
| 1107 | H | 3,4-F$_2$ | Br |
| 1108 | H | 3,5-F$_2$ | Br |
| 1109 | H | 2,3-Cl$_2$ | Br |
| 1110 | H | 2,4-Cl$_2$ | Br |
| 1111 | H | 2,5-Cl$_2$ | Br |
| 1112 | H | 2,6-Cl$_2$ | Br |
| 1113 | H | 3,4-Cl$_2$ | Br |
| 1114 | H | 3,5-Cl$_2$ | Br |
| 1115 | H | 2-F, 3-Cl | Br |
| 1116 | H | 2-F, 4-Cl | Br |
| 1117 | H | 2-F, 5-Cl | Br |
| 1118 | H | 2-F, 6-Cl | Br |
| 1119 | H | 2,6-F$_2$, 4-Cl | Br |
| 1120 | H | 3-F, 4-Cl | Br |
| 1121 | H | 3-Cl, 5-F | Br |
| 1122 | H | 2-Cl, 5-F | Br |
| 1123 | H | 3-CN, 4-Cl | Br |
| 1124 | H | 3-NO$_2$, 4-Cl | Br |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1125 | H | 2-F, 4-Br | Br |
| 1126 | 6-F | 4-F | Br |
| 1127 | 6-F | 4-Cl | Br |
| 1128 | 6-F | 4-Br | Br |
| 1129 | 6-F | H | Br |
| 1130 | 6-F | 4-Me | Br |
| 1131 | 6-F | 4-CN | Br |
| 1132 | 6-F | 4-NO$_2$ | Br |
| 1133 | 6-F | 4-OMe | Br |
| 1134 | 6-F | 3-F | Br |
| 1135 | 6-F | 3-Cl | Br |
| 1136 | 6-F | 3-Br | Br |
| 1137 | 6-F | 3-Me | Br |
| 1138 | 6-F | 3-CN | Br |
| 1139 | 6-F | 3-NO$_2$ | Br |
| 1140 | 6-F | 3-OMe | Br |
| 1141 | 6-F | 2-F | Br |
| 1142 | 6-F | 2-Cl | Br |
| 1143 | 6-F | 2-Br | Br |
| 1144 | 6-F | 2-Me | Br |
| 1145 | 6-F | 2-CN | Br |
| 1146 | 6-F | 2-NO$_2$ | Br |
| 1147 | 6-F | 2-OMe | Br |
| 1148 | 6-F | 2,3-F$_2$ | Br |
| 1149 | 6-F | 2,4-F$_2$ | Br |
| 1150 | 6-F | 2,5-F$_2$ | Br |
| 1151 | 6-F | 2,6-F$_2$ | Br |
| 1152 | 6-F | 3,4-F$_2$ | Br |
| 1153 | 6-F | 3,5-F$_2$ | Br |
| 1154 | 6-F | 2,3-Cl$_2$ | Br |
| 1155 | 6-F | 2,4-Cl$_2$ | Br |
| 1156 | 6-F | 2,5-Cl$_2$ | Br |
| 1157 | 6-F | 2,6-Cl$_2$ | Br |
| 1158 | 6-F | 3,4-Cl$_2$ | Br |
| 1159 | 6-F | 3,5-Cl$_2$ | Br |
| 1160 | 6-F | 2-F, 3-Cl | Br |
| 1161 | 6-F | 2-F, 4-Cl | Br |
| 1162 | 6-F | 2-F, 5-Cl | Br |
| 1163 | 6-F | 2-F, 6-Cl | Br |
| 1164 | 6-F | 2,6-F$_2$, 4-Cl | Br |
| 1165 | 6-F | 3-F, 4-Cl | Br |
| 1166 | 6-F | 3-Cl, 5-F | Br |
| 1167 | 6-F | 2-Cl, 5-F | Br |
| 1168 | 6-F | 3-CN, 4-Cl | Br |
| 1169 | 6-F | 3-NO$_2$, 4-Cl | Br |
| 1170 | 6-F | 2-F, 4-Br | Br |
| 1171 | 6-Cl | 4-F | Br |
| 1172 | 6-Cl | 4-Cl | Br |
| 1173 | 6-Cl | 4-Br | Br |
| 1174 | 6-Cl | H | Br |
| 1175 | 6-Cl | 4-Me | Br |
| 1176 | 6-Cl | 4-CN | Br |
| 1177 | 6-Cl | 4-NO$_2$ | Br |
| 1178 | 6-Cl | 4-OMe | Br |
| 1179 | 6-Cl | 3-F | Br |
| 1180 | 6-Cl | 3-Cl | Br |
| 1181 | 6-Cl | 3-Br | Br |
| 1182 | 6-Cl | 3-Me | Br |
| 1183 | 6-Cl | 3-CN | Br |
| 1184 | 6-Cl | 3-NO$_2$ | Br |
| 1185 | 6-Cl | 3-OMe | Br |
| 1186 | 6-Cl | 2-F | Br |
| 1187 | 6-Cl | 2-Cl | Br |
| 1188 | 6-Cl | 2-Br | Br |
| 1189 | 6-Cl | 2-Me | Br |
| 1190 | 6-Cl | 2-CN | Br |
| 1191 | 6-Cl | 2-NO$_2$ | Br |
| 1192 | 6-Cl | 2-OMe | Br |
| 1193 | 6-Cl | 2,3-F$_2$ | Br |
| 1194 | 6-Cl | 2,4-F$_2$ | Br |
| 1195 | 6-Cl | 2,5-F$_2$ | Br |
| 1196 | 6-Cl | 2,6-F$_2$ | Br |
| 1197 | 6-Cl | 3,4-F$_2$ | Br |
| 1198 | 6-Cl | 3,5-F$_2$ | Br |
| 1199 | 6-Cl | 2,3-Cl$_2$ | Br |
| 1200 | 6-Cl | 2,4-Cl$_2$ | Br |
| 1201 | 6-Cl | 2,5-Cl$_2$ | Br |
| 1202 | 6-Cl | 2,6-Cl$_2$ | Br |
| 1203 | 6-Cl | 3,4-Cl$_2$ | Br |
| 1204 | 6-Cl | 3,5-Cl$_2$ | Br |
| 1205 | 6-Cl | 2-F, 3-Cl | Br |
| 1206 | 6-Cl | 2-F, 4-Cl | Br |
| 1207 | 6-Cl | 2-F, 5-Cl | Br |
| 1208 | 6-Cl | 2-F, 6-Cl | Br |
| 1209 | 6-Cl | 2,6-F$_2$, 4-Cl | Br |
| 1210 | 6-Cl | 3-F, 4-Cl | Br |
| 1211 | 6-Cl | 3-Cl, 5-F | Br |
| 1212 | 6-Cl | 2-Cl, 5-F | Br |
| 1213 | 6-Cl | 3-CN, 4-Cl | Br |
| 1214 | 6-Cl | 3-NO$_2$, 4-Cl | Br |
| 1215 | 6-Cl | 2-F, 4-Br | Br |
| 1216 | 6-Br | 4-F | Br |
| 1217 | 6-Br | 4-Cl | Br |
| 1218 | 6-Br | 4-Br | Br |
| 1219 | 6-Br | H | Br |
| 1220 | 6-Br | 4-Me | Br |
| 1221 | 6-Br | 4-CN | Br |
| 1222 | 6-Br | 4-NO$_2$ | Br |
| 1223 | 6-Br | 4-OMe | Br |
| 1224 | 6-Br | 3-F | Br |
| 1225 | 6-Br | 3-Cl | Br |
| 1226 | 6-Br | 3-Br | Br |
| 1227 | 6-Br | 3-Me | Br |
| 1228 | 6-Br | 3-CN | Br |
| 1229 | 6-Br | 3-NO$_2$ | Br |
| 1230 | 6-Br | 3-OMe | Br |
| 1231 | 6-Br | 2-F | Br |
| 1232 | 6-Br | 2-Cl | Br |
| 1233 | 6-Br | 2-Br | Br |
| 1234 | 6-Br | 2-Me | Br |
| 1235 | 6-Br | 2-CN | Br |
| 1236 | 6-Br | 2-NO$_2$ | Br |
| 1237 | 6-Br | 2-OMe | Br |
| 1238 | 6-Br | 2,3-F$_2$ | Br |
| 1239 | 6-Br | 2,4-F$_2$ | Br |
| 1240 | 6-Br | 2,5-F$_2$ | Br |
| 1241 | 6-Br | 2,6-F$_2$ | Br |
| 1242 | 6-Br | 3,4-F$_2$ | Br |
| 1243 | 6-Br | 3,5-F$_2$ | Br |
| 1244 | 6-Br | 2,3-Cl$_2$ | Br |
| 1245 | 6-Br | 2,4-Cl$_2$ | Br |
| 1246 | 6-Br | 2,5-Cl$_2$ | Br |
| 1247 | 6-Br | 2,6-Cl$_2$ | Br |
| 1248 | 6-Br | 3,4-Cl$_2$ | Br |
| 1249 | 6-Br | 3,5-Cl$_2$ | Br |
| 1250 | 6-Br | 2-F, 3-Cl | Br |
| 1251 | 6-Br | 2-F, 4-Cl | Br |
| 1252 | 6-Br | 2-F, 5-Cl | Br |
| 1253 | 6-Br | 2-F, 6-Cl | Br |
| 1254 | 6-Br | 2,6-F$_2$, 4-Cl | Br |
| 1255 | 6-Br | 3-F, 4-Cl | Br |
| 1256 | 6-Br | 3-Cl, 5-F | Br |
| 1257 | 6-Br | 2-Cl, 5-F | Br |
| 1258 | 6-Br | 3-CN, 4-Cl | Br |
| 1259 | 6-Br | 3-NO$_2$, 4-Cl | Br |
| 1260 | 6-Br | 2-F, 4-Br | Br |
| 1261 | 6-CN | 4-F | Br |
| 1262 | 6-CN | 4-Cl | Br |
| 1263 | 6-CN | 4-Br | Br |
| 1264 | 6-CN | H | Br |
| 1265 | 6-CN | 4-Me | Br |
| 1266 | 6-CN | 4-CN | Br |
| 1267 | 6-CN | 4-NO$_2$ | Br |
| 1268 | 6-CN | 4-OMe | Br |
| 1269 | 6-CN | 3-F | Br |
| 1270 | 6-CN | 3-Cl | Br |
| 1271 | 6-CN | 3-Br | Br |
| 1272 | 6-CN | 3-Me | Br |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1273 | 6-CN | 3-CN | Br |
| 1274 | 6-CN | 3-NO$_2$ | Br |
| 1275 | 6-CN | 3-OMe | Br |
| 1276 | 6-CN | 2-F | Br |
| 1277 | 6-CN | 2-Cl | Br |
| 1278 | 6-CN | 2-Br | Br |
| 1279 | 6-CN | 2-Me | Br |
| 1280 | 6-CN | 2-CN | Br |
| 1281 | 6-CN | 2-NO$_2$ | Br |
| 1282 | 6-CN | 2-OMe | Br |
| 1283 | 6-CN | 2,3-F$_2$ | Br |
| 1284 | 6-CN | 2,4-F$_2$ | Br |
| 1285 | 6-CN | 2,5-F$_2$ | Br |
| 1286 | 6-CN | 2,6-F$_2$ | Br |
| 1287 | 6-CN | 3,4-F$_2$ | Br |
| 1288 | 6-CN | 3,5-F$_2$ | Br |
| 1289 | 6-CN | 2,3-Cl$_2$ | Br |
| 1290 | 6-CN | 2,4-Cl$_2$ | Br |
| 1291 | 6-CN | 2,5-Cl$_2$ | Br |
| 1292 | 6-CN | 2,6-Cl$_2$ | Br |
| 1293 | 6-CN | 3,4-Cl$_2$ | Br |
| 1294 | 6-CN | 3,5-Cl$_2$ | Br |
| 1295 | 6-CN | 2-F, 3-Cl | Br |
| 1296 | 6-CN | 2-F, 4-Cl | Br |
| 1297 | 6-CN | 2-F, 5-Cl | Br |
| 1298 | 6-CN | 2-F, 6-Cl | Br |
| 1299 | 6-CN | 2,6-F$_2$, 4-Cl | Br |
| 1300 | 6-CN | 3-F, 4-Cl | Br |
| 1301 | 6-CN | 3-Cl, 5-F | Br |
| 1302 | 6-CN | 2-Cl, 5-F | Br |
| 1303 | 6-CN | 3-CN, 4-Cl | Br |
| 1304 | 6-CN | 3-NO$_2$, 4-Cl | Br |
| 1305 | 6-CN | 2-F, 4-Br | Br |
| 1306 | 6-Me | 4-F | Br |
| 1307 | 6-Me | 4-Cl | Br |
| 1308 | 6-Me | 4-Br | Br |
| 1309 | 6-Me | H | Br |
| 1310 | 6-Me | 4-Me | Br |
| 1311 | 6-Me | 4-CN | Br |
| 1312 | 6-Me | 4-NO$_2$ | Br |
| 1313 | 6-Me | 4-OMe | Br |
| 1314 | 6-Me | 3-F | Br |
| 1315 | 6-Me | 3-Cl | Br |
| 1316 | 6-Me | 3-Br | Br |
| 1317 | 6-Me | 3-Me | Br |
| 1318 | 6-Me | 3-CN | Br |
| 1319 | 6-Me | 3-NO$_2$ | Br |
| 1320 | 6-Me | 3-OMe | Br |
| 1321 | 6-Me | 2-F | Br |
| 1322 | 6-Me | 2-Cl | Br |
| 1323 | 6-Me | 2-Br | Br |
| 1324 | 6-Me | 2-Me | Br |
| 1325 | 6-Me | 2-CN | Br |
| 1326 | 6-Me | 2-NO$_2$ | Br |
| 1327 | 6-Me | 2-OMe | Br |
| 1328 | 6-Me | 2,3-F$_2$ | Br |
| 1329 | 6-Me | 2,4-F$_2$ | Br |
| 1330 | 6-Me | 2,5-F$_2$ | Br |
| 1331 | 6-Me | 2,6-F$_2$ | Br |
| 1332 | 6-Me | 3,4-F$_2$ | Br |
| 1333 | 6-Me | 3,5-F$_2$ | Br |
| 1334 | 6-Me | 2,3-Cl$_2$ | Br |
| 1335 | 6-Me | 2,4-Cl$_2$ | Br |
| 1336 | 6-Me | 2,5-Cl$_2$ | Br |
| 1337 | 6-Me | 2,6-Cl$_2$ | Br |
| 1338 | 6-Me | 3,4-Cl$_2$ | Br |
| 1339 | 6-Me | 3,5-Cl$_2$ | Br |
| 1340 | 6-Me | 2-F, 3-Cl | Br |
| 1341 | 6-Me | 2-F, 4-Cl | Br |
| 1342 | 6-Me | 2-F, 5-Cl | Br |
| 1343 | 6-Me | 2-F, 6-Cl | Br |
| 1344 | 6-Me | 2,6-F$_2$, 4-Cl | Br |
| 1345 | 6-Me | 3-F, 4-Cl | Br |
| 1346 | 6-Me | 3-Cl, 5-F | Br |
| 1347 | 6-Me | 2-Cl, 5-F | Br |
| 1348 | 6-Me | 3-CN, 4-Cl | Br |
| 1349 | 6-Me | 3-NO$_2$, 4-Cl | Br |
| 1350 | 6-Me | 2-F, 4-Br | Br |
| 1351 | 6-OMe | 4-F | Br |
| 1352 | 6-OMe | 4-Cl | Br |
| 1353 | 6-OMe | 4-Br | Br |
| 1354 | 6-OMe | H | Br |
| 1355 | 6-OMe | 4-Me | Br |
| 1356 | 6-OMe | 4-CN | Br |
| 1357 | 6-OMe | 4-NO$_2$ | Br |
| 1358 | 6-OMe | 4-OMe | Br |
| 1359 | 6-OMe | 3-F | Br |
| 1360 | 6-OMe | 3-Cl | Br |
| 1361 | 6-OMe | 3-Br | Br |
| 1362 | 6-OMe | 3-Me | Br |
| 1363 | 6-OMe | 3-CN | Br |
| 1364 | 6-OMe | 3-NO$_2$ | Br |
| 1365 | 6-OMe | 3-OMe | Br |
| 1366 | 6-OMe | 2-F | Br |
| 1367 | 6-OMe | 2-Cl | Br |
| 1368 | 6-OMe | 2-Br | Br |
| 1369 | 6-OMe | 2-Me | Br |
| 1370 | 6-OMe | 2-CN | Br |
| 1371 | 6-OMe | 2-NO$_2$ | Br |
| 1372 | 6-OMe | 2-OMe | Br |
| 1373 | 6-OMe | 2,3-F$_2$ | Br |
| 1374 | 6-OMe | 2,4-F$_2$ | Br |
| 1375 | 6-OMe | 2,5-F$_2$ | Br |
| 1376 | 6-OMe | 2,6-F$_2$ | Br |
| 1377 | 6-OMe | 3,4-F$_2$ | Br |
| 1378 | 6-OMe | 3,5-F$_2$ | Br |
| 1379 | 6-OMe | 2,3-Cl$_2$ | Br |
| 1380 | 6-OMe | 2,4-Cl$_2$ | Br |
| 1381 | 6-OMe | 2,5-Cl$_2$ | Br |
| 1382 | 6-OMe | 2,6-Cl$_2$ | Br |
| 1383 | 6-OMe | 3,4-Cl$_2$ | Br |
| 1384 | 6-OMe | 3,5-Cl$_2$ | Br |
| 1385 | 6-OMe | 2-F, 3-Cl | Br |
| 1386 | 6-OMe | 2-F, 4-Cl | Br |
| 1387 | 6-OMe | 2-F, 5-Cl | Br |
| 1388 | 6-OMe | 2-F, 6-Cl | Br |
| 1389 | 6-OMe | 2,6-F$_2$, 4-Cl | Br |
| 1390 | 6-OMe | 3-F, 4-Cl | Br |
| 1391 | 6-OMe | 3-Cl, 5-F | Br |
| 1392 | 6-OMe | 2-Cl, 5-F | Br |
| 1393 | 6-OMe | 3-CN, 4-Cl | Br |
| 1394 | 6-OMe | 3-NO$_2$, 4-Cl | Br |
| 1395 | 6-OMe | 2-F, 4-Br | Br |
| 1396 | 2-F | 4-F | Br |
| 1397 | 2-F | 4-Cl | Br |
| 1398 | 2-F | 4-Br | Br |
| 1399 | 2-F | H | Br |
| 1400 | 2-F | 4-Me | Br |
| 1401 | 2-F | 4-CN | Br |
| 1402 | 2-F | 4-NO$_2$ | Br |
| 1403 | 2-F | 4-OMe | Br |
| 1404 | 2-F | 3-F | Br |
| 1405 | 2-F | 3-Cl | Br |
| 1406 | 2-F | 3-Br | Br |
| 1407 | 2-F | 3-Me | Br |
| 1408 | 2-F | 3-CN | Br |
| 1409 | 2-F | 3-NO$_2$ | Br |
| 1410 | 2-F | 3-OMe | Br |
| 1411 | 2-F | 2-F | Br |
| 1412 | 2-F | 2-Cl | Br |
| 1413 | 2-F | 2-Br | Br |
| 1414 | 2-F | 2-Me | Br |
| 1415 | 2-F | 2-CN | Br |
| 1416 | 2-F | 2-NO$_2$ | Br |
| 1417 | 2-F | 2-OMe | Br |
| 1418 | 2-F | 2,3-F$_2$ | Br |
| 1419 | 2-F | 2,4-F$_2$ | Br |
| 1420 | 2-F | 2,5-F$_2$ | Br |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1421 | 2-F | 2,6-F$_2$ | Br |
| 1422 | 2-F | 3,4-F$_2$ | Br |
| 1423 | 2-F | 3,5-F$_2$ | Br |
| 1424 | 2-F | 2,3-Cl$_2$ | Br |
| 1425 | 2-F | 2,4-Cl$_2$ | Br |
| 1426 | 2-F | 2,5-Cl$_2$ | Br |
| 1427 | 2-F | 2,6-Cl$_2$ | Br |
| 1428 | 2-F | 3,4-Cl$_2$ | Br |
| 1429 | 2-F | 3,5-Cl$_2$ | Br |
| 1430 | 2-F | 2-F, 3-Cl | Br |
| 1431 | 2-F | 2-F, 4-Cl | Br |
| 1432 | 2-F | 2-F, 5-Cl | Br |
| 1433 | 2-F | 2-F, 6-Cl | Br |
| 1434 | 2-F | 2,6-F$_2$, 4-Cl | Br |
| 1435 | 2-F | 3-F, 4-Cl | Br |
| 1436 | 2-F | 3-Cl, 5-F | Br |
| 1437 | 2-F | 2-Cl, 5-F | Br |
| 1438 | 2-F | 3-CN, 4-Cl | Br |
| 1439 | 2-F | 3-NO$_2$, 4-Cl | Br |
| 1440 | 2-F | 2-F, 4-Br | Br |
| 1441 | 4-F | 4-F | Br |
| 1442 | 4-F | 4-Cl | Br |
| 1443 | 4-F | 4-Br | Br |
| 1444 | 4-F | H | Br |
| 1445 | 4-F | 4-Me | Br |
| 1446 | 4-F | 4-CN | Br |
| 1447 | 4-F | 4-NO$_2$ | Br |
| 1448 | 4-F | 4-OMe | Br |
| 1449 | 4-F | 3-F | Br |
| 1450 | 4-F | 3-Cl | Br |
| 1451 | 4-F | 3-Br | Br |
| 1452 | 4-F | 3-Me | Br |
| 1453 | 4-F | 3-CN | Br |
| 1454 | 4-F | 3-NO$_2$ | Br |
| 1455 | 4-F | 3-OMe | Br |
| 1456 | 4-F | 2-F | Br |
| 1457 | 4-F | 2-Cl | Br |
| 1458 | 4-F | 2-Br | Br |
| 1459 | 4-F | 2-Me | Br |
| 1460 | 4-F | 2-CN | Br |
| 1461 | 4-F | 2-NO$_2$ | Br |
| 1462 | 4-F | 2-OMe | Br |
| 1463 | 4-F | 2,3-F$_2$ | Br |
| 1464 | 4-F | 2,4-F$_2$ | Br |
| 1465 | 4-F | 2,5-F$_2$ | Br |
| 1466 | 4-F | 2,6-F$_2$ | Br |
| 1467 | 4-F | 3,4-F$_2$ | Br |
| 1468 | 4-F | 3,5-F$_2$ | Br |
| 1469 | 4-F | 2,3-Cl$_2$ | Br |
| 1470 | 4-F | 2,4-Cl$_2$ | Br |
| 1471 | 4-F | 2,5-Cl$_2$ | Br |
| 1472 | 4-F | 2,6-Cl$_2$ | Br |
| 1473 | 4-F | 3,4-Cl$_2$ | Br |
| 1474 | 4-F | 3,5-Cl$_2$ | Br |
| 1475 | 4-F | 2-F, 3-Cl | Br |
| 1476 | 4-F | 2-F, 4-Cl | Br |
| 1477 | 4-F | 2-F, 5-Cl | Br |
| 1478 | 4-F | 2-F, 6-Cl | Br |
| 1479 | 4-F | 2,6-F$_2$, 4-Cl | Br |
| 1480 | 4-F | 3-F, 4-Cl | Br |
| 1481 | 4-F | 3-Cl, 5-F | Br |
| 1482 | 4-F | 2-Cl, 5-F | Br |
| 1483 | 4-F | 3-CN, 4-Cl | Br |
| 1484 | 4-F | 3-NO$_2$, 4-Cl | Br |
| 1485 | 4-F | 2-F, 4-Br | Br |
| 1486 | 2-Cl | 4-F | Br |
| 1487 | 2-Cl | 4-Cl | Br |
| 1488 | 2-Cl | 4-Br | Br |
| 1489 | 2-Cl | H | Br |
| 1490 | 2-Cl | 4-Me | Br |
| 1491 | 2-Cl | 4-CN | Br |
| 1492 | 2-Cl | 4-NO$_2$ | Br |
| 1493 | 2-Cl | 4-OMe | Br |
| 1494 | 2-Cl | 3-F | Br |
| 1495 | 2-Cl | 3-Cl | Br |
| 1496 | 2-Cl | 3-Br | Br |
| 1497 | 2-Cl | 3-Me | Br |
| 1498 | 2-Cl | 3-CN | Br |
| 1499 | 2-Cl | 3-NO$_2$ | Br |
| 1500 | 2-Cl | 3-OMe | Br |
| 1501 | 2-Cl | 2-F | Br |
| 1502 | 2-Cl | 2-Cl | Br |
| 1503 | 2-Cl | 2-Br | Br |
| 1504 | 2-Cl | 2-Me | Br |
| 1505 | 2-Cl | 2-CN | Br |
| 1506 | 2-Cl | 2-NO$_2$ | Br |
| 1507 | 2-Cl | 2-OMe | Br |
| 1508 | 2-Cl | 2,3-F$_2$ | Br |
| 1509 | 2-Cl | 2,4-F$_2$ | Br |
| 1510 | 2-Cl | 2,5-F$_2$ | Br |
| 1511 | 2-Cl | 2,6-F$_2$ | Br |
| 1512 | 2-Cl | 3,4-F$_2$ | Br |
| 1513 | 2-Cl | 3,5-F$_2$ | Br |
| 1514 | 2-Cl | 2,3-Cl$_2$ | Br |
| 1515 | 2-Cl | 2,4-Cl$_2$ | Br |
| 1516 | 2-Cl | 2,5-Cl$_2$ | Br |
| 1517 | 2-Cl | 2,6-Cl$_2$ | Br |
| 1518 | 2-Cl | 3,4-Cl$_2$ | Br |
| 1519 | 2-Cl | 3,5-Cl$_2$ | Br |
| 1520 | 2-Cl | 2-F, 3-Cl | Br |
| 1521 | 2-Cl | 2-F, 4-Cl | Br |
| 1522 | 2-Cl | 2-F, 5-Cl | Br |
| 1523 | 2-Cl | 2-F, 6-Cl | Br |
| 1524 | 2-Cl | 2,6-F$_2$, 4-Cl | Br |
| 1525 | 2-Cl | 3-F, 4-Cl | Br |
| 1526 | 2-Cl | 3-Cl, 5-F | Br |
| 1527 | 2-Cl | 2-Cl, 5-F | Br |
| 1528 | 2-Cl | 3-CN, 4-Cl | Br |
| 1529 | 2-Cl | 3-NO$_2$, 4-Cl | Br |
| 1530 | 2-Cl | 2-F, 4-Br | Br |
| 1531 | 4-Cl | 4-F | Br |
| 1532 | 4-Cl | 4-Cl | Br |
| 1533 | 4-Cl | 4-Br | Br |
| 1534 | 4-Cl | H | Br |
| 1535 | 4-Cl | 4-Me | Br |
| 1536 | 4-Cl | 4-CN | Br |
| 1537 | 4-Cl | 4-NO$_2$ | Br |
| 1538 | 4-Cl | 4-OMe | Br |
| 1539 | 4-Cl | 3-F | Br |
| 1540 | 4-Cl | 3-Cl | Br |
| 1541 | 4-Cl | 3-Br | Br |
| 1542 | 4-Cl | 3-Me | Br |
| 1543 | 4-Cl | 3-CN | Br |
| 1544 | 4-Cl | 3-NO$_2$ | Br |
| 1545 | 4-Cl | 3-OMe | Br |
| 1546 | 4-Cl | 2-F | Br |
| 1547 | 4-Cl | 2-Cl | Br |
| 1548 | 4-Cl | 2-Br | Br |
| 1549 | 4-Cl | 2-Me | Br |
| 1550 | 4-Cl | 2-CN | Br |
| 1551 | 4-Cl | 2-NO$_2$ | Br |
| 1552 | 4-Cl | 2-OMe | Br |
| 1553 | 4-Cl | 2,3-F$_2$ | Br |
| 1554 | 4-Cl | 2,4-F$_2$ | Br |
| 1555 | 4-Cl | 2,5-F$_2$ | Br |
| 1556 | 4-Cl | 2,6-F$_2$ | Br |
| 1557 | 4-Cl | 3,4-F$_2$ | Br |
| 1558 | 4-Cl | 3,5-F$_2$ | Br |
| 1559 | 4-Cl | 2,3-Cl$_2$ | Br |
| 1560 | 4-Cl | 2,4-Cl$_2$ | Br |
| 1561 | 4-Cl | 2,5-Cl$_2$ | Br |
| 1562 | 4-Cl | 2,6-Cl$_2$ | Br |
| 1563 | 4-Cl | 3,4-Cl$_2$ | Br |
| 1564 | 4-Cl | 3,5-Cl$_2$ | Br |
| 1565 | 4-Cl | 2-F, 3-Cl | Br |
| 1566 | 4-Cl | 2-F, 4-Cl | Br |
| 1567 | 4-Cl | 2-F, 5-Cl | Br |
| 1568 | 4-Cl | 2-F, 6-Cl | Br |

TABLE 1-continued

Definitions of structural combinations of groups (R¹)ₘ, (R²)ₙ and R³ for the tables of compounds of the general formula (I) according to the invention below

| No. | (R¹)ₘ | (R²)ₙ | R³ |
|---|---|---|---|
| 1569 | 4-Cl | 2,6-F$_2$, 4-Cl | Br |
| 1570 | 4-Cl | 3-F, 4-Cl | Br |
| 1571 | 4-Cl | 3-Cl, 5-F | Br |
| 1572 | 4-Cl | 2-Cl, 5-F | Br |
| 1573 | 4-Cl | 3-CN, 4-Cl | Br |
| 1574 | 4-Cl | 3-NO$_2$, 4-Cl | Br |
| 1575 | 4-Cl | 2-F, 4-Br | Br |
| 1576 | 6-OCF$_2$H | 4-F | Br |
| 1577 | 6-OCF$_2$H | 4-Cl | Br |
| 1578 | 6-OCF$_2$H | 4-Br | Br |
| 1579 | 6-OCF$_2$H | H | Br |
| 1580 | 6-OCF$_2$H | 4-Me | Br |
| 1581 | 6-OCF$_2$H | 4-CN | Br |
| 1582 | 6-OCF$_2$H | 4-NO$_2$ | Br |
| 1583 | 6-OCF$_2$H | 4-OMe | Br |
| 1584 | 6-OCF$_2$H | 3-F | Br |
| 1585 | 6-OCF$_2$H | 3-Cl | Br |
| 1586 | 6-OCF$_2$H | 3-Br | Br |
| 1587 | 6-OCF$_2$H | 3-Me | Br |
| 1588 | 6-OCF$_2$H | 3-CN | Br |
| 1589 | 6-OCF$_2$H | 3-NO$_2$ | Br |
| 1590 | 6-OCF$_2$H | 3-OMe | Br |
| 1591 | 6-OCF$_2$H | 2-F | Br |
| 1592 | 6-OCF$_2$H | 2-Cl | Br |
| 1593 | 6-OCF$_2$H | 2-Br | Br |
| 1594 | 6-OCF$_2$H | 2-Me | Br |
| 1595 | 6-OCF$_2$H | 2-CN | Br |
| 1596 | 6-OCF$_2$H | 2-NO$_2$ | Br |
| 1597 | 6-OCF$_2$H | 2-OMe | Br |
| 1598 | 6-OCF$_2$H | 2,3-F$_2$ | Br |
| 1599 | 6-OCF$_2$H | 2,4-F$_2$ | Br |
| 1600 | 6-OCF$_2$H | 2,5-F$_2$ | Br |
| 1601 | 6-OCF$_2$H | 2,6-F$_2$ | Br |
| 1602 | 6-OCF$_2$H | 3,4-F$_2$ | Br |
| 1603 | 6-OCF$_2$H | 3,5-F$_2$ | Br |
| 1604 | 6-OCF$_2$H | 2,3-Cl$_2$ | Br |
| 1605 | 6-OCF$_2$H | 2,4-Cl$_2$ | Br |
| 1606 | 6-OCF$_2$H | 2,5-Cl$_2$ | Br |
| 1607 | 6-OCF$_2$H | 2,6-Cl$_2$ | Br |
| 1608 | 6-OCF$_2$H | 3,4-Cl$_2$ | Br |
| 1609 | 6-OCF$_2$H | 3,5-Cl$_2$ | Br |
| 1610 | 6-OCF$_2$H | 2-F, 3-Cl | Br |
| 1611 | 6-OCF$_2$H | 2-F, 4-Cl | Br |
| 1612 | 6-OCF$_2$H | 2-F, 5-Cl | Br |
| 1613 | 6-OCF$_2$H | 2-F, 6-Cl | Br |
| 1614 | 6-OCF$_2$H | 2,6-F$_2$, 4-Cl | Br |
| 1615 | 6-OCF$_2$H | 3-F, 4-Cl | Br |
| 1616 | 6-OCF$_2$H | 3-Cl, 5-F | Br |
| 1617 | 6-OCF$_2$H | 2-Cl, 5-F | Br |
| 1618 | 6-OCF$_2$H | 3-CN, 4-Cl | Br |
| 1619 | 6-OCF$_2$H | 3-NO$_2$, 4-Cl | Br |
| 1620 | 6-OCF$_2$H | 2-F, 4-Br | Br |
| 1621 | H | 4-F | Me |
| 1622 | H | 4-Cl | Me |
| 1623 | H | 4-Br | Me |
| 1624 | H | H | Me |
| 1625 | H | 4-Me | Me |
| 1626 | H | 4-CN | Me |
| 1627 | H | 4-NO$_2$ | Me |
| 1628 | H | 4-OMe | Me |
| 1629 | H | 3-F | Me |
| 1630 | H | 3-Cl | Me |
| 1631 | H | 3-Br | Me |
| 1632 | H | 3-Me | Me |
| 1633 | H | 3-CN | Me |
| 1634 | H | 3-NO$_2$ | Me |
| 1635 | H | 3-OMe | Me |
| 1636 | H | 2-F | Me |
| 1637 | H | 2-Cl | Me |
| 1638 | H | 2-Br | Me |
| 1639 | H | 2-Me | Me |
| 1640 | H | 2-CN | Me |
| 1641 | H | 2-NO$_2$ | Me |
| 1642 | H | 2-OMe | Me |
| 1643 | H | 2,3-F$_2$ | Me |
| 1644 | H | 2,4-F$_2$ | Me |
| 1645 | H | 2,5-F$_2$ | Me |
| 1646 | H | 2,6-F$_2$ | Me |
| 1647 | H | 3,4-F$_2$ | Me |
| 1648 | H | 3,5-F$_2$ | Me |
| 1649 | H | 2,3-Cl$_2$ | Me |
| 1650 | H | 2,4-Cl$_2$ | Me |
| 1651 | H | 2,5-Cl$_2$ | Me |
| 1652 | H | 2,6-Cl$_2$ | Me |
| 1653 | H | 3,4-Cl$_2$ | Me |
| 1654 | H | 3,5-Cl$_2$ | Me |
| 1655 | H | 2-F, 3-Cl | Me |
| 1656 | H | 2-F, 4-Cl | Me |
| 1657 | H | 2-F, 5-Cl | Me |
| 1658 | H | 2-F, 6-Cl | Me |
| 1659 | H | 2,6-F$_2$, 4-Cl | Me |
| 1660 | H | 3-F, 4-Cl | Me |
| 1661 | H | 3-Cl, 5-F | Me |
| 1662 | H | 2-Cl, 5-F | Me |
| 1663 | H | 3-CN, 4-Cl | Me |
| 1664 | H | 3-NO$_2$, 4-Cl | Me |
| 1665 | H | 2-F, 4-Br | Me |
| 1666 | 6-F | 4-F | Me |
| 1667 | 6-F | 4-Cl | Me |
| 1668 | 6-F | 4-Br | Me |
| 1669 | 6-F | H | Me |
| 1670 | 6-F | 4-Me | Me |
| 1671 | 6-F | 4-CN | Me |
| 1672 | 6-F | 4-NO$_2$ | Me |
| 1673 | 6-F | 4-OMe | Me |
| 1674 | 6-F | 3-F | Me |
| 1675 | 6-F | 3-Cl | Me |
| 1676 | 6-F | 3-Br | Me |
| 1677 | 6-F | 3-Me | Me |
| 1678 | 6-F | 3-CN | Me |
| 1679 | 6-F | 3-NO$_2$ | Me |
| 1680 | 6-F | 3-OMe | Me |
| 1681 | 6-F | 2-F | Me |
| 1682 | 6-F | 2-Cl | Me |
| 1683 | 6-F | 2-Br | Me |
| 1684 | 6-F | 2-Me | Me |
| 1685 | 6-F | 2-CN | Me |
| 1686 | 6-F | 2-NO$_2$ | Me |
| 1687 | 6-F | 2-OMe | Me |
| 1688 | 6-F | 2,3-F$_2$ | Me |
| 1689 | 6-F | 2,4-F$_2$ | Me |
| 1690 | 6-F | 2,5-F$_2$ | Me |
| 1691 | 6-F | 2,6-F$_2$ | Me |
| 1692 | 6-F | 3,4-F$_2$ | Me |
| 1693 | 6-F | 3,5-F$_2$ | Me |
| 1694 | 6-F | 2,3-Cl$_2$ | Me |
| 1695 | 6-F | 2,4-Cl$_2$ | Me |
| 1696 | 6-F | 2,5-Cl$_2$ | Me |
| 1697 | 6-F | 2,6-Cl$_2$ | Me |
| 1698 | 6-F | 3,4-Cl$_2$ | Me |
| 1699 | 6-F | 3,5-Cl$_2$ | Me |
| 1700 | 6-F | 2-F, 3-Cl | Me |
| 1701 | 6-F | 2-F, 4-Cl | Me |
| 1702 | 6-F | 2-F, 5-Cl | Me |
| 1703 | 6-F | 2-F, 6-Cl | Me |
| 1704 | 6-F | 2,6-F$_2$, 4-Cl | Me |
| 1705 | 6-F | 3-F, 4-Cl | Me |
| 1706 | 6-F | 3-Cl, 5-F | Me |
| 1707 | 6-F | 2-Cl, 5-F | Me |
| 1708 | 6-F | 3-CN, 4-Cl | Me |
| 1709 | 6-F | 3-NO$_2$, 4-Cl | Me |
| 1710 | 6-F | 2-F, 4-Br | Me |
| 1711 | 6-Cl | 4-F | Me |
| 1712 | 6-Cl | 4-Cl | Me |
| 1713 | 6-Cl | 4-Br | Me |
| 1714 | 6-Cl | H | Me |
| 1715 | 6-Cl | 4-Me | Me |
| 1716 | 6-Cl | 4-CN | Me |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1717 | 6-Cl | 4-NO$_2$ | Me |
| 1718 | 6-Cl | 4-OMe | Me |
| 1719 | 6-Cl | 3-F | Me |
| 1720 | 6-Cl | 3-Cl | Me |
| 1721 | 6-Cl | 3-Br | Me |
| 1722 | 6-Cl | 3-Me | Me |
| 1723 | 6-Cl | 3-CN | Me |
| 1724 | 6-Cl | 3-NO$_2$ | Me |
| 1725 | 6-Cl | 3-OMe | Me |
| 1726 | 6-Cl | 2-F | Me |
| 1727 | 6-Cl | 2-Cl | Me |
| 1728 | 6-Cl | 2-Br | Me |
| 1729 | 6-Cl | 2-Me | Me |
| 1730 | 6-Cl | 2-CN | Me |
| 1731 | 6-Cl | 2-NO$_2$ | Me |
| 1732 | 6-Cl | 2-OMe | Me |
| 1733 | 6-Cl | 2,3-F$_2$ | Me |
| 1734 | 6-Cl | 2,4-F$_2$ | Me |
| 1735 | 6-Cl | 2,5-F$_2$ | Me |
| 1736 | 6-Cl | 2,6-F$_2$ | Me |
| 1737 | 6-Cl | 3,4-F$_2$ | Me |
| 1738 | 6-Cl | 3,5-F$_2$ | Me |
| 1739 | 6-Cl | 2,3-Cl$_2$ | Me |
| 1740 | 6-Cl | 2,4-Cl$_2$ | Me |
| 1741 | 6-Cl | 2,5-Cl$_2$ | Me |
| 1742 | 6-Cl | 2,6-Cl$_2$ | Me |
| 1743 | 6-Cl | 3,4-Cl$_2$ | Me |
| 1744 | 6-Cl | 3,5-Cl$_2$ | Me |
| 1745 | 6-Cl | 2-F, 3-Cl | Me |
| 1746 | 6-Cl | 2-F, 4-Cl | Me |
| 1747 | 6-Cl | 2-F, 5-Cl | Me |
| 1748 | 6-Cl | 2-F, 6-Cl | Me |
| 1749 | 6-Cl | 2,6-F$_2$, 4-Cl | Me |
| 1750 | 6-Cl | 3-F, 4-Cl | Me |
| 1751 | 6-Cl | 3-Cl, 5-F | Me |
| 1752 | 6-Cl | 2-Cl, 5-F | Me |
| 1753 | 6-Cl | 3-CN, 4-Cl | Me |
| 1754 | 6-Cl | 3-NO$_2$, 4-Cl | Me |
| 1755 | 6-Cl | 2-F, 4-Br | Me |
| 1756 | 6-Br | 4-F | Me |
| 1757 | 6-Br | 4-Cl | Me |
| 1758 | 6-Br | 4-Br | Me |
| 1759 | 6-Br | H | Me |
| 1760 | 6-Br | 4-Me | Me |
| 1761 | 6-Br | 4-CN | Me |
| 1762 | 6-Br | 4-NO$_2$ | Me |
| 1763 | 6-Br | 4-OMe | Me |
| 1764 | 6-Br | 3-F | Me |
| 1765 | 6-Br | 3-Cl | Me |
| 1766 | 6-Br | 3-Br | Me |
| 1767 | 6-Br | 3-Me | Me |
| 1768 | 6-Br | 3-CN | Me |
| 1769 | 6-Br | 3-NO$_2$ | Me |
| 1770 | 6-Br | 3-OMe | Me |
| 1771 | 6-Br | 2-F | Me |
| 1772 | 6-Br | 2-Cl | Me |
| 1773 | 6-Br | 2-Br | Me |
| 1774 | 6-Br | 2-Me | Me |
| 1775 | 6-Br | 2-CN | Me |
| 1776 | 6-Br | 2-NO$_2$ | Me |
| 1777 | 6-Br | 2-OMe | Me |
| 1778 | 6-Br | 2,3-F$_2$ | Me |
| 1779 | 6-Br | 2,4-F$_2$ | Me |
| 1780 | 6-Br | 2,5-F$_2$ | Me |
| 1781 | 6-Br | 2,6-F$_2$ | Me |
| 1782 | 6-Br | 3,4-F$_2$ | Me |
| 1783 | 6-Br | 3,5-F$_2$ | Me |
| 1784 | 6-Br | 2,3-Cl$_2$ | Me |
| 1785 | 6-Br | 2,4-Cl$_2$ | Me |
| 1786 | 6-Br | 2,5-Cl$_2$ | Me |
| 1787 | 6-Br | 2,6-Cl$_2$ | Me |
| 1788 | 6-Br | 3,4-Cl$_2$ | Me |
| 1789 | 6-Br | 3,5-Cl$_2$ | Me |
| 1790 | 6-Br | 2-F, 3-Cl | Me |
| 1791 | 6-Br | 2-F, 4-Cl | Me |
| 1792 | 6-Br | 2-F, 5-Cl | Me |
| 1793 | 6-Br | 2-F, 6-Cl | Me |
| 1794 | 6-Br | 2,6-F$_2$, 4-Cl | Me |
| 1795 | 6-Br | 3-F, 4-Cl | Me |
| 1796 | 6-Br | 3-Cl, 5-F | Me |
| 1797 | 6-Br | 2-Cl, 5-F | Me |
| 1798 | 6-Br | 3-CN, 4-Cl | Me |
| 1799 | 6-Br | 3-NO$_2$, 4-Cl | Me |
| 1800 | 6-Br | 2-F, 4-Br | Me |
| 1801 | 6-CN | 4-F | Me |
| 1802 | 6-CN | 4-Cl | Me |
| 1803 | 6-CN | 4-Br | Me |
| 1804 | 6-CN | H | Me |
| 1805 | 6-CN | 4-Me | Me |
| 1806 | 6-CN | 4-CN | Me |
| 1807 | 6-CN | 4-NO$_2$ | Me |
| 1808 | 6-CN | 4-OMe | Me |
| 1809 | 6-CN | 3-F | Me |
| 1810 | 6-CN | 3-Cl | Me |
| 1811 | 6-CN | 3-Br | Me |
| 1812 | 6-CN | 3-Me | Me |
| 1813 | 6-CN | 3-CN | Me |
| 1814 | 6-CN | 3-NO$_2$ | Me |
| 1815 | 6-CN | 3-OMe | Me |
| 1816 | 6-CN | 2-F | Me |
| 1817 | 6-CN | 2-Cl | Me |
| 1818 | 6-CN | 2-Br | Me |
| 1819 | 6-CN | 2-Me | Me |
| 1820 | 6-CN | 2-CN | Me |
| 1821 | 6-CN | 2-NO$_2$ | Me |
| 1822 | 6-CN | 2-OMe | Me |
| 1823 | 6-CN | 2,3-F$_2$ | Me |
| 1824 | 6-CN | 2,4-F$_2$ | Me |
| 1825 | 6-CN | 2,5-F$_2$ | Me |
| 1826 | 6-CN | 2,6-F$_2$ | Me |
| 1827 | 6-CN | 3,4-F$_2$ | Me |
| 1828 | 6-CN | 3,5-F$_2$ | Me |
| 1829 | 6-CN | 2,3-Cl$_2$ | Me |
| 1830 | 6-CN | 2,4-Cl$_2$ | Me |
| 1831 | 6-CN | 2,5-Cl$_2$ | Me |
| 1832 | 6-CN | 2,6-Cl$_2$ | Me |
| 1833 | 6-CN | 3,4-Cl$_2$ | Me |
| 1834 | 6-CN | 3,5-Cl$_2$ | Me |
| 1835 | 6-CN | 2-F, 3-Cl | Me |
| 1836 | 6-CN | 2-F, 4-Cl | Me |
| 1837 | 6-CN | 2-F, 5-Cl | Me |
| 1838 | 6-CN | 2-F, 6-Cl | Me |
| 1839 | 6-CN | 2,6-F$_2$, 4-Cl | Me |
| 1840 | 6-CN | 3-F, 4-Cl | Me |
| 1841 | 6-CN | 3-Cl, 5-F | Me |
| 1842 | 6-CN | 2-Cl, 5-F | Me |
| 1843 | 6-CN | 3-CN, 4-Cl | Me |
| 1844 | 6-CN | 3-NO$_2$, 4-Cl | Me |
| 1845 | 6-CN | 2-F, 4-Br | Me |
| 1846 | 6-Me | 4-F | Me |
| 1847 | 6-Me | 4-Cl | Me |
| 1848 | 6-Me | 4-Br | Me |
| 1849 | 6-Me | H | Me |
| 1850 | 6-Me | 4-Me | Me |
| 1851 | 6-Me | 4-CN | Me |
| 1852 | 6-Me | 4-NO$_2$ | Me |
| 1853 | 6-Me | 4-OMe | Me |
| 1854 | 6-Me | 3-F | Me |
| 1855 | 6-Me | 3-Cl | Me |
| 1856 | 6-Me | 3-Br | Me |
| 1857 | 6-Me | 3-Me | Me |
| 1858 | 6-Me | 3-CN | Me |
| 1859 | 6-Me | 3-NO$_2$ | Me |
| 1860 | 6-Me | 3-OMe | Me |
| 1861 | 6-Me | 2-F | Me |
| 1862 | 6-Me | 2-Cl | Me |
| 1863 | 6-Me | 2-Br | Me |
| 1864 | 6-Me | 2-Me | Me |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 1865 | 6-Me | 2-CN | Me |
| 1866 | 6-Me | 2-NO$_2$ | Me |
| 1867 | 6-Me | 2-OMe | Me |
| 1868 | 6-Me | 2,3-F$_2$ | Me |
| 1869 | 6-Me | 2,4-F$_2$ | Me |
| 1870 | 6-Me | 2,5-F$_2$ | Me |
| 1871 | 6-Me | 2,6-F$_2$ | Me |
| 1872 | 6-Me | 3,4-F$_2$ | Me |
| 1873 | 6-Me | 3,5-F$_2$ | Me |
| 1874 | 6-Me | 2,3-Cl$_2$ | Me |
| 1875 | 6-Me | 2,4-Cl$_2$ | Me |
| 1876 | 6-Me | 2,5-Cl$_2$ | Me |
| 1877 | 6-Me | 2,6-Cl$_2$ | Me |
| 1878 | 6-Me | 3,4-Cl$_2$ | Me |
| 1879 | 6-Me | 3,5-Cl$_2$ | Me |
| 1880 | 6-Me | 2-F, 3-Cl | Me |
| 1881 | 6-Me | 2-F, 4-Cl | Me |
| 1882 | 6-Me | 2-F, 5-Cl | Me |
| 1883 | 6-Me | 2-F, 6-Cl | Me |
| 1884 | 6-Me | 2,6-F$_2$, 4-Cl | Me |
| 1885 | 6-Me | 3-F, 4-Cl | Me |
| 1886 | 6-Me | 3-Cl, 5-F | Me |
| 1887 | 6-Me | 2-Cl, 5-F | Me |
| 1888 | 6-Me | 3-CN, 4-Cl | Me |
| 1889 | 6-Me | 3-NO$_2$, 4-Cl | Me |
| 1890 | 6-Me | 2-F, 4-Br | Me |
| 1891 | 6-OMe | 4-F | Me |
| 1892 | 6-OMe | 4-Cl | Me |
| 1893 | 6-OMe | 4-Br | Me |
| 1894 | 6-OMe | H | Me |
| 1895 | 6-OMe | 4-Me | Me |
| 1896 | 6-OMe | 4-CN | Me |
| 1897 | 6-OMe | 4-NO$_2$ | Me |
| 1898 | 6-OMe | 4-OMe | Me |
| 1899 | 6-OMe | 3-F | Me |
| 1900 | 6-OMe | 3-Cl | Me |
| 1901 | 6-OMe | 3-Br | Me |
| 1902 | 6-OMe | 3-Me | Me |
| 1903 | 6-OMe | 3-CN | Me |
| 1904 | 6-OMe | 3-NO$_2$ | Me |
| 1905 | 6-OMe | 3-OMe | Me |
| 1906 | 6-OMe | 2-F | Me |
| 1907 | 6-OMe | 2-Cl | Me |
| 1908 | 6-OMe | 2-Br | Me |
| 1909 | 6-OMe | 2-Me | Me |
| 1910 | 6-OMe | 2-CN | Me |
| 1911 | 6-OMe | 2-NO$_2$ | Me |
| 1912 | 6-OMe | 2-OMe | Me |
| 1913 | 6-OMe | 2,3-F$_2$ | Me |
| 1914 | 6-OMe | 2,4-F$_2$ | Me |
| 1915 | 6-OMe | 2,5-F$_2$ | Me |
| 1916 | 6-OMe | 2,6-F$_2$ | Me |
| 1917 | 6-OMe | 3,4-F$_2$ | Me |
| 1918 | 6-OMe | 3,5-F$_2$ | Me |
| 1919 | 6-OMe | 2,3-Cl$_2$ | Me |
| 1920 | 6-OMe | 2,4-Cl$_2$ | Me |
| 1921 | 6-OMe | 2,5-Cl$_2$ | Me |
| 1922 | 6-OMe | 2,6-Cl$_2$ | Me |
| 1923 | 6-OMe | 3,4-Cl$_2$ | Me |
| 1924 | 6-OMe | 3,5-Cl$_2$ | Me |
| 1925 | 6-OMe | 2-F, 3-Cl | Me |
| 1926 | 6-OMe | 2-F, 4-Cl | Me |
| 1927 | 6-OMe | 2-F, 5-Cl | Me |
| 1928 | 6-OMe | 2-F, 6-Cl | Me |
| 1929 | 6-OMe | 2,6-F$_2$, 4-Cl | Me |
| 1930 | 6-OMe | 3-F, 4-Cl | Me |
| 1931 | 6-OMe | 3-Cl, 5-F | Me |
| 1932 | 6-OMe | 2-Cl, 5-F | Me |
| 1933 | 6-OMe | 3-CN, 4-Cl | Me |
| 1934 | 6-OMe | 3-NO$_2$, 4-Cl | Me |
| 1935 | 6-OMe | 2-F, 4-Br | Me |
| 1936 | 2-F | 4-F | Me |
| 1937 | 2-F | 4-Cl | Me |
| 1938 | 2-F | 4-Br | Me |
| 1939 | 2-F | H | Me |
| 1940 | 2-F | 4-Me | Me |
| 1941 | 2-F | 4-CN | Me |
| 1942 | 2-F | 4-NO$_2$ | Me |
| 1943 | 2-F | 4-OMe | Me |
| 1944 | 2-F | 3-F | Me |
| 1945 | 2-F | 3-Cl | Me |
| 1946 | 2-F | 3-Br | Me |
| 1947 | 2-F | 3-Me | Me |
| 1948 | 2-F | 3-CN | Me |
| 1949 | 2-F | 3-NO$_2$ | Me |
| 1950 | 2-F | 3-OMe | Me |
| 1951 | 2-F | 2-F | Me |
| 1952 | 2-F | 2-Cl | Me |
| 1953 | 2-F | 2-Br | Me |
| 1954 | 2-F | 2-Me | Me |
| 1955 | 2-F | 2-CN | Me |
| 1956 | 2-F | 2-NO$_2$ | Me |
| 1957 | 2-F | 2-OMe | Me |
| 1958 | 2-F | 2,3-F$_2$ | Me |
| 1959 | 2-F | 2,4-F$_2$ | Me |
| 1960 | 2-F | 2,5-F$_2$ | Me |
| 1961 | 2-F | 2,6-F$_2$ | Me |
| 1962 | 2-F | 3,4-F$_2$ | Me |
| 1963 | 2-F | 3,5-F$_2$ | Me |
| 1964 | 2-F | 2,3-Cl$_2$ | Me |
| 1965 | 2-F | 2,4-Cl$_2$ | Me |
| 1966 | 2-F | 2,5-Cl$_2$ | Me |
| 1967 | 2-F | 2,6-Cl$_2$ | Me |
| 1968 | 2-F | 3,4-Cl$_2$ | Me |
| 1969 | 2-F | 3,5-Cl$_2$ | Me |
| 1970 | 2-F | 2-F, 3-Cl | Me |
| 1971 | 2-F | 2-F, 4-Cl | Me |
| 1972 | 2-F | 2-F, 5-Cl | Me |
| 1973 | 2-F | 2-F, 6-Cl | Me |
| 1974 | 2-F | 2,6-F$_2$, 4-Cl | Me |
| 1975 | 2-F | 3-F, 4-Cl | Me |
| 1976 | 2-F | 3-Cl, 5-F | Me |
| 1977 | 2-F | 2-Cl, 5-F | Me |
| 1978 | 2-F | 3-CN, 4-Cl | Me |
| 1979 | 2-F | 3-NO$_2$, 4-Cl | Me |
| 1980 | 2-F | 2-F, 4-Br | Me |
| 1981 | 4-F | 4-F | Me |
| 1982 | 4-F | 4-Cl | Me |
| 1983 | 4-F | 4-Br | Me |
| 1984 | 4-F | H | Me |
| 1985 | 4-F | 4-Me | Me |
| 1986 | 4-F | 4-CN | Me |
| 1987 | 4-F | 4-NO$_2$ | Me |
| 1988 | 4-F | 4-OMe | Me |
| 1989 | 4-F | 3-F | Me |
| 1990 | 4-F | 3-Cl | Me |
| 1991 | 4-F | 3-Br | Me |
| 1992 | 4-F | 3-Me | Me |
| 1993 | 4-F | 3-CN | Me |
| 1994 | 4-F | 3-NO$_2$ | Me |
| 1995 | 4-F | 3-OMe | Me |
| 1996 | 4-F | 2-F | Me |
| 1997 | 4-F | 2-Cl | Me |
| 1998 | 4-F | 2-Br | Me |
| 1999 | 4-F | 2-Me | Me |
| 2000 | 4-F | 2-CN | Me |
| 2001 | 4-F | 2-NO$_2$ | Me |
| 2002 | 4-F | 2-OMe | Me |
| 2003 | 4-F | 2,3-F$_2$ | Me |
| 2004 | 4-F | 2,4-F$_2$ | Me |
| 2005 | 4-F | 2,5-F$_2$ | Me |
| 2006 | 4-F | 2,6-F$_2$ | Me |
| 2007 | 4-F | 3,4-F$_2$ | Me |
| 2008 | 4-F | 3,5-F$_2$ | Me |
| 2009 | 4-F | 2,3-Cl$_2$ | Me |
| 2010 | 4-F | 2,4-Cl$_2$ | Me |
| 2011 | 4-F | 2,5-Cl$_2$ | Me |
| 2012 | 4-F | 2,6-Cl$_2$ | Me |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2013 | 4-F | 3,4-Cl$_2$ | Me |
| 2014 | 4-F | 3,5-Cl$_2$ | Me |
| 2015 | 4-F | 2-F, 3-Cl | Me |
| 2016 | 4-F | 2-F, 4-Cl | Me |
| 2017 | 4-F | 2-F, 5-Cl | Me |
| 2018 | 4-F | 2-F, 6-Cl | Me |
| 2019 | 4-F | 2,6-F$_2$, 4-Cl | Me |
| 2020 | 4-F | 3-F, 4-Cl | Me |
| 2021 | 4-F | 3-Cl, 5-F | Me |
| 2022 | 4-F | 2-Cl, 5-F | Me |
| 2023 | 4-F | 3-CN, 4-Cl | Me |
| 2024 | 4-F | 3-NO$_2$, 4-Cl | Me |
| 2025 | 4-F | 2-F, 4-Br | Me |
| 2026 | 2-Cl | 4-F | Me |
| 2027 | 2-Cl | 4-Cl | Me |
| 2028 | 2-Cl | 4-Br | Me |
| 2029 | 2-Cl | H | Me |
| 2030 | 2-Cl | 4-Me | Me |
| 2031 | 2-Cl | 4-CN | Me |
| 2032 | 2-Cl | 4-NO$_2$ | Me |
| 2033 | 2-Cl | 4-OMe | Me |
| 2034 | 2-Cl | 3-F | Me |
| 2035 | 2-Cl | 3-Cl | Me |
| 2036 | 2-Cl | 3-Br | Me |
| 2037 | 2-Cl | 3-Me | Me |
| 2038 | 2-Cl | 3-CN | Me |
| 2039 | 2-Cl | 3-NO$_2$ | Me |
| 2040 | 2-Cl | 3-OMe | Me |
| 2041 | 2-Cl | 2-F | Me |
| 2042 | 2-Cl | 2-Cl | Me |
| 2043 | 2-Cl | 2-Br | Me |
| 2044 | 2-Cl | 2-Me | Me |
| 2045 | 2-Cl | 2-CN | Me |
| 2046 | 2-Cl | 2-NO$_2$ | Me |
| 2047 | 2-Cl | 2-OMe | Me |
| 2048 | 2-Cl | 2,3-F$_2$ | Me |
| 2049 | 2-Cl | 2,4-F$_2$ | Me |
| 2050 | 2-Cl | 2,5-F$_2$ | Me |
| 2051 | 2-Cl | 2,6-F$_2$ | Me |
| 2052 | 2-Cl | 3,4-F$_2$ | Me |
| 2053 | 2-Cl | 3,5-F$_2$ | Me |
| 2054 | 2-Cl | 2,3-Cl$_2$ | Me |
| 2055 | 2-Cl | 2,4-Cl$_2$ | Me |
| 2056 | 2-Cl | 2,5-Cl$_2$ | Me |
| 2057 | 2-Cl | 2,6-Cl$_2$ | Me |
| 2058 | 2-Cl | 3,4-Cl$_2$ | Me |
| 2059 | 2-Cl | 3,5-Cl$_2$ | Me |
| 2060 | 2-Cl | 2-F, 3-Cl | Me |
| 2061 | 2-Cl | 2-F, 4-Cl | Me |
| 2062 | 2-Cl | 2-F, 5-Cl | Me |
| 2063 | 2-Cl | 2-F, 6-Cl | Me |
| 2064 | 2-Cl | 2,6-F$_2$, 4-Cl | Me |
| 2065 | 2-Cl | 3-F, 4-Cl | Me |
| 2066 | 2-Cl | 3-Cl, 5-F | Me |
| 2067 | 2-Cl | 2-Cl, 5-F | Me |
| 2068 | 2-Cl | 3-CN, 4-Cl | Me |
| 2069 | 2-Cl | 3-NO$_2$, 4-Cl | Me |
| 2070 | 2-Cl | 2-F, 4-Br | Me |
| 2071 | 4-Cl | 4-F | Me |
| 2072 | 4-Cl | 4-Cl | Me |
| 2073 | 4-Cl | 4-Br | Me |
| 2074 | 4-Cl | H | Me |
| 2075 | 4-Cl | 4-Me | Me |
| 2076 | 4-Cl | 4-CN | Me |
| 2077 | 4-Cl | 4-NO$_2$ | Me |
| 2078 | 4-Cl | 4-OMe | Me |
| 2079 | 4-Cl | 3-F | Me |
| 2080 | 4-Cl | 3-Cl | Me |
| 2081 | 4-Cl | 3-Br | Me |
| 2082 | 4-Cl | 3-Me | Me |
| 2083 | 4-Cl | 3-CN | Me |
| 2084 | 4-Cl | 3-NO$_2$ | Me |
| 2085 | 4-Cl | 3-OMe | Me |
| 2086 | 4-Cl | 2-F | Me |
| 2087 | 4-Cl | 2-Cl | Me |
| 2088 | 4-Cl | 2-Br | Me |
| 2089 | 4-Cl | 2-Me | Me |
| 2090 | 4-Cl | 2-CN | Me |
| 2091 | 4-Cl | 2-NO$_2$ | Me |
| 2092 | 4-Cl | 2-OMe | Me |
| 2093 | 4-Cl | 2,3-F$_2$ | Me |
| 2094 | 4-Cl | 2,4-F$_2$ | Me |
| 2095 | 4-Cl | 2,5-F$_2$ | Me |
| 2096 | 4-Cl | 2,6-F$_2$ | Me |
| 2097 | 4-Cl | 3,4-F$_2$ | Me |
| 2098 | 4-Cl | 3,5-F$_2$ | Me |
| 2099 | 4-Cl | 2,3-Cl$_2$ | Me |
| 2100 | 4-Cl | 2,4-Cl$_2$ | Me |
| 2101 | 4-Cl | 2,5-Cl$_2$ | Me |
| 2102 | 4-Cl | 2,6-Cl$_2$ | Me |
| 2103 | 4-Cl | 3,4-Cl$_2$ | Me |
| 2104 | 4-Cl | 3,5-Cl$_2$ | Me |
| 2105 | 4-Cl | 2-F, 3-Cl | Me |
| 2106 | 4-Cl | 2-F, 4-Cl | Me |
| 2107 | 4-Cl | 2-F, 5-Cl | Me |
| 2108 | 4-Cl | 2-F, 6-Cl | Me |
| 2109 | 4-Cl | 2,6-F$_2$, 4-Cl | Me |
| 2110 | 4-Cl | 3-F, 4-Cl | Me |
| 2111 | 4-Cl | 3-Cl, 5-F | Me |
| 2112 | 4-Cl | 2-Cl, 5-F | Me |
| 2113 | 4-Cl | 3-CN, 4-Cl | Me |
| 2114 | 4-Cl | 3-NO$_2$, 4-Cl | Me |
| 2115 | 4-Cl | 2-F, 4-Br | Me |
| 2116 | 6-OCF$_2$H | 4-F | Me |
| 2117 | 6-OCF$_2$H | 4-Cl | Me |
| 2118 | 6-OCF$_2$H | 4-Br | Me |
| 2119 | 6-OCF$_2$H | H | Me |
| 2120 | 6-OCF$_2$H | 4-Me | Me |
| 2121 | 6-OCF$_2$H | 4-CN | Me |
| 2122 | 6-OCF$_2$H | 4-NO$_2$ | Me |
| 2123 | 6-OCF$_2$H | 4-OMe | Me |
| 2124 | 6-OCF$_2$H | 3-F | Me |
| 2125 | 6-OCF$_2$H | 3-Cl | Me |
| 2126 | 6-OCF$_2$H | 3-Br | Me |
| 2127 | 6-OCF$_2$H | 3-Me | Me |
| 2128 | 6-OCF$_2$H | 3-CN | Me |
| 2129 | 6-OCF$_2$H | 3-NO$_2$ | Me |
| 2130 | 6-OCF$_2$H | 3-OMe | Me |
| 2131 | 6-OCF$_2$H | 2-F | Me |
| 2132 | 6-OCF$_2$H | 2-Cl | Me |
| 2133 | 6-OCF$_2$H | 2-Br | Me |
| 2134 | 6-OCF$_2$H | 2-Me | Me |
| 2135 | 6-OCF$_2$H | 2-CN | Me |
| 2136 | 6-OCF$_2$H | 2-NO$_2$ | Me |
| 2137 | 6-OCF$_2$H | 2-OMe | Me |
| 2138 | 6-OCF$_2$H | 2,3-F$_2$ | Me |
| 2139 | 6-OCF$_2$H | 2,4-F$_2$ | Me |
| 2140 | 6-OCF$_2$H | 2,5-F$_2$ | Me |
| 2141 | 6-OCF$_2$H | 2,6-F$_2$ | Me |
| 2142 | 6-OCF$_2$H | 3,4-F$_2$ | Me |
| 2143 | 6-OCF$_2$H | 3,5-F$_2$ | Me |
| 2144 | 6-OCF$_2$H | 2,3-Cl$_2$ | Me |
| 2145 | 6-OCF$_2$H | 2,4-Cl$_2$ | Me |
| 2146 | 6-OCF$_2$H | 2,5-Cl$_2$ | Me |
| 2147 | 6-OCF$_2$H | 2,6-Cl$_2$ | Me |
| 2148 | 6-OCF$_2$H | 3,4-Cl$_2$ | Me |
| 2149 | 6-OCF$_2$H | 3,5-Cl$_2$ | Me |
| 2150 | 6-OCF$_2$H | 2-F, 3-Cl | Me |
| 2151 | 6-OCF$_2$H | 2-F, 4-Cl | Me |
| 2152 | 6-OCF$_2$H | 2-F, 5-Cl | Me |
| 2153 | 6-OCF$_2$H | 2-F, 6-Cl | Me |
| 2154 | 6-OCF$_2$H | 2,6-F$_2$, 4-Cl | Me |
| 2155 | 6-OCF$_2$H | 3-F, 4-Cl | Me |
| 2156 | 6-OCF$_2$H | 3-Cl, 5-F | Me |
| 2157 | 6-OCF$_2$H | 2-Cl, 5-F | Me |
| 2158 | 6-OCF$_2$H | 3-CN, 4-Cl | Me |
| 2159 | 6-OCF$_2$H | 3-NO$_2$, 4-Cl | Me |
| 2160 | 6-OCF$_2$H | 2-F, 4-Br | Me |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2161 | H | 4-F | CN |
| 2162 | H | 4-Cl | CN |
| 2163 | H | 4-Br | CN |
| 2164 | H | H | CN |
| 2165 | H | 4-Me | CN |
| 2166 | H | 4-CN | CN |
| 2167 | H | 4-$NO_2$ | CN |
| 2168 | H | 4-OMe | CN |
| 2169 | H | 3-F | CN |
| 2170 | H | 3-Cl | CN |
| 2171 | H | 3-Br | CN |
| 2172 | H | 3-Me | CN |
| 2173 | H | 3-CN | CN |
| 2174 | H | 3-$NO_2$ | CN |
| 2175 | H | 3-OMe | CN |
| 2176 | H | 2-F | CN |
| 2177 | H | 2-Cl | CN |
| 2178 | H | 2-Br | CN |
| 2179 | H | 2-Me | CN |
| 2180 | H | 2-CN | CN |
| 2181 | H | 2-$NO_2$ | CN |
| 2182 | H | 2-OMe | CN |
| 2183 | H | 2,3-$F_2$ | CN |
| 2184 | H | 2,4-$F_2$ | CN |
| 2185 | H | 2,5-$F_2$ | CN |
| 2186 | H | 2,6-$F_2$ | CN |
| 2187 | H | 3,4-$F_2$ | CN |
| 2188 | H | 3,5-$F_2$ | CN |
| 2189 | H | 2,3-$Cl_2$ | CN |
| 2190 | H | 2,4-$Cl_2$ | CN |
| 2191 | H | 2,5-$Cl_2$ | CN |
| 2192 | H | 2,6-$Cl_2$ | CN |
| 2193 | H | 3,4-$Cl_2$ | CN |
| 2194 | H | 3,5-$Cl_2$ | CN |
| 2195 | H | 2-F, 3-Cl | CN |
| 2196 | H | 2-F, 4-Cl | CN |
| 2197 | H | 2-F, 5-Cl | CN |
| 2198 | H | 2-F, 6-Cl | CN |
| 2199 | H | 2,6-$F_2$, 4-Cl | CN |
| 2200 | H | 3-F, 4-Cl | CN |
| 2201 | H | 3-Cl, 5-F | CN |
| 2202 | H | 2-Cl, 5-F | CN |
| 2203 | H | 3-CN, 4-Cl | CN |
| 2204 | H | 3-$NO_2$, 4-Cl | CN |
| 2205 | H | 2-F, 4-Br | CN |
| 2206 | 6-F | 4-F | CN |
| 2207 | 6-F | 4-Cl | CN |
| 2208 | 6-F | 4-Br | CN |
| 2209 | 6-F | H | CN |
| 2210 | 6-F | 4-Me | CN |
| 2211 | 6-F | 4-CN | CN |
| 2212 | 6-F | 4-$NO_2$ | CN |
| 2213 | 6-F | 4-OMe | CN |
| 2214 | 6-F | 3-F | CN |
| 2215 | 6-F | 3-Cl | CN |
| 2216 | 6-F | 3-Br | CN |
| 2217 | 6-F | 3-Me | CN |
| 2218 | 6-F | 3-CN | CN |
| 2219 | 6-F | 3-$NO_2$ | CN |
| 2220 | 6-F | 3-OMe | CN |
| 2221 | 6-F | 2-F | CN |
| 2222 | 6-F | 2-Cl | CN |
| 2223 | 6-F | 2-Br | CN |
| 2224 | 6-F | 2-Me | CN |
| 2225 | 6-F | 2-CN | CN |
| 2226 | 6-F | 2-$NO_2$ | CN |
| 2227 | 6-F | 2-OMe | CN |
| 2228 | 6-F | 2,3-$F_2$ | CN |
| 2229 | 6-F | 2,4-$F_2$ | CN |
| 2230 | 6-F | 2,5-$F_2$ | CN |
| 2231 | 6-F | 2,6-$F_2$ | CN |
| 2232 | 6-F | 3,4-$F_2$ | CN |
| 2233 | 6-F | 3,5-$F_2$ | CN |
| 2234 | 6-F | 2,3-$Cl_2$ | CN |
| 2235 | 6-F | 2,4-$Cl_2$ | CN |
| 2236 | 6-F | 2,5-$Cl_2$ | CN |
| 2237 | 6-F | 2,6-$Cl_2$ | CN |
| 2238 | 6-F | 3,4-$Cl_2$ | CN |
| 2239 | 6-F | 3,5-$Cl_2$ | CN |
| 2240 | 6-F | 2-F, 3-Cl | CN |
| 2241 | 6-F | 2-F, 4-Cl | CN |
| 2242 | 6-F | 2-F, 5-Cl | CN |
| 2243 | 6-F | 2-F, 6-Cl | CN |
| 2244 | 6-F | 2,6-$F_2$, 4-Cl | CN |
| 2245 | 6-F | 3-F, 4-Cl | CN |
| 2246 | 6-F | 3-Cl, 5-F | CN |
| 2247 | 6-F | 2-Cl, 5-F | CN |
| 2248 | 6-F | 3-CN, 4-Cl | CN |
| 2249 | 6-F | 3-$NO_2$, 4-Cl | CN |
| 2250 | 6-F | 2-F, 4-Br | CN |
| 2251 | 6-Cl | 4-F | CN |
| 2252 | 6-Cl | 4-Cl | CN |
| 2253 | 6-Cl | 4-Br | CN |
| 2254 | 6-Cl | H | CN |
| 2255 | 6-Cl | 4-Me | CN |
| 2256 | 6-Cl | 4-CN | CN |
| 2257 | 6-Cl | 4-$NO_2$ | CN |
| 2258 | 6-Cl | 4-OMe | CN |
| 2259 | 6-Cl | 3-F | CN |
| 2260 | 6-Cl | 3-Cl | CN |
| 2261 | 6-Cl | 3-Br | CN |
| 2262 | 6-Cl | 3-Me | CN |
| 2263 | 6-Cl | 3-CN | CN |
| 2264 | 6-Cl | 3-$NO_2$ | CN |
| 2265 | 6-Cl | 3-OMe | CN |
| 2266 | 6-Cl | 2-F | CN |
| 2267 | 6-Cl | 2-Cl | CN |
| 2268 | 6-Cl | 2-Br | CN |
| 2269 | 6-Cl | 2-Me | CN |
| 2270 | 6-Cl | 2-CN | CN |
| 2271 | 6-Cl | 2-$NO_2$ | CN |
| 2272 | 6-Cl | 2-OMe | CN |
| 2273 | 6-Cl | 2,3-$F_2$ | CN |
| 2274 | 6-Cl | 2,4-$F_2$ | CN |
| 2275 | 6-Cl | 2,5-$F_2$ | CN |
| 2276 | 6-Cl | 2,6-$F_2$ | CN |
| 2277 | 6-Cl | 3,4-$F_2$ | CN |
| 2278 | 6-Cl | 3,5-$F_2$ | CN |
| 2279 | 6-Cl | 2,3-$Cl_2$ | CN |
| 2280 | 6-Cl | 2,4-$Cl_2$ | CN |
| 2281 | 6-Cl | 2,5-$Cl_2$ | CN |
| 2282 | 6-Cl | 2,6-$Cl_2$ | CN |
| 2283 | 6-Cl | 3,4-$Cl_2$ | CN |
| 2284 | 6-Cl | 3,5-$Cl_2$ | CN |
| 2285 | 6-Cl | 2-F, 3-Cl | CN |
| 2286 | 6-Cl | 2-F, 4-Cl | CN |
| 2287 | 6-Cl | 2-F, 5-Cl | CN |
| 2288 | 6-Cl | 2-F, 6-Cl | CN |
| 2289 | 6-Cl | 2,6-$F_2$, 4-Cl | CN |
| 2290 | 6-Cl | 3-F, 4-Cl | CN |
| 2291 | 6-Cl | 3-Cl, 5-F | CN |
| 2292 | 6-Cl | 2-Cl, 5-F | CN |
| 2293 | 6-Cl | 3-CN, 4-Cl | CN |
| 2294 | 6-Cl | 3-$NO_2$, 4-Cl | CN |
| 2295 | 6-Cl | 2-F, 4-Br | CN |
| 2296 | 6-Br | 4-F | CN |
| 2297 | 6-Br | 4-Cl | CN |
| 2298 | 6-Br | 4-Br | CN |
| 2299 | 6-Br | H | CN |
| 2300 | 6-Br | 4-Me | CN |
| 2301 | 6-Br | 4-CN | CN |
| 2302 | 6-Br | 4-$NO_2$ | CN |
| 2303 | 6-Br | 4-OMe | CN |
| 2304 | 6-Br | 3-F | CN |
| 2305 | 6-Br | 3-Cl | CN |
| 2306 | 6-Br | 3-Br | CN |
| 2307 | 6-Br | 3-Me | CN |
| 2308 | 6-Br | 3-CN | CN |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2309 | 6-Br | 3-NO$_2$ | CN |
| 2310 | 6-Br | 3-OMe | CN |
| 2311 | 6-Br | 2-F | CN |
| 2312 | 6-Br | 2-Cl | CN |
| 2313 | 6-Br | 2-Br | CN |
| 2314 | 6-Br | 2-Me | CN |
| 2315 | 6-Br | 2-CN | CN |
| 2316 | 6-Br | 2-NO$_2$ | CN |
| 2317 | 6-Br | 2-OMe | CN |
| 2318 | 6-Br | 2,3-F$_2$ | CN |
| 2319 | 6-Br | 2,4-F$_2$ | CN |
| 2320 | 6-Br | 2,5-F$_2$ | CN |
| 2321 | 6-Br | 2,6-F$_2$ | CN |
| 2322 | 6-Br | 3,4-F$_2$ | CN |
| 2323 | 6-Br | 3,5-F$_2$ | CN |
| 2324 | 6-Br | 2,3-Cl$_2$ | CN |
| 2325 | 6-Br | 2,4-Cl$_2$ | CN |
| 2326 | 6-Br | 2,5-Cl$_2$ | CN |
| 2327 | 6-Br | 2,6-Cl$_2$ | CN |
| 2328 | 6-Br | 3,4-Cl$_2$ | CN |
| 2329 | 6-Br | 3,5-Cl$_2$ | CN |
| 2330 | 6-Br | 2-F, 3-Cl | CN |
| 2331 | 6-Br | 2-F, 4-Cl | CN |
| 2332 | 6-Br | 2-F, 5-Cl | CN |
| 2333 | 6-Br | 2-F, 6-Cl | CN |
| 2334 | 6-Br | 2,6-F$_2$, 4-Cl | CN |
| 2335 | 6-Br | 3-F, 4-Cl | CN |
| 2336 | 6-Br | 3-Cl, 5-F | CN |
| 2337 | 6-Br | 2-Cl, 5-F | CN |
| 2338 | 6-Br | 3-CN, 4-Cl | CN |
| 2339 | 6-Br | 3-NO$_2$, 4-Cl | CN |
| 2340 | 6-Br | 2-F, 4-Br | CN |
| 2341 | 6-CN | 4-F | CN |
| 2342 | 6-CN | 4-Cl | CN |
| 2343 | 6-CN | 4-Br | CN |
| 2344 | 6-CN | H | CN |
| 2345 | 6-CN | 4-Me | CN |
| 2346 | 6-CN | 4-CN | CN |
| 2347 | 6-CN | 4-NO$_2$ | CN |
| 2348 | 6-CN | 4-OMe | CN |
| 2349 | 6-CN | 3-F | CN |
| 2350 | 6-CN | 3-Cl | CN |
| 2351 | 6-CN | 3-Br | CN |
| 2352 | 6-CN | 3-Me | CN |
| 2353 | 6-CN | 3-CN | CN |
| 2354 | 6-CN | 3-NO$_2$ | CN |
| 2355 | 6-CN | 3-OMe | CN |
| 2356 | 6-CN | 2-F | CN |
| 2357 | 6-CN | 2-Cl | CN |
| 2358 | 6-CN | 2-Br | CN |
| 2359 | 6-CN | 2-Me | CN |
| 2360 | 6-CN | 2-CN | CN |
| 2361 | 6-CN | 2-NO$_2$ | CN |
| 2362 | 6-CN | 2-OMe | CN |
| 2363 | 6-CN | 2,3-F$_2$ | CN |
| 2364 | 6-CN | 2,4-F$_2$ | CN |
| 2365 | 6-CN | 2,5-F$_2$ | CN |
| 2366 | 6-CN | 2,6-F$_2$ | CN |
| 2367 | 6-CN | 3,4-F$_2$ | CN |
| 2368 | 6-CN | 3,5-F$_2$ | CN |
| 2369 | 6-CN | 2,3-Cl$_2$ | CN |
| 2370 | 6-CN | 2,4-Cl$_2$ | CN |
| 2371 | 6-CN | 2,5-Cl$_2$ | CN |
| 2372 | 6-CN | 2,6-Cl$_2$ | CN |
| 2373 | 6-CN | 3,4-Cl$_2$ | CN |
| 2374 | 6-CN | 3,5-Cl$_2$ | CN |
| 2375 | 6-CN | 2-F, 3-Cl | CN |
| 2376 | 6-CN | 2-F, 4-Cl | CN |
| 2377 | 6-CN | 2-F, 5-Cl | CN |
| 2378 | 6-CN | 2-F, 6-Cl | CN |
| 2379 | 6-CN | 2,6-F$_2$, 4-Cl | CN |
| 2380 | 6-CN | 3-F, 4-Cl | CN |
| 2381 | 6-CN | 3-Cl, 5-F | CN |
| 2382 | 6-CN | 2-Cl, 5-F | CN |
| 2383 | 6-CN | 3-CN, 4-Cl | CN |
| 2384 | 6-CN | 3-NO$_2$, 4-Cl | CN |
| 2385 | 6-CN | 2-F, 4-Br | CN |
| 2386 | 6-Me | 4-F | CN |
| 2387 | 6-Me | 4-Cl | CN |
| 2388 | 6-Me | 4-Br | CN |
| 2389 | 6-Me | H | CN |
| 2390 | 6-Me | 4-Me | CN |
| 2391 | 6-Me | 4-CN | CN |
| 2392 | 6-Me | 4-NO$_2$ | CN |
| 2393 | 6-Me | 4-OMe | CN |
| 2394 | 6-Me | 3-F | CN |
| 2395 | 6-Me | 3-Cl | CN |
| 2396 | 6-Me | 3-Br | CN |
| 2397 | 6-Me | 3-Me | CN |
| 2398 | 6-Me | 3-CN | CN |
| 2399 | 6-Me | 3-NO$_2$ | CN |
| 2400 | 6-Me | 3-OMe | CN |
| 2401 | 6-Me | 2-F | CN |
| 2402 | 6-Me | 2-Cl | CN |
| 2403 | 6-Me | 2-Br | CN |
| 2404 | 6-Me | 2-Me | CN |
| 2405 | 6-Me | 2-CN | CN |
| 2406 | 6-Me | 2-NO$_2$ | CN |
| 2407 | 6-Me | 2-OMe | CN |
| 2408 | 6-Me | 2,3-F$_2$ | CN |
| 2409 | 6-Me | 2,4-F$_2$ | CN |
| 2410 | 6-Me | 2,5-F$_2$ | CN |
| 2411 | 6-Me | 2,6-F$_2$ | CN |
| 2412 | 6-Me | 3,4-F$_2$ | CN |
| 2413 | 6-Me | 3,5-F$_2$ | CN |
| 2414 | 6-Me | 2,3-Cl$_2$ | CN |
| 2415 | 6-Me | 2,4-Cl$_2$ | CN |
| 2416 | 6-Me | 2,5-Cl$_2$ | CN |
| 2417 | 6-Me | 2,6-Cl$_2$ | CN |
| 2418 | 6-Me | 3,4-Cl$_2$ | CN |
| 2419 | 6-Me | 3,5-Cl$_2$ | CN |
| 2420 | 6-Me | 2-F, 3-Cl | CN |
| 2421 | 6-Me | 2-F, 4-Cl | CN |
| 2422 | 6-Me | 2-F, 5-Cl | CN |
| 2423 | 6-Me | 2-F, 6-Cl | CN |
| 2424 | 6-Me | 2,6-F$_2$, 4-Cl | CN |
| 2425 | 6-Me | 3-F, 4-Cl | CN |
| 2426 | 6-Me | 3-Cl, 5-F | CN |
| 2427 | 6-Me | 2-Cl, 5-F | CN |
| 2428 | 6-Me | 3-CN, 4-Cl | CN |
| 2429 | 6-Me | 3-NO$_2$, 4-Cl | CN |
| 2430 | 6-Me | 2-F, 4-Br | CN |
| 2431 | 6-OMe | 4-F | CN |
| 2432 | 6-OMe | 4-Cl | CN |
| 2433 | 6-OMe | 4-Br | CN |
| 2434 | 6-OMe | H | CN |
| 2435 | 6-OMe | 4-Me | CN |
| 2436 | 6-OMe | 4-CN | CN |
| 2437 | 6-OMe | 4-NO$_2$ | CN |
| 2438 | 6-OMe | 4-OMe | CN |
| 2439 | 6-OMe | 3-F | CN |
| 2440 | 6-OMe | 3-Cl | CN |
| 2441 | 6-OMe | 3-Br | CN |
| 2442 | 6-OMe | 3-Me | CN |
| 2443 | 6-OMe | 3-CN | CN |
| 2444 | 6-OMe | 3-NO$_2$ | CN |
| 2445 | 6-OMe | 3-OMe | CN |
| 2446 | 6-OMe | 2-F | CN |
| 2447 | 6-OMe | 2-Cl | CN |
| 2448 | 6-OMe | 2-Br | CN |
| 2449 | 6-OMe | 2-Me | CN |
| 2450 | 6-OMe | 2-CN | CN |
| 2451 | 6-OMe | 2-NO$_2$ | CN |
| 2452 | 6-OMe | 2-OMe | CN |
| 2453 | 6-OMe | 2,3-F$_2$ | CN |
| 2454 | 6-OMe | 2,4-F$_2$ | CN |
| 2455 | 6-OMe | 2,5-F$_2$ | CN |
| 2456 | 6-OMe | 2,6-F$_2$ | CN |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2457 | 6-OMe | 3,4-$F_2$ | CN |
| 2458 | 6-OMe | 3,5-$F_2$ | CN |
| 2459 | 6-OMe | 2,3-$Cl_2$ | CN |
| 2460 | 6-OMe | 2,4-$Cl_2$ | CN |
| 2461 | 6-OMe | 2,5-$Cl_2$ | CN |
| 2462 | 6-OMe | 2,6-$Cl_2$ | CN |
| 2463 | 6-OMe | 3,4-$Cl_2$ | CN |
| 2464 | 6-OMe | 3,5-$Cl_2$ | CN |
| 2465 | 6-OMe | 2-F, 3-Cl | CN |
| 2466 | 6-OMe | 2-F, 4-Cl | CN |
| 2467 | 6-OMe | 2-F, 5-Cl | CN |
| 2468 | 6-OMe | 2-F, 6-Cl | CN |
| 2469 | 6-OMe | 2,6-$F_2$, 4-Cl | CN |
| 2470 | 6-OMe | 3-F, 4-Cl | CN |
| 2471 | 6-OMe | 3-Cl, 5-F | CN |
| 2472 | 6-OMe | 2-Cl, 5-F | CN |
| 2473 | 6-OMe | 3-CN, 4-Cl | CN |
| 2474 | 6-OMe | 3-$NO_2$, 4-Cl | CN |
| 2475 | 6-OMe | 2-F, 4-Br | CN |
| 2476 | 2-F | 4-F | CN |
| 2477 | 2-F | 4-Cl | CN |
| 2478 | 2-F | 4-Br | CN |
| 2479 | 2-F | H | CN |
| 2480 | 2-F | 4-Me | CN |
| 2481 | 2-F | 4-CN | CN |
| 2482 | 2-F | 4-$NO_2$ | CN |
| 2483 | 2-F | 4-OMe | CN |
| 2484 | 2-F | 3-F | CN |
| 2485 | 2-F | 3-Cl | CN |
| 2486 | 2-F | 3-Br | CN |
| 2487 | 2-F | 3-Me | CN |
| 2488 | 2-F | 3-CN | CN |
| 2489 | 2-F | 3-$NO_2$ | CN |
| 2490 | 2-F | 3-OMe | CN |
| 2491 | 2-F | 2-F | CN |
| 2492 | 2-F | 2-Cl | CN |
| 2493 | 2-F | 2-Br | CN |
| 2494 | 2-F | 2-Me | CN |
| 2495 | 2-F | 2-CN | CN |
| 2496 | 2-F | 2-$NO_2$ | CN |
| 2497 | 2-F | 2-OMe | CN |
| 2498 | 2-F | 2,3-$F_2$ | CN |
| 2499 | 2-F | 2,4-$F_2$ | CN |
| 2500 | 2-F | 2,5-$F_2$ | CN |
| 2501 | 2-F | 2,6-$F_2$ | CN |
| 2502 | 2-F | 3,4-$F_2$ | CN |
| 2503 | 2-F | 3,5-$F_2$ | CN |
| 2504 | 2-F | 2,3-$Cl_2$ | CN |
| 2505 | 2-F | 2,4-$Cl_2$ | CN |
| 2506 | 2-F | 2,5-$Cl_2$ | CN |
| 2507 | 2-F | 2,6-$Cl_2$ | CN |
| 2508 | 2-F | 3,4-$Cl_2$ | CN |
| 2509 | 2-F | 3,5-$Cl_2$ | CN |
| 2510 | 2-F | 2-F, 3-Cl | CN |
| 2511 | 2-F | 2-F, 4-Cl | CN |
| 2512 | 2-F | 2-F, 5-Cl | CN |
| 2513 | 2-F | 2-F, 6-Cl | CN |
| 2514 | 2-F | 2,6-$F_2$, 4-Cl | CN |
| 2515 | 2-F | 3-F, 4-Cl | CN |
| 2516 | 2-F | 3-Cl, 5-F | CN |
| 2517 | 2-F | 2-Cl, 5-F | CN |
| 2518 | 2-F | 3-CN, 4-Cl | CN |
| 2519 | 2-F | 3-$NO_2$, 4-Cl | CN |
| 2520 | 2-F | 2-F, 4-Br | CN |
| 2521 | 4-F | 4-F | CN |
| 2522 | 4-F | 4-Cl | CN |
| 2523 | 4-F | 4-Br | CN |
| 2524 | 4-F | H | CN |
| 2525 | 4-F | 4-Me | CN |
| 2526 | 4-F | 4-CN | CN |
| 2527 | 4-F | 4-$NO_2$ | CN |
| 2528 | 4-F | 4-OMe | CN |
| 2529 | 4-F | 3-F | CN |
| 2530 | 4-F | 3-Cl | CN |
| 2531 | 4-F | 3-Br | CN |
| 2532 | 4-F | 3-Me | CN |
| 2533 | 4-F | 3-CN | CN |
| 2534 | 4-F | 3-$NO_2$ | CN |
| 2535 | 4-F | 3-OMe | CN |
| 2536 | 4-F | 2-F | CN |
| 2537 | 4-F | 2-Cl | CN |
| 2538 | 4-F | 2-Br | CN |
| 2539 | 4-F | 2-Me | CN |
| 2540 | 4-F | 2-CN | CN |
| 2541 | 4-F | 2-$NO_2$ | CN |
| 2542 | 4-F | 2-OMe | CN |
| 2543 | 4-F | 2,3-$F_2$ | CN |
| 2544 | 4-F | 2,4-$F_2$ | CN |
| 2545 | 4-F | 2,5-$F_2$ | CN |
| 2546 | 4-F | 2,6-$F_2$ | CN |
| 2547 | 4-F | 3,4-$F_2$ | CN |
| 2548 | 4-F | 3,5-$F_2$ | CN |
| 2549 | 4-F | 2,3-$Cl_2$ | CN |
| 2550 | 4-F | 2,4-$Cl_2$ | CN |
| 2551 | 4-F | 2,5-$Cl_2$ | CN |
| 2552 | 4-F | 2,6-$Cl_2$ | CN |
| 2553 | 4-F | 3,4-$Cl_2$ | CN |
| 2554 | 4-F | 3,5-$Cl_2$ | CN |
| 2555 | 4-F | 2-F, 3-Cl | CN |
| 2556 | 4-F | 2-F, 4-Cl | CN |
| 2557 | 4-F | 2-F, 5-Cl | CN |
| 2558 | 4-F | 2-F, 6-Cl | CN |
| 2559 | 4-F | 2,6-$F_2$, 4-Cl | CN |
| 2560 | 4-F | 3-F, 4-Cl | CN |
| 2561 | 4-F | 3-Cl, 5-F | CN |
| 2562 | 4-F | 2-Cl, 5-F | CN |
| 2563 | 4-F | 3-CN, 4-Cl | CN |
| 2564 | 4-F | 3-$NO_2$, 4-Cl | CN |
| 2565 | 4-F | 2-F, 4-Br | CN |
| 2566 | 2-Cl | 4-F | CN |
| 2567 | 2-Cl | 4-Cl | CN |
| 2568 | 2-Cl | 4-Br | CN |
| 2569 | 2-Cl | H | CN |
| 2570 | 2-Cl | 4-Me | CN |
| 2571 | 2-Cl | 4-CN | CN |
| 2572 | 2-Cl | 4-$NO_2$ | CN |
| 2573 | 2-Cl | 4-OMe | CN |
| 2574 | 2-Cl | 3-F | CN |
| 2575 | 2-Cl | 3-Cl | CN |
| 2576 | 2-Cl | 3-Br | CN |
| 2577 | 2-Cl | 3-Me | CN |
| 2578 | 2-Cl | 3-CN | CN |
| 2579 | 2-Cl | 3-$NO_2$ | CN |
| 2580 | 2-Cl | 3-OMe | CN |
| 2581 | 2-Cl | 2-F | CN |
| 2582 | 2-Cl | 2-Cl | CN |
| 2583 | 2-Cl | 2-Br | CN |
| 2584 | 2-Cl | 2-Me | CN |
| 2585 | 2-Cl | 2-CN | CN |
| 2586 | 2-Cl | 2-$NO_2$ | CN |
| 2587 | 2-Cl | 2-OMe | CN |
| 2588 | 2-Cl | 2,3-$F_2$ | CN |
| 2589 | 2-Cl | 2,4-$F_2$ | CN |
| 2590 | 2-Cl | 2,5-$F_2$ | CN |
| 2591 | 2-Cl | 2,6-$F_2$ | CN |
| 2592 | 2-Cl | 3,4-$F_2$ | CN |
| 2593 | 2-Cl | 3,5-$F_2$ | CN |
| 2594 | 2-Cl | 2,3-$Cl_2$ | CN |
| 2595 | 2-Cl | 2,4-$Cl_2$ | CN |
| 2596 | 2-Cl | 2,5-$Cl_2$ | CN |
| 2597 | 2-Cl | 2,6-$Cl_2$ | CN |
| 2598 | 2-Cl | 3,4-$Cl_2$ | CN |
| 2599 | 2-Cl | 3,5-$Cl_2$ | CN |
| 2600 | 2-Cl | 2-F, 3-Cl | CN |
| 2601 | 2-Cl | 2-F, 4-Cl | CN |
| 2602 | 2-Cl | 2-F, 5-Cl | CN |
| 2603 | 2-Cl | 2-F, 6-Cl | CN |
| 2604 | 2-Cl | 2,6-$F_2$, 4-Cl | CN |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2605 | 2-Cl | 3-F, 4-Cl | CN |
| 2606 | 2-Cl | 3-Cl, 5-F | CN |
| 2607 | 2-Cl | 2-Cl, 5-F | CN |
| 2608 | 2-Cl | 3-CN, 4-Cl | CN |
| 2609 | 2-Cl | 3-$NO_2$, 4-Cl | CN |
| 2610 | 2-Cl | 2-F, 4-Br | CN |
| 2611 | 4-Cl | 4-F | CN |
| 2612 | 4-Cl | 4-Cl | CN |
| 2613 | 4-Cl | 4-Br | CN |
| 2614 | 4-Cl | H | CN |
| 2615 | 4-Cl | 4-Me | CN |
| 2616 | 4-Cl | 4-CN | CN |
| 2617 | 4-Cl | 4-$NO_2$ | CN |
| 2618 | 4-Cl | 4-OMe | CN |
| 2619 | 4-Cl | 3-F | CN |
| 2620 | 4-Cl | 3-Cl | CN |
| 2621 | 4-Cl | 3-Br | CN |
| 2622 | 4-Cl | 3-Me | CN |
| 2623 | 4-Cl | 3-CN | CN |
| 2624 | 4-Cl | 3-$NO_2$ | CN |
| 2625 | 4-Cl | 3-OMe | CN |
| 2626 | 4-Cl | 2-F | CN |
| 2627 | 4-Cl | 2-Cl | CN |
| 2628 | 4-Cl | 2-Br | CN |
| 2629 | 4-Cl | 2-Me | CN |
| 2630 | 4-Cl | 2-CN | CN |
| 2631 | 4-Cl | 2-$NO_2$ | CN |
| 2632 | 4-Cl | 2-OMe | CN |
| 2633 | 4-Cl | 2,3-$F_2$ | CN |
| 2634 | 4-Cl | 2,4-$F_2$ | CN |
| 2635 | 4-Cl | 2,5-$F_2$ | CN |
| 2636 | 4-Cl | 2,6-$F_2$ | CN |
| 2637 | 4-Cl | 3,4-$F_2$ | CN |
| 2638 | 4-Cl | 3,5-$F_2$ | CN |
| 2639 | 4-Cl | 2,3-$Cl_2$ | CN |
| 2640 | 4-Cl | 2,4-$Cl_2$ | CN |
| 2641 | 4-Cl | 2,5-$Cl_2$ | CN |
| 2642 | 4-Cl | 2,6-$Cl_2$ | CN |
| 2643 | 4-Cl | 3,4-$Cl_2$ | CN |
| 2644 | 4-Cl | 3,5-$Cl_2$ | CN |
| 2645 | 4-Cl | 2-F, 3-Cl | CN |
| 2646 | 4-Cl | 2-F, 4-Cl | CN |
| 2647 | 4-Cl | 2-F, 5-Cl | CN |
| 2648 | 4-Cl | 2-F, 6-Cl | CN |
| 2649 | 4-Cl | 2,6-$F_2$, 4-Cl | CN |
| 2650 | 4-Cl | 3-F, 4-Cl | CN |
| 2651 | 4-Cl | 3-Cl, 5-F | CN |
| 2652 | 4-Cl | 2-Cl, 5-F | CN |
| 2653 | 4-Cl | 3-CN, 4-Cl | CN |
| 2654 | 4-Cl | 3-$NO_2$, 4-Cl | CN |
| 2655 | 4-Cl | 2-F, 4-Br | CN |
| 2656 | 6-$OCF_2H$ | 4-F | CN |
| 2657 | 6-$OCF_2H$ | 4-Cl | CN |
| 2658 | 6-$OCF_2H$ | 4-Br | CN |
| 2659 | 6-$OCF_2H$ | H | CN |
| 2660 | 6-$OCF_2H$ | 4-Me | CN |
| 2661 | 6-$OCF_2H$ | 4-CN | CN |
| 2662 | 6-$OCF_2H$ | 4-$NO_2$ | CN |
| 2663 | 6-$OCF_2H$ | 4-OMe | CN |
| 2664 | 6-$OCF_2H$ | 3-F | CN |
| 2665 | 6-$OCF_2H$ | 3-Cl | CN |
| 2666 | 6-$OCF_2H$ | 3-Br | CN |
| 2667 | 6-$OCF_2H$ | 3-Me | CN |
| 2668 | 6-$OCF_2H$ | 3-CN | CN |
| 2669 | 6-$OCF_2H$ | 3-$NO_2$ | CN |
| 2670 | 6-$OCF_2H$ | 3-OMe | CN |
| 2671 | 6-$OCF_2H$ | 2-F | CN |
| 2672 | 6-$OCF_2H$ | 2-Cl | CN |
| 2673 | 6-$OCF_2H$ | 2-Br | CN |
| 2674 | 6-$OCF_2H$ | 2-Me | CN |
| 2675 | 6-$OCF_2H$ | 2-CN | CN |
| 2676 | 6-$OCF_2H$ | 2-$NO_2$ | CN |
| 2677 | 6-$OCF_2H$ | 2-OMe | CN |
| 2678 | 6-$OCF_2H$ | 2,3-$F_2$ | CN |
| 2679 | 6-$OCF_2H$ | 2,4-$F_2$ | CN |
| 2680 | 6-$OCF_2H$ | 2,5-$F_2$ | CN |
| 2681 | 6-$OCF_2H$ | 2,6-$F_2$ | CN |
| 2682 | 6-$OCF_2H$ | 3,4-$F_2$ | CN |
| 2683 | 6-$OCF_2H$ | 3,5-$F_2$ | CN |
| 2684 | 6-$OCF_2H$ | 2,3-$Cl_2$ | CN |
| 2685 | 6-$OCF_2H$ | 2,4-$Cl_2$ | CN |
| 2686 | 6-$OCF_2H$ | 2,5-$Cl_2$ | CN |
| 2687 | 6-$OCF_2H$ | 2,6-$Cl_2$ | CN |
| 2688 | 6-$OCF_2H$ | 3,4-$Cl_2$ | CN |
| 2689 | 6-$OCF_2H$ | 3,5-$Cl_2$ | CN |
| 2690 | 6-$OCF_2H$ | 2-F, 3-Cl | CN |
| 2691 | 6-$OCF_2H$ | 2-F, 4-Cl | CN |
| 2692 | 6-$OCF_2H$ | 2-F, 5-Cl | CN |
| 2693 | 6-$OCF_2H$ | 2-F, 6-Cl | CN |
| 2694 | 6-$OCF_2H$ | 2,6-$F_2$, 4-Cl | CN |
| 2695 | 6-$OCF_2H$ | 3-F, 4-Cl | CN |
| 2696 | 6-$OCF_2H$ | 3-Cl, 5-F | CN |
| 2697 | 6-$OCF_2H$ | 2-Cl, 5-F | CN |
| 2698 | 6-$OCF_2H$ | 3-CN, 4-Cl | CN |
| 2699 | 6-$OCF_2H$ | 3-$NO_2$, 4-Cl | CN |
| 2700 | 6-$OCF_2H$ | 2-F, 4-Br | CN |
| 2701 | H | 4-F | $NO_2$ |
| 2702 | H | 4-Cl | $NO_2$ |
| 2703 | H | 4-Br | $NO_2$ |
| 2704 | H | H | $NO_2$ |
| 2705 | H | 4-Me | $NO_2$ |
| 2706 | H | 4-CN | $NO_2$ |
| 2707 | H | 4-$NO_2$ | $NO_2$ |
| 2708 | H | 4-OMe | $NO_2$ |
| 2709 | H | 3-F | $NO_2$ |
| 2710 | H | 3-Cl | $NO_2$ |
| 2711 | H | 3-Br | $NO_2$ |
| 2712 | H | 3-Me | $NO_2$ |
| 2713 | H | 3-CN | $NO_2$ |
| 2714 | H | 3-$NO_2$ | $NO_2$ |
| 2715 | H | 3-OMe | $NO_2$ |
| 2716 | H | 2-F | $NO_2$ |
| 2717 | H | 2-Cl | $NO_2$ |
| 2718 | H | 2-Br | $NO_2$ |
| 2719 | H | 2-Me | $NO_2$ |
| 2720 | H | 2-CN | $NO_2$ |
| 2721 | H | 2-$NO_2$ | $NO_2$ |
| 2722 | H | 2-OMe | $NO_2$ |
| 2723 | H | 2,3-$F_2$ | $NO_2$ |
| 2724 | H | 2,4-$F_2$ | $NO_2$ |
| 2725 | H | 2,5-$F_2$ | $NO_2$ |
| 2726 | H | 2,6-$F_2$ | $NO_2$ |
| 2727 | H | 3,4-$F_2$ | $NO_2$ |
| 2728 | H | 3,5-$F_2$ | $NO_2$ |
| 2729 | H | 2,3-$Cl_2$ | $NO_2$ |
| 2730 | H | 2,4-$Cl_2$ | $NO_2$ |
| 2731 | H | 2,5-$Cl_2$ | $NO_2$ |
| 2732 | H | 2,6-$Cl_2$ | $NO_2$ |
| 2733 | H | 3,4-$Cl_2$ | $NO_2$ |
| 2734 | H | 3,5-$Cl_2$ | $NO_2$ |
| 2735 | H | 2-F, 3-Cl | $NO_2$ |
| 2736 | H | 2-F, 4-Cl | $NO_2$ |
| 2737 | H | 2-F, 5-Cl | $NO_2$ |
| 2738 | H | 2-F, 6-Cl | $NO_2$ |
| 2739 | H | 2,6-$F_2$, 4-Cl | $NO_2$ |
| 2740 | H | 3-F, 4-Cl | $NO_2$ |
| 2741 | H | 3-Cl, 5-F | $NO_2$ |
| 2742 | H | 2-Cl, 5-F | $NO_2$ |
| 2743 | H | 3-CN, 4-Cl | $NO_2$ |
| 2744 | H | 3-$NO_2$, 4-Cl | $NO_2$ |
| 2745 | H | 2-F, 4-Br | $NO_2$ |
| 2746 | 6-F | 4-F | $NO_2$ |
| 2747 | 6-F | 4-Cl | $NO_2$ |
| 2748 | 6-F | 4-Br | $NO_2$ |
| 2749 | 6-F | H | $NO_2$ |
| 2750 | 6-F | 4-Me | $NO_2$ |
| 2751 | 6-F | 4-CN | $NO_2$ |
| 2752 | 6-F | 4-$NO_2$ | $NO_2$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2753 | 6-F | 4-OMe | $NO_2$ |
| 2754 | 6-F | 3-F | $NO_2$ |
| 2755 | 6-F | 3-Cl | $NO_2$ |
| 2756 | 6-F | 3-Br | $NO_2$ |
| 2757 | 6-F | 3-Me | $NO_2$ |
| 2758 | 6-F | 3-CN | $NO_2$ |
| 2759 | 6-F | 3-$NO_2$ | $NO_2$ |
| 2760 | 6-F | 3-OMe | $NO_2$ |
| 2761 | 6-F | 2-F | $NO_2$ |
| 2762 | 6-F | 2-Cl | $NO_2$ |
| 2763 | 6-F | 2-Br | $NO_2$ |
| 2764 | 6-F | 2-Me | $NO_2$ |
| 2765 | 6-F | 2-CN | $NO_2$ |
| 2766 | 6-F | 2-$NO_2$ | $NO_2$ |
| 2767 | 6-F | 2-OMe | $NO_2$ |
| 2768 | 6-F | 2,3-$F_2$ | $NO_2$ |
| 2769 | 6-F | 2,4-$F_2$ | $NO_2$ |
| 2770 | 6-F | 2,5-$F_2$ | $NO_2$ |
| 2771 | 6-F | 2,6-$F_2$ | $NO_2$ |
| 2772 | 6-F | 3,4-$F_2$ | $NO_2$ |
| 2773 | 6-F | 3,5-$F_2$ | $NO_2$ |
| 2774 | 6-F | 2,3-$Cl_2$ | $NO_2$ |
| 2775 | 6-F | 2,4-$Cl_2$ | $NO_2$ |
| 2776 | 6-F | 2,5-$Cl_2$ | $NO_2$ |
| 2777 | 6-F | 2,6-$Cl_2$ | $NO_2$ |
| 2778 | 6-F | 3,4-$Cl_2$ | $NO_2$ |
| 2779 | 6-F | 3,5-$Cl_2$ | $NO_2$ |
| 2780 | 6-F | 2-F, 3-Cl | $NO_2$ |
| 2781 | 6-F | 2-F, 4-Cl | $NO_2$ |
| 2782 | 6-F | 2-F, 5-Cl | $NO_2$ |
| 2783 | 6-F | 2-F, 6-Cl | $NO_2$ |
| 2784 | 6-F | 2,6-$F_2$, 4-Cl | $NO_2$ |
| 2785 | 6-F | 3-F, 4-Cl | $NO_2$ |
| 2786 | 6-F | 3-Cl, 5-F | $NO_2$ |
| 2787 | 6-F | 2-Cl, 5-F | $NO_2$ |
| 2788 | 6-F | 3-CN, 4-Cl | $NO_2$ |
| 2789 | 6-F | 3-$NO_2$, 4-Cl | $NO_2$ |
| 2790 | 6-F | 2-F, 4-Br | $NO_2$ |
| 2791 | 6-Cl | 4-F | $NO_2$ |
| 2792 | 6-Cl | 4-Cl | $NO_2$ |
| 2793 | 6-Cl | 4-Br | $NO_2$ |
| 2794 | 6-Cl | H | $NO_2$ |
| 2795 | 6-Cl | 4-Me | $NO_2$ |
| 2796 | 6-Cl | 4-CN | $NO_2$ |
| 2797 | 6-Cl | 4-$NO_2$ | $NO_2$ |
| 2798 | 6-Cl | 4-OMe | $NO_2$ |
| 2799 | 6-Cl | 3-F | $NO_2$ |
| 2800 | 6-Cl | 3-Cl | $NO_2$ |
| 2801 | 6-Cl | 3-Br | $NO_2$ |
| 2802 | 6-Cl | 3-Me | $NO_2$ |
| 2803 | 6-Cl | 3-CN | $NO_2$ |
| 2804 | 6-Cl | 3-$NO_2$ | $NO_2$ |
| 2805 | 6-Cl | 3-OMe | $NO_2$ |
| 2806 | 6-Cl | 2-F | $NO_2$ |
| 2807 | 6-Cl | 2-Cl | $NO_2$ |
| 2808 | 6-Cl | 2-Br | $NO_2$ |
| 2809 | 6-Cl | 2-Me | $NO_2$ |
| 2810 | 6-Cl | 2-CN | $NO_2$ |
| 2811 | 6-Cl | 2-$NO_2$ | $NO_2$ |
| 2812 | 6-Cl | 2-OMe | $NO_2$ |
| 2813 | 6-Cl | 2,3-$F_2$ | $NO_2$ |
| 2814 | 6-Cl | 2,4-$F_2$ | $NO_2$ |
| 2815 | 6-Cl | 2,5-$F_2$ | $NO_2$ |
| 2816 | 6-Cl | 2,6-$F_2$ | $NO_2$ |
| 2817 | 6-Cl | 3,4-$F_2$ | $NO_2$ |
| 2818 | 6-Cl | 3,5-$F_2$ | $NO_2$ |
| 2819 | 6-Cl | 2,3-$Cl_2$ | $NO_2$ |
| 2820 | 6-Cl | 2,4-$Cl_2$ | $NO_2$ |
| 2821 | 6-Cl | 2,5-$Cl_2$ | $NO_2$ |
| 2822 | 6-Cl | 2,6-$Cl_2$ | $NO_2$ |
| 2823 | 6-Cl | 3,4-$Cl_2$ | $NO_2$ |
| 2824 | 6-Cl | 3,5-$Cl_2$ | $NO_2$ |
| 2825 | 6-Cl | 2-F, 3-Cl | $NO_2$ |
| 2826 | 6-Cl | 2-F, 4-Cl | $NO_2$ |
| 2827 | 6-Cl | 2-F, 5-Cl | $NO_2$ |
| 2828 | 6-Cl | 2-F, 6-Cl | $NO_2$ |
| 2829 | 6-Cl | 2,6-$F_2$, 4-Cl | $NO_2$ |
| 2830 | 6-Cl | 3-F, 4-Cl | $NO_2$ |
| 2831 | 6-Cl | 3-Cl, 5-F | $NO_2$ |
| 2832 | 6-Cl | 2-Cl, 5-F | $NO_2$ |
| 2833 | 6-Cl | 3-CN, 4-Cl | $NO_2$ |
| 2834 | 6-Cl | 3-$NO_2$, 4-Cl | $NO_2$ |
| 2835 | 6-Cl | 2-F, 4-Br | $NO_2$ |
| 2836 | 6-Br | 4-F | $NO_2$ |
| 2837 | 6-Br | 4-Cl | $NO_2$ |
| 2838 | 6-Br | 4-Br | $NO_2$ |
| 2839 | 6-Br | H | $NO_2$ |
| 2840 | 6-Br | 4-Me | $NO_2$ |
| 2841 | 6-Br | 4-CN | $NO_2$ |
| 2842 | 6-Br | 4-$NO_2$ | $NO_2$ |
| 2843 | 6-Br | 4-OMe | $NO_2$ |
| 2844 | 6-Br | 3-F | $NO_2$ |
| 2845 | 6-Br | 3-Cl | $NO_2$ |
| 2846 | 6-Br | 3-Br | $NO_2$ |
| 2847 | 6-Br | 3-Me | $NO_2$ |
| 2848 | 6-Br | 3-CN | $NO_2$ |
| 2849 | 6-Br | 3-$NO_2$ | $NO_2$ |
| 2850 | 6-Br | 3-OMe | $NO_2$ |
| 2851 | 6-Br | 2-F | $NO_2$ |
| 2852 | 6-Br | 2-Cl | $NO_2$ |
| 2853 | 6-Br | 2-Br | $NO_2$ |
| 2854 | 6-Br | 2-Me | $NO_2$ |
| 2855 | 6-Br | 2-CN | $NO_2$ |
| 2856 | 6-Br | 2-$NO_2$ | $NO_2$ |
| 2857 | 6-Br | 2-OMe | $NO_2$ |
| 2858 | 6-Br | 2,3-$F_2$ | $NO_2$ |
| 2859 | 6-Br | 2,4-$F_2$ | $NO_2$ |
| 2860 | 6-Br | 2,5-$F_2$ | $NO_2$ |
| 2861 | 6-Br | 2,6-$F_2$ | $NO_2$ |
| 2862 | 6-Br | 3,4-$F_2$ | $NO_2$ |
| 2863 | 6-Br | 3,5-$F_2$ | $NO_2$ |
| 2864 | 6-Br | 2,3-$Cl_2$ | $NO_2$ |
| 2865 | 6-Br | 2,4-$Cl_2$ | $NO_2$ |
| 2866 | 6-Br | 2,5-$Cl_2$ | $NO_2$ |
| 2867 | 6-Br | 2,6-$Cl_2$ | $NO_2$ |
| 2868 | 6-Br | 3,4-$Cl_2$ | $NO_2$ |
| 2869 | 6-Br | 3,5-$Cl_2$ | $NO_2$ |
| 2870 | 6-Br | 2-F, 3-Cl | $NO_2$ |
| 2871 | 6-Br | 2-F, 4-Cl | $NO_2$ |
| 2872 | 6-Br | 2-F, 5-Cl | $NO_2$ |
| 2873 | 6-Br | 2-F, 6-Cl | $NO_2$ |
| 2874 | 6-Br | 2,6-$F_2$, 4-Cl | $NO_2$ |
| 2875 | 6-Br | 3-F, 4-Cl | $NO_2$ |
| 2876 | 6-Br | 3-Cl, 5-F | $NO_2$ |
| 2877 | 6-Br | 2-Cl, 5-F | $NO_2$ |
| 2878 | 6-Br | 3-CN, 4-Cl | $NO_2$ |
| 2879 | 6-Br | 3-$NO_2$, 4-Cl | $NO_2$ |
| 2880 | 6-Br | 2-F, 4-Br | $NO_2$ |
| 2881 | 6-CN | 4-F | $NO_2$ |
| 2882 | 6-CN | 4-Cl | $NO_2$ |
| 2883 | 6-CN | 4-Br | $NO_2$ |
| 2884 | 6-CN | H | $NO_2$ |
| 2885 | 6-CN | 4-Me | $NO_2$ |
| 2886 | 6-CN | 4-CN | $NO_2$ |
| 2887 | 6-CN | 4-$NO_2$ | $NO_2$ |
| 2888 | 6-CN | 4-OMe | $NO_2$ |
| 2889 | 6-CN | 3-F | $NO_2$ |
| 2890 | 6-CN | 3-Cl | $NO_2$ |
| 2891 | 6-CN | 3-Br | $NO_2$ |
| 2892 | 6-CN | 3-Me | $NO_2$ |
| 2893 | 6-CN | 3-CN | $NO_2$ |
| 2894 | 6-CN | 3-$NO_2$ | $NO_2$ |
| 2895 | 6-CN | 3-OMe | $NO_2$ |
| 2896 | 6-CN | 2-F | $NO_2$ |
| 2897 | 6-CN | 2-Cl | $NO_2$ |
| 2898 | 6-CN | 2-Br | $NO_2$ |
| 2899 | 6-CN | 2-Me | $NO_2$ |
| 2900 | 6-CN | 2-CN | $NO_2$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 2901 | 6-CN | 2-NO$_2$ | NO$_2$ |
| 2902 | 6-CN | 2-OMe | NO$_2$ |
| 2903 | 6-CN | 2,3-F$_2$ | NO$_2$ |
| 2904 | 6-CN | 2,4-F$_2$ | NO$_2$ |
| 2905 | 6-CN | 2,5-F$_2$ | NO$_2$ |
| 2906 | 6-CN | 2,6-F$_2$ | NO$_2$ |
| 2907 | 6-CN | 3,4-F$_2$ | NO$_2$ |
| 2908 | 6-CN | 3,5-F$_2$ | NO$_2$ |
| 2909 | 6-CN | 2,3-Cl$_2$ | NO$_2$ |
| 2910 | 6-CN | 2,4-Cl$_2$ | NO$_2$ |
| 2911 | 6-CN | 2,5-Cl$_2$ | NO$_2$ |
| 2912 | 6-CN | 2,6-Cl$_2$ | NO$_2$ |
| 2913 | 6-CN | 3,4-Cl$_2$ | NO$_2$ |
| 2914 | 6-CN | 3,5-Cl$_2$ | NO$_2$ |
| 2915 | 6-CN | 2-F, 3-Cl | NO$_2$ |
| 2916 | 6-CN | 2-F, 4-Cl | NO$_2$ |
| 2917 | 6-CN | 2-F, 5-Cl | NO$_2$ |
| 2918 | 6-CN | 2-F, 6-Cl | NO$_2$ |
| 2919 | 6-CN | 2,6-F$_2$, 4-Cl | NO$_2$ |
| 2920 | 6-CN | 3-F, 4-Cl | NO$_2$ |
| 2921 | 6-CN | 3-Cl, 5-F | NO$_2$ |
| 2922 | 6-CN | 2-Cl, 5-F | NO$_2$ |
| 2923 | 6-CN | 3-CN, 4-Cl | NO$_2$ |
| 2924 | 6-CN | 3-NO$_2$, 4-Cl | NO$_2$ |
| 2925 | 6-CN | 2-F, 4-Br | NO$_2$ |
| 2926 | 6-Me | 4-F | NO$_2$ |
| 2927 | 6-Me | 4-Cl | NO$_2$ |
| 2928 | 6-Me | 4-Br | NO$_2$ |
| 2929 | 6-Me | H | NO$_2$ |
| 2930 | 6-Me | 4-Me | NO$_2$ |
| 2931 | 6-Me | 4-CN | NO$_2$ |
| 2932 | 6-Me | 4-NO$_2$ | NO$_2$ |
| 2933 | 6-Me | 4-OMe | NO$_2$ |
| 2934 | 6-Me | 3-F | NO$_2$ |
| 2935 | 6-Me | 3-Cl | NO$_2$ |
| 2936 | 6-Me | 3-Br | NO$_2$ |
| 2937 | 6-Me | 3-Me | NO$_2$ |
| 2938 | 6-Me | 3-CN | NO$_2$ |
| 2939 | 6-Me | 3-NO$_2$ | NO$_2$ |
| 2940 | 6-Me | 3-OMe | NO$_2$ |
| 2941 | 6-Me | 2-F | NO$_2$ |
| 2942 | 6-Me | 2-Cl | NO$_2$ |
| 2943 | 6-Me | 2-Br | NO$_2$ |
| 2944 | 6-Me | 2-Me | NO$_2$ |
| 2945 | 6-Me | 2-CN | NO$_2$ |
| 2946 | 6-Me | 2-NO$_2$ | NO$_2$ |
| 2947 | 6-Me | 2-OMe | NO$_2$ |
| 2948 | 6-Me | 2,3-F$_2$ | NO$_2$ |
| 2949 | 6-Me | 2,4-F$_2$ | NO$_2$ |
| 2950 | 6-Me | 2,5-F$_2$ | NO$_2$ |
| 2951 | 6-Me | 2,6-F$_2$ | NO$_2$ |
| 2952 | 6-Me | 3,4-F$_2$ | NO$_2$ |
| 2953 | 6-Me | 3,5-F$_2$ | NO$_2$ |
| 2954 | 6-Me | 2,3-Cl$_2$ | NO$_2$ |
| 2955 | 6-Me | 2,4-Cl$_2$ | NO$_2$ |
| 2956 | 6-Me | 2,5-Cl$_2$ | NO$_2$ |
| 2957 | 6-Me | 2,6-Cl$_2$ | NO$_2$ |
| 2958 | 6-Me | 3,4-Cl$_2$ | NO$_2$ |
| 2959 | 6-Me | 3,5-Cl$_2$ | NO$_2$ |
| 2960 | 6-Me | 2-F, 3-Cl | NO$_2$ |
| 2961 | 6-Me | 2-F, 4-Cl | NO$_2$ |
| 2962 | 6-Me | 2-F, 5-Cl | NO$_2$ |
| 2963 | 6-Me | 2-F, 6-Cl | NO$_2$ |
| 2964 | 6-Me | 2,6-F$_2$, 4-Cl | NO$_2$ |
| 2965 | 6-Me | 3-F, 4-Cl | NO$_2$ |
| 2966 | 6-Me | 3-Cl, 5-F | NO$_2$ |
| 2967 | 6-Me | 2-Cl, 5-F | NO$_2$ |
| 2968 | 6-Me | 3-CN, 4-Cl | NO$_2$ |
| 2969 | 6-Me | 3-NO$_2$, 4-Cl | NO$_2$ |
| 2970 | 6-Me | 2-F, 4-Br | NO$_2$ |
| 2971 | 6-OMe | 4-F | NO$_2$ |
| 2972 | 6-OMe | 4-Cl | NO$_2$ |
| 2973 | 6-OMe | 4-Br | NO$_2$ |
| 2974 | 6-OMe | H | NO$_2$ |
| 2975 | 6-OMe | 4-Me | NO$_2$ |
| 2976 | 6-OMe | 4-CN | NO$_2$ |
| 2977 | 6-OMe | 4-NO$_2$ | NO$_2$ |
| 2978 | 6-OMe | 4-OMe | NO$_2$ |
| 2979 | 6-OMe | 3-F | NO$_2$ |
| 2980 | 6-OMe | 3-Cl | NO$_2$ |
| 2981 | 6-OMe | 3-Br | NO$_2$ |
| 2982 | 6-OMe | 3-Me | NO$_2$ |
| 2983 | 6-OMe | 3-CN | NO$_2$ |
| 2984 | 6-OMe | 3-NO$_2$ | NO$_2$ |
| 2985 | 6-OMe | 3-OMe | NO$_2$ |
| 2986 | 6-OMe | 2-F | NO$_2$ |
| 2987 | 6-OMe | 2-Cl | NO$_2$ |
| 2988 | 6-OMe | 2-Br | NO$_2$ |
| 2989 | 6-OMe | 2-Me | NO$_2$ |
| 2990 | 6-OMe | 2-CN | NO$_2$ |
| 2991 | 6-OMe | 2-NO$_2$ | NO$_2$ |
| 2992 | 6-OMe | 2-OMe | NO$_2$ |
| 2993 | 6-OMe | 2,3-F$_2$ | NO$_2$ |
| 2994 | 6-OMe | 2,4-F$_2$ | NO$_2$ |
| 2995 | 6-OMe | 2,5-F$_2$ | NO$_2$ |
| 2996 | 6-OMe | 2,6-F$_2$ | NO$_2$ |
| 2997 | 6-OMe | 3,4-F$_2$ | NO$_2$ |
| 2998 | 6-OMe | 3,5-F$_2$ | NO$_2$ |
| 2999 | 6-OMe | 2,3-Cl$_2$ | NO$_2$ |
| 3000 | 6-OMe | 2,4-Cl$_2$ | NO$_2$ |
| 3001 | 6-OMe | 2,5-Cl$_2$ | NO$_2$ |
| 3002 | 6-OMe | 2,6-Cl$_2$ | NO$_2$ |
| 3003 | 6-OMe | 3,4-Cl$_2$ | NO$_2$ |
| 3004 | 6-OMe | 3,5-Cl$_2$ | NO$_2$ |
| 3005 | 6-OMe | 2-F, 3-Cl | NO$_2$ |
| 3006 | 6-OMe | 2-F, 4-Cl | NO$_2$ |
| 3007 | 6-OMe | 2-F, 5-Cl | NO$_2$ |
| 3008 | 6-OMe | 2-F, 6-Cl | NO$_2$ |
| 3009 | 6-OMe | 2,6-F$_2$, 4-Cl | NO$_2$ |
| 3010 | 6-OMe | 3-F, 4-Cl | NO$_2$ |
| 3011 | 6-OMe | 3-Cl, 5-F | NO$_2$ |
| 3012 | 6-OMe | 2-Cl, 5-F | NO$_2$ |
| 3013 | 6-OMe | 3-CN, 4-Cl | NO$_2$ |
| 3014 | 6-OMe | 3-NO$_2$, 4-Cl | NO$_2$ |
| 3015 | 6-OMe | 2-F, 4-Br | NO$_2$ |
| 3016 | 2-F | 4-F | NO$_2$ |
| 3017 | 2-F | 4-Cl | NO$_2$ |
| 3018 | 2-F | 4-Br | NO$_2$ |
| 3019 | 2-F | H | NO$_2$ |
| 3020 | 2-F | 4-Me | NO$_2$ |
| 3021 | 2-F | 4-CN | NO$_2$ |
| 3022 | 2-F | 4-NO$_2$ | NO$_2$ |
| 3023 | 2-F | 4-OMe | NO$_2$ |
| 3024 | 2-F | 3-F | NO$_2$ |
| 3025 | 2-F | 3-Cl | NO$_2$ |
| 3026 | 2-F | 3-Br | NO$_2$ |
| 3027 | 2-F | 3-Me | NO$_2$ |
| 3028 | 2-F | 3-CN | NO$_2$ |
| 3029 | 2-F | 3-NO$_2$ | NO$_2$ |
| 3030 | 2-F | 3-OMe | NO$_2$ |
| 3031 | 2-F | 2-F | NO$_2$ |
| 3032 | 2-F | 2-Cl | NO$_2$ |
| 3033 | 2-F | 2-Br | NO$_2$ |
| 3034 | 2-F | 2-Me | NO$_2$ |
| 3035 | 2-F | 2-CN | NO$_2$ |
| 3036 | 2-F | 2-NO$_2$ | NO$_2$ |
| 3037 | 2-F | 2-OMe | NO$_2$ |
| 3038 | 2-F | 2,3-F$_2$ | NO$_2$ |
| 3039 | 2-F | 2,4-F$_2$ | NO$_2$ |
| 3040 | 2-F | 2,5-F$_2$ | NO$_2$ |
| 3041 | 2-F | 2,6-F$_2$ | NO$_2$ |
| 3042 | 2-F | 3,4-F$_2$ | NO$_2$ |
| 3043 | 2-F | 3,5-F$_2$ | NO$_2$ |
| 3044 | 2-F | 2,3-Cl$_2$ | NO$_2$ |
| 3045 | 2-F | 2,4-Cl$_2$ | NO$_2$ |
| 3046 | 2-F | 2,5-Cl$_2$ | NO$_2$ |
| 3047 | 2-F | 2,6-Cl$_2$ | NO$_2$ |
| 3048 | 2-F | 3,4-Cl$_2$ | NO$_2$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3049 | 2-F | 3,5-Cl$_2$ | NO$_2$ |
| 3050 | 2-F | 2-F, 3-Cl | NO$_2$ |
| 3051 | 2-F | 2-F, 4-Cl | NO$_2$ |
| 3052 | 2-F | 2-F, 5-Cl | NO$_2$ |
| 3053 | 2-F | 2-F, 6-Cl | NO$_2$ |
| 3054 | 2-F | 2,6-F$_2$, 4-Cl | NO$_2$ |
| 3055 | 2-F | 3-F, 4-Cl | NO$_2$ |
| 3056 | 2-F | 3-Cl, 5-F | NO$_2$ |
| 3057 | 2-F | 2-Cl, 5-F | NO$_2$ |
| 3058 | 2-F | 3-CN, 4-Cl | NO$_2$ |
| 3059 | 2-F | 3-NO$_2$, 4-Cl | NO$_2$ |
| 3060 | 2-F | 2-F, 4-Br | NO$_2$ |
| 3061 | 4-F | 4-F | NO$_2$ |
| 3062 | 4-F | 4-Cl | NO$_2$ |
| 3063 | 4-F | 4-Br | NO$_2$ |
| 3064 | 4-F | H | NO$_2$ |
| 3065 | 4-F | 4-Me | NO$_2$ |
| 3066 | 4-F | 4-CN | NO$_2$ |
| 3067 | 4-F | 4-NO$_2$ | NO$_2$ |
| 3068 | 4-F | 4-OMe | NO$_2$ |
| 3069 | 4-F | 3-F | NO$_2$ |
| 3070 | 4-F | 3-Cl | NO$_2$ |
| 3071 | 4-F | 3-Br | NO$_2$ |
| 3072 | 4-F | 3-Me | NO$_2$ |
| 3073 | 4-F | 3-CN | NO$_2$ |
| 3074 | 4-F | 3-NO$_2$ | NO$_2$ |
| 3075 | 4-F | 3-OMe | NO$_2$ |
| 3076 | 4-F | 2-F | NO$_2$ |
| 3077 | 4-F | 2-Cl | NO$_2$ |
| 3078 | 4-F | 2-Br | NO$_2$ |
| 3079 | 4-F | 2-Me | NO$_2$ |
| 3080 | 4-F | 2-CN | NO$_2$ |
| 3081 | 4-F | 2-NO$_2$ | NO$_2$ |
| 3082 | 4-F | 2-OMe | NO$_2$ |
| 3083 | 4-F | 2,3-F$_2$ | NO$_2$ |
| 3084 | 4-F | 2,4-F$_2$ | NO$_2$ |
| 3085 | 4-F | 2,5-F$_2$ | NO$_2$ |
| 3086 | 4-F | 2,6-F$_2$ | NO$_2$ |
| 3087 | 4-F | 3,4-F$_2$ | NO$_2$ |
| 3088 | 4-F | 3,5-F$_2$ | NO$_2$ |
| 3089 | 4-F | 2,3-Cl$_2$ | NO$_2$ |
| 3090 | 4-F | 2,4-Cl$_2$ | NO$_2$ |
| 3091 | 4-F | 2,5-Cl$_2$ | NO$_2$ |
| 3092 | 4-F | 2,6-Cl$_2$ | NO$_2$ |
| 3093 | 4-F | 3,4-Cl$_2$ | NO$_2$ |
| 3094 | 4-F | 3,5-Cl$_2$ | NO$_2$ |
| 3095 | 4-F | 2-F, 3-Cl | NO$_2$ |
| 3096 | 4-F | 2-F, 4-Cl | NO$_2$ |
| 3097 | 4-F | 2-F, 5-Cl | NO$_2$ |
| 3098 | 4-F | 2-F, 6-Cl | NO$_2$ |
| 3099 | 4-F | 2,6-F$_2$, 4-Cl | NO$_2$ |
| 3100 | 4-F | 3-F, 4-Cl | NO$_2$ |
| 3101 | 4-F | 3-Cl, 5-F | NO$_2$ |
| 3102 | 4-F | 2-Cl, 5-F | NO$_2$ |
| 3103 | 4-F | 3-CN, 4-Cl | NO$_2$ |
| 3104 | 4-F | 3-NO$_2$, 4-Cl | NO$_2$ |
| 3105 | 4-F | 2-F, 4-Br | NO$_2$ |
| 3106 | 2-Cl | 4-F | NO$_2$ |
| 3107 | 2-Cl | 4-Cl | NO$_2$ |
| 3108 | 2-Cl | 4-Br | NO$_2$ |
| 3109 | 2-Cl | H | NO$_2$ |
| 3110 | 2-Cl | 4-Me | NO$_2$ |
| 3111 | 2-Cl | 4-CN | NO$_2$ |
| 3112 | 2-Cl | 4-NO$_2$ | NO$_2$ |
| 3113 | 2-Cl | 4-OMe | NO$_2$ |
| 3114 | 2-Cl | 3-F | NO$_2$ |
| 3115 | 2-Cl | 3-Cl | NO$_2$ |
| 3116 | 2-Cl | 3-Br | NO$_2$ |
| 3117 | 2-Cl | 3-Me | NO$_2$ |
| 3118 | 2-Cl | 3-CN | NO$_2$ |
| 3119 | 2-Cl | 3-NO$_2$ | NO$_2$ |
| 3120 | 2-Cl | 3-OMe | NO$_2$ |
| 3121 | 2-Cl | 2-F | NO$_2$ |
| 3122 | 2-Cl | 2-Cl | NO$_2$ |
| 3123 | 2-Cl | 2-Br | NO$_2$ |
| 3124 | 2-Cl | 2-Me | NO$_2$ |
| 3125 | 2-Cl | 2-CN | NO$_2$ |
| 3126 | 2-Cl | 2-NO$_2$ | NO$_2$ |
| 3127 | 2-Cl | 2-OMe | NO$_2$ |
| 3128 | 2-Cl | 2,3-F$_2$ | NO$_2$ |
| 3129 | 2-Cl | 2,4-F$_2$ | NO$_2$ |
| 3130 | 2-Cl | 2,5-F$_2$ | NO$_2$ |
| 3131 | 2-Cl | 2,6-F$_2$ | NO$_2$ |
| 3132 | 2-Cl | 3,4-F$_2$ | NO$_2$ |
| 3133 | 2-Cl | 3,5-F$_2$ | NO$_2$ |
| 3134 | 2-Cl | 2,3-Cl$_2$ | NO$_2$ |
| 3135 | 2-Cl | 2,4-Cl$_2$ | NO$_2$ |
| 3136 | 2-Cl | 2,5-Cl$_2$ | NO$_2$ |
| 3137 | 2-Cl | 2,6-Cl$_2$ | NO$_2$ |
| 3138 | 2-Cl | 3,4-Cl$_2$ | NO$_2$ |
| 3139 | 2-Cl | 3,5-Cl$_2$ | NO$_2$ |
| 3140 | 2-Cl | 2-F, 3-Cl | NO$_2$ |
| 3141 | 2-Cl | 2-F, 4-Cl | NO$_2$ |
| 3142 | 2-Cl | 2-F, 5-Cl | NO$_2$ |
| 3143 | 2-Cl | 2-F, 6-Cl | NO$_2$ |
| 3144 | 2-Cl | 2,6-F$_2$, 4-Cl | NO$_2$ |
| 3145 | 2-Cl | 3-F, 4-Cl | NO$_2$ |
| 3146 | 2-Cl | 3-Cl, 5-F | NO$_2$ |
| 3147 | 2-Cl | 2-Cl, 5-F | NO$_2$ |
| 3148 | 2-Cl | 3-CN, 4-Cl | NO$_2$ |
| 3149 | 2-Cl | 3-NO$_2$, 4-Cl | NO$_2$ |
| 3150 | 2-Cl | 2-F, 4-Br | NO$_2$ |
| 3151 | 4-Cl | 4-F | NO$_2$ |
| 3152 | 4-Cl | 4-Cl | NO$_2$ |
| 3153 | 4-Cl | 4-Br | NO$_2$ |
| 3154 | 4-Cl | H | NO$_2$ |
| 3155 | 4-Cl | 4-Me | NO$_2$ |
| 3156 | 4-Cl | 4-CN | NO$_2$ |
| 3157 | 4-Cl | 4-NO$_2$ | NO$_2$ |
| 3158 | 4-Cl | 4-OMe | NO$_2$ |
| 3159 | 4-Cl | 3-F | NO$_2$ |
| 3160 | 4-Cl | 3-Cl | NO$_2$ |
| 3161 | 4-Cl | 3-Br | NO$_2$ |
| 3162 | 4-Cl | 3-Me | NO$_2$ |
| 3163 | 4-Cl | 3-CN | NO$_2$ |
| 3164 | 4-Cl | 3-NO$_2$ | NO$_2$ |
| 3165 | 4-Cl | 3-OMe | NO$_2$ |
| 3166 | 4-Cl | 2-F | NO$_2$ |
| 3167 | 4-Cl | 2-Cl | NO$_2$ |
| 3168 | 4-Cl | 2-Br | NO$_2$ |
| 3169 | 4-Cl | 2-Me | NO$_2$ |
| 3170 | 4-Cl | 2-CN | NO$_2$ |
| 3171 | 4-Cl | 2-NO$_2$ | NO$_2$ |
| 3172 | 4-Cl | 2-OMe | NO$_2$ |
| 3173 | 4-Cl | 2,3-F$_2$ | NO$_2$ |
| 3174 | 4-Cl | 2,4-F$_2$ | NO$_2$ |
| 3175 | 4-Cl | 2,5-F$_2$ | NO$_2$ |
| 3176 | 4-Cl | 2,6-F$_2$ | NO$_2$ |
| 3177 | 4-Cl | 3,4-F$_2$ | NO$_2$ |
| 3178 | 4-Cl | 3,5-F$_2$ | NO$_2$ |
| 3179 | 4-Cl | 2,3-Cl$_2$ | NO$_2$ |
| 3180 | 4-Cl | 2,4-Cl$_2$ | NO$_2$ |
| 3181 | 4-Cl | 2,5-Cl$_2$ | NO$_2$ |
| 3182 | 4-Cl | 2,6-Cl$_2$ | NO$_2$ |
| 3183 | 4-Cl | 3,4-Cl$_2$ | NO$_2$ |
| 3184 | 4-Cl | 3,5-Cl$_2$ | NO$_2$ |
| 3185 | 4-Cl | 2-F, 3-Cl | NO$_2$ |
| 3186 | 4-Cl | 2-F, 4-Cl | NO$_2$ |
| 3187 | 4-Cl | 2-F, 5-Cl | NO$_2$ |
| 3188 | 4-Cl | 2-F, 6-Cl | NO$_2$ |
| 3189 | 4-Cl | 2,6-F$_2$, 4-Cl | NO$_2$ |
| 3190 | 4-Cl | 3-F, 4-Cl | NO$_2$ |
| 3191 | 4-Cl | 3-Cl, 5-F | NO$_2$ |
| 3192 | 4-Cl | 2-Cl, 5-F | NO$_2$ |
| 3193 | 4-Cl | 3-CN, 4-Cl | NO$_2$ |
| 3194 | 4-Cl | 3-NO$_2$, 4-Cl | NO$_2$ |
| 3195 | 4-Cl | 2-F, 4-Br | NO$_2$ |
| 3196 | 6-OCF$_2$H | 4-F | NO$_2$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3197 | 6-OCF$_2$H | 4-Cl | NO$_2$ |
| 3198 | 6-OCF$_2$H | 4-Br | NO$_2$ |
| 3199 | 6-OCF$_2$H | H | NO$_2$ |
| 3200 | 6-OCF$_2$H | 4-Me | NO$_2$ |
| 3201 | 6-OCF$_2$H | 4-CN | NO$_2$ |
| 3202 | 6-OCF$_2$H | 4-NO$_2$ | NO$_2$ |
| 3203 | 6-OCF$_2$H | 4-OMe | NO$_2$ |
| 3204 | 6-OCF$_2$H | 3-F | NO$_2$ |
| 3205 | 6-OCF$_2$H | 3-Cl | NO$_2$ |
| 3206 | 6-OCF$_2$H | 3-Br | NO$_2$ |
| 3207 | 6-OCF$_2$H | 3-Me | NO$_2$ |
| 3208 | 6-OCF$_2$H | 3-CN | NO$_2$ |
| 3209 | 6-OCF$_2$H | 3-NO$_2$ | NO$_2$ |
| 3210 | 6-OCF$_2$H | 3-OMe | NO$_2$ |
| 3211 | 6-OCF$_2$H | 2-F | NO$_2$ |
| 3212 | 6-OCF$_2$H | 2-Cl | NO$_2$ |
| 3213 | 6-OCF$_2$H | 2-Br | NO$_2$ |
| 3214 | 6-OCF$_2$H | 2-Me | NO$_2$ |
| 3215 | 6-OCF$_2$H | 2-CN | NO$_2$ |
| 3216 | 6-OCF$_2$H | 2-NO$_2$ | NO$_2$ |
| 3217 | 6-OCF$_2$H | 2-OMe | NO$_2$ |
| 3218 | 6-OCF$_2$H | 2,3-F$_2$ | NO$_2$ |
| 3219 | 6-OCF$_2$H | 2,4-F$_2$ | NO$_2$ |
| 3220 | 6-OCF$_2$H | 2,5-F$_2$ | NO$_2$ |
| 3221 | 6-OCF$_2$H | 2,6-F$_2$ | NO$_2$ |
| 3222 | 6-OCF$_2$H | 3,4-F$_2$ | NO$_2$ |
| 3223 | 6-OCF$_2$H | 3,5-F$_2$ | NO$_2$ |
| 3224 | 6-OCF$_2$H | 2,3-Cl$_2$ | NO$_2$ |
| 3225 | 6-OCF$_2$H | 2,4-Cl$_2$ | NO$_2$ |
| 3226 | 6-OCF$_2$H | 2,5-Cl$_2$ | NO$_2$ |
| 3227 | 6-OCF$_2$H | 2,6-Cl$_2$ | NO$_2$ |
| 3228 | 6-OCF$_2$H | 3,4-Cl$_2$ | NO$_2$ |
| 3229 | 6-OCF$_2$H | 3,5-Cl$_2$ | NO$_2$ |
| 3230 | 6-OCF$_2$H | 2-F, 3-Cl | NO$_2$ |
| 3231 | 6-OCF$_2$H | 2-F, 4-Cl | NO$_2$ |
| 3232 | 6-OCF$_2$H | 2-F, 5-Cl | NO$_2$ |
| 3233 | 6-OCF$_2$H | 2-F, 6-Cl | NO$_2$ |
| 3234 | 6-OCF$_2$H | 2,6-F$_2$, 4-Cl | NO$_2$ |
| 3235 | 6-OCF$_2$H | 3-F, 4-Cl | NO$_2$ |
| 3236 | 6-OCF$_2$H | 3-Cl, 5-F | NO$_2$ |
| 3237 | 6-OCF$_2$H | 2-Cl, 5-F | NO$_2$ |
| 3238 | 6-OCF$_2$H | 3-CN, 4-Cl | NO$_2$ |
| 3239 | 6-OCF$_2$H | 3-NO$_2$, 4-Cl | NO$_2$ |
| 3240 | 6-OCF$_2$H | 2-F, 4-Br | NO$_2$ |
| 3241 | H | 4-F | CO$_2$Me |
| 3242 | H | 4-Cl | CO$_2$Me |
| 3243 | H | 4-Br | CO$_2$Me |
| 3244 | H | H | CO$_2$Me |
| 3245 | H | 4-Me | CO$_2$Me |
| 3246 | H | 4-CN | CO$_2$Me |
| 3247 | H | 4-NO$_2$ | CO$_2$Me |
| 3248 | H | 4-OMe | CO$_2$Me |
| 3249 | H | 3-F | CO$_2$Me |
| 3250 | H | 3-Cl | CO$_2$Me |
| 3251 | H | 3-Br | CO$_2$Me |
| 3252 | H | 3-Me | CO$_2$Me |
| 3253 | H | 3-CN | CO$_2$Me |
| 3254 | H | 3-NO$_2$ | CO$_2$Me |
| 3255 | H | 3-OMe | CO$_2$Me |
| 3256 | H | 2-F | CO$_2$Me |
| 3257 | H | 2-Cl | CO$_2$Me |
| 3258 | H | 2-Br | CO$_2$Me |
| 3259 | H | 2-Me | CO$_2$Me |
| 3260 | H | 2-CN | CO$_2$Me |
| 3261 | H | 2-NO$_2$ | CO$_2$Me |
| 3262 | H | 2-OMe | CO$_2$Me |
| 3263 | H | 2,3-F$_2$ | CO$_2$Me |
| 3264 | H | 2,4-F$_2$ | CO$_2$Me |
| 3265 | H | 2,5-F$_2$ | CO$_2$Me |
| 3266 | H | 2,6-F$_2$ | CO$_2$Me |
| 3267 | H | 3,4-F$_2$ | CO$_2$Me |
| 3268 | H | 3,5-F$_2$ | CO$_2$Me |
| 3269 | H | 2,3-Cl$_2$ | CO$_2$Me |
| 3270 | H | 2,4-Cl$_2$ | CO$_2$Me |
| 3271 | H | 2,5-Cl$_2$ | CO$_2$Me |
| 3272 | H | 2,6-Cl$_2$ | CO$_2$Me |
| 3273 | H | 3,4-Cl$_2$ | CO$_2$Me |
| 3274 | H | 3,5-Cl$_2$ | CO$_2$Me |
| 3275 | H | 2-F, 3-Cl | CO$_2$Me |
| 3276 | H | 2-F, 4-Cl | CO$_2$Me |
| 3277 | H | 2-F, 5-Cl | CO$_2$Me |
| 3278 | H | 2-F, 6-Cl | CO$_2$Me |
| 3279 | H | 2,6-F$_2$, 4-Cl | CO$_2$Me |
| 3280 | H | 3-F, 4-Cl | CO$_2$Me |
| 3281 | H | 3-Cl, 5-F | CO$_2$Me |
| 3282 | H | 2-Cl, 5-F | CO$_2$Me |
| 3283 | H | 3-CN, 4-Cl | CO$_2$Me |
| 3284 | H | 3-NO$_2$, 4-Cl | CO$_2$Me |
| 3285 | H | 2-F, 4-Br | CO$_2$Me |
| 3286 | 6-F | 4-F | CO$_2$Me |
| 3287 | 6-F | 4-Cl | CO$_2$Me |
| 3288 | 6-F | 4-Br | CO$_2$Me |
| 3289 | 6-F | H | CO$_2$Me |
| 3290 | 6-F | 4-Me | CO$_2$Me |
| 3291 | 6-F | 4-CN | CO$_2$Me |
| 3292 | 6-F | 4-NO$_2$ | CO$_2$Me |
| 3293 | 6-F | 4-OMe | CO$_2$Me |
| 3294 | 6-F | 3-F | CO$_2$Me |
| 3295 | 6-F | 3-Cl | CO$_2$Me |
| 3296 | 6-F | 3-Br | CO$_2$Me |
| 3297 | 6-F | 3-Me | CO$_2$Me |
| 3298 | 6-F | 3-CN | CO$_2$Me |
| 3299 | 6-F | 3-NO$_2$ | CO$_2$Me |
| 3300 | 6-F | 3-OMe | CO$_2$Me |
| 3301 | 6-F | 2-F | CO$_2$Me |
| 3302 | 6-F | 2-Cl | CO$_2$Me |
| 3303 | 6-F | 2-Br | CO$_2$Me |
| 3304 | 6-F | 2-Me | CO$_2$Me |
| 3305 | 6-F | 2-CN | CO$_2$Me |
| 3306 | 6-F | 2-NO$_2$ | CO$_2$Me |
| 3307 | 6-F | 2-OMe | CO$_2$Me |
| 3308 | 6-F | 2,3-F$_2$ | CO$_2$Me |
| 3309 | 6-F | 2,4-F$_2$ | CO$_2$Me |
| 3310 | 6-F | 2,5-F$_2$ | CO$_2$Me |
| 3311 | 6-F | 2,6-F$_2$ | CO$_2$Me |
| 3312 | 6-F | 3,4-F$_2$ | CO$_2$Me |
| 3313 | 6-F | 3,5-F$_2$ | CO$_2$Me |
| 3314 | 6-F | 2,3-Cl$_2$ | CO$_2$Me |
| 3315 | 6-F | 2,4-Cl$_2$ | CO$_2$Me |
| 3316 | 6-F | 2,5-Cl$_2$ | CO$_2$Me |
| 3317 | 6-F | 2,6-Cl$_2$ | CO$_2$Me |
| 3318 | 6-F | 3,4-Cl$_2$ | CO$_2$Me |
| 3319 | 6-F | 3,5-Cl$_2$ | CO$_2$Me |
| 3320 | 6-F | 2-F, 3-Cl | CO$_2$Me |
| 3321 | 6-F | 2-F, 4-Cl | CO$_2$Me |
| 3322 | 6-F | 2-F, 5-Cl | CO$_2$Me |
| 3323 | 6-F | 2-F, 6-Cl | CO$_2$Me |
| 3324 | 6-F | 2,6-F$_2$, 4-Cl | CO$_2$Me |
| 3325 | 6-F | 3-F, 4-Cl | CO$_2$Me |
| 3326 | 6-F | 3-Cl, 5-F | CO$_2$Me |
| 3327 | 6-F | 2-Cl, 5-F | CO$_2$Me |
| 3328 | 6-F | 3-CN, 4-Cl | CO$_2$Me |
| 3329 | 6-F | 3-NO$_2$, 4-Cl | CO$_2$Me |
| 3330 | 6-F | 2-F, 4-Br | CO$_2$Me |
| 3331 | 6-Cl | 4-F | CO$_2$Me |
| 3332 | 6-Cl | 4-Cl | CO$_2$Me |
| 3333 | 6-Cl | 4-Br | CO$_2$Me |
| 3334 | 6-Cl | H | CO$_2$Me |
| 3335 | 6-Cl | 4-Me | CO$_2$Me |
| 3336 | 6-Cl | 4-CN | CO$_2$Me |
| 3337 | 6-Cl | 4-NO$_2$ | CO$_2$Me |
| 3338 | 6-Cl | 4-OMe | CO$_2$Me |
| 3339 | 6-Cl | 3-F | CO$_2$Me |
| 3340 | 6-Cl | 3-Cl | CO$_2$Me |
| 3341 | 6-Cl | 3-Br | CO$_2$Me |
| 3342 | 6-Cl | 3-Me | CO$_2$Me |
| 3343 | 6-Cl | 3-CN | CO$_2$Me |
| 3344 | 6-Cl | 3-NO$_2$ | CO$_2$Me |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3345 | 6-Cl | 3-OMe | $CO_2Me$ |
| 3346 | 6-Cl | 2-F | $CO_2Me$ |
| 3347 | 6-Cl | 2-Cl | $CO_2Me$ |
| 3348 | 6-Cl | 2-Br | $CO_2Me$ |
| 3349 | 6-Cl | 2-Me | $CO_2Me$ |
| 3350 | 6-Cl | 2-CN | $CO_2Me$ |
| 3351 | 6-Cl | 2-$NO_2$ | $CO_2Me$ |
| 3352 | 6-Cl | 2-OMe | $CO_2Me$ |
| 3353 | 6-Cl | 2,3-$F_2$ | $CO_2Me$ |
| 3354 | 6-Cl | 2,4-$F_2$ | $CO_2Me$ |
| 3355 | 6-Cl | 2,5-$F_2$ | $CO_2Me$ |
| 3356 | 6-Cl | 2,6-$F_2$ | $CO_2Me$ |
| 3357 | 6-Cl | 3,4-$F_2$ | $CO_2Me$ |
| 3358 | 6-Cl | 3,5-$F_2$ | $CO_2Me$ |
| 3359 | 6-Cl | 2,3-$Cl_2$ | $CO_2Me$ |
| 3360 | 6-Cl | 2,4-$Cl_2$ | $CO_2Me$ |
| 3361 | 6-Cl | 2,5-$Cl_2$ | $CO_2Me$ |
| 3362 | 6-Cl | 2,6-$Cl_2$ | $CO_2Me$ |
| 3363 | 6-Cl | 3,4-$Cl_2$ | $CO_2Me$ |
| 3364 | 6-Cl | 3,5-$Cl_2$ | $CO_2Me$ |
| 3365 | 6-Cl | 2-F, 3-Cl | $CO_2Me$ |
| 3366 | 6-Cl | 2-F, 4-Cl | $CO_2Me$ |
| 3367 | 6-Cl | 2-F, 5-Cl | $CO_2Me$ |
| 3368 | 6-Cl | 2-F, 6-Cl | $CO_2Me$ |
| 3369 | 6-Cl | 2,6-$F_2$, 4-Cl | $CO_2Me$ |
| 3370 | 6-Cl | 3-F, 4-Cl | $CO_2Me$ |
| 3371 | 6-Cl | 3-Cl, 5-F | $CO_2Me$ |
| 3372 | 6-Cl | 2-Cl, 5-F | $CO_2Me$ |
| 3373 | 6-Cl | 3-CN, 4-Cl | $CO_2Me$ |
| 3374 | 6-Cl | 3-$NO_2$, 4-Cl | $CO_2Me$ |
| 3375 | 6-Cl | 2-F, 4-Br | $CO_2Me$ |
| 3376 | 6-Br | 4-F | $CO_2Me$ |
| 3377 | 6-Br | 4-Cl | $CO_2Me$ |
| 3378 | 6-Br | 4-Br | $CO_2Me$ |
| 3379 | 6-Br | H | $CO_2Me$ |
| 3380 | 6-Br | 4-Me | $CO_2Me$ |
| 3381 | 6-Br | 4-CN | $CO_2Me$ |
| 3382 | 6-Br | 4-$NO_2$ | $CO_2Me$ |
| 3383 | 6-Br | 4-OMe | $CO_2Me$ |
| 3384 | 6-Br | 3-F | $CO_2Me$ |
| 3385 | 6-Br | 3-Cl | $CO_2Me$ |
| 3386 | 6-Br | 3-Br | $CO_2Me$ |
| 3387 | 6-Br | 3-Me | $CO_2Me$ |
| 3388 | 6-Br | 3-CN | $CO_2Me$ |
| 3389 | 6-Br | 3-$NO_2$ | $CO_2Me$ |
| 3390 | 6-Br | 3-OMe | $CO_2Me$ |
| 3391 | 6-Br | 2-F | $CO_2Me$ |
| 3392 | 6-Br | 2-Cl | $CO_2Me$ |
| 3393 | 6-Br | 2-Br | $CO_2Me$ |
| 3394 | 6-Br | 2-Me | $CO_2Me$ |
| 3395 | 6-Br | 2-CN | $CO_2Me$ |
| 3396 | 6-Br | 2-$NO_2$ | $CO_2Me$ |
| 3397 | 6-Br | 2-OMe | $CO_2Me$ |
| 3398 | 6-Br | 2,3-$F_2$ | $CO_2Me$ |
| 3399 | 6-Br | 2,4-$F_2$ | $CO_2Me$ |
| 3400 | 6-Br | 2,5-$F_2$ | $CO_2Me$ |
| 3401 | 6-Br | 2,6-$F_2$ | $CO_2Me$ |
| 3402 | 6-Br | 3,4-$F_2$ | $CO_2Me$ |
| 3403 | 6-Br | 3,5-$F_2$ | $CO_2Me$ |
| 3404 | 6-Br | 2,3-$Cl_2$ | $CO_2Me$ |
| 3405 | 6-Br | 2,4-$Cl_2$ | $CO_2Me$ |
| 3406 | 6-Br | 2,5-$Cl_2$ | $CO_2Me$ |
| 3407 | 6-Br | 2,6-$Cl_2$ | $CO_2Me$ |
| 3408 | 6-Br | 3,4-$Cl_2$ | $CO_2Me$ |
| 3409 | 6-Br | 3,5-$Cl_2$ | $CO_2Me$ |
| 3410 | 6-Br | 2-F, 3-Cl | $CO_2Me$ |
| 3411 | 6-Br | 2-F, 4-Cl | $CO_2Me$ |
| 3412 | 6-Br | 2-F, 5-Cl | $CO_2Me$ |
| 3413 | 6-Br | 2-F, 6-Cl | $CO_2Me$ |
| 3414 | 6-Br | 2,6-$F_2$, 4-Cl | $CO_2Me$ |
| 3415 | 6-Br | 3-F, 4-Cl | $CO_2Me$ |
| 3416 | 6-Br | 3-Cl, 5-F | $CO_2Me$ |
| 3417 | 6-Br | 2-Cl, 5-F | $CO_2Me$ |
| 3418 | 6-Br | 3-CN, 4-Cl | $CO_2Me$ |
| 3419 | 6-Br | 3-$NO_2$, 4-Cl | $CO_2Me$ |
| 3420 | 6-Br | 2-F, 4-Br | $CO_2Me$ |
| 3421 | 6-CN | 4-F | $CO_2Me$ |
| 3422 | 6-CN | 4-Cl | $CO_2Me$ |
| 3423 | 6-CN | 4-Br | $CO_2Me$ |
| 3424 | 6-CN | H | $CO_2Me$ |
| 3425 | 6-CN | 4-Me | $CO_2Me$ |
| 3426 | 6-CN | 4-CN | $CO_2Me$ |
| 3427 | 6-CN | 4-$NO_2$ | $CO_2Me$ |
| 3428 | 6-CN | 4-OMe | $CO_2Me$ |
| 3429 | 6-CN | 3-F | $CO_2Me$ |
| 3430 | 6-CN | 3-Cl | $CO_2Me$ |
| 3431 | 6-CN | 3-Br | $CO_2Me$ |
| 3432 | 6-CN | 3-Me | $CO_2Me$ |
| 3433 | 6-CN | 3-CN | $CO_2Me$ |
| 3434 | 6-CN | 3-$NO_2$ | $CO_2Me$ |
| 3435 | 6-CN | 3-OMe | $CO_2Me$ |
| 3436 | 6-CN | 2-F | $CO_2Me$ |
| 3437 | 6-CN | 2-Cl | $CO_2Me$ |
| 3438 | 6-CN | 2-Br | $CO_2Me$ |
| 3439 | 6-CN | 2-Me | $CO_2Me$ |
| 3440 | 6-CN | 2-CN | $CO_2Me$ |
| 3441 | 6-CN | 2-$NO_2$ | $CO_2Me$ |
| 3442 | 6-CN | 2-OMe | $CO_2Me$ |
| 3443 | 6-CN | 2,3-$F_2$ | $CO_2Me$ |
| 3444 | 6-CN | 2,4-$F_2$ | $CO_2Me$ |
| 3445 | 6-CN | 2,5-$F_2$ | $CO_2Me$ |
| 3446 | 6-CN | 2,6-$F_2$ | $CO_2Me$ |
| 3447 | 6-CN | 3,4-$F_2$ | $CO_2Me$ |
| 3448 | 6-CN | 3,5-$F_2$ | $CO_2Me$ |
| 3449 | 6-CN | 2,3-$Cl_2$ | $CO_2Me$ |
| 3450 | 6-CN | 2,4-$Cl_2$ | $CO_2Me$ |
| 3451 | 6-CN | 2,5-$Cl_2$ | $CO_2Me$ |
| 3452 | 6-CN | 2,6-$Cl_2$ | $CO_2Me$ |
| 3453 | 6-CN | 3,4-$Cl_2$ | $CO_2Me$ |
| 3454 | 6-CN | 3,5-$Cl_2$ | $CO_2Me$ |
| 3455 | 6-CN | 2-F, 3-Cl | $CO_2Me$ |
| 3456 | 6-CN | 2-F, 4-Cl | $CO_2Me$ |
| 3457 | 6-CN | 2-F, 5-Cl | $CO_2Me$ |
| 3458 | 6-CN | 2-F, 6-Cl | $CO_2Me$ |
| 3459 | 6-CN | 2,6-$F_2$, 4-Cl | $CO_2Me$ |
| 3460 | 6-CN | 3-F, 4-Cl | $CO_2Me$ |
| 3461 | 6-CN | 3-Cl, 5-F | $CO_2Me$ |
| 3462 | 6-CN | 2-Cl, 5-F | $CO_2Me$ |
| 3463 | 6-CN | 3-CN, 4-Cl | $CO_2Me$ |
| 3464 | 6-CN | 3-$NO_2$, 4-Cl | $CO_2Me$ |
| 3465 | 6-CN | 2-F, 4-Br | $CO_2Me$ |
| 3466 | 6-Me | 4-F | $CO_2Me$ |
| 3467 | 6-Me | 4-Cl | $CO_2Me$ |
| 3468 | 6-Me | 4-Br | $CO_2Me$ |
| 3469 | 6-Me | H | $CO_2Me$ |
| 3470 | 6-Me | 4-Me | $CO_2Me$ |
| 3471 | 6-Me | 4-CN | $CO_2Me$ |
| 3472 | 6-Me | 4-$NO_2$ | $CO_2Me$ |
| 3473 | 6-Me | 4-OMe | $CO_2Me$ |
| 3474 | 6-Me | 3-F | $CO_2Me$ |
| 3475 | 6-Me | 3-Cl | $CO_2Me$ |
| 3476 | 6-Me | 3-Br | $CO_2Me$ |
| 3477 | 6-Me | 3-Me | $CO_2Me$ |
| 3478 | 6-Me | 3-CN | $CO_2Me$ |
| 3479 | 6-Me | 3-$NO_2$ | $CO_2Me$ |
| 3480 | 6-Me | 3-OMe | $CO_2Me$ |
| 3481 | 6-Me | 2-F | $CO_2Me$ |
| 3482 | 6-Me | 2-Cl | $CO_2Me$ |
| 3483 | 6-Me | 2-Br | $CO_2Me$ |
| 3484 | 6-Me | 2-Me | $CO_2Me$ |
| 3485 | 6-Me | 2-CN | $CO_2Me$ |
| 3486 | 6-Me | 2-$NO_2$ | $CO_2Me$ |
| 3487 | 6-Me | 2-OMe | $CO_2Me$ |
| 3488 | 6-Me | 2,3-$F_2$ | $CO_2Me$ |
| 3489 | 6-Me | 2,4-$F_2$ | $CO_2Me$ |
| 3490 | 6-Me | 2,5-$F_2$ | $CO_2Me$ |
| 3491 | 6-Me | 2,6-$F_2$ | $CO_2Me$ |
| 3492 | 6-Me | 3,4-$F_2$ | $CO_2Me$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3493 | 6-Me | 3,5-$F_2$ | $CO_2Me$ |
| 3494 | 6-Me | 2,3-$Cl_2$ | $CO_2Me$ |
| 3495 | 6-Me | 2,4-$Cl_2$ | $CO_2Me$ |
| 3496 | 6-Me | 2,5-$Cl_2$ | $CO_2Me$ |
| 3497 | 6-Me | 2,6-$Cl_2$ | $CO_2Me$ |
| 3498 | 6-Me | 3,4-$Cl_2$ | $CO_2Me$ |
| 3499 | 6-Me | 3,5-$Cl_2$ | $CO_2Me$ |
| 3500 | 6-Me | 2-F, 3-Cl | $CO_2Me$ |
| 3501 | 6-Me | 2-F, 4-Cl | $CO_2Me$ |
| 3502 | 6-Me | 2-F, 5-Cl | $CO_2Me$ |
| 3503 | 6-Me | 2-F, 6-Cl | $CO_2Me$ |
| 3504 | 6-Me | 2,6-$F_2$, 4-Cl | $CO_2Me$ |
| 3505 | 6-Me | 3-F, 4-Cl | $CO_2Me$ |
| 3506 | 6-Me | 3-Cl, 5-F | $CO_2Me$ |
| 3507 | 6-Me | 2-Cl, 5-F | $CO_2Me$ |
| 3508 | 6-Me | 3-CN, 4-Cl | $CO_2Me$ |
| 3509 | 6-Me | 3-$NO_2$, 4-Cl | $CO_2Me$ |
| 3510 | 6-Me | 2-F, 4-Br | $CO_2Me$ |
| 3511 | 6-OMe | 4-F | $CO_2Me$ |
| 3512 | 6-OMe | 4-Cl | $CO_2Me$ |
| 3513 | 6-OMe | 4-Br | $CO_2Me$ |
| 3514 | 6-OMe | H | $CO_2Me$ |
| 3515 | 6-OMe | 4-Me | $CO_2Me$ |
| 3516 | 6-OMe | 4-CN | $CO_2Me$ |
| 3517 | 6-OMe | 4-$NO_2$ | $CO_2Me$ |
| 3518 | 6-OMe | 4-OMe | $CO_2Me$ |
| 3519 | 6-OMe | 3-F | $CO_2Me$ |
| 3520 | 6-OMe | 3-Cl | $CO_2Me$ |
| 3521 | 6-OMe | 3-Br | $CO_2Me$ |
| 3522 | 6-OMe | 3-Me | $CO_2Me$ |
| 3523 | 6-OMe | 3-CN | $CO_2Me$ |
| 3524 | 6-OMe | 3-$NO_2$ | $CO_2Me$ |
| 3525 | 6-OMe | 3-OMe | $CO_2Me$ |
| 3526 | 6-OMe | 2-F | $CO_2Me$ |
| 3527 | 6-OMe | 2-Cl | $CO_2Me$ |
| 3528 | 6-OMe | 2-Br | $CO_2Me$ |
| 3529 | 6-OMe | 2-Me | $CO_2Me$ |
| 3530 | 6-OMe | 2-CN | $CO_2Me$ |
| 3531 | 6-OMe | 2-$NO_2$ | $CO_2Me$ |
| 3532 | 6-OMe | 2-OMe | $CO_2Me$ |
| 3533 | 6-OMe | 2,3-$F_2$ | $CO_2Me$ |
| 3534 | 6-OMe | 2,4-$F_2$ | $CO_2Me$ |
| 3535 | 6-OMe | 2,5-$F_2$ | $CO_2Me$ |
| 3536 | 6-OMe | 2,6-$F_2$ | $CO_2Me$ |
| 3537 | 6-OMe | 3,4-$F_2$ | $CO_2Me$ |
| 3538 | 6-OMe | 3,5-$F_2$ | $CO_2Me$ |
| 3539 | 6-OMe | 2,3-$Cl_2$ | $CO_2Me$ |
| 3540 | 6-OMe | 2,4-$Cl_2$ | $CO_2Me$ |
| 3541 | 6-OMe | 2,5-$Cl_2$ | $CO_2Me$ |
| 3542 | 6-OMe | 2,6-$Cl_2$ | $CO_2Me$ |
| 3543 | 6-OMe | 3,4-$Cl_2$ | $CO_2Me$ |
| 3544 | 6-OMe | 3,5-$Cl_2$ | $CO_2Me$ |
| 3545 | 6-OMe | 2-F, 3-Cl | $CO_2Me$ |
| 3546 | 6-OMe | 2-F, 4-Cl | $CO_2Me$ |
| 3547 | 6-OMe | 2-F, 5-Cl | $CO_2Me$ |
| 3548 | 6-OMe | 2-F, 6-Cl | $CO_2Me$ |
| 3549 | 6-OMe | 2,6-$F_2$, 4-Cl | $CO_2Me$ |
| 3550 | 6-OMe | 3-F, 4-Cl | $CO_2Me$ |
| 3551 | 6-OMe | 3-Cl, 5-F | $CO_2Me$ |
| 3552 | 6-OMe | 2-Cl, 5-F | $CO_2Me$ |
| 3553 | 6-OMe | 3-CN, 4-Cl | $CO_2Me$ |
| 3554 | 6-OMe | 3-$NO_2$, 4-Cl | $CO_2Me$ |
| 3555 | 6-OMe | 2-F, 4-Br | $CO_2Me$ |
| 3556 | 2-F | 4-F | $CO_2Me$ |
| 3557 | 2-F | 4-Cl | $CO_2Me$ |
| 3558 | 2-F | 4-Br | $CO_2Me$ |
| 3559 | 2-F | H | $CO_2Me$ |
| 3560 | 2-F | 4-Me | $CO_2Me$ |
| 3561 | 2-F | 4-CN | $CO_2Me$ |
| 3562 | 2-F | 4-$NO_2$ | $CO_2Me$ |
| 3563 | 2-F | 4-OMe | $CO_2Me$ |
| 3564 | 2-F | 3-F | $CO_2Me$ |
| 3565 | 2-F | 3-Cl | $CO_2Me$ |
| 3566 | 2-F | 3-Br | $CO_2Me$ |
| 3567 | 2-F | 3-Me | $CO_2Me$ |
| 3568 | 2-F | 3-CN | $CO_2Me$ |
| 3569 | 2-F | 3-$NO_2$ | $CO_2Me$ |
| 3570 | 2-F | 3-OMe | $CO_2Me$ |
| 3571 | 2-F | 2-F | $CO_2Me$ |
| 3572 | 2-F | 2-Cl | $CO_2Me$ |
| 3573 | 2-F | 2-Br | $CO_2Me$ |
| 3574 | 2-F | 2-Me | $CO_2Me$ |
| 3575 | 2-F | 2-CN | $CO_2Me$ |
| 3576 | 2-F | 2-$NO_2$ | $CO_2Me$ |
| 3577 | 2-F | 2-OMe | $CO_2Me$ |
| 3578 | 2-F | 2,3-$F_2$ | $CO_2Me$ |
| 3579 | 2-F | 2,4-$F_2$ | $CO_2Me$ |
| 3580 | 2-F | 2,5-$F_2$ | $CO_2Me$ |
| 3581 | 2-F | 2,6-$F_2$ | $CO_2Me$ |
| 3582 | 2-F | 3,4-$F_2$ | $CO_2Me$ |
| 3583 | 2-F | 3,5-$F_2$ | $CO_2Me$ |
| 3584 | 2-F | 2,3-$Cl_2$ | $CO_2Me$ |
| 3585 | 2-F | 2,4-$Cl_2$ | $CO_2Me$ |
| 3586 | 2-F | 2,5-$Cl_2$ | $CO_2Me$ |
| 3587 | 2-F | 2,6-$Cl_2$ | $CO_2Me$ |
| 3588 | 2-F | 3,4-$Cl_2$ | $CO_2Me$ |
| 3589 | 2-F | 3,5-$Cl_2$ | $CO_2Me$ |
| 3590 | 2-F | 2-F, 3-Cl | $CO_2Me$ |
| 3591 | 2-F | 2-F, 4-Cl | $CO_2Me$ |
| 3592 | 2-F | 2-F, 5-Cl | $CO_2Me$ |
| 3593 | 2-F | 2-F, 6-Cl | $CO_2Me$ |
| 3594 | 2-F | 2,6-$F_2$, 4-Cl | $CO_2Me$ |
| 3595 | 2-F | 3-F, 4-Cl | $CO_2Me$ |
| 3596 | 2-F | 3-Cl, 5-F | $CO_2Me$ |
| 3597 | 2-F | 2-Cl, 5-F | $CO_2Me$ |
| 3598 | 2-F | 3-CN, 4-Cl | $CO_2Me$ |
| 3599 | 2-F | 3-$NO_2$, 4-Cl | $CO_2Me$ |
| 3600 | 2-F | 2-F, 4-Br | $CO_2Me$ |
| 3601 | 4-F | 4-F | $CO_2Me$ |
| 3602 | 4-F | 4-Cl | $CO_2Me$ |
| 3603 | 4-F | 4-Br | $CO_2Me$ |
| 3604 | 4-F | H | $CO_2Me$ |
| 3605 | 4-F | 4-Me | $CO_2Me$ |
| 3606 | 4-F | 4-CN | $CO_2Me$ |
| 3607 | 4-F | 4-$NO_2$ | $CO_2Me$ |
| 3608 | 4-F | 4-OMe | $CO_2Me$ |
| 3609 | 4-F | 3-F | $CO_2Me$ |
| 3610 | 4-F | 3-Cl | $CO_2Me$ |
| 3611 | 4-F | 3-Br | $CO_2Me$ |
| 3612 | 4-F | 3-Me | $CO_2Me$ |
| 3613 | 4-F | 3-CN | $CO_2Me$ |
| 3614 | 4-F | 3-$NO_2$ | $CO_2Me$ |
| 3615 | 4-F | 3-OMe | $CO_2Me$ |
| 3616 | 4-F | 2-F | $CO_2Me$ |
| 3617 | 4-F | 2-Cl | $CO_2Me$ |
| 3618 | 4-F | 2-Br | $CO_2Me$ |
| 3619 | 4-F | 2-Me | $CO_2Me$ |
| 3620 | 4-F | 2-CN | $CO_2Me$ |
| 3621 | 4-F | 2-$NO_2$ | $CO_2Me$ |
| 3622 | 4-F | 2-OMe | $CO_2Me$ |
| 3623 | 4-F | 2,3-$F_2$ | $CO_2Me$ |
| 3624 | 4-F | 2,4-$F_2$ | $CO_2Me$ |
| 3625 | 4-F | 2,5-$F_2$ | $CO_2Me$ |
| 3626 | 4-F | 2,6-$F_2$ | $CO_2Me$ |
| 3627 | 4-F | 3,4-$F_2$ | $CO_2Me$ |
| 3628 | 4-F | 3,5-$F_2$ | $CO_2Me$ |
| 3629 | 4-F | 2,3-$Cl_2$ | $CO_2Me$ |
| 3630 | 4-F | 2,4-$Cl_2$ | $CO_2Me$ |
| 3631 | 4-F | 2,5-$Cl_2$ | $CO_2Me$ |
| 3632 | 4-F | 2,6-$Cl_2$ | $CO_2Me$ |
| 3633 | 4-F | 3,4-$Cl_2$ | $CO_2Me$ |
| 3634 | 4-F | 3,5-$Cl_2$ | $CO_2Me$ |
| 3635 | 4-F | 2-F, 3-Cl | $CO_2Me$ |
| 3636 | 4-F | 2-F, 4-Cl | $CO_2Me$ |
| 3637 | 4-F | 2-F, 5-Cl | $CO_2Me$ |
| 3638 | 4-F | 2-F, 6-Cl | $CO_2Me$ |
| 3639 | 4-F | 2,6-$F_2$, 4-Cl | $CO_2Me$ |
| 3640 | 4-F | 3-F, 4-Cl | $CO_2Me$ |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3641 | 4-F | 3-Cl, 5-F | $CO_2Me$ |
| 3642 | 4-F | 2-Cl, 5-F | $CO_2Me$ |
| 3643 | 4-F | 3-CN, 4-Cl | $CO_2Me$ |
| 3644 | 4-F | 3-$NO_2$, 4-Cl | $CO_2Me$ |
| 3645 | 4-F | 2-F, 4-Br | $CO_2Me$ |
| 3646 | 2-Cl | 4-F | $CO_2Me$ |
| 3647 | 2-Cl | 4-Cl | $CO_2Me$ |
| 3648 | 2-Cl | 4-Br | $CO_2Me$ |
| 3649 | 2-Cl | H | $CO_2Me$ |
| 3650 | 2-Cl | 4-Me | $CO_2Me$ |
| 3651 | 2-Cl | 4-CN | $CO_2Me$ |
| 3652 | 2-Cl | 4-$NO_2$ | $CO_2Me$ |
| 3653 | 2-Cl | 4-OMe | $CO_2Me$ |
| 3654 | 2-Cl | 3-F | $CO_2Me$ |
| 3655 | 2-Cl | 3-Cl | $CO_2Me$ |
| 3656 | 2-Cl | 3-Br | $CO_2Me$ |
| 3657 | 2-Cl | 3-Me | $CO_2Me$ |
| 3658 | 2-Cl | 3-CN | $CO_2Me$ |
| 3659 | 2-Cl | 3-$NO_2$ | $CO_2Me$ |
| 3660 | 2-Cl | 3-OMe | $CO_2Me$ |
| 3661 | 2-Cl | 2-F | $CO_2Me$ |
| 3662 | 2-Cl | 2-Cl | $CO_2Me$ |
| 3663 | 2-Cl | 2-Br | $CO_2Me$ |
| 3664 | 2-Cl | 2-Me | $CO_2Me$ |
| 3665 | 2-Cl | 2-CN | $CO_2Me$ |
| 3666 | 2-Cl | 2-$NO_2$ | $CO_2Me$ |
| 3667 | 2-Cl | 2-OMe | $CO_2Me$ |
| 3668 | 2-Cl | 2,3-$F_2$ | $CO_2Me$ |
| 3669 | 2-Cl | 2,4-$F_2$ | $CO_2Me$ |
| 3670 | 2-Cl | 2,5-$F_2$ | $CO_2Me$ |
| 3671 | 2-Cl | 2,6-$F_2$ | $CO_2Me$ |
| 3672 | 2-Cl | 3,4-$F_2$ | $CO_2Me$ |
| 3673 | 2-Cl | 3,5-$F_2$ | $CO_2Me$ |
| 3674 | 2-Cl | 2,3-$Cl_2$ | $CO_2Me$ |
| 3675 | 2-Cl | 2,4-$Cl_2$ | $CO_2Me$ |
| 3676 | 2-Cl | 2,5-$Cl_2$ | $CO_2Me$ |
| 3677 | 2-Cl | 2,6-$Cl_2$ | $CO_2Me$ |
| 3678 | 2-Cl | 3,4-$Cl_2$ | $CO_2Me$ |
| 3679 | 2-Cl | 3,5-$Cl_2$ | $CO_2Me$ |
| 3680 | 2-Cl | 2-F, 3-Cl | $CO_2Me$ |
| 3681 | 2-Cl | 2-F, 4-Cl | $CO_2Me$ |
| 3682 | 2-Cl | 2-F, 5-Cl | $CO_2Me$ |
| 3683 | 2-Cl | 2-F, 6-Cl | $CO_2Me$ |
| 3684 | 2-Cl | 2,6-$F_2$, 4-Cl | $CO_2Me$ |
| 3685 | 2-Cl | 3-F, 4-Cl | $CO_2Me$ |
| 3686 | 2-Cl | 3-Cl, 5-F | $CO_2Me$ |
| 3687 | 2-Cl | 2-Cl, 5-F | $CO_2Me$ |
| 3688 | 2-Cl | 3-CN, 4-Cl | $CO_2Me$ |
| 3689 | 2-Cl | 3-$NO_2$, 4-Cl | $CO_2Me$ |
| 3690 | 2-Cl | 2-F, 4-Br | $CO_2Me$ |
| 3691 | 4-Cl | 4-F | $CO_2Me$ |
| 3692 | 4-Cl | 4-Cl | $CO_2Me$ |
| 3693 | 4-Cl | 4-Br | $CO_2Me$ |
| 3694 | 4-Cl | H | $CO_2Me$ |
| 3695 | 4-Cl | 4-Me | $CO_2Me$ |
| 3696 | 4-Cl | 4-CN | $CO_2Me$ |
| 3697 | 4-Cl | 4-$NO_2$ | $CO_2Me$ |
| 3698 | 4-Cl | 4-OMe | $CO_2Me$ |
| 3699 | 4-Cl | 3-F | $CO_2Me$ |
| 3700 | 4-Cl | 3-Cl | $CO_2Me$ |
| 3701 | 4-Cl | 3-Br | $CO_2Me$ |
| 3702 | 4-Cl | 3-Me | $CO_2Me$ |
| 3703 | 4-Cl | 3-CN | $CO_2Me$ |
| 3704 | 4-Cl | 3-$NO_2$ | $CO_2Me$ |
| 3705 | 4-Cl | 3-OMe | $CO_2Me$ |
| 3706 | 4-Cl | 2-F | $CO_2Me$ |
| 3707 | 4-Cl | 2-Cl | $CO_2Me$ |
| 3708 | 4-Cl | 2-Br | $CO_2Me$ |
| 3709 | 4-Cl | 2-Me | $CO_2Me$ |
| 3710 | 4-Cl | 2-CN | $CO_2Me$ |
| 3711 | 4-Cl | 2-$NO_2$ | $CO_2Me$ |
| 3712 | 4-Cl | 2-OMe | $CO_2Me$ |
| 3713 | 4-Cl | 2,3-$F_2$ | $CO_2Me$ |
| 3714 | 4-Cl | 2,4-$F_2$ | $CO_2Me$ |
| 3715 | 4-Cl | 2,5-$F_2$ | $CO_2Me$ |
| 3716 | 4-Cl | 2,6-$F_2$ | $CO_2Me$ |
| 3717 | 4-Cl | 3,4-$F_2$ | $CO_2Me$ |
| 3718 | 4-Cl | 3,5-$F_2$ | $CO_2Me$ |
| 3719 | 4-Cl | 2,3-$Cl_2$ | $CO_2Me$ |
| 3720 | 4-Cl | 2,4-$Cl_2$ | $CO_2Me$ |
| 3721 | 4-Cl | 2,5-$Cl_2$ | $CO_2Me$ |
| 3722 | 4-Cl | 2,6-$Cl_2$ | $CO_2Me$ |
| 3723 | 4-Cl | 3,4-$Cl_2$ | $CO_2Me$ |
| 3724 | 4-Cl | 3,5-$Cl_2$ | $CO_2Me$ |
| 3725 | 4-Cl | 2-F, 3-Cl | $CO_2Me$ |
| 3726 | 4-Cl | 2-F, 4-Cl | $CO_2Me$ |
| 3727 | 4-Cl | 2-F, 5-Cl | $CO_2Me$ |
| 3728 | 4-Cl | 2-F, 6-Cl | $CO_2Me$ |
| 3729 | 4-Cl | 2,6-$F_2$, 4-Cl | $CO_2Me$ |
| 3730 | 4-Cl | 3-F, 4-Cl | $CO_2Me$ |
| 3731 | 4-Cl | 3-Cl, 5-F | $CO_2Me$ |
| 3732 | 4-Cl | 2-Cl, 5-F | $CO_2Me$ |
| 3733 | 4-Cl | 3-CN, 4-Cl | $CO_2Me$ |
| 3734 | 4-Cl | 3-$NO_2$, 4-Cl | $CO_2Me$ |
| 3735 | 4-Cl | 2-F, 4-Br | $CO_2Me$ |
| 3736 | 6-$OCF_2H$ | 4-F | $CO_2Me$ |
| 3737 | 6-$OCF_2H$ | 4-Cl | $CO_2Me$ |
| 3738 | 6-$OCF_2H$ | 4-Br | $CO_2Me$ |
| 3739 | 6-$OCF_2H$ | H | $CO_2Me$ |
| 3740 | 6-$OCF_2H$ | 4-Me | $CO_2Me$ |
| 3741 | 6-$OCF_2H$ | 4-CN | $CO_2Me$ |
| 3742 | 6-$OCF_2H$ | 4-$NO_2$ | $CO_2Me$ |
| 3743 | 6-$OCF_2H$ | 4-OMe | $CO_2Me$ |
| 3744 | 6-$OCF_2H$ | 3-F | $CO_2Me$ |
| 3745 | 6-$OCF_2H$ | 3-Cl | $CO_2Me$ |
| 3746 | 6-$OCF_2H$ | 3-Br | $CO_2Me$ |
| 3747 | 6-$OCF_2H$ | 3-Me | $CO_2Me$ |
| 3748 | 6-$OCF_2H$ | 3-CN | $CO_2Me$ |
| 3749 | 6-$OCF_2H$ | 3-$NO_2$ | $CO_2Me$ |
| 3750 | 6-$OCF_2H$ | 3-OMe | $CO_2Me$ |
| 3751 | 6-$OCF_2H$ | 2-F | $CO_2Me$ |
| 3752 | 6-$OCF_2H$ | 2-Cl | $CO_2Me$ |
| 3753 | 6-$OCF_2H$ | 2-Br | $CO_2Me$ |
| 3754 | 6-$OCF_2H$ | 2-Me | $CO_2Me$ |
| 3755 | 6-$OCF_2H$ | 2-CN | $CO_2Me$ |
| 3756 | 6-$OCF_2H$ | 2-$NO_2$ | $CO_2Me$ |
| 3757 | 6-$OCF_2H$ | 2-OMe | $CO_2Me$ |
| 3758 | 6-$OCF_2H$ | 2,3-$F_2$ | $CO_2Me$ |
| 3759 | 6-$OCF_2H$ | 2,4-$F_2$ | $CO_2Me$ |
| 3760 | 6-$OCF_2H$ | 2,5-$F_2$ | $CO_2Me$ |
| 3761 | 6-$OCF_2H$ | 2,6-$F_2$ | $CO_2Me$ |
| 3762 | 6-$OCF_2H$ | 3,4-$F_2$ | $CO_2Me$ |
| 3763 | 6-$OCF_2H$ | 3,5-$F_2$ | $CO_2Me$ |
| 3764 | 6-$OCF_2H$ | 2,3-$Cl_2$ | $CO_2Me$ |
| 3765 | 6-$OCF_2H$ | 2,4-$Cl_2$ | $CO_2Me$ |
| 3766 | 6-$OCF_2H$ | 2,5-$Cl_2$ | $CO_2Me$ |
| 3767 | 6-$OCF_2H$ | 2,6-$Cl_2$ | $CO_2Me$ |
| 3768 | 6-$OCF_2H$ | 3,4-$Cl_2$ | $CO_2Me$ |
| 3769 | 6-$OCF_2H$ | 3,5-$Cl_2$ | $CO_2Me$ |
| 3770 | 6-$OCF_2H$ | 2-F, 3-Cl | $CO_2Me$ |
| 3771 | 6-$OCF_2H$ | 2-F, 4-Cl | $CO_2Me$ |
| 3772 | 6-$OCF_2H$ | 2-F, 5-Cl | $CO_2Me$ |
| 3773 | 6-$OCF_2H$ | 2-F, 6-Cl | $CO_2Me$ |
| 3774 | 6-$OCF_2H$ | 2,6-$F_2$, 4-Cl | $CO_2Me$ |
| 3775 | 6-$OCF_2H$ | 3-F, 4-Cl | $CO_2Me$ |
| 3776 | 6-$OCF_2H$ | 3-Cl, 5-F | $CO_2Me$ |
| 3777 | 6-$OCF_2H$ | 2-Cl, 5-F | $CO_2Me$ |
| 3778 | 6-$OCF_2H$ | 3-CN, 4-Cl | $CO_2Me$ |
| 3779 | 6-$OCF_2H$ | 3-$NO_2$, 4-Cl | $CO_2Me$ |
| 3780 | 6-$OCF_2H$ | 2-F, 4-Br | $CO_2Me$ |
| 3781 | H | 3-F, 4-OMe | F |
| 3782 | H | 3-F, 4-OMe | Cl |
| 3783 | H | 3-F, 4-OMe | Br |
| 3784 | H | 3-F, 4-OMe | Me |
| 3785 | H | 3-F, 4-OMe | CN |
| 3786 | H | 3-F, 4-OMe | $NO_2$ |
| 3787 | H | 3-F, 4-OMe | $CO_2Me$ |
| 3788 | 6-F | 3-F, 4-OMe | F |

TABLE 1-continued

Definitions of structural combinations of groups $(R^1)_m$, $(R^2)_n$ and $R^3$ for the tables of compounds of the general formula (I) according to the invention below

| No. | $(R^1)_m$ | $(R^2)_n$ | $R^3$ |
|---|---|---|---|
| 3789 | 6-F | 3-F, 4-OMe | Cl |
| 3790 | 6-F | 3-F, 4-OMe | Br |
| 3791 | 6-F | 3-F, 4-OMe | Me |
| 3792 | 6-F | 3-F, 4-OMe | CN |
| 3793 | 6-F | 3-F, 4-OMe | $NO_2$ |
| 3794 | 6-F | 3-F, 4-OMe | $CO_2Me$ |
| 3795 | H | 3-F, 4-CN | F |
| 3796 | H | 3-F, 4-CN | Cl |
| 3797 | H | 3-F, 4-CN | Br |
| 3798 | H | 3-F, 4-CN | Me |
| 3799 | H | 3-F, 4-CN | CN |
| 3800 | H | 3-F, 4-CN | $NO_2$ |
| 3801 | H | 3-F, 4-CN | $CO_2Me$ |
| 3802 | 6-F | 3-F, 4-CN | F |
| 3803 | 6-F | 3-F, 4-CN | Cl |
| 3804 | 6-F | 3-F, 4-CN | Br |
| 3805 | 6-F | 3-F, 4-CN | Me |
| 3806 | 6-F | 3-F, 4-CN | CN |
| 3807 | 6-F | 3-F, 4-CN | $NO_2$ |
| 3808 | 6-F | 3-F, 4-CN | $CO_2Me$ |
| 3809 | 6-Cl | 3-F, 4-CN | F |
| 3810 | 6-Cl | 3-F, 4-CN | Cl |
| 3811 | 6-Cl | 3-F, 4-CN | Br |
| 3812 | 6-Cl | 3-F, 4-CN | Me |
| 3813 | 6-Cl | 3-F, 4-CN | CN |
| 3814 | 6-Cl | 3-F, 4-CN | $NO_2$ |
| 3815 | 6-Cl | 3-F, 4-CN | $CO_2Me$ |
| 3816 | 6-CN | 3-F, 4-CN | F |
| 3817 | 6-CN | 3-F, 4-CN | Cl |
| 3818 | 6-CN | 3-F, 4-CN | Br |
| 3819 | 6-CN | 3-F, 4-CN | Me |
| 3820 | 6-CN | 3-F, 4-CN | CN |
| 3821 | 6-CN | 3-F, 4-CN | $NO_2$ |
| 3822 | 6-CN | 3-F, 4-CN | $CO_2Me$ |
| 3823 | H | 3-F, 4-$NO_2$ | F |
| 3824 | H | 3-F, 4-$NO_2$ | Cl |
| 3825 | H | 3-F, 4-$NO_2$ | Br |
| 3826 | H | 3-F, 4-$NO_2$ | Me |
| 3827 | H | 3-F, 4-$NO_2$ | CN |
| 3828 | H | 3-F, 4-$NO_2$ | $NO_2$ |
| 3829 | H | 3-F, 4-$NO_2$ | $CO_2Me$ |
| 3830 | 6-F | 3-F, 4-$NO_2$ | F |
| 3831 | 6-F | 3-F, 4-$NO_2$ | Cl |
| 3832 | 6-F | 3-F, 4-$NO_2$ | Br |
| 3833 | 6-F | 3-F, 4-$NO_2$ | Me |
| 3834 | 6-F | 3-F, 4-$NO_2$ | CN |
| 3835 | 6-F | 3-F, 4-$NO_2$ | $NO_2$ |
| 3836 | 6-F | 3-F, 4-$NO_2$ | $CO_2Me$ |
| 3837 | 6-Cl | 3-F, 4-$NO_2$ | F |
| 3838 | 6-Cl | 3-F, 4-$NO_2$ | Cl |
| 3839 | 6-Cl | 3-F, 4-$NO_2$ | Br |
| 3840 | 6-Cl | 3-F, 4-$NO_2$ | Me |
| 3841 | 6-Cl | 3-F, 4-$NO_2$ | CN |
| 3842 | 6-Cl | 3-F, 4-$NO_2$ | $NO_2$ |
| 3843 | 6-Cl | 3-F, 4-$NO_2$ | $CO_2Me$ |
| 3844 | 6-CN | 3-F, 4-$NO_2$ | F |
| 3845 | 6-CN | 3-F, 4-$NO_2$ | Cl |
| 3846 | 6-CN | 3-F, 4-$NO_2$ | Br |
| 3847 | 6-CN | 3-F, 4-$NO_2$ | Me |
| 3848 | 6-CN | 3-F, 4-$NO_2$ | CN |
| 3849 | 6-CN | 3-F, 4-$NO_2$ | $NO_2$ |
| 3850 | 6-CN | 3-F, 4-$NO_2$ | $CO_2Me$ |
| 3851 | H | 3-Cl, 4-F | F |
| 3852 | H | 3-Cl, 4-F | Cl |
| 3853 | H | 3-Cl, 4-F | Br |
| 3854 | H | 3-Cl, 4-F | Me |
| 3855 | H | 3-Cl, 4-F | CN |
| 3856 | H | 3-Cl, 4-F | $NO_2$ |
| 3857 | H | 3-Cl, 4-F | $CO_2Me$ |
| 3858 | 6-F | 3-Cl, 4-F | F |
| 3859 | 6-F | 3-Cl, 4-F | Cl |
| 3860 | 6-F | 3-Cl, 4-F | Br |
| 3861 | 6-F | 3-Cl, 4-F | Me |
| 3862 | 6-F | 3-Cl, 4-F | CN |
| 3863 | 6-F | 3-Cl, 4-F | $NO_2$ |
| 3864 | 6-F | 3-Cl, 4-F | $CO_2Me$ |
| 3865 | 6-Cl | 3-Cl, 4-F | F |
| 3866 | 6-Cl | 3-Cl, 4-F | Cl |
| 3867 | 6-Cl | 3-Cl, 4-F | Br |
| 3868 | 6-Cl | 3-Cl, 4-F | Me |
| 3869 | 6-Cl | 3-Cl, 4-F | CN |
| 3870 | 6-Cl | 3-Cl, 4-F | $NO_2$ |
| 3871 | 6-Cl | 3-Cl, 4-F | $CO_2Me$ |
| 3872 | 6-CN | 3-Cl, 4-F | F |
| 3873 | 6-CN | 3-Cl, 4-F | Cl |
| 3874 | 6-CN | 3-Cl, 4-F | Br |
| 3875 | 6-CN | 3-Cl, 4-F | Me |
| 3876 | 6-CN | 3-Cl, 4-F | CN |
| 3877 | 6-CN | 3-Cl, 4-F | $NO_2$ |
| 3878 | 6-CN | 3-Cl, 4-F | $CO_2Me$ |
| 3879 | H | 3-F, 4-Br | F |
| 3880 | H | 3-F, 4-Br | Cl |
| 3881 | H | 3-F, 4-Br | Br |
| 3882 | H | 3-F, 4-Br | Me |
| 3883 | H | 3-F, 4-Br | CN |
| 3884 | H | 3-F, 4-Br | $NO_2$ |
| 3885 | H | 3-F, 4-Br | $CO_2Me$ |
| 3886 | 6-F | 3-F, 4-Br | F |
| 3887 | 6-F | 3-F, 4-Br | Cl |
| 3888 | 6-F | 3-F, 4-Br | Br |
| 3889 | 6-F | 3-F, 4-Br | Me |
| 3890 | 6-F | 3-F, 4-Br | CN |
| 3891 | 6-F | 3-F, 4-Br | $NO_2$ |
| 3892 | 6-F | 3-F, 4-Br | $CO_2Me$ |
| 3893 | 6-Cl | 3-F, 4-Br | F |
| 3894 | 6-Cl | 3-F, 4-Br | Cl |
| 3895 | 6-Cl | 3-F, 4-Br | Br |
| 3896 | 6-Cl | 3-F, 4-Br | Me |
| 3897 | 6-Cl | 3-F, 4-Br | CN |
| 3898 | 6-Cl | 3-F, 4-Br | $NO_2$ |
| 3899 | 6-Cl | 3-F, 4-Br | $CO_2Me$ |
| 3900 | 6-CN | 3-F, 4-Br | F |
| 3901 | 6-CN | 3-F, 4-Br | Cl |
| 3902 | 6-CN | 3-F, 4-Br | Br |
| 3903 | 6-CN | 3-F, 4-Br | Me |
| 3904 | 6-CN | 3-F, 4-Br | CN |
| 3905 | 6-CN | 3-F, 4-Br | $NO_2$ |
| 3906 | 6-CN | 3-F, 4-Br | $CO_2Me$ |
| 3907 | H | 3-CN, 4-F | F |
| 3908 | H | 3-CN, 4-F | Cl |
| 3909 | H | 3-CN, 4-F | Br |
| 3910 | H | 3-CN, 4-F | Me |
| 3911 | H | 3-CN, 4-F | CN |
| 3912 | H | 3-CN, 4-F | $NO_2$ |
| 3913 | H | 3-CN, 4-F | $CO_2Me$ |
| 3914 | 6-F | 3-CN, 4-F | F |
| 3915 | 6-F | 3-CN, 4-F | Cl |
| 3916 | 6-F | 3-CN, 4-F | Br |
| 3917 | 6-F | 3-CN, 4-F | Me |
| 3918 | 6-F | 3-CN, 4-F | CN |
| 3919 | 6-F | 3-CN, 4-F | $NO_2$ |
| 3920 | 6-F | 3-CN, 4-F | $CO_2Me$ |
| 3921 | 6-Cl | 3-CN, 4-F | F |
| 3922 | 6-Cl | 3-CN, 4-F | Cl |
| 3923 | 6-Cl | 3-CN, 4-F | Br |
| 3924 | 6-Cl | 3-CN, 4-F | Me |
| 3925 | 6-Cl | 3-CN, 4-F | CN |
| 3926 | 6-Cl | 3-CN, 4-F | $NO_2$ |
| 3927 | 6-Cl | 3-CN, 4-F | $CO_2Me$ |
| 3928 | 6-CN | 3-CN, 4-F | F |
| 3929 | 6-CN | 3-CN, 4-F | Cl |
| 3930 | 6-CN | 3-CN, 4-F | Br |
| 3931 | 6-CN | 3-CN, 4-F | Me |
| 3932 | 6-CN | 3-CN, 4-F | CN |
| 3933 | 6-CN | 3-CN, 4-F | $NO_2$ |
| 3934 | 6-CN | 3-CN, 4-F | $CO_2Me$ |
| 3935 | H | 4-$CF_3$ | F |
| 3936 | H | 4-$CF_3$ | Cl |

TABLE 1-continued

Definitions of structural combinations of groups
$(R^1)_m$, $(R^2)_n$ and $R^3$ for the tables of compounds of
the general formula (I) according to the invention below

| No. | $(R^1)_m$ | $(R^2)_n$ | $R^3$ |
|---|---|---|---|
| 3937 | H | 4-$CF_3$ | Br |
| 3938 | H | 4-$CF_3$ | Me |
| 3939 | H | 4-$CF_3$ | CN |
| 3940 | H | 4-$CF_3$ | $NO_2$ |
| 3941 | H | 4-$CF_3$ | $CO_2Me$ |
| 3942 | 6-F | 4-$CF_3$ | F |
| 3943 | 6-F | 4-$CF_3$ | Cl |
| 3944 | 6-F | 4-$CF_3$ | Br |
| 3945 | 6-F | 4-$CF_3$ | Me |
| 3946 | 6-F | 4-$CF_3$ | CN |
| 3947 | 6-F | 4-$CF_3$ | $NO_2$ |
| 3948 | 6-F | 4-$CF_3$ | $CO_2Me$ |
| 3949 | 6-Cl | 4-$CF_3$ | F |
| 3950 | 6-Cl | 4-$CF_3$ | Cl |
| 3951 | 6-Cl | 4-$CF_3$ | Br |
| 3952 | 6-Cl | 4-$CF_3$ | Me |
| 3953 | 6-Cl | 4-$CF_3$ | CN |
| 3954 | 6-Cl | 4-$CF_3$ | $NO_2$ |
| 3955 | 6-Cl | 4-$CF_3$ | $CO_2Me$ |
| 3956 | 6-CN | 4-$CF_3$ | F |
| 3957 | 6-CN | 4-$CF_3$ | Cl |
| 3958 | 6-CN | 4-$CF_3$ | Br |
| 3959 | 6-CN | 4-$CF_3$ | Me |
| 3960 | 6-CN | 4-$CF_3$ | CN |
| 3961 | 6-CN | 4-$CF_3$ | $NO_2$ |
| 3962 | 6-CN | 4-$CF_3$ | $CO_2Me$ |
| 3963 | H | 4-$OCF_3$ | F |
| 3964 | H | 4-$OCF_3$ | Cl |
| 3965 | H | 4-$OCF_3$ | Br |
| 3966 | H | 4-$OCF_3$ | Me |
| 3967 | H | 4-$OCF_3$ | CN |
| 3968 | H | 4-$OCF_3$ | $NO_2$ |
| 3969 | H | 4-$OCF_3$ | $CO_2Me$ |
| 3970 | 6-F | 4-$OCF_3$ | F |
| 3971 | 6-F | 4-$OCF_3$ | Cl |
| 3972 | 6-F | 4-$OCF_3$ | Br |
| 3973 | 6-F | 4-$OCF_3$ | Me |
| 3974 | 6-F | 4-$OCF_3$ | CN |
| 3975 | 6-F | 4-$OCF_3$ | $NO_2$ |
| 3976 | 6-F | 4-$OCF_3$ | $CO_2Me$ |
| 3977 | 6-Cl | 4-$OCF_3$ | F |
| 3978 | 6-Cl | 4-$OCF_3$ | Cl |
| 3979 | 6-Cl | 4-$OCF_3$ | Br |
| 3980 | 6-Cl | 4-$OCF_3$ | Me |
| 3981 | 6-Cl | 4-$OCF_3$ | CN |
| 3982 | 6-Cl | 4-$OCF_3$ | $NO_2$ |
| 3983 | 6-Cl | 4-$OCF_3$ | $CO_2Me$ |
| 3984 | 6-CN | 4-$OCF_3$ | F |
| 3985 | 6-CN | 4-$OCF_3$ | Cl |
| 3986 | 6-CN | 4-$OCF_3$ | Br |
| 3987 | 6-CN | 4-$OCF_3$ | Me |
| 3988 | 6-CN | 4-$OCF_3$ | CN |
| 3989 | 6-CN | 4-$OCF_3$ | $NO_2$ |
| 3990 | 6-CN | 4-$OCF_3$ | $CO_2Me$ |

Definition of the Examples in Tables 2 to 2f below:

For reference purposes, specific numbers (=Example Numbers) have been assigned to the individual compounds in Tables 2 to 2f below, where the Example Number in question is composed of the number of the chemical formula assigned to the respective table and a "row number" (row number) which refers to the same number in the row of the first column of Table 1. The chemical structure of Example No. "(formula number) (row number)" is thus defined unambiguously by the formula above the respective table by formula number and row number of Table 1, for example:

The example of No. "Iba1" from Table 2 is the compound of the formula (Ib) in which $R^4$=H (=hydrogen) [=formula (Iba)] and $(R^1)_m$=H, $(R^2)_n$=4-F and $R^3$=F, defined according to row 1 of Table 1.

The example of No. "Ibd1801" from Table 2 is the compound of the formula (Ib) in which $R^4$=n-propyl [=formula (Ibd)] and $(R^1)_m$=6-CN, $(R^2)_n$=4-F and $R^3$=Me=$CH_3$, defined according to row 1801 of Table 1.

This applies correspondingly to the assignment of racemic or optically active threo stereoisomers or erythro stereoisomers. For example, for reference purposes, specific numbers (=Example Numbers) have been assigned to the compounds of Table 2a, where the number "threo-Iba (row number)" refers to the racemic mixture of the threo enantiomers having the chemical structure of the formulae (threo-1-Iba) and (threo-2-Iba), each of which has the structural combination of groups $(R^1)_m$, $(R^2)_n$ and $R^3$ according to the row number of Table 1.

TABLE 2

Compounds of the formulae (Ib), (Iba), (Ibb), (Ibc), (Ibd), (Ibe), (Ibf), (Ibg)
(Ibh), (Ibi), (Ibj), (Ibk), (Ibl), (Ibm), (Ibn), (Ibo), (Ibp), (Ibq), (Ibr) (Ibs), (Ibt),
(Ibu), (Ibv), (Ibw), (Ibx), (Iby) and (Ibz) where $(R^1)_m$, $(R^2)_n$ and $R^3$ are each
as defined in Table 1

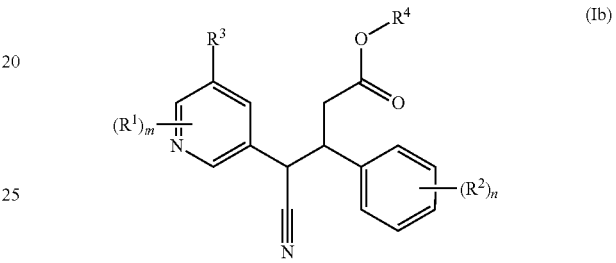

For definitions of subformulae of formula (Ib), see Table U1 below:

TABLE U1

| Formula | Radical $R^4$ in formula (Ib) |
|---|---|
| (Iba) | H (hydrogen atom) |
| (Ibb) | methyl |
| (Ibc) | ethyl |
| (Ibd) | n-propyl |
| (Ibe) | isopropyl |
| (Ibf) | 2,2-difluoroethyl |
| (Ibg) | 2,2,2-trifluoroethyl |
| (Ibh) | 2-methoxyethyl |
| (Ibi) | cyclopropylmethyl |
| (Ibj) | (1-methylcyclopropyl)methyl |
| (Ibk) | allyl |
| (Ibl) | prop-2-yn-1-yl |
| (Ibm) | ethynyl |
| (Ibn) | prop-1-yn-1-yl |
| (Ibo) | benzyl |
| (Ibp) | 4-chlorobenzyl |
| (Ibq) | phenyl |
| (Ibr) | methoxymethyl |
| (Ibs) | difluoromethyl |
| (Ibt) | oxetan-3-yl |
| (Ibu) | thietan-3-yl |
| (Ibv) | 2-(phenylsulphanyl)ethyl |
| (Ibw) | 2-(phenylsulphinyl)ethyl |
| (Ibx) | 2-(ethylsulphanyl)ethyl |
| (Iby) | 2-(ethylsulphinyl)ethyl |
| (Ibz) | tetrahydrofuran-2-ylmethyl |

Erythro/Threo Mixtures of the Formulae (Iba) to (Ibz):

Examples of compounds of the formulae (Iba) to (Ibz) are the compounds of the respective formulae (Iba) to (Ibz) in the form of a racemic erythro/threo mixture (ratio 70:30 to 30:70), where the structural combination of the groups $(R^1)_m$, $(R^2)_n$ and $R^3$ is defined according to a row number of Table 1.

The numeration is carried out according to "(formula)(row number)" without any brackets, for example Iba200=compound of the formula (Iba) having the structural combination of row 200 of Table 1.

TABLES 2a, 2b and 2c

Threo, threo-1 and threo-2 compounds of the compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby) and (Ibz) where $(R^1)_m$, $(R^2)_n$ and $R^3$ are each as defined in Table 1

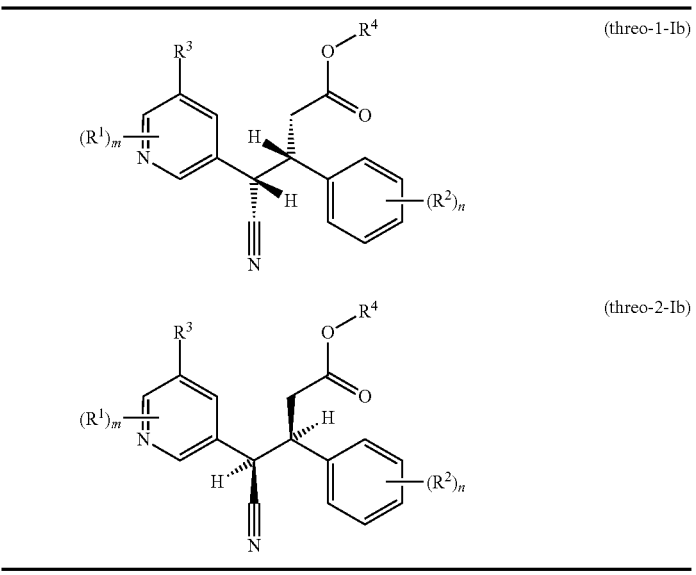

(threo-Ib) = (threo-1-Ib) + (threo-2-Ib) (50:50) = (rac.)

For definitions of subformulae of formulae (threo-Ib), (threo-1-Ib) and (threo-2-Ib), see Table U2 below:

TABLE U2

| Formula | Radical $R^4$ in formula (threo-Ib) |
|---|---|
| (threo-Iba) | H (hydrogen atom) |
| (threo-1-Iba) | H (hydrogen atom) |
| (threo-2-Iba) | H (hydrogen atom) |
| (threo-Ibb) | methyl |
| (threo-1-Ibb) | methyl |
| (threo-2-Ibb) | methyl |
| (threo-Ibc) | ethyl |
| (threo-1-Ibc) | ethyl |
| (threo-2-Ibc) | ethyl |
| (threo-Ibd) | n-propyl |
| (threo-1-Ibd) | n-propyl |
| (threo-2-Ibd) | n-propyl |
| (threo-Ibe) | isopropyl |
| (threo-1-Ibe) | isopropyl |
| (threo-2-Ibe) | isopropyl |
| (threo-Ibf) | 2,2-difluoroethyl |
| (threo-1-Ibf) | 2,2-difluoroethyl |
| (threo-2-Ibf) | 2,2-difluoroethyl |
| (threo-Ibg) | 2,2,2-trifluoroethyl |
| (threo-1-Ibg) | 2,2,2-trifluoroethyl |
| (threo-2-Ibg) | 2,2,2-trifluoroethyl |
| (threo-Ibh) | 2-methoxyethyl |
| (threo-1-Ibh) | 2-methoxyethyl |
| (threo-2-Ibh) | 2-methoxyethyl |
| (threo-Ibi) | cyclopropylmethyl |
| (threo-1-Ibi) | cyclopropylmethyl |
| (threo-2-Ibi) | cyclopropylmethyl |
| (threo-Ibj) | (1-methylcyclopropyl)methyl |
| (threo-1-Ibj) | (1-methylcyclopropyl)methyl |
| (threo-2-Ibj) | (1-methylcyclopropyl)methyl |
| (threo-Ibk) | allyl |
| (threo-1-Ibk) | allyl |
| (threo-2-Ibk) | allyl |
| (threo-Ibl) | prop-2-yn-1-yl |
| (threo-1-Ibl) | prop-2-yn-1-yl |
| (threo-2-Ibl) | prop-2-yn-1-yl |
| (threo-Ibm) | ethynyl |

TABLE U2-continued

| Formula | Radical $R^4$ in formula (threo-Ib) |
|---|---|
| (threo-1-Ibm) | ethynyl |
| (threo-2-Ibm) | ethynyl |
| (threo-Ibn) | prop-1-yn-1-yl |
| (threo-1-Ibn) | prop-1-yn-1-yl |
| (threo-2-Ibn) | prop-1-yn-1-yl |
| (threo-Ibo) | benzyl |
| (threo-1-Ibo) | benzyl |
| (threo-2-Ibo) | benzyl |
| (threo-Ibp) | 4-chlorobenzyl |
| (threo-1-Ibp) | 4-chlorobenzyl |
| (threo-2-Ibp) | 4-chlorobenzyl |
| (threo-Ibq) | phenyl |
| (threo-1-Ibq) | phenyl |
| (threo-2-Ibq) | phenyl |
| (threo-Ibr) | methoxymethyl |
| (threo-1-Ibr) | methoxymethyl |
| (threo-2-Ibr) | methoxymethyl |
| (threo-Ibs) | difluoromethyl |
| (threo-1-Ibs) | difluoromethyl |
| (threo-2-Ibs) | difluoromethyl |
| (threo-Ibt) | oxetan-3-yl |
| (threo-1-Ibt) | oxetan-3-yl |
| (threo-2-Ibt) | oxetan-3-yl |
| (threo-Ibu) | thietan-3-yl |
| (threo-1-Ibu) | thietan-3-yl |
| (threo-2-Ibu) | thietan-3-yl |
| (threo-Ibv) | 2-(phenylsulphanyl)ethyl |
| (threo-1-Ibv) | 2-(phenylsulphanyl)ethyl |
| (threo-2-Ibv) | 2-(phenylsulphanyl)ethyl |
| (threo-Ibw) | 2-(phenylsulphinyl)ethyl |
| (threo-1-Ibw) | 2-(phenylsulphinyl)ethyl |
| (threo-2-Ibw) | 2-(phenylsulphinyl)ethyl |
| (threo-Ibx) | 2-(ethylsulphanyl)ethyl |
| (threo-1-Ibx) | 2-(ethylsulphanyl)ethyl |
| (threo-2-Ibx) | 2-(ethylsulphanyl)ethyl |
| (threo-Iby) | 2-(ethylsulphinyl)ethyl |
| (threo-1-Iby) | 2-(ethylsulphinyl)ethyl |
| (threo-2-Iby) | 2-(ethylsulphinyl)ethyl |

TABLE U2-continued

| Formula | Radical $R^4$ in formula (threo-Ib) |
|---|---|
| (threo-Ibz) | tetrahydrofuran-2-ylmethyl |
| (threo-1-Ibz) | tetrahydrofuran-2-ylmethyl |
| (threo-2-Ibz) | tetrahydrofuran-2-ylmethyl |

Table 2a (Threo Racemates), Examples:

Examples of the compounds of the formulae (threo-Iba) to (threo-Ibz) (see Table U2) are the compounds of the formulae in question in the form of the racemic mixture of the threo isomers where the structural combination of groups $(R^1)_m$, $(R^2)_n$ and $R^3$ is defined according to a row number of Table 1.

The numeration is carried out according to "(formula)(row number)" without any brackets, for example threo-Iba200=compound of the formula (threo-Iba) having the structural combination of row 200 of Table 1.

Table 2b (Optically Active Threo-2 Enantiomers): Examples:

Examples of the compounds of the formulae (threo-2-Iba) to (threo-2-Ibz) (see Table U2) are the optically active threo-2 compounds of the formulae in question in enriched form [=(3R,4R)-form having more than 90% ee] where the structural combination of groups $(R^1)_m$, $(R^2)_n$ and $R^3$ is defined according to a row number of Table 1.

Compounds are numbered "(formula)(row number)", without any brackets. For example, No. threo-2-Iba1789 refers to the compound of the formula (threo-2-Iba) in which $(R^1)_m$=6-Br, $(R^2)_n$=3,5-Cl$_2$ and $R^3$=Me.

Table 2c (Optically Active Threo-1 Enantiomers): Examples:

Examples of the compounds of the formulae (threo-1-Iba) to (threo-1-Ibz) (see Table U2) are the optically active threo-1 compounds of the formulae in question in enriched form [=(3S,4S)-form having more than 90% ee] where the structural combination of groups $(R^1)_m$, $(R^2)_n$ and $R^3$ is defined according to a row number of Table 1.

Compounds are numbered "(formula)(row number)", without any brackets. For example, No. threo-1-Ibb5 refers to the compound of the formula (threo-1-Ibb) in which $(R^1)_m$=H, $(R^2)_n$=4-Me and $R^3$=F.

TABLES 2d, 2e and 2f

Erythro, erythro-1 and erythro-2 compounds of the compounds of the formulae (Ib), (Iba), (Ibb), (Ibc), (Ibd), (Ibe), (Ibf), (Ibg) (Ibh), (Ibi), (Ibj), (Ibk), (Ibl), (Ibm), (Ibn), (Ibo), (Ibp), (Ibq), (Ibr) (Ibs), (Ibt), (Ibu), (Ibv), (Ibw), (Ibx), (Iby) and (Ibz) where $(R^1)_m$, $(R^2)_n$ and $R^3$ are each as defined in Table 1

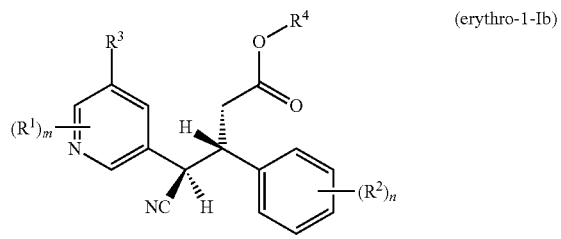
(erythro-1-Ib)

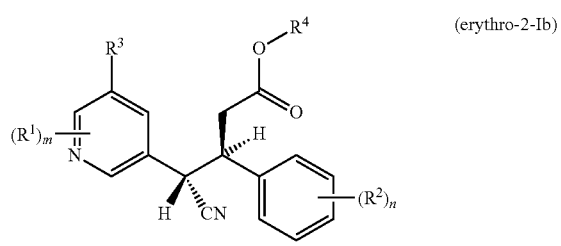
(erythro-2-Ib)

(erythro-Ib) = (erythro-1-Ib) + (erythro-2-Ib) (50:50) = (rac.)

For definitions of subformulae of formulae (erythro-Ib), (erythro-1-Ib) and (erythro-2-Ib), see Table U3 below:

TABLE U3

| Formula | Radical $R^4$ in formula (erythro-Ib) |
|---|---|
| (erythro-Iba) | H (hydrogen atom) |
| (erythro-1-Iba) | H (hydrogen atom) |
| (erythro-2-Iba) | H (hydrogen atom) |
| (erythro-Ibb) | methyl |
| (erythro-1-Ibb) | methyl |
| (erythro-2-Ibb) | methyl |
| (erythro-Ibc) | ethyl |
| (erythro-1-Ibc) | ethyl |
| (erythro-2-Ibc) | ethyl |
| (erythro-Ibd) | n-propyl |
| (erythro-1-Ibd) | n-propyl |
| (erythro-2-Ibd) | n-propyl |
| (erythro-Ibe) | isopropyl |
| (erythro-1-Ibe) | isopropyl |
| (erythro-2-Ibe) | isopropyl |
| (erythro-Ibf) | 2,2-difluoroethyl |
| (erythro-1-Ibf) | 2,2-difluoroethyl |
| (erythro-2-Ibf) | 2,2-difluoroethyl |
| (erythro-Ibg) | 2,2,2-trifluoroethyl |
| (erythro-1-Ibg) | 2,2,2-trifluoroethyl |
| (erythro-2-Ibg) | 2,2,2-trifluoroethyl |
| (erythro-Ibh) | 2-methoxyethyl |
| (erythro-1-Ibh) | 2-methoxyethyl |
| (erythro-2-Ibh) | 2-methoxyethyl |
| (erythro-Ibi) | cyclopropylmethyl |
| (erythro-1-Ibi) | cyclopropylmethyl |
| (erythro-2-Ibi) | cyclopropylmethyl |
| (erythro-Ibj) | (1-methylcyclopropyl)methyl |
| (erythro-1-Ibj) | (1-methylcyclopropyl)methyl |
| (erythro-2-Ibj) | (1-methylcyclopropyl)methyl |
| (erythro-Ibk) | allyl |
| (erythro-1-Ibk) | allyl |
| (erythro-2-Ibk) | allyl |
| (erythro-Ibl) | prop-2-yn-1-yl |
| (erythro-1-Ibl) | prop-2-yn-1-yl |
| (erythro-2-Ibl) | prop-2-yn-1-yl |
| (erythro-Ibm) | ethynyl |
| (erythro-1-Ibm) | ethynyl |
| (erythro-2-Ibm) | ethynyl |
| (erythro-Ibn) | prop-1-yn-1-yl |
| (erythro-1-Ibn) | prop-1-yn-1-yl |
| (erythro-2-Ibn) | prop-1-yn-1-yl |
| (erythro-Ibo) | benzyl |
| (erythro-1-Ibo) | benzyl |
| (erythro-2-Ibo) | benzyl |
| (erythro-Ibp) | 4-chlorobenzyl |
| (erythro-1-Ibp) | 4-chlorobenzyl |
| (erythro-2-Ibp) | 4-chlorobenzyl |
| (erythro-Ibq) | phenyl |
| (erythro-1-Ibq) | phenyl |
| (erythro-2-Ibq) | phenyl |
| (erythro-Ibr) | methoxymethyl |
| (erythro-1-Ibr) | methoxymethyl |
| (erythro-2-Ibr) | methoxymethyl |
| (erythro-Ibs) | difluoromethyl |
| (erythro-1-Ibs) | difluoromethyl |
| (erythro-2-Ibs) | difluoromethyl |
| (erythro-Ibt) | oxetan-3-yl |
| (erythro-1-Ibt) | oxetan-3-yl |
| (erythro-2-Ibt) | oxetan-3-yl |
| (erythro-Ibu) | thietan-3-yl |
| (erythro-1-Ibu) | thietan-3-yl |
| (erythro-2-Ibu) | thietan-3-yl |
| (erythro-Ibv) | 2-(phenylsulphanyl)ethyl |

TABLE U3-continued

| Formula | Radical R⁴ in formula (erythro-Ib) |
|---|---|
| (erythro-1-Ibv) | 2-(phenylsulphanyl)ethyl |
| (erythro-2-Ibv) | 2-(phenylsulphanyl)ethyl |
| (erythro-Ibw) | 2-(phenylsulphinyl)ethyl |
| (erythro-1-Ibw) | 2-(phenylsulphinyl)ethyl |
| (erythro-2-Ibw) | 2-(phenylsulphinyl)ethyl |
| (erythro-Ibx) | 2-(ethylsulphanyl)ethyl |
| (erythro-1-Ibx) | 2-(ethylsulphanyl)ethyl |
| (erythro-2-Ibx) | 2-(ethylsulphanyl)ethyl |
| (erythro-Iby) | 2-(ethylsulphinyl)ethyl |
| (erythro-1-Iby) | 2-(ethylsulphinyl)ethyl |
| (erythro-2-Iby) | 2-(ethylsulphinyl)ethyl |
| (erythro-Ibz) | tetrahydrofuran-2-ylmethyl |
| (erythro-1-Ibz) | tetrahydrofuran-2-ylmethyl |
| (erythro-2-Ibz) | tetrahydrofuran-2-ylmethyl |

Table 2d (Erythro Racemates), Examples:

Examples of the compounds of the formulae (erythro-Iba) to (erythro-Ibz) (see Table U3) are the compounds of the formulae in question in the form of the racemic mixture of the erythro isomers where the structural combination of groups $(R^1)_m$, $(R^2)_n$ and $R^3$ is defined according to a row number of Table 1.

The numeration is carried out according to "(formula)(row number)" without any brackets, for example erythro-Iba200=compound of the formula (erythro-Iba) having the structural combination of row 200 of Table 1.

Table 2e (Optically Active Erythro-2 Enantiomers): Examples:

Examples of the compounds of the formulae (erythro-2-Iba) to (erythro-2-Ibz) (see Table U3) are the optically active erythro-2 compounds of the formulae in question in enriched form [=(3R,4S)-form having more than 90% ee] where the structural combination of groups $(R^1)_m$, $(R^2)_n$ and $R^3$ is defined according to a row number of Table 1.

Compounds are numbered "(formula)(row number)", without any brackets. For example, No. erythro-2-Iba1789 refers to the compound of the formula (erythro-2-Iba) in which $(R^1)_m$=6-Br, $(R^2)_n$=3,5-Cl$_2$ and $R^3$=Me.

Table 2f (Optically Active Erythro-1 Enantiomers): Examples:

Examples of the compounds of the formulae (erythro-1-Iba) to (erythro-1-Ibz) (see Table U3) are the optically active erythro-1 compounds of the formulae in question in enriched form [=(3S,4R)-form having more than 90% ee] where the structural combination of groups $(R^1)_m$, $(R^2)_n$ and $R^3$ is defined according to a row number of Table 1.

Compounds are numbered "(formula)(row number)", without any brackets. For example, No. erythro-1-Ibb5 refers to the compound of the formula (erythro-1-Ibb) in which $(R^1)_m$=H, $(R^2)_n$=4-Me and $R^3$=F.

Physical Data for Tables 2a-2f:

Test Methods:
1) NMR=¹H-NMR data (400 MHz, CDCl₃); characteristic chemical shifts [in ppm] are indicated for the example in question,
2) MS=mass spectrum, measured using a quadrupole instrument; electrospray ionization (+−), mass range 100-1000; molecular peak M or [M+H]+ or [M−1]+ or [M−2]+ or [M+1]+ indicated for the example in question,
3) HPLC=High Performance Liquid Chromatography, column: Zorbax Eclipse, 50×3.0, C18 1.8 ym, mobile phase: water+0.06% formic acid/acrylonitrile+0.06% formic acid, gradient: 90:10, after 2 min 5:95; detector: DAD (210-400 nm); retention time (rt) indicated for the example in question,
4) chiral HPLC=HPLC on a chiral column, column: Chiralpak IC, 250×4.6 mm, 5 μm DAIC 83325, detector wavelength: 210 nm; column temperature 25° C.,
   mobile phase a: (n-heptane:2-propanol), (60:40), Chromasolv, flow rate: 1.0 ml/min
   mobile phase b: (n-heptane:2-propanol), (70:30), Chromasolv, flow rate: 1.0 ml/min
   mobile phase c: (n-heptane:2-propanol), (80:20), Chromasolv, flow rate: 1.0 ml/min
   mobile phase d: (n-heptane:2-propanol), (90:10), Chromasolv, flow rate: 0.6 ml/min Ex. erythro-Ibb2, NMR: 2.85 (dd, 1H), 3.06 (dd, 1H), 3.53 (m, 1H), 3.71 (s, 3H), 4.56 (d, 1H), 6.95 (d, 2H), 7.08 (dt, 1H), 7.25 (d, 2H), 8.24 (bs, 1H), 8.43 (d, 1H)

Ex. erythro-1-Ibb2, NMR: 2.85 (dd, 1H), 3.06 (dd, 1H), 3.53 (m, 1H), 3.71 (s, 3H), 4.56 (d, 1H), 6.95 (d, 2H), 7.08 (dt, 1H), 7.25 (d, 2H), 8.24 (bs, 1H), 8.43 (d, 1H)); chiral HPLC: 29.9 min, mobile phase d Ex. erythro-2-Ibb2, NMR: 2.85 (dd, 1H), 3.06 (dd, 1H), 3.53 (m, 1H), 3.71 (s, 3H), 4.56 (d, 1H), 6.95 (d, 2H), 7.08 (dt, 1H), 7.25 (d, 2H), 8.24 (bs, 1H), 8.43 (d, 1H)); chiral HPLC: 32.9 min, mobile phase d Ex. threo-Ibb2, NMR: 2.92 (m, 2H), 3.60 (s, 3H), 3.66 (q, 1H), 4.18 (d, 1H), 7.04 (d, 2H), 7.25 (dt, 1H), 7.28 (d, 2H), 8.15 (bs, 1H), 8.44 (d, 1H)

Ex. threo-1-Ibb2, NMR: 2.92 (m, 2H), 3.60 (s, 3H), 3.66 (q, 1H), 4.18 (d, 1H), 7.04 (d, 2H), 7.25 (dt, 1H), 7.28 (d, 2H), 8.15 (bs, 1H), 8.44 (d, 1H)); chiral HPLC: 11.7 min, mobile phase c Ex. threo-2-Ibb2, NMR: 2.92 (m, 2H), 3.60 (s, 3H), 3.66 (q, 1H), 4.18 (d, 1H), 7.04 (d, 2H), 7.25 (dt, 1H), 7.28 (d, 2H), 8.15 (bs, 1H), 8.44 (d, 1H)); chiral HPLC: 23.2 min, mobile phase c Ex. erythro-Ibb4, NMR: 2.89 (dd, 1H), 3.10 (dd, 1H), 3.53 (m, 1H), 3.71 (s, 3H), 4.57 (d, 1H), 7.01 (m, 3H), 8.22 (m, 1H), 8.40 (d, 1H)

Ex. threo-Ibb4, NMR: 2.94 (d, 2H), 3.59 (s, 3H), 3.66 (q, 1H), 4.20 (d, 1H), 7.07 (m, 2H), 7.20 (m, 1H), 8.14 (m, 1H), 8.40 (d, 1H)

Ex. erythro-Ibb7, NMR: 2.90 (dd, 1H), 3.11 (dd, 1H), 3.69 (m, 1H), 3.71 (s, 3H), 4.62 (d, 1H), 7.12 (dt, 1H), 7.23 (d, 2H), 8.15 (d, 2H), 8.27 (bs, 1H), 8.46 (d, 1H)

Ex. threo-Ibb7, NMR: 2.98 (d, 2H), 3.60 (s, 3H), 3.80 (q, 1H), 4.25 (d, 1H), 7.32 (m, 1H), 7.33 (d, 2H), 8.19 (d, 2H), 8.19 (m, 1H), 8.44 (bs, 1H)

Ex. erythro-Ibb9, NMR: 2.87 (dd, 1H), 3.06 (dd, 1H), 3.54 (m, 1H), 3.71 (s, 3H), 4.56 (d, 1H), 6.78 (m, 2H), 7.00 (m, 1H), 7.08 (t, 1H), 8.25 (m, 1H), 8.43 (d, 1H)

Ex. threo-Ibb9, NMR: 2.93 (m, 2H), 3.60 (s, 3H), 3.66 (q, 1H), 4.19 (d, 1H), 6.83 (m, 1H), 6.88 (d, 1H), 6.98 (m. 1H), 8.17 (t, 1H), 8.43 (d, 1H)

Ex. threo-Ibb10, NMR: 2.93 (d, 2H), 3.61 (s, 3H), 3.64 (q, 1H), 4.19 (d, 1H), 6.99 (m, 1H), 7.09 (m, 1H), 8.17 (bs, 1H), 8.44 (d, 1H)

Ex. erythro-Ibb25, NMR: 2.81 (dd, 1H), 3.00 (dd, 1H), 3.70 (s, 3H), 3.96 (q, 1H), 4.59 (d, 1H), 6.91 (m, 1H), 6.99 (m, 1H), 7.11 (m, 1H), 7.21 (dt, 1H), 8.28 (bs, 1H), 8.45 (d, 1H)

Ex. threo-Ibb25, NMR: 3.00 (m, 2H), 3.60 (s, 3H), 3.91 (q, 1H), 4.26 (d, 1H), 6.85 (m, 1H), 7.00 (m. 2H), 7.40 (dt, 1H), 8.25 (bs, 1H), 8.44 (d, 1H)

Ex. erythro-Ibb26, NMR: 2.88 (d, 2H), 3.59 (s, 3H), 4.11 (q, 1H), 4.46 (d, 1H), 6.92 (t, 2H), 7.44 (dt, 1H), 8.39 (bs, 1H), 8.49 (d, 1H)

Ex. erythro-1-Ibb26, NMR: 2.88 (d, 2H), 3.59 (s, 3H), 4.11 (q, 1H), 4.46 (d, 1H), 6.92 (t, 2H), 7.44 (dt, 1H), 8.39 (bs, 1H), 8.49 (d, 1H); chiral HPLC: 12.5 min, mobile phase c Ex. erythro-2-Ibb26, NMR: 2.88 (d, 2H), 3.59 (s, 3H), 4.11 (q, 1H), 4.46 (d, 1H), 6.92 (t, 2H), 7.44 (dt, 1H), 8.39 (bs, 1H), 8.49 (d, 1H); chiral HPLC: 13.5 min, mobile phase c Ex. threo-Ibb26, NMR: 3.15 (dd, 1H), 3.23 (dd, 1H), 3.63 (s, 3H), 4.17 (m, 1H), 4.26 (d, 1H), 6.78 (t, 2H), 7.39 (dt, 1H), 8.10 (bs, 1H), 8.36 (bs, 1H)

Ex. threo-1-Ibb26, NMR: 3.15 (dd, 1H), 3.23 (dd, 1H), 3.63 (s, 3H), 4.17 (m, 1H), 4.26 (d, 1H), 6.78 (t, 2H), 7.39 (dt, 1H), 8.10 (bs, 1H), 8.36 (bs, 1H); chiral HPLC: 11.7 min, mobile phase c Ex. threo-2-Ibb26, NMR: 3.15 (dd, 1H), 3.23 (dd, 1H), 3.63 (s, 3H), 4.17 (m, 1H), 4.26 (d, 1H), 6.78 (t, 2H), 7.39 (dt, 1H), 8.10 (bs, 1H), 8.36 (bs, 1H); chiral HPLC: 16.5 min, mobile phase c Ex. erythro-Ibb541, NMR: 2.86 (dd, 1H), 3.06 (dd, 1H), 3.52 (m, 1H), 3.71 (s, 3H), 4.50 (d, 1H), 6.98 (d, 2H), 7.32 (t, 1H), 8.24 (d, 1H), 8.52 (d, 1H)

Ex. threo-Ibb541, NMR: 2.90 (m, 2H), 3.60 (s, 3H), 3.66 (q, 1H), 4.14 (d, 1H), 7.00 (m, 2H), 7.06 (m, 2H), 7.48 (t, 1H), 8.18 (d, 1H), 8.52 (d, 1H)

Ex. erythro-Ibb542, NMR: 2.85 (dd, 1H), 3.05 (dd, 1H), 3.51 (m, 1H), 3.70 (s, 3H), 4.50 (d, 1H), 6.95 (d, 2H), 7.27 (d, 2H), 7.35 (t, 1H), 8.25 (d, 1H), 8.52 (d, 1H)

Ex. threo-Ibb542, NMR: 2.89 (d, 2H), 3.60 (s, 3H), 3.64 (q, 1H), 4.14 (d, 1H), 7.04 (d, 2H), 7.29 (d, 2H), 7.50 (t, 1H), 8.19 (d, 1H), 8.53 (d, 1H)

Ex. threo-1-Ibb542, NMR: 2.89 (d, 2H), 3.60 (s, 3H), 3.64 (q, 1H), 4.14 (d, 1H), 7.04 (d, 2H), 7.29 (d, 2H), 7.50 (t, 1H), 8.19 (d, 1H), 8.53 (d, 1H); chiral HPLC: 11.0 min, mobile phase c Ex. threo-2-Ibb542, NMR: 2.89 (d, 2H), 3.60 (s, 3H), 3.64 (q, 1H), 4.14 (d, 1H), 7.04 (d, 2H), 7.29 (d, 2H), 7.50 (t, 1H), 8.19 (d, 1H), 8.53 (d, 1H); chiral HPLC: 18.5 min, mobile phase c Ex. erythro-Ibb543, NMR: 2.85 (dd, 1H), 3.05 (dd, 1H), 3.50 (m, 1H), 3.70 (s, 3H), 4.50 (d, 1H), 6.89 (d, 2H), 7.36 (s, 1H), 7.42 (d, 2H), 8.25 (s, 1H), 8.53 (s, 1H)

Ex. threo-Ibb543, NMR: 2.90 (d, 2H), 3.60 (s, 3H), 3.63 (q, 1H), 4.14 (d, 1H), 6.98 (d, 2H), 7.44 (d, 2H), 7.51 (t, 1H), 8.19 (d, 1H), 8.53 (d, 1H)

Ex. erythro-Ibb544, NMR: 2.89 (dd, 1H), 3.10 (dd, 1H), 3.52 (m, 1H), 3.70 (s, 3H), 4.52 (d, 1H), 7.00 (m, 2H), 7.29 (m, 4H), 8.23 (d, 1H), 8.50 (d, 1H)

Ex. threo-Ibb544, NMR: 2.94 (d, 2H), 3.59 (s, 3H), 3.65 (q, 1H), 4.16 (d, 1H), 7.07 (m, 2H), 7.29 (m, 3H), 7.45 (t, 1H), 8.16 (d, 1H), 8.60 (d, 1H)

Ex. erythro-Ibb546, NMR: 2.87 (dd, 1H), 3.08 (dd, 1H), 3.60 (m, 1H), 3.71 (s, 3H), 4.55 (d, 1H), 7.15 (d, 2H), 7.35 (t, 1H), 7.60 (d, 2H), 8.27 (d, 1H), 8.55 (d, 1H)

Ex. threo-Ibb546, NMR: 2.94 (d, 2H), 3.60 (s, 3H), 3.73 (q, 1H), 4.18 (d, 1H), 7.26 (d, 2H), 7.51 (t, 1H), 7.63 (d, 2H), 8.21 (bs, 1H), 8.55 (bs, 1H)

Ex. erythro-Ibb547, NMR: 2.90 (dd, 1H), 3.10 (dd, 1H), 3.68 (m, 1H), 3.71 (s, 3H), 4.57 (d, 1H), 7.22 (d, 2H), 7.40 (t, 1H), 8.17 (d, 2H), 8.28 (d, 1H), 8.55 (d, 1H)

Ex. threo-Ibb547, NMR: 2.97 (d, 2H), 3.60 (s, 3H), 3.80 (q, 1H), 4.21 (d, 1H), 7.34 (d, 2H), 7.55 (t, 1H), 8.20 (d, 2H), 8.23 (bs, 1H), 8.56 (bs, 1H)

Ex. erythro-Ibb548, NMR: 2.85 (dd, 1H), 3.06 (dd, 1H), 3.47 (m, 1H), 3.70 (s, 3H), 3.78 (s, 3H), 4.47 (d, 1H), 6.80 (d, 2H), 6.91 (d, 2H), 7.31 (m, 1H), 8.22 (d, 1H), 8.50 (d, 1H)

Ex. threo-Ibb548, NMR: 2.89 (m, 2H), 3.59 (s, 3H), 3.60 (m, 1H), 3.78 (s, 3H), 4.12 (d, 1H), 6.81 (d, 2H), 6.98 (d, 2H), 7.46 (t, 1H), 8.15 (d, 1H), 8.50 (d, 1H)

Ex. erythro-Ibb553, NMR: 2.87 (dd, 1H), 3.07 (dd, 1H), 3.58 (m, 1H), 3.71 (s, 3H), 4.53 (d, 1H), 7.31 (m, 2H), 7.36 (t, 1H), 7.44 (t, 1H), 7.62 (m, 1H), 8.27 (d, 1H), 8.55 (d, 1H)

Ex. threo-Ibb553, NMR: 2.93 (d, 2H), 3.61 (s, 3H), 3.71 (q, 1H), 4.17 (d, 1H), 7.41 (m, 2H), 7.46 (t, 1H), 7.51 (t, 1H), 7.62 (m, 1H), 8.21 (d, 1H), 8.55 (d, 1H)

Ex. erythro-Ibb565, NMR: 2.81 (dd, 1H), 2.99 (dd, 1H), 3.69 (s, 3H), 3.94 (q, 1H), 4.54 (d, 1H), 6.93 (m, 1H), 6.99 (m, 1H), 7.10 (m, 1H), 7.45 (t, 1H), 8.31 (bs, 1H), 8.54 (d, 1H)

Ex. threo-Ibb565, NMR: 2.99 (m, 2H), 3.60 (s, 3H), 3.91 (q, 1H), 4.22 (d, 1H), 6.86 (m, 1H), 6.98 (m. 1H), 7.01 (m, 1H), 7.65 (t, 1H), 8.30 (d, 1H), 8.53 (d, 1H)

Ex. erythro-Ibb566, NMR: 2.88 (d, 2H), 3.59 (s, 3H), 4.10 (q, 1H), 4.41 (d, 1H), 6.92 (t, 2H), 7.32 (m, 1H), 7.69 (t, 1H), 8.44 (bs, 1H), 8.59 (bs, 1H)

Ex. threo-Ibb566, NMR: 3.12 (dd, 1H), 3.23 (dd, 1H), 3.63 (s, 3H), 4.18 (m, 1H), 4.22 (d, 1H), 6.79 (t, 2H), 7.18 (m, 1H), 7.64 (t, 1H), 8.15 (d, 1H), 8.45 (d, 1H)

Ex. threo-1-Ibb566, NMR: 3.12 (dd, 1H), 3.23 (dd, 1H), 3.63 (s, 3H), 4.18 (m, 1H), 4.22 (d, 1H), 6.79 (t, 2H), 7.18 (m, 1H), 7.64 (t, 1H), 8.15 (d, 1H), 8.45 (d, 1H)); chiral HPLC: 11.5 min, mobile phase c Ex. threo-2-Ibb566, NMR: 3.12 (dd, 1H), 3.23 (dd, 1H), 3.63 (s, 3H), 4.18 (m, 1H), 4.22 (d, 1H), 6.79 (t, 2H), 7.18 (m, 1H), 7.64 (t, 1H), 8.15 (d, 1H), 8.45 (d, 1H)); chiral HPLC: 15.4 min, mobile phase c Ex. Ibb587 (erythro-Ibb587: threo-Ibb587=50:50), NMR:
erythro-Ibb587: 2.85 (dd, 1H), 3.06 (dd, 1H), 3.48 (m, 1H), 3.71 (s, 3H), 4.53 (d, 1H), 6.96 (d, 2H), 7.28 (d, 2H), 7.46 (dd, 1H), 7.83 (m, 1H)

threo-Ibb587: 2.89 (m, 2H), 3.61 (s, 3H), 3.63 (q, 1H), 4.16 (d, 1H), 7.03 (d, 2H), 7.30 (d, 2H), 7.61 (dd, 1H), 7.77 (m, 1H)

Ex. erythro-Ibb587: 2.85 (dd, 1H), 3.06 (dd, 1H), 3.48 (m, 1H), 3.71 (s, 3H), 4.53 (d, 1H), 6.96 (d, 2H), 7.28 (d, 2H), 7.46 (dd, 1H), 7.83 (m, 1H)

Ex. threo-Ibb587: 2.89 (m, 2H), 3.61 (s, 3H), 3.63 (q, 1H), 4.16 (d, 1H), 7.03 (d, 2H), 7.30 (d, 2H), 7.61 (dd, 1H), 7.77 (m, 1H)

Ex. Ibb589 (erythro-Ibb589: threo-Ibb589=50:50), NMR:
erythro-Ibb589: 2.90 (dd, 1H), 3.11 (dd, 1H), 3.48 (m, 1H), 3.71 (s, 3H), 4.55 (d, 1H), 7.00 (m, 2H), 7.30 (m, 3H), 7.37 (dd, 1H), 7.81 (m, 1H)

threo-Ibb589: 2.94 (m, 2H), 3.61 (s, 3H), 3.63 (q, 1H), 4.17 (d, 1H), 7.05 (m, 2H), 7.54 (dd, 1H), 7.74 (m, 1H)

Ex. erythro-Ibb589: 2.90 (dd, 1H), 3.11 (dd, 1H), 3.48 (m, 1H), 3.71 (s, 3H), 4.55 (d, 1H), 7.00 (m, 2H), 7.30 (m, 3H), 7.37 (dd, 1H), 7.81 (m, 1H)

Ex. erythro-Ibb592: 2.90 (dd, 1H), 3.10 (dd, 1H), 3.65 (m, 1H), 3.72 (s, 3H), 4.59 (d, 1H), 7.25 (d, 2H), 7.53 (dd, 1H), 7.87 (m, 1H), 8.18 (d, 2H)

Ex. threo-Ibb592: 2.97 (d, 2H), 3.61 (s, 3H), 3.78 (q, 1H), 4.23 (d, 1H), 7.33 (d, 2H), 7.68 (dd, 1H), 7.82 (m, 1H), 8.20 (d, 2H)

Ex. Ibb594 (erythro-Ibb594: threo-Ibb594=54:46), NMR:
erythro-Ibb594: 2.87 (dd, 1H), 3.06 (dd, 1H), 3.50 (m, 1H), 3.72 (s, 3H), 4.54 (d, 1H), 6.79 (m, 2H), 7.00 (m, 1H), 7.28 (m, 1H), 7.45 (dd, 1H), 7.85 (m, 1H)

threo-Ibb594: 2.92 (m, 2H), 3.62 (s, 3H), 3.63 (q, 1H), 4.17 (d, 1H), 6.83 (m, 2H), 7.01 (m, 1H), 7.28 (m, 1H), 7.61 (dd, 1H), 7.78 (m, 1H)

Ex. erythro-Ibb594: 2.87 (dd, 1H), 3.06 (dd, 1H), 3.50 (m, 1H), 3.72 (s, 3H), 4.54 (d, 1H), 6.79 (m, 2H), 7.00 (m, 1H), 7.28 (m, 1H), 7.45 (dd, 1H), 7.85 (m, 1H)

Ex. Ibb595 (erythro-Ibb595: threo-Ibb595=48:52), NMR:
erythro-Ibb595: 2.85 (dd, 1H), 3.05 (dd, 1H), 3.47 (m, 1H), 3.71 (s, 3H), 4.53 (d, 1H), 6.91 (dt, 1H), 7.04 (t, 1H), 7.45 (dd, 1H), 7.86 (m, 1H)

threo-Ibb595: 2.91 (m, 2H), 3.61 (q, 1H), 3.62 (s, 3H), 4.18 (d, 1H), 6.98 (dt, 1H), 7.10 (t, 1H), 7.62 (dd, 1H), 7.80 (m, 1H)

Ex. erythro-Ibb595: 2.85 (dd, 1H), 3.05 (dd, 1H), 3.47 (m, 1H), 3.71 (s, 3H), 4.53 (d, 1H), 6.91 (dt, 1H), 7.04 (t, 1H), 7.24 (t, 1H), 7.30 (m, 1H), 7.45 (dd, 1H), 7.86 (m, 1H)

Ex. Ibb610 (erythro-Ibb610: threo-Ibb610=55:45), NMR:
erythro-Ibb610: 2.82 (dd, 1H), 3.01 (dd, 1H), 3.71 (s, 3H), 3.93 (m, 1H), 4.58 (d, 1H), 6.94 (m, 1H), 6.99 (m, 1H), 7.12 (m, 1H), 7.59 (dd, 1H), 7.90 (m, 1H)
threo-Ibb610: 2.99 (m, 2H), 3.61 (s, 3H), 3.90 (q, 1H), 4.22 (d, 1H), 6.86 (m, 1H), 7.00 (m, 2H), 7.79 (m, 1H), 7.88 (m, 2H)

Ex. erythro-Ibb610: 2.82 (dd, 1H), 3.01 (dd, 1H), 3.71 (s, 3H), 3.93 (m, 1H), 4.58 (d, 1H), 6.94 (m, 1H), 6.99 (m, 1H), 7.12 (m, 1H), 7.59 (dd, 1H), 7.90 (m, 1H)

Ex. Ibb611 (erythro-Ibb611: threo-Ibb611=50:50), NMR:
erythro-Ibb611: 2.88 (dd, 1H), 2.93 (dd, 1H), 3.62 (s, 3H), 4.07 (q, 1H), 4.45 (d, 1H), 6.92 (t, 2H), 7.31 (m, 1H), 7.81 (dd, 1H), 8.02 (m, 1H)
threo-Ibb611: 3.11 (dd, 1H), 3.24 (dd, 1H), 3.63 (s, 3H), 4.16 (m, 1H), 4.22 (d, 1H), 6.81 (t, 2H), 7.23 (m, 1H), 7.74 (m, 1H), 7.78 (dd, 1H)

Ex. erythro-Ibb624: 2.87 (m, 2H), 3.63 (s, 3H), 4.01 (q, 1H), 4.40 (d, 1H), 6.98 (d, 2H), 7.84 (dd, 1H), 8.03 (m, 1H)

Ex. threo-Ibb624: 3.07 (dd, 1H), 3.22 (dd, 1H), 3.64 (s, 3H), 4.10 (m, 1H), 4.18 (d, 1H), 6.87 (d, 2H), 7.76 (m, 1H), 7.80 (dd, 1H)

Ex. erythro-Ibb1081, NMR: 2.86 (dd, 1H), 3.06 (dd, 1H), 3.51 (m, 1H), 3.70 (s, 3H), 4.49 (d, 1H), 6.98 (d, 4H), 7.46 (t, 1H), 8.27 (d, 1H), 8.62 (d, 1H)

Ex. threo-Ibb1081, NMR: 2.90 (m, 2H), 3.60 (s, 3H), 3.65 (q, 1H), 4.12 (d, 1H), 7.03 (m, 4H), 7.62 (t, 1H), 8.22 (d, 1H), 8.62 (d, 1H)

Ex. Iba1082 (erythro-Iba1082:threo-Iba1082=35:65):
erythro-Iba1082, NMR: 2.90 (dd, 1H), 3.10 (dd, 1H), 3.49 (m, 1H), 4.50 (d, 1H), 6.95 (d, 2H), 7.30 (d, 2H), 7.49 (m, 1H)
threo-Iba1082, NMR: 2.93 (m, 2H), 3.64 (q, 1H), 4.14 (d, 1H), 7.05 (d, 2H), 7.27 (d, 2H), 7.65 (m, 1H)

Ex. Ibb1082 (erythro-Ibb1082:threo-Ibb1082=58:42):
erythro-Ibb1082, NMR: 2.85 (dd, 1H), 3.06 (dd, 1H), 3.51 (m, 1H), 3.71 (s, 3H), 4.49 (d, 1H), 6.95 (d, 2H), 7.27 (d, 2H), 7.49 (m, 1H)
threo-Ibb1082, NMR: 2.89 (d, 2H), 3.60 (s, 3H), 3.64 (q, 1H), 4.12 (d, 1H), 7.04 (d, 2H), 7.29 (d, 2H), 7.64 (m, 1H)

Ex. erythro-Ibb1082, NMR: 2.85 (dd, 1H), 3.06 (dd, 1H), 3.51 (m, 1H), 3.71 (s, 3H), 4.49 (d, 1H), 6.95 (d, 2H), 7.27 (d, 2H), 7.49 (m, 1H), 8.27 (d, 1H), 8.62 (d, 1H)

Ex. erythro-1-Ibb1082, NMR: 2.85 (dd, 1H), 3.06 (dd, 1H), 3.51 (m, 1H), 3.71 (s, 3H), 4.49 (d, 1H), 6.95 (d, 2H), 7.27 (d, 2H), 7.49 (m, 1H), 8.27 (d, 1H), 8.62 (d, 1H); chiral HPLC: 28.2 min, mobile phase d Ex. erythro-2-Ibb1082, NMR: 2.85 (dd, 1H), 3.06 (dd, 1H), 3.51 (m, 1H), 3.71 (s, 3H), 4.49 (d, 1H), 6.95 (d, 2H), 7.27 (d, 2H), 7.49 (m, 1H), 8.27 (d, 1H), 8.62 (d, 1H); chiral HPLC: rt=30.4 min, mobile phase d Ex. threo-Ibb1082, NMR: 2.89 (d, 2H), 3.60 (s, 3H), 3.64 (q, 1H), 4.12 (d, 1H), 7.04 (d, 2H), 7.29 (d, 2H), 7.64 (m, 1H), 8.22 (d, 1H), 8.63 (d, 1H)

Ex. threo-1-Ibb1082, NMR: 2.89 (d, 2H), 3.60 (s, 3H), 3.64 (q, 1H), 4.12 (d, 1H), 7.04 (d, 2H), 7.29 (d, 2H), 7.64 (t, 1H), 8.22 (d, 1H), 8.63 (d, 1H); chiral HPLC: rt=6.9 min, mobile phase a Ex. threo-2-Ibb1082, NMR: 2.89 (d, 2H), 3.60 (s, 3H), 3.64 (q, 1H), 4.12 (d, 1H), 7.04 (d, 2H), 7.29 (d, 2H), 7.64 (t, 1H), 8.22 (d, 1H), 8.63 (d, 1H); chiral HPLC: rt=9.9 min, mobile phase a Ex. Ibc1082 (erythro-Ibc1082:threo-Ibc1082=58:42):
erythro-Ibc1082, NMR: 1.24 (t, 3H), 2.83 (dd, 1H), 3.03 (dd, 1H), 3.51 (m, 1H), 4.14 (q, 2H), 4.48 (d, 1H), 6.95 (d, 2H), 7.28 (d, 2H), 7.49 (m, 1H), 8.27 (m, 1H), 8.63 (m, 1H)
threo-Ibc1082, NMR: 1.16 (t, 3H), 2.89 (d, 2H), 3.63 (q, 1H), 4.03 (m, 2H), 4.12 (d, 1H), 7.04 (d, 2H), 7.26 (d, 2H), 7.64 (m, 1H), 8.22 (m, 1H), 8.63 (m, 1H)
erythro-Ibc1082, NMR: 1.24 (t, 3H), 2.83 (dd, 1H), 3.03 (dd, 1H), 3.51 (m, 1H), 4.14 (q, 2H), 4.48 (d, 1H), 6.95 (d, 2H), 7.28 (d, 2H), 7.49 (m, 1H), 8.27 (m, 1H), 8.63 (m, 1H)
threo-Ibc1082, NMR: 1.16 (t, 3H), 2.89 (d, 2H), 3.63 (q, 1H), 4.03 (m, 2H), 4.12 (d, 1H), 7.04 (d, 2H), 7.26 (d, 2H), 7.64 (m, 1H), 8.22 (m, 1H), 8.63 (m, 1H)

Ex. Ibv1082 (erythro-Ibv1082:threo-Ibv1082=58:42):
erythro-Ibv1082, NMR: 3.09 (t, 2H), 3.47 (m, 1H), 4.28 (t, 2H), 4.47 (d, 1H), 6.93 (d, 2H), 7.49 (t, 1H), 8.28 (d, 1H), 8.63 (d, 1H)
threo-Ibv1082, NMR: 3.02 (t, 2H), 3.59 (q, 1H), 4.12 (d, 1H), 4.16 (m, 2H), 7.01 (d, 2H), 7.67 (t, 1H), 8.21 (d, 1H), 8.63 (d, 1H)

Ex. erythro-Ibb1083, NMR in [D$_6$-DMSO]: 2.63 (dd, 1H), 2.76 (dd, 1H), 3.39 (s, 3H), 3.75 (m, 1H), 4.75 (d, 1H), 7.28 (d, 2H), 7.57 (d, 2H), 8.11 (t, 1H), 8.50 (d, 1H), 8.72 (d, 1H)

Ex. threo-Ibb1083, NMR in [D$_6$-DMSO]: 2.94 (m, 2H), 3.45 (s, 3H), 3.85 (m, 1H), 4.74 (d, 1H), 7.18 (d, 2H), 7.46 (d, 2H), 8.06 (t, 1H), 8.33 (d, 1H), 8.61 (d, 1H)

Ex. erythro-Ibb1084, NMR: 2.89 (dd, 1H), 3.10 (dd, 1H), 3.51 (m, 1H), 3.70 (s, 3H), 4.51 (d, 1H), 7.00 (m, 2H), 7.29 (m, 3H), 7.42 (t, 1H), 8.25 (d, 1H), 8.60 (d, 1H)

Ex. threo-Ibb1084, NMR: 2.94 (d, 2H), 3.64 (s, 3H), 3.65 (q, 1H), 4.14 (d, 1H), 7.08 (m, 2H), 7.30 (m, 3H), 7.60 (s, 1H), 8.20 (s, 1H), 8.60 (s, 1H)

Ex. erythro-Ibb1085, NMR: 2.31 (s, 3H), 2.87 (dd, 1H), 3.07 (dd, 1H), 3.48 (m, 1H), 3.70 (s, 3H), 4.47 (d, 1H), 6.87 (d, 2H), 7.08 (d, 2H), 7.44 (m, 1H), 8.23 (d, 1H), 8.60 (d, 1H)

Ex. threo-Ibb1085, NMR: 2.31 (s, 3H), 2.91 (d, 2H), 3.59 (s, 3H), 3.61 (q, 1H), 4.12 (d, 1H), 6.95 (d, 2H), 7.10 (d, 2H), 7.62 (t, 1H), 8.18 (d, 1H), 8.60 (d, 1H)

Ex. erythro-Ibb1087, NMR: 2.90 (dd, 1H), 3.10 (dd, 1H), 3.67 (m, 1H), 3.71 (s, 3H), 4.55 (d, 1H), 7.22 (d, 2H), 7.53 (t, 1H), 8.17 (d, 2H), 8.31 (d, 1H), 8.65 (d, 1H)

Ex. threo-Ibb1087, NMR: 2.97 (d, 2H), 3.60 (s, 3H), 3.79 (q, 1H), 4.19 (d, 1H), 7.33 (d, 2H), 7.69 (t, 1H), 8.20 (d, 2H), 8.26 (bs, 1H), 8.65 (bs, 1H)

Ex. erythro-Ibb1088, NMR: 2.85 (dd, 1H), 3.06 (dd, 1H), 3.47 (m, 1H), 3.70 (s, 3H), 3.78 (s, 3H), 4.46 (d, 1H), 6.80 (d, 2H), 6.91 (d, 2H), 7.44 (s, 1H), 8.25 (s, 1H), 8.60 (s, 1H)

Ex. threo-Ibb1088, NMR: 2.89 (m, 2H), 3.59 (s, 3H), 3.60 (m, 1H), 3.78 (s, 3H), 4.11 (d, 1H), 6.81 (d, 2H), 6.99 (d, 2H), 7.61 (t, 1H), 8.19 (d, 1H), 8.60 (d, 1H)

Ex. erythro-Ibb1089, NMR: 2.87 (dd, 1H), 3.05 (dd, 1H), 3.52 (m, 1H), 3.71 (s, 3H), 4.50 (d, 1H), 6.77 (m, 2H), 7.02 (m, 1H), 7.49 (m, 1H), 8.29 (d, 1H), 8.62 (d, 1H)

Ex. threo-Ibb1089, NMR: 2.92 (d, 2H), 3.61 (s, 3H), 3.65 (q, 1H), 4.13 (d, 1H), 6.83 (m, 1H), 6.88 (d, 1H), 6.99 (m. 1H), 7.65 (m, 1H), 8.23 (d, 1H), 8.62 (d, 1H)

Ex. threo-Ibb1090, NMR: 2.91 (d, 2H), 3.61 (s, 3H), 3.63 (q, 1H), 4.14 (d, 1H), 6.99 (m, 2H), 7.65 (m, 1H), 8.25 (d, 1H), 8.64 (d, 1H)

Ex. erythro-Ibb1092, NMR: 2.28 (s, 3H), 2.87 (dd, 1H), 3.07 (dd, 1H), 3.47 (m, 1H), 3.70 (s, 3H), 4.49 (d, 1H), 6.77 (s, 1H), 6.80 (d, 1H), 7.11 (d, 1H), 7.17 (t, 1H), 7.40 (t, 1H), 8.26 (d, 1H), 8.60 (d, 1H)

Ex. threo-Ibb1092, NMR: 2.28 (s, 3H), 2.91 (d, 2H), 3.60 (s, 3H), 3.61 (q, 1H), 4.14 (d, 1H), 6.87 (m, 2H), 7.09 (d, 1H), 7.19 (t, 1H), 7.59 (t, 1H), 8.21 (d, 1H), 8.61 (d, 1H)

Ex. erythro-Ibb1093, NMR: 2.87 (dd, 1H), 3.06 (dd, 1H), 3.57 (m, 1H), 3.71 (s, 3H), 4.51 (d, 1H), 7.32 (m, 2H), 7.44 (t, 1H), 7.50 (t, 1H), 7.62 (m, 1H), 8.30 (d, 1H), 8.65 (d, 1H)

Ex. threo-Ibb1093, NMR: 2.93 (d, 2H), 3.61 (s, 3H), 3.70 (q, 1H), 4.16 (d, 1H), 7.39 (m, 2H), 7.46 (t, 1H), 7.62 (m, 1H), 7.63 (m, 1H), 8.25 (bs, 1H), 8.66 (bs, 1H)

Ex. erythro-Ibb1094, NMR: 2.90 (dd, 1H), 3.09 (dd, 1H), 3.68 (m, 1H), 3.70 (s, 3H), 4.53 (d, 1H), 7.42 (m, 1H), 7.55 (m, 2H), 7.89 (t, 1H), 8.19 (m, 1H), 8.32 (d, 1H), 8.66 (d, 1H)

Ex. threo-Ibb1094, NMR: 2.98 (d, 2H), 3.61 (s, 3H), 3.80 (q, 1H), 4.21 (d, 1H), 7.51 (m, 2H), 7.68 (t, 1H), 8.00 (t, 1H), 8.17 (m, 1H), 8.26 (d, 1H), 8.65 (d, 1H)

Ex. Ibb1096 (erythro-Ibb1096: threo-Ibb1096=55:45), NMR:

erythro-Ibb1096: 2.83 (dd, 1H), 3.04 (dd, 1H), 3.68 (s, 3H), 3.97 (q, 1H), 4.53 (d, 1H), 7.54 (t, 1H), 8.30 (d, 1H), 8.62 (d, 1H)

threo-Ibb1096: 3.01 (m, 2H), 3.58 (s, 3H), 3.93 (m, 1H), 4.22 (d, 1H), 7.77 (t, 1H), 8.30 (d, 1H), 8.60 (d, 1H)

Ex. erythro-Ibb1103, NMR: 2.84 (dd, 1H), 3.03 (dd, 1H), 3.69 (s, 3H), 3.98 (m, 1H), 4.54 (d, 1H), 7.14 (m, 3H), 7.59 (t, 1H), 8.33 (d, 1H), 8.65 (d, 1H)

Ex. threo-Ibb1103, NMR: 3.00 (m, 2H), 3.59 (s, 3H), 3.97 (m, 1H), 4.20 (d, 1H), 6.91 (m, 1H), 7.13 (m, 2H), 7.80 (t, 1H), 8.34 (d, 1H), 8.64 (d, 1H)

Ex. erythro-Ibb1104, NMR: 2.81 (dd, 1H), 3.01 (dd, 1H), 3.691 (s, 3H), 3.92 (q, 1H), 4.51 (d, 1H), 6.71 (m, 1H), 6.94 (m, 1H), 7.36 (m, 1H), 7.58 (t, 1H), 8.32 (d, 1H), 8.64 (d, 1H)

Ex. threo-Ibb1104, NMR: 2.98 (m, 2H), 3.58 (s, 3H), 3.90 (q, 1H), 4.19 (d, 1H), 6.82 (m, 2H), 7.10 (m, 1H), 7.78 (t, 1H), 8.32 (d, 1H), 8.62 (d, 1H)

Ex. erythro-Ibb1105, NMR: 2.81 (dd, 1H), 2.99 (dd, 1H), 3.71 (s, 3H), 3.95 (q, 1H), 4.53 (d, 1H), 6.92 (m, 1H), 6.99 (m, 1H), 7.10 (m, 1H), 7.60 (m, 1H), 8.36 (d, 1H), 8.66 (d, 1H)

Ex. erythro-1-Ibb1105, NMR: 2.81 (dd, 1H), 2.99 (dd, 1H), 3.69 (s, 3H), 3.94 (q, 1H), 4.53 (d, 1H), 6.92 (m, 1H), 6.99 (m, 1H), 7.10 (m, 1H), 7.60 (t, 1H), 8.35 (d, 1H), 8.65 (d, 1H), chiral HPLC: rt=26.9 min, mobile phase d Ex. erythro-2-Ibb1105, NMR: 2.81 (dd, 1H), 2.99 (dd, 1H), 3.69 (s, 3H), 3.94 (q, 1H), 4.53 (d, 1H), 6.92 (m, 1H), 6.99 (m, 1H), 7.10 (m, 1H), 7.60 (t, 1H), 8.35 (d, 1H), 8.65 (d, 1H), chiral HPLC: rt=29.2 min, mobile phase d Ex. threo-Ibb1105, NMR: 2.98 (m, 2H), 3.60 (s, 3H), 3.89 (q, 1H), 4.20 (d, 1H), 6.86 (m, 1H), 7.00 (m, 2H), 7.80 (m, 1H), 8.35 (d, 1H), 8.63 (d, 1H)

Ex. threo-1-Ibb1105, NMR: 2.98 (m, 2H), 3.60 (s, 3H), 3.90 (q, 1H), 4.20 (d, 1H), 6.86 (m, 1H), 7.00 (m, 2H), 7.80 (t, 1H), 8.34 (d, 1H), 8.63 (d, 1H), chiral HPLC: rt=10.9 min, mobile phase c Ex. threo-2-Ibb1105, NMR: 2.98 (m, 2H), 3.60 (s, 3H), 3.90 (q, 1H), 4.20 (d, 1H), 6.85 (m, 1H), 7.00 (m, 2H), 7.80 (t, 1H), 8.34 (d, 1H), 8.63 (d, 1H), chiral HPLC: rt=15.1 min, mobile phase c Ex. erythro-Ibb1106, NMR: 2.88 (d, 2H), 3.60 (s, 3H), 4.09 (q, 1H), 4.39 (d, 1H), 6.92 (t, 2H), 7.82 (m, 1H), 8.47 (d, 1H), 8.68 (d, 1H)

Ex. erythro-1-Ibb1106, NMR: 2.88 (d, 2H), 3.60 (s, 3H), 4.09 (q, 1H), 4.39 (d, 1H), 6.92 (t, 2H), 7.83 (m, 1H), 8.47 (d, 1H), 8.69 (d, 1H); chiral HPLC: rt 8.7 min, mobile phase b Ex. erythro-2-Ibb1106, NMR: 2.88 (d, 2H), 3.60 (s, 3H), 4.09 (q, 1H), 4.39 (d, 1H), 6.92 (t, 2H), 7.83 (m, 1H), 8.47 (d, 1H), 8.69 (d, 1H); chiral HPLC: rt 9.8 min, mobile phase b Ex. threo-Ibb1106, NMR: 3.12 (dd, 1H), 3.23 (dd, 1H), 3.63 (s, 3H), 4.17 (m, 2H), 6.79 (t, 2H), 7.78 (m, 1H), 8.18 (d, 1H), 8.55 (d, 1H)

Ex. threo-1-Ibb1106, NMR: 3.12 (dd, 1H), 3.23 (dd, 1H), 3.63 (s, 3H), 4.17 (m, 2H), 6.79 (t, 2H), 7.18 (m, 1H), 7.78 (t, 1H), 8.18 (d, 1H), 8.55 (d, 1H); chiral HPLC: rt 7.3 min, mobile phase a Ex. threo-2-Ibb1106, NMR: 3.12 (dd, 1H), 3.23 (dd, 1H), 3.63 (s, 3H), 4.17 (m, 2H), 6.79 (t, 2H), 7.18 (m, 1H), 7.78 (t, 1H), 8.18 (d, 1H), 8.55 (d, 1H); 7.3 min, chiral HPLC: rt 9.0 min, mobile phase a Ex. erythro-Ibb1107, NMR: 2.84 (dd, 1H), 3.02 (dd, 1H), 3.50 (m, 1H), 3.71 (s, 3H), 4.48 (d, 1H), 6.74 (m, 1H), 6.91 (m, 1H), 7.09 (m, 1H), 7.53 (t, 1H), 8.30 (d, 1H), 8.64 (d, 1H)

Ex. threo-Ibb1107, NMR: 2.88 (d, 2H), 3.61 (s, 3H), 3.62 (q, 1H), 4.12 (d, 1H), 6.86 (m, 1H), 6.96 (m, 1H), 7.11 (m, 1H), 7.67 (t, 1H), 8.24 (d, 1H), 8.64 (d, 1H)

Ex. threo-Ibb1108, NMR: 2.90 (d, 2H), 3.62 (s, 3H), 3.64 (q, 1H), 4.13 (d, 1H), 6.67 (m, 2H), 6.75 (m. 1H), 7.70 (m, 1H), 8.27 (d, 1H), 8.65 (d, 1H)

Ex. erythro-Ibb1119, NMR: 2.84 (d, 2H), 3.60 (s, 3H), 4.03 (q, 1H), 4.35 (d, 1H), 6.98 (m, 2H), 7.85 (t, 1H), 8.48 (d, 1H), 8.70 (d, 1H)

Ex. threo-Ibb1119, NMR: 3.11 (dd, 1H), 3.21 (dd, 1H), 3.64 (s, 3H), 4.14 (m, 2H), 6.85 (m, 2H), 7.81 (m, 1H), 8.20 (d, 1H), 8.59 (d, 1H)

Ex. erythro-Ibb1123, NMR: 2.84 (dd, 1H), 3.03 (dd, 1H), 3.57 (q, 1H), 3.71 (s, 3H), 4.50 (d, 1H), 7.25 (m, 1H), 7.32 (m, 1H), 7.47 (m, 1H), 7.57 (m, 1H), 8.32 (m, 1H), 8.68 (m, 1H)

Ex. threo-Ibb1123, NMR: 2.90 (d, 2H), 3.61 (s, 3H), 3.69 (q, 1H), 4.15 (d, 1H), 7.34 (d, 1H), 7.45 (s, 1H), 7.50 (dd, 1H), 7.71 (s, 1H), 8.28 (s, 1H), 8.69 (s, 1H)

Ex. Ibb1126 (erythro-Ibb1126: threo-Ibb26=56:44), NMR: erythro-Ibb1126: 2.87 (dd, 1H), 3.07 (dd, 1H), 3.47 (m, 1H), 3.71 (s, 3H), 4.52 (d, 1H), 6.99 (m, 4H), 7.56 (dd, 1H), 7.86 (m, 1H) threo-Ibb1126: 2.90 (m, 2H), 3.61 (s, 3H), 3.64 (q, 1H), 4.15 (d, 1H), 7.04 (m, 4H), 7.72 (dd, 1H), 7.80 (m, 1H)

Ex. threo-Ibb1126: 2.90 (m, 2H), 3.61 (s, 3H), 3.64 (q, 1H), 4.15 (d, 1H), 7.04 (m, 4H), 7.72 (dd, 1H), 7.80 (m, 1H)

Ex. Ibb1127 (erythro-Ibb1127: threo-Ibb1127=34:66), NMR:

erythro-Ibb1127: 2.86 (dd, 1H), 3.06 (dd, 1H), 3.48 (m, 1H), 3.71 (s, 3H), 4.52 (d, 1H), 6.96 (d, 2H), 7.29 (d, 2H), 7.61 (dd, 1H), 7.86 (m, 1H)

threo-Ibb1127: 2.89 (m, 2H), 3.61 (s, 3H), 3.63 (q, 1H), 4.15 (d, 1H), 7.02 (d, 2H), 7.30 (d, 2H), 7.75 (dd, 1H), 7.81 (m, 1H)

Ex. erythro-Ibb1127: 2.86 (dd, 1H), 3.06 (dd, 1H), 3.48 (m, 1H), 3.71 (s, 3H), 4.52 (d, 1H), 6.96 (d, 2H), 7.29 (d, 2H), 7.61 (dd, 1H), 7.86 (m, 1H)

Ex. threo-Ibb1127: 2.89 (m, 2H), 3.61 (s, 3H), 3.63 (q, 1H), 4.15 (d, 1H), 7.02 (d, 2H), 7.30 (d, 2H), 7.75 (dd, 1H), 7.81 (m, 1H)

Ex. Ibb1128 (erythro-Ibb1128: threo-Ibb1128=68:32), NMR:

erythro-Ibb1128: 2.85 (dd, 1H), 3.06 (dd, 1H), 3.46 (m, 1H), 3.71 (s, 3H), 4.52 (d, 1H), 6.89 (d, 2H), 7.44 (d, 2H), 7.61 (dd, 1H), 7.86 (m, 1H)

threo-Ibb1128: 2.88 (m, 2H), 3.61 (s, 3H), 3.62 (q, 1H), 4.15 (d, 1H), 6.96 (d, 2H), 7.46 (d, 2H), 7.75 (dd, 1H), 7.81 (m, 1H)

Ex. erythro-Ibb1128: 2.85 (dd, 1H), 3.06 (dd, 1H), 3.46 (m, 1H), 3.71 (s, 3H), 4.52 (d, 1H), 6.89 (d, 2H), 7.44 (d, 2H), 7.61 (dd, 1H), 7.86 (m, 1H)

Ex. threo-Ibb1128: 2.88 (m, 2H), 3.61 (s, 3H), 3.62 (q, 1H), 4.15 (d, 1H), 6.96 (d, 2H), 7.46 (d, 2H), 7.75 (dd, 1H), 7.81 (m, 1H)

Ex. Ibb1129 (erythro-Ibb1129: threo-Ibb1129=59:41), NMR:
erythro-Ibb1129: 2.90 (dd, 1H), 3.11 (dd, 1H), 3.48 (m, 1H), 3.71 (s, 3H), 4.54 (d, 1H), 6.99 (m, 2H), 7.51 (dd, 1H), 7.84 (m, 1H)
threo-Ibb1129: 2.94 (m, 2H), 3.61 (s, 3H), 3.63 (q, 1H), 4.16 (d, 1H), 7.05 (m, 2H), 7.69 (dd, 1H), 7.78 (m, 1H)
Ex. Ibb1131 (erythro-Ibb1131: threo-Ibb1131=40:60), NMR:
erythro-Ibb1131: 2.89 (dd, 1H), 3.08 (dd, 1H), 3.57 (m, 1H), 3.72 (s, 3H), 4.56 (d, 1H), 7.17 (d, 2H), 7.63 (m, 3H), 7.89 (m, 1H)
threo-Ibb1131: 2.91 (m, 2H), 3.61 (s, 3H), 3.71 (q, 1H), 4.20 (d, 1H), 7.26 (d, 2H), 7.62 (d, 2H), 7.76 (dd, 1H), 7.85 (m, 1H)
Ex. Ibb1132 (erythro-Ibb1132: threo-Ibb1132=34:66), NMR:
erythro-Ibb1132: 2.90 (dd, 1H), 3.10 (dd, 1H), 3.65 (m, 1H), 3.72 (s, 3H), 4.59 (d, 1H), 7.25 (d, 2H), 7.68 (dd, 1H), 7.91 (m, 1H), 8.19 (d, 2H)
threo-Ibb1132: 2.97 (m, 2H), 3.61 (s, 3H), 3.78 (q, 1H), 4.23 (d, 1H), 7.34 (d, 2H), 7.82 (dd, 1H), 7.86 (m, 1H), 8.21 (d, 2H)
Ex. Ibb1133 (erythro-Ibb1133: threo-Ibb1133=57:43), NMR:
erythro-Ibb1133: 2.86 (dd, 1H), 3.07 (dd, 1H), 3.43 (m, 1H), 3.71 (s, 3H), 3.79 (s, 3H), 4.50 (d, 1H), 6.82 (d, 2H), 6.91 (d, 2H), 7.53 (dd, 1H), 7.83 (m, 1H)
threo-Ibb1133: 2.89 (m, 2H), 3.58 (q, 1H), 3.61 (s, 3H), 3.78 (s, 3H), 4.12 (d, 1H), 6.83 (d, 2H), 6.96 (d, 2H), 7.69 (dd, 1H), 7.76 (m, 1H)
Ex. erythro-Ibb1133: 2.86 (dd, 1H), 3.07 (dd, 1H), 3.43 (m, 1H), 3.71 (s, 3H), 3.79 (s, 3H), 4.50 (d, 1H), 6.82 (d, 2H), 6.91 (d, 2H), 7.53 (dd, 1H), 7.83 (m, 1H)
Ex. Ibb1134 (erythro-Ibb1134: threo-Ibb1134=54:46), NMR:
erythro-Ibb1134: 2.87 (dd, 1H), 3.06 (dd, 1H), 3.50 (m, 1H), 3.72 (s, 3H), 4.53 (d, 1H), 7.60 (dd, 1H), 7.89 (d, 1H)
threo-Ibb1134: 2.92 (m, 2H), 3.62 (s, 3H), 3.63 (q, 1H), 4.16 (d, 1H), 7.76 (dd, 1H), 7.82 (d, 1H)
Ex. erythro-Ibb1134: 2.87 (dd, 1H), 3.06 (dd, 1H), 3.50 (m, 1H), 3.72 (s, 3H), 4.53 (d, 1H), 7.60 (dd, 1H), 7.89 (d, 1H)
Ex. erythro-1-Ibb1134: 2.87 (dd, 1H), 3.06 (dd, 1H), 3.50 (m, 1H), 3.72 (s, 3H), 4.53 (d, 1H), 7.60 (dd, 1H), 7.89 (d, 1H)
Ex. erythro-2-Ibb1134: 2.87 (dd, 1H), 3.06 (dd, 1H), 3.50 (m, 1H), 3.72 (s, 3H), 4.53 (d, 1H), 7.60 (dd, 1H), 7.89 (d, 1H)
Ex. threo-Ibb1134: 2.92 (m, 2H), 3.62 (s, 3H), 3.63 (q, 1H), 4.16 (d, 1H), 7.76 (dd, 1H), 7.82 (d, 1H)
Ex. threo-1-Ibb1134: 2.92 (m, 2H), 3.62 (s, 3H), 3.63 (q, 1H), 4.16 (d, 1H), 7.76 (dd, 1H), 7.82 (d, 1H)
Ex. threo-2-Ibb1134: 2.92 (m, 2H), 3.62 (s, 3H), 3.63 (q, 1H), 4.16 (d, 1H), 7.76 (dd, 1H), 7.82 (d, 1H); chiral HPLC: 30.7 min, mobile phase d
Ex. Ibb1139 (erythro-Ibb1139: threo-Ibb1139=37:63), NMR:
erythro-Ibb1139, NMR: 2.90 (dd, 1H), 3.09 (dd, 1H), 3.65 (m, 1H), 3.71 (s, 3H), 4.57 (d, 1H), 7.41 (dt, 1H), 7.53 (t, 1H), 7.68 (dd, 1H), 7.93 (m, 2H), 8.21 (m, 1H)
threo-Ibb1139, NMR: 2.98 (d, 2H), 3.62 (s, 3H), 3.80 (q, 1H), 4.26 (d, 1H), 7.48 (dt, 1H), 7.52 (t, 1H), 7.82 (dd, 1H), 7.88 (m, 1H), 8.02 (m, 1H), 8.20 (m, 1H)
Ex. erythro-Ibb1148, NMR: 2.84 (dd, 1H), 3.05 (dd, 1H), 3.70 (s, 3H), 3.96 (m, 1H), 4.58 (d, 1H), 7.16 (m, 3H), 7.72 (dd, 1H), 7.92 (m, 1H)
Ex. threo-Ibb1148, NMR: 3.02 (m, 2H), 3.60 (s, 3H), 3.96 (q, 1H), 4.22 (d, 1H), 6.90 (m, 1H), 7.06 (m, 1H), 7.13 (m, 1H), 7.93 (m, 2H)

Ex. erythro-Ibb1149, NMR: 2.82 (dd, 1H), 3.04 (dd, 1H), 3.70 (s, 3H), 3.90 (q, 1H), 4.55 (d, 1H), 6.71 (m, 1H), 6.96 (m, 1H), 7.38 (m, 1H), 7.70 (dd, 1H), 7.91 (m, 1H)
Ex. threo-Ibb1149, NMR: 2.99 (m, 2H), 3.60 (s, 3H), 3.88 (q, 1H), 4.20 (d, 1H), 6.82 (m, 2H), 7.10 (m, 1H), 7.91 (m, 2H)
Ex. Ibb1150 (erythro-Ibb1150: threo-Ibb1150=53:47), NMR:
erythro-Ibb1150: 2.81 (dd, 1H), 2.99 (dd, 1H), 3.71 (s, 3H), 3.91 (m, 1H), 4.57 (d, 1H), 6.94 (m, 1H), 7.00 (m, 1H), 7.12 (m, 1H), 7.71 (dd, 1H), 7.93 (m, 1H)
threo-Ibb1150: 2.99 (m, 2H), 3.61 (s, 3H), 3.89 (q, 1H), 4.22 (d, 1H), 6.86 (m, 1H), 7.00 (m, 2H), 7.12 (m, 1H), 7.93 (m, 2H)
Ex. erythro-Ibb1150: 2.81 (dd, 1H), 2.99 (dd, 1H), 3.71 (s, 3H), 3.91 (m, 1H), 4.57 (d, 1H), 6.94 (m, 1H), 7.00 (m, 1H), 7.12 (m, 1H), 7.71 (dd, 1H), 7.93 (m, 1H)
Ex. Ibb1151 (erythro-Ibb1151: threo-Ibb1151=52:48), NMR:
erythro-Ibb1151: 2.88 (dd, 1H), 2.95 (dd, 1H), 3.62 (s, 3H), 4.16 (m, 1H), 4.45 (d, 1H), 6.93 (t, 2H), 7.31 (m, 1H), 7.96 (dd, 1H), 8.07 (m, 1H)
threo-Ibb1151: 3.11 (dd, 1H), 3.23 (dd, 1H), 3.63 (s, 3H), 4.07 (q, 1H), 4.21 (d, 1H), 6.81 (t, 2H), 7.21 (m, 1H), 7.78 (m, 1H), 7.94 (dd, 1H)
Ex. Ibb1152 (erythro-Ibb1152: threo-Ibb1152=63:37), NMR:
erythro-Ibb1152, NMR: 2.83 (dd, 1H), 3.02 (dd, 1H), 3.47 (m, 1H), 3.72 (s, 3H), 4.51 (d, 1H), 6.73 (m, 1H), 6.94 (m, 1H), 7.10 (m, 1H), 7.65 (dd, 1H), 7.90 (m, 1H)
threo-Ibb1152, NMR: 2.88 (d, 2H), 3.61 (q, 1H), 3.62 (s, 3H), 4.15 (d, 1H), 6.82 (m, 1H), 6.96 (m, 1H), 7.11 (m, 1H), 7.77 (dd, 1H), 7.84 (m, 1H)
Ex. erythro-Ibb1152, NMR: 2.83 (dd, 1H), 3.02 (dd, 1H), 3.47 (m, 1H), 3.72 (s, 3H), 4.51 (d, 1H), 6.73 (m, 1H), 6.94 (m, 1H), 7.10 (m, 1H), 7.65 (dd, 1H), 7.90 (m, 1H)
Ex. erythro-Ibb1164: 2.87 (m, 2H), 3.62 (s, 3H), 4.00 (q, 1H), 4.39 (d, 1H), 6.99 (d, 2H), 7.79 (dd, 1H), 8.07 (m, 1H)
Ex. threo-Ibb1164: 3.08 (dd, 1H), 3.22 (dd, 1H), 3.64 (s, 3H), 4.10 (m, 1H), 4.18 (d, 1H), 6.87 (d, 2H), 7.80 (m, 1H), 7.95 (dd, 1H)
Ex. erythro-Ibb1622, NMR: 2.28 (s, 3H), 2.83 (dd, 1H), 3.00 (dd, 1H), 3.52 (m, 1H), 3.67 (s, 3H), 4.40 (d, 1H), 6.95 (d, 2H), 7.15 (t, 1H), 7.24 (d, 2H), 8.19 (bs, 1H), 8.39 (bs, 1H)
Ex. threo-Ibb1622, NMR: 2.33 (s, 3H), 2.89 (d, 2H), 3.58 (s, 3H), 3.64 (q, 1H), 4.10 (d, 1H), 7.04 (d, 2H), 7.27 (d, 2H), 7.29 (t, 1H), 8.14 (d, 1H), 8.39 (d, 1H)
Ex. erythro-Ibb2162, NMR: 2.87 (dd, 1H), 3.11 (dd, 1H), 3.50 (m, 1H), 3.73 (s, 3H), 4.65 (d, 1H), 6.92 (d, 2H), 7.27 (d, 2H), 7.62 (m, 1H), 8.55 (d, 1H), 8.82 (d, 1H)
Ex. threo-Ibb2162, NMR: 2.91 (m, 2H), 3.61 (s, 3H), 3.64 (q, 1H), 4.23 (d, 1H), 7.01 (d, 2H), 7.30 (d, 2H), 7.76 (m, 1H), 8.48 (d, 1H), 8.82 (d, 1H)
Ex. erythro-Ibb2186, NMR: 2.90 (dd, 1H), 3.05 (dd, 1H), 3.66 (s, 3H), 4.10 (m, 1H), 4.58 (d, 1H), 6.90 (t, 2H), 7.33 (m, 1H), 7.90 (t, 1H), 8.75 (d, 1H), 8.87 (d, 1H)
Ex. threo-Ibb2186, NMR: 3.15 (dd, 1H), 3.24 (dd, 1H), 3.64 (s, 3H), 4.17 (m, 1H), 4.27 (d, 1H), 6.80 (t, 2H), 7.21 (m, 1H), 7.85 (t, 1H), 8.50 (d, 1H), 8.76 (d, 1H)
Ex. erythro-Ibb3909, NMR: 2.87 (dd, 1H), 3.02 (dd, 1H), 3.57 (m, 1H), 3.71 (s, 3H), 4.50 (d, 1H), 7.21 (m, 3H), 7.55 (m, 1H), 8.31 (m, 1H), 8.68 (m, 1H)
Ex. threo-Ibb3909, NMR: 2.89 (d, 2H), 3.61 (s, 3H), 3.70 (q, 1H), 4.15 (d, 1H), 7.21 (m, 1H), 7.40 (d, 1H), 8.27 (d, 1H), 8.68 (d, 1H)

Ex. erythro-Ibb3783, NMR: 2.84 (dd, 1H), 3.02 (dd, 1H), 3.46 (m, 1H), 3.70 (s, 3H), 3.87 (s, 3H), 4.46 (d, 1H), 6.69 (m, 1H), 6.80 (dd, 1H), 6.85 (t, 1H), 7.50 (t, 1H), 8.28 (d, 1H), 8.63 (d, 1H)

Ex. threo-Ibb3783, NMR: 2.88 (m, 2H), 3.58 (q, 1H), 3.61 (s, 3H), 3.87 (s, 3H), 4.10 (d, 1H), 6.85 (m, 3H), 7.66 (t, 1H), 8.21 (d, 1H), 8.62 (d, 1H)

Ex. erythro-Ibb3937, NMR: 2.89 (dd, 1H), 3.09 (dd, 1H), 3.60 (m, 1H), 3.71 (s, 3H), 4.53 (d, 1H), 7.15 (d, 2H), 7.47 (m, 1H), 7.56 (d, 2H), 8.30 (bs, 1H), 8.64 (bs, 1H)

Ex. threo-Ibb3937, NMR: 2.94 (m, 2H), 3.60 (s, 3H), 3.74 (q, 1H), 4.17 (d, 1H), 7.26 (d, 2H), 7.59 (d, 2H), 7.64 (t, 1H), 8.26 (d, 1H), 8.64 (d, 1H)

(B) Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulphonate and 1 part by weight of sodium oleoylmethyltaurate as wetting agent and dispersant, and grinding the mixture in a pinned-disc mill.

c) A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing
   75 parts by weight of a compound of the formula (I),
   10 parts by weight of calcium lignosulphonate,
   5 parts by weight of sodium laurylsulphate,
   3 parts by weight of polyvinyl alcohol and
   7 parts by weight of kaolin,
   grinding the mixture in a pinned-disc mill, and granulating the powder in a fluidized bed by spray application of water as a granulating liquid.

f) Water-dispersible granules are also obtained by homogenizing and precomminuting
   25 parts by weight of a compound of the formula (I),
   5 parts by weight of sodium 2,2'-dinaphthylmethane-6,6'-disulphonate,
   2 parts by weight of sodium oleoylmethyltaurinate,
   1 part by weight of polyvinyl alcohol,
   17 parts by weight of calcium carbonate and
   50 parts by weight of water,
   on a colloid mill, subsequently grinding the mixture in a bead mill and atomizing and drying the resulting suspension in a spray tower by means of a single-substance nozzle.

(C) Biological Examples

1. Herbicidal Pre-Emergence Action

Seeds of monocotyledonous and dicotyledonous weed plants and crop plants were placed in wood-fibre pots in sandy loam and covered with soil. The compounds (I) according to the invention, formulated in the form of wettable powders (WP), were then applied as aqueous suspension or emulsion at a water application rate of 600 l/ha (converted) with the addition of 0.2% of wetting agent to the surface of the covering soil.

After the treatment, the pots were placed in a greenhouse and kept under good growth conditions for the test plants. After about 3 weeks, the effect of the preparations was scored visually in comparison with untreated controls as percentages. For example, 100% activity=the plants have died, 50% herbicidal activity or damage=the plants have been reduced by 50% or the plant mass has been reduced by 50%, 0% activity=like control plants.

Compounds (I) according to the invention, for example the compounds Nos. erythro-Ibb2, threo-Ibb2, erythro-Ibb9, threo-Ibb9, threo-Ibb10, erythro-Ibb25, threo-Ibb25, erythro-Ibb26, threo-Ibb26, erythro-Ibb542, threo-Ibb542, erythro-Ibb565, threo-Ibb565, erythro-Ibb566, threo-Ibb566, erythro-Ibb1081, threo-Ibb1081, Ibb1082, erythro-Ibb1082, erythro-1-Ibb1082, erythro-2-Ibb1082, threo-Ibb1082, threo-1-Ibb1082, threo-2-Ibb1082, erythro-Ibb1084, threo-Ibb1084, erythro-Ibb1085, threo-Ibb1085, erythro-Ibb1088, threo-Ibb1088, erythro-Ibb1089, threo-Ibb1089, threo-Ibb1090, erythro-Ibb1092, erythro-Ibb1093, threo-Ibb1093, erythro-Ibb1094, threo-Ibb1094, Ibb1096, erythro-Ibb1096, threo-Ibb1096, erythro-Ibb1103, threo-Ibb1103, erythro-Ibb1104, threo-Ibb1104, erythro-Ibb1105, erythro-1-Ibb1105, erythro-2-Ibb1105, threo-Ibb1105, threo-1-Ibb1105, threo-2-Ibb1105, erythro-Ibb1106, erythro-1-Ibb1106, erythro-2-Ibb1106, threo-Ibb1106, threo-1-Ibb1106, threo-2-Ibb1106, erythro-Ibb1107, threo-Ibb1107, threo-Ibb1108, erythro-Ibb1622, threo-Ibb1622, erythro-Ibb3783, threo-Ibb3783 from the above Tables 2 to 2f have good herbicidal activity (70% to 100% activity) against a plurality of harmful plants at an application rate of 320 g or less of active substance per hectare when applied by the pre-emergence method.

Here, for example, the compounds Nos. erythro-Ibb2, threo-Ibb2, threo-Ibb9, threo-Ibb10, erythro-Ibb25, threo-Ibb25, erythro-Ibb26, threo-Ibb26, Ibb1082, threo-Ibb1082, erythro-Ibb1084, threo-Ibb1084, erythro-Ibb1088, threo-Ibb1088, threo-Ibb1089, threo-Ibb1090, threo-Ibb1105, erythro-Ibb1106, threo-Ibb1106 and threo-Ibb1108 have very good activity (90-100%) against harmful plants such as *Echinochloa crus-galli* when applied by the pre-emergence method at an application rate of 0.32 kg of active substance per hectare.

For example, the compounds Nos. erythro-Ibb2, threo-Ibb2, erythro-Ibb9, threo-Ibb10, erythro-Ibb26, Ibb1082, threo-Ibb1082, threo-Ibb1084, threo-Ibb1088, threo-Ibb1089, threo-Ibb1090, threo-Ibb1105, erythro-Ibb1106, threo-Ibb1106 and threo-Ibb1108 have very good activity (90-100%) against harmful plants such as *Setaria virides* when applied by the pre-emergence method at an application rate of 0.32 kg of active substance per hectare.

For example, the compounds Nos. erythro-Ibb26, threo-Ibb26, threo-Ibb1089, erythro-Ibb1105, erythro-Ibb1106 and threo-Ibb1106 have very good activity (80-100%) against harmful plants such as *Polygonum convolvulus* when applied by the pre-emergence method at an application rate of 0.32 kg of active substance per hectare. For example, the compounds Nos. erythro-Ibb9, threo-Ibb9, Ibb1082, threo-Ibb1082, erythro-Ibb1088, threo-Ibb1088, erythro-Ibb1089, threo-Ibb1089, threo-Ibb1090, erythro-Ibb1105, threo-Ibb1105, erythro-Ibb1106, threo-Ibb1106 and threo-Ibb1108 have very good activity (90-100%) against harmful plants such as

*Veronica persica* when applied by the pre-emergence method at an application rate of 0.32 kg of active substance per hectare.

For example, the compounds Nos. erythro-Ibb9, threo-Ibb9, erythro-Ibb26, threo-Ibb26, Ibb1082, threo-Ibb1082, threo-Ibb1084, threo-Ibb1088, erythro-Ibb1105, threo-Ibb1105, erythro-Ibb1106 and threo-Ibb1106 have very good activity (90-100%) against harmful plants such as Viola tricolor when applied by the pre-emergence method at an application rate of 0.32 kg of active substance per hectare.

For example, the compounds Nos. erythro-Ibb2, threo-Ibb2, erythro-Ibb9, threo-Ibb9, threo-Ibb10, erythro-Ibb26, threo-Ibb26, Ibb1082, threo-Ibb1082, erythro-Ibb1088, threo-Ibb1088, threo-Ibb1090, erythro-Ibb1106 and threo-Ibb1106 have very good activity (80-100%) against harmful plants such as *Alopecurus myosuroides* when applied by the pre-emergence method at an application rate of 0.32 kg of active substance per hectare.

For example, the compounds Nos. erythro-Ibb2, threo-Ibb10, erythro-Ibb26, threo-Ibb26, threo-Ibb1082, erythro-Ibb1105, threo-Ibb1105, erythro-Ibb1106 and threo-Ibb1106 have very good activity (80-100%) against harmful plants such as *Amaranthus retroflexus* when applied by the pre-emergence method at an application rate of 0.32 kg of active substance per hectare.

2. Herbicidal Post-Emergence Action

Seeds of monocotyledonous and dicotyledonous weeds and crop plants were placed in sandy loam in wood-fibre pots, covered with soil and cultivated in a greenhouse under good growth conditions. 2 to 3 weeks after sowing, the test plants were treated at the one-leaf stage, where the compounds (I) according to the invention, formulated in the form of wettable powders (WP), were applied by spraying as aqueous suspension or emulsion at a water application rate of 600 l/ha (converted) with the addition of 0.2% of wetting agent to the green parts of the plants. After the test plants had been kept in the greenhouse under optimum growth conditions for about 3 weeks, the activity of the preparations was rated visually in comparison to untreated controls in percent (%). For example, 100% activity=the plants have died, 50% herbicidal activity or damage=the plants have been reduced by 50% or the plant mass has been reduced by 50%, 0% activity=like control plants.

As shown by the results, compounds (I) according to the invention, for example the compounds Nos. erythro-Ibb2, threo-Ibb2, erythro-Ibb9, threo-Ibb9, threo-Ibb10, erythro-Ibb25, threo-Ibb25, erythro-Ibb26, threo-Ibb26, erythro-Ibb542, threo-Ibb542, erythro-Ibb565, threo-Ibb565, erythro-Ibb566, threo-Ibb566, erythro-Ibb1081, threo-Ibb1081, Ibb1082, erythro-Ibb1082, erythro-1-Ibb1082, erythro-2-Ibb1082, threo-Ibb1082, threo-1-Ibb1082, threo-2-Ibb1082, erythro-Ibb1084, threo-Ibb1084, erythro-Ibb1085, threo-Ibb1085, erythro-Ibb1088, threo-Ibb1088, erythro-Ibb1089, threo-Ibb1089, threo-Ibb1090, erythro-Ibb1092, erythro-Ibb1093, threo-Ibb1093, erythro-Ibb1094, threo-Ibb1094, Ibb1096, erythro-Ibb1096, threo-Ibb1096, erythro-Ibb1103, threo-Ibb1103, erythro-Ibb1104, threo-Ibb1104, erythro-Ibb1105, erythro-1-Ibb1105, erythro-2-Ibb1105, threo-Ibb1105, threo-1-Ibb1105, threo-2-Ibb1105, erythro-Ibb1106, erythro-1-Ibb1106, erythro-2-Ibb1106, threo-Ibb1106, threo-1-Ibb1106, threo-2-Ibb1106, erythro-Ibb1107, threo-Ibb1107, threo-Ibb1108, erythro-Ibb1622, threo-Ibb1622, erythro-Ibb3783, threo-Ibb3783 from the above Tables 2 to 2f have good herbicidal activity (70% to 100% activity) against a plurality of harmful plants at an application rate of 320 g or less of active substance per hectare when applied by the post-emergence method.

Here, for example, the compounds Nos. erythro-Ibb2, threo-Ibb2, threo-Ibb9, threo-Ibb10, erythro-Ibb25, threo-Ibb25, erythro-Ibb26, threo-Ibb26, Ibb1082, threo-Ibb1082, erythro-Ibb1084, threo-Ibb1084, erythro-Ibb1088, threo-Ibb1088, erythro-Ibb1089, threo-Ibb1089, threo-Ibb1090, erythro-Ibb1105, threo-Ibb1105, erythro-Ibb1106, threo-Ibb1106 and threo-Ibb1108 have very good activity (80-100%) against harmful plants such as *Echinochloa crus-galli* when applied by the post-emergence method at an application rate of 0.32 kg of active substance per hectare.

Here, for example, the compounds Nos. erythro-Ibb2, threo-Ibb2, threo-Ibb9, threo-Ibb10, erythro-Ibb25, threo-Ibb25, erythro-Ibb26, threo-Ibb26, Ibb1082, threo-Ibb1082, erythro-Ibb1084, threo-Ibb1084, threo-Ibb1088, erythro-Ibb1089, threo-Ibb1089, threo-Ibb1090, erythro-Ibb1105, threo-Ibb1105, erythro-Ibb1106, threo-Ibb1106 and threo-Ibb1108 also have very good activity (80-100%) against harmful plants such as *Setaria virides* when applied by the post-emergence method at an application rate of 0.32 kg of active substance per hectare.

Here, for example, the compounds Nos. erythro-Ibb2, threo-Ibb2, erythro-Ibb9, threo-Ibb9, threo-Ibb10, erythro-Ibb25, threo-Ibb25, erythro-Ibb26, threo-Ibb26, Ibb1082, threo-Ibb1082, erythro-Ibb1084, threo-Ibb1088, erythro-Ibb1089, threo-Ibb1089, threo-Ibb1090, erythro-Ibb1105, threo-Ibb1105, threo-Ibb1106 and threo-Ibb1108 also have very good activity (80-100%) against harmful plants such as *Veronica persica* when applied by the post-emergence method at an application rate of 0.32 kg of active substance per hectare.

Here, for example, the compounds Nos. erythro-Ibb2, threo-Ibb2, erythro-Ibb9, threo-Ibb9, threo-Ibb10, erythro-Ibb25, threo-Ibb25, erythro-Ibb26, threo-Ibb26, Ibb1082, threo-Ibb1082, threo-Ibb1084, erythro-Ibb1088, threo-Ibb1088, threo-Ibb1090, erythro-Ibb1105, threo-Ibb1105, erythro-Ibb1106, threo-Ibb1106 and threo-Ibb1108 also have very good activity (80-100%) against harmful plants such as *Avena fatua* when applied by the post-emergence method at an application rate of 0.32 kg of active substance per hectare.

Here, for example, the compounds Nos. erythro-Ibb2, threo-Ibb2, threo-Ibb9, threo-Ibb10, erythro-Ibb25, threo-Ibb25, erythro-Ibb26, threo-Ibb26, Ibb1082, threo-Ibb1082, threo-Ibb1084, threo-Ibb1088, threo-Ibb1090 and threo-Ibb1105 also have very good activity (80-100%) against harmful plants such as *Alopecurus myosuroides* when applied by the post-emergence method at an application rate of 0.32 kg of active substance per hectare.

Here, for example, the compounds Nos. threo-Ibb10, erythro-Ibb25, threo-Ibb25, erythro-Ibb26, threo-Ibb26, threo-Ibb1082, threo-Ibb1084, erythro-Ibb1105, threo-Ibb1105 and threo-Ibb1108 also have very good activity (80-100%) against harmful plants such as *Cyprus esculentus* when applied by the post-emergence method at an application rate of 0.32 kg of active substance per hectare.

Here, for example, the compounds Nos. erythro-Ibb2, threo-Ibb26 and threo-Ibb1082 also have very good activity (80-100%) against harmful plants such as *Lolium multiflorum* when applied by the post-emergence method at an application rate of 0.32 kg of active substance per hectare.

Here, for example, the compounds Nos. erythro-Ibb9 and threo-Ibb26 also have very good activity (80-100%) against harmful plants such as *Stellaria media* when applied by the post-emergence method at an application rate of 0.32 kg of active substance per hectare.

Here, for example, the compounds Nos. erythro-Ibb2, threo-Ibb2, threo-Ibb9, threo-Ibb25, erythro-Ibb26, threo-Ibb26, threo-Ibb1082, threo-Ibb1084, erythro-Ibb1088, threo-Ibb1088, threo-Ibb1090, erythro-Ibb1105, threo-Ibb1105, erythro-Ibb1106, threo-Ibb1106 and threo-Ibb1108 also have very good activity (80-100%) against harmful plants such as *Abutilon theophrasti* when applied by the post-emergence method at an application rate of 0.32 kg of active substance per hectare.

Here, for example, the compounds Nos. erythro-Ibb2, threo-Ibb2, threo-Ibb9, erythro-Ibb25, threo-Ibb25, erythro-Ibb26, Ibb1082, threo-Ibb1082, threo-Ibb1084 and erythro-Ibb1105 also have very good activity (80-100%) against harmful plants such as *Amaranthus retroflexus* when applied by the post-emergence method at an application rate of 0.32 kg of active substance per hectare.

Here, for example, the compounds Nos. threo-Ibb10, erythro-Ibb25, threo-Ibb25, erythro-Ibb26, threo-Ibb26, Ibb1082, threo-Ibb1082, erythro-Ibb1084, threo-Ibb1084, erythro-Ibb1088, threo-Ibb1088, threo-Ibb1090, erythro-Ibb1105, threo-Ibb1105 and threo-Ibb1108 also have very good activity (80-100%) against harmful plants such as *Polygonum convolvulus* when applied by the post-emergence method at an application rate of 0.32 kg of active substance per hectare.

Here, for example, the compounds Nos. erythro-Ibb2, threo-Ibb2, threo-Ibb9, erythro-Ibb26, threo-Ibb26, Ibb1082, threo-Ibb1090 and threo-Ibb1105 also have very good activity (80-100%) against harmful plants such as *Viola tricolor virides* when applied by the post-emergence method at an application rate of 0.32 kg of active substance per hectare.

Here, for example, the compounds Nos. erythro-Ibb2, erythro-Ibb26, threo-Ibb26, Ibb1082, threo-Ibb1084, threo-Ibb1088, threo-Ibb1090, threo-Ibb1105 and threo-Ibb1106 also have very good activity (80-100%) against harmful plants such as *Pharbitis purpurea* when applied by the post-emergence method at an application rate of 0.32 kg of active substance per hectare.

The invention claimed is:

1. A compound of formula (I) and/or a salt thereof

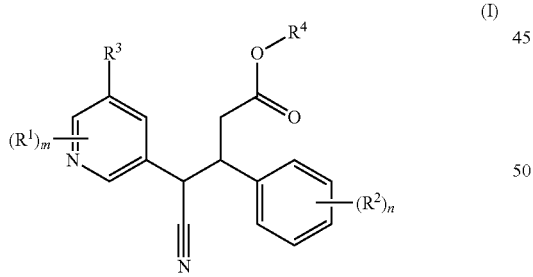

(I)

in which $(R^1)_m$ represents m substituents $R^1$, where $R^1$, if m=1, or each of the substituents $R^1$, if m is greater than 1, independently of the others represents halogen, cyano, $(C_1-C_8)$-alkyl, $(C_2-C_6)$-alkenyl, $(C_2-C_6)$-alkynyl, $(C_1-C_8)$-alkoxy, $(C_1-C_6)$-haloalkyl, $(C_1-C_6)$-haloalkoxy, $(C_2-C_6)$-haloalkenyl, or $(C_2-C_6)$-haloalkynyl, $(R^2)_n$ represents n substituents $R^2$, where $R^2$, if n=1, or each of the substituents $R^2$, if n is greater than 1, independently of the others represents halogen, cyano, nitro, $(C_1-C_8)$-alkyl, $(C_2-C_6)$-alkenyl, $(C_2-C_6)$-alkynyl, $(C_1-C_8)$-alkoxy, $(C_1-C_6)$-haloalkyl, $(C_1-C_6)$-haloalkoxy, or a radical of the formula $C(O)OR^{10}$, $R^3$ represents halogen, cyano, nitro, $(C_1-C_8)$-alkyl, $(C_2-C_6)$-alkenyl, $(C_2-C_6)$-alkynyl, $(C_1-C_8)$-alkoxy, $(C_1-C_6)$-haloalkyl, $(C_1-C_6)$-haloalkoxy, or a radical of the formula $C(O)OR^{15}$, $R^4$ represents hydrogen or a hydrolyzable optionally substituted hydrocarbon radical or optionally substituted heterocyclyl radical, where each of the two last-mentioned carbon-containing radicals including substituents has 1 to 30 carbon atoms, or represents a hydrolyzable radical of the formula $SiR^aR^bR^c$, —$NR^aR^b$ or —$N=CR^cR^d$, where in the 3 last-mentioned formulae each of the radicals $R^a$, $R^b$, $R^c$ and $R^d$ independently of the others represents hydrogen or an optionally substituted hydrocarbon radical, where, however, $SiR^aR^bR^c$ is not $SiH_3$, where each of the radicals $R^a$, $R^b$, $R^c$ and $R^d$ including substituents has up to 30 carbon atoms, or represents a hydrolyzable radical of the formula —$C(=O)$—$R^e$ or —$P(=O)(R^f)_2$, where $R^e$ and the radicals $R^f$ independently of one another each represent hydrogen, OH, $(C_1-C_8)$-alkyl, $(C_1-C_4)$-haloalkyl, $(C_2-C_8)$-alkenyl, $(C_2-C_8)$-alkynyl, $(C_1-C_6)$-alkoxy, $(C_1-C_6)$-alkoxy-$(C_1-C_8)$-alkyl, $(C_1-C_4)$-haloalkoxy, $(C_1-C_4)$-haloalkoxy-$(C_1-C_8)$-alkyl, $(C_3-C_8)$-alkenyloxy, $(C_3-C_8)$-alkenyloxy-$(C_1-C_8)$-alkyl, $(C_3-C_8)$-alkynyloxy, $(C_3-C_8)$-alkynyloxy-$(C_1-C_8)$-alkyl, —$NR*R**$, tri-$[(C_1-C_4)$-alkyl]silyl, tri-$[(C_1-C_4)$-alkyl]silyl-$(C_1-C_8)$alkyl, $(C_3-C_6)$-cycloalkyl, $(C_3-C_6)$-cycloalkyl-$(C_1-C_8)$-alkyl, $(C_5-C_6)$-cycloalkenyl, $(C_5-C_6)$-cycloalkenyl-$(C_1-C_8)$-alkyl, $(C_5-C_6)$-cycloalkynyl, $(C_5-C_6)$-cycloalkynyl-$(C_1-C_8)$-alkyl, phenyl, phenyl-$(C_1-C_8)$-alkyl, phenoxy, phenoxy-$(C_1-C_8)$-alkyl, phenylamino, or phenylamino-$(C_1-C_8)$-alkyl, $R^{10}$ and $R^{15}$ independently of one another each represent hydrogen, $(C_1-C_6)$-alkyl, $(C_1-C_4)$-haloalkyl, $(C_3-C_6)$-cycloalkyl, $(C_3-C_6)$-halocycloalkyl, $(C_2-C_4)$-alkenyl, $(C_2-C_4)$-haloalkenyl, $(C_2-C_4)$-alkynyl or a group M, $R*$ and $R**$ independently each represent H, $(C_1-C_8)$-alkyl, $(C_2-C_8)$-alkenyl, $(C_2-C_8)$-alkynyl, $(C_1-C_4)$-alkoxy-$(C_1-C_4)$-alkyl, $(C_1-C_6)$-alkanoyl, $[(C_1-C_4)$-haloalkyl]carbonyl, $[(C_1-C_4)$-alkoxy]carbonyl, $[(C_1-C_4)$-haloalkoxy]carbonyl, $(C_3-C_6)$-cycloalkyl, $(C_3-C_6)$-cycloalkyl-$(C_1-C_4)$-alkyl, phenyl, or phenyl-$(C_1-C_4)$-alkyl, where each of the 4 last-mentioned radicals is optionally substituted in the cycle by one or more identical or different radicals from the group consisting of halogen, $(C_1-C_4)$-alkyl, $(C_1-C_4)$-haloalkyl, $(C_1-C_4)$-alkoxy and $(C_1-C_4)$-haloalkoxy or, in the case of saturated or partially unsaturated cyclic base groups, also oxo, or $R*$ and $R**$ together with the nitrogen atom represent a 3- to 8-membered heterocycle which, in addition to the nitrogen atom, may contain one or two further ring heteroatoms from the group consisting of N, O and S and which may be unsubstituted or substituted by one or more radicals from the group consisting of $(C_1-C_4)$-alkyl, $(C_1-C_4)$-haloalkyl and oxo, M represents an equivalent of a cation that is a metal ion, an ammonium ion which is optionally substituted by 1 to 4 identical or different radicals from the group consisting of $(C_1-C_6)$-alkyl, $(C_2-C_6)$-alkenyl, $(C_2-C_6)$-alkynyl, ($C_3$-$C_6$)-cycloalkyl, ($C_5$-$C_6$)-cycloalkenyl, ($C_5$-$C_6$)-cycloalkynyl, phenyl, ($C_3$-$C_6$)-cycloalkyl-($C_1$-$C_4$)-alkyl, ($C_5$-$C_6$)-cycloalkenyl-($C_1$-$C_4$)-alkyl, phenyl-($C_1$-$C_4$)-alkyl, or a tertiary sulphonium ion which is optionally substituted by 3 identical or different radicals from the group consisting of ($C_1$-$C_6$)-alkyl, ($C_2$-$C_6$)-alkenyl, ($C_2$-$C_6$)-alkynyl, ($C_3$-$C_6$)-cycloalkyl, ($C_5$-$C_6$)-cycloalkenyl, ($C_5$-$C_6$)-cycloalkynyl, phenyl, ($C_3$-$C_6$)-cycloalkyl-($C_1$-$C_4$)-alkyl, ($C_5$-$C_6$)-cycloalkenyl-($C_1$-$C_4$)-alkyl, phenyl-($C_1$-$C_4$)-alkyl, optionally ($C_1$-$C_4$)-alkyl, m represents 0, 1, 2 or 3, and n represents 0, 1, 2, 3, 4 or 5.

2. A compound and/or salt thereof according to claim 1, wherein $R^4$ represents hydrogen or a hydrolyzable optionally substituted hydrocarbon radical or an optionally substituted heterocyclyl radical, where each of the two last-mentioned carbon-containing radicals including substituents has 1 to 30 carbon atoms, or represents a hydrolyzable radical of the formula $SiR^aR^bR^c$, —$NR^aR^b$ or —N=$CR^cR^d$, where in the 3 last-mentioned formulae each of the radicals $R^a$, $R^b$, $R^c$ and $R^d$ independently of the others represents hydrogen or an optionally substituted hydrocarbon radical, where, however, $SiR^aR^bR^c$ is not $SiH_3$, where each of the radicals $R^a$, $R^b$, $R^c$ and $R^d$ including substituents has up to 30 carbon atoms, or represents a hydrolyzable radical of the formula —C(=O)—$R^e$ or —P(=O)($R^f$)$_2$, where $R^e$ and the radicals $R^f$ independently of one another each represent hydrogen, OH, ($C_1$-$C_8$)-alkyl, ($C_1$-$C_4$-haloalkyl, ($C_2$-$C_8$)-alkenyl, ($C_2$-$C_8$)-alkynyl, ($C_1$-$C_6$)-alkoxy, ($C_1$-$C_6$)-alkoxy-($C_1$-$C_8$)-alkyl, ($C_1$-$C_4$)-haloalkoxy, ($C_1$-$C_4$)-haloalkoxy-($C_1$-$C_8$)-alkyl, ($C_3$-$C_8$)-alkenyloxy, ($C_3$-$C_8$)-alkenyloxy-($C_1$-$C_8$)-alkyl, ($C_3$-$C_8$)-alkynyloxy, ($C_3$-$C_8$)-alkynyloxy-($C_1$-$C_8$)-alkyl, —NR*R**, tri-[($C_1$-$C_4$)-alkyl]silyl, tri-[($C_1$-$C_4$)-alkyl]silyl-($C_1$-$C_8$)alkyl, ($C_3$-$C_6$)-cycloalkyl, ($C_3$-$C_6$)-cycloalkyl-($C_1$-$C_8$)-alkyl, ($C_5$-$C_6$)-cycloalkenyl, ($C_5$-$C_6$)-cycloalkenyl-($C_1$-$C_8$)-alkyl, ($C_5$-$C_6$)-cycloalkynyl, ($C_5$-$C_6$)-cycloalkynyl-($C_1$-$C_8$)-alkyl, phenyl, phenyl-($C_1$-$C_8$)-alkyl, phenoxy, phenoxy-($C_1$-$C_8$)-alkyl, phenylamino, or phenylamino-($C_1$-$C_8$)-alkyl, and R* and R** independently each represent H, ($C_1$-$C_8$)-alkyl, ($C_2$-$C_8$)-alkenyl, ($C_2$-$C_8$)-alkynyl, ($C_1$-$C_4$)-alkoxy-($C_1$-$C_4$)-alkyl, ($C_1$-$C_6$)-alkanoyl, [($C_1$-$C_4$)-haloalkyl]carbonyl, [($C_1$-$C_4$)-alkoxy]carbonyl, [($C_1$-$C_4$)-haloalkoxy]carbonyl, ($C_3$-$C_6$)-cycloalkyl, ($C_3$-$C_6$)-cycloalkyl-($C_1$-$C_4$)-alkyl, phenyl, phenyl-($C_1$-$C_4$)-alkyl, where each of the 4 last-mentioned radicals is optionally substituted in the cycle by one or more identical or different radicals from the group consisting of halogen, ($C_1$-$C_4$)-alkyl, ($C_1$-$C_4$)-haloalkyl, ($C_1$-$C_4$)-alkoxy and ($C_1$-$C_4$)-haloalkoxy or, in the case of saturated or partially unsaturated cyclic base groups, also oxo, or R* and R** together with the nitrogen atom represent a 3- to 8-membered heterocycle which, in addition to the nitrogen atom, may contain one or two further ring heteroatoms from the group consisting of N, O and S and which may be unsubstituted or substituted by one or more radicals from the group consisting of ($C_1$-$C_4$)-alkyl, ($C_1$-$C_4$)-haloalkyl and oxo.

3. A compound and/or salt thereof according to claim 1, wherein $(R^1)_m$ represents m substituents $R^1$, where $R^1$, if m=1, or each of the substituents $R^1$, if m is greater than 1, independently of the others represents halogen, cyano, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_4$)-haloalkyl, ($C_1$-$C_4$)-haloalkoxy, ($C_2$-$C_4$)-haloalkenyl, or ($C_2$-$C_4$)-haloalkynyl, M represents an equivalent of a cation and m represents 0, 1, 2 or 3.

4. A compound and/or salt thereof according to claim 1, wherein $(R^2)_n$ represents n substituents $R^2$, where $R^2$, if n=1, or each of the substituents $R^2$, if n is greater than 1, independently of the others represents halogen, cyano, nitro, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_4$)-haloalkyl, ($C_1$-$C_4$)-haloalkoxy, ($C_2$-$C_4$)-haloalkenyl, ($C_2$-$C_4$)-haloalkynyl, or a radical of the formula C(O)OR$^{10}$, $R^{10}$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or a group M, M represents an equivalent of a cation and n represents 0, 1, 2, 3, 4 or 5.

5. compound and/or salt thereof according to claim 1, wherein $R^3$ represents halogen, cyano, nitro, ($C_1$-$C_6$)-alkyl, ($C_2$-$C_4$)-alkenyl, ($C_2$-$C_4$)-alkynyl, ($C_1$-$C_6$)-alkoxy, ($C_1$-$C_4$)-haloalkyl, ($C_1$-$C_4$)-haloalkoxy, or a radical of the formula C(O)OR$^{15}$, $R^{15}$ represents hydrogen, ($C_1$-$C_4$)-alkyl, ($C_1$-$C_4$)-haloalkyl, ($C_3$-$C_6$)-cycloalkyl, ($C_3$-$C_6$)-halocycloalkyl, ($C_2$-$C_4$)-alkenyl, ($C_2$-$C_4$)-haloalkenyl, ($C_2$-$C_4$)-alkynyl or a group M, and M represents an equivalent of a cation.

6. A compound and/or salt thereof according to claim 1, wherein $(R^1)_m$ represents m substituents $R^1$, where R1, if m=1, or each of the substituents $R^1$, if m is greater than 1, independently of the others represents halogen, cyano, ($C_1$-$C_4$)-alkyl, ($C_1$-$C_4$)-alkoxy, ($C_1$-$C_4$)-haloalkyl, ($C_1$-$C_4$)-haloalkoxy, or a radical of the formula C(O)OR$^5$, $R^5$ represents hydrogen, ($C_1$-$C_4$)-alkyl or a group M, m represents 0, 1, 2 or 3, $(R^2)_n$ represents n substituents $R^2$, where $R^2$, if n=1, or each of the substituents $R^2$, if n is greater than 1, independently of one another represent halogen, cyano, nitro, ($C_1$-$C_4$)-alkyl, ($C_1$-$C_4$)-alkoxy, ($C_1$-$C_4$)-haloalkyl, ($C_1$-$C_4$)-haloalkoxy, or a radical of the formula C(O)OR$^{10}$, $R^{10}$ represents hydrogen, ($C_1$-$C_4$)-alkyl or a group M, n represents 0, 1, 2, 3, 4 or 5, $R^3$ represents halogen, cyano, nitro, ($C_1$-$C_4$)-alkyl, ($C_1$-$C_4$)-alkoxy, ($C_1$-$C_4$)-haloalkyl, ($C_1$-$C_4$)-haloalkoxy, or a radical of the formula C(O)OR$^{15}$, $R^{15}$ represents hydrogen, ($C_1$-$C_4$)-alkyl or a group M, and M represents an equivalent of a cation.

7. A process for preparing a compound of formula (I) and/or a salt thereof as defined in claim 1 comprising obtaining a diastereomer mixture of the compound and/or salt of formula (I) comprising the compound (I) to be prepared wherein
(a) in the case of preparation of a diastereomer mixture of the compound and/or salt of formula (I), reacting a compound of formula (II)

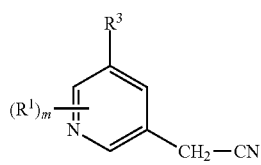

(II)

with a compound of formula (III) and/or salt thereof

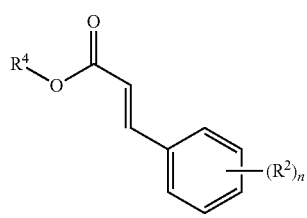

(III)

to give a compound of the formula (I)

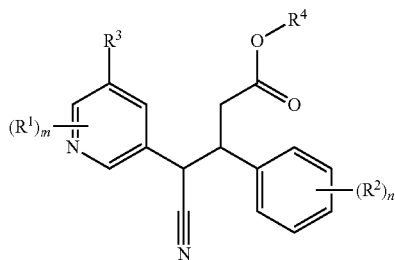

(I)

where $R^1$, $R^2$, $R^3$, $R^4$, m and n in the compounds (II) and (III) are as defined in the respective compound of the formula (I) to be prepared, and/or (b) reacting a compound of the formula (I*)

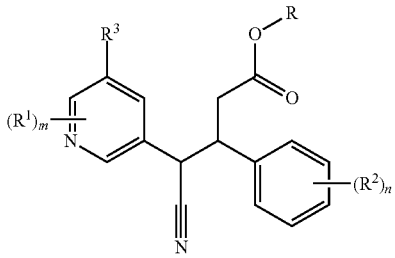

(I*)

in which R is a radical from the group consisting of the radicals possible for $R^4$ but different from the radical $R^4$ in the compound (I) to be prepared, with a compound of formula $R^4$—OH in which $R^4$ is defined as in formula (I), to give compound (I) and/or salt thereof, where $R^1$, $R^2$, $R^3$, m and n in the compound (I*) are as defined in the compound of the formula (I) to be prepared in each case and/or (c) reacting a compound of formula (I*) in which R represents a hydrogen atom with a compound of formula $R^4$—OH in which $R^4$ is as defined in formula (I), to give a compound of the formula (I) and/or salt thereof, or (d) in the case in which an optically active compound of a diastereomeric form of the compound of the formula (I) and/or salt is prepared, subjecting the racemic mixture of the diastereomeric form of the compound of the formula (I) and/or salt to an optical resolution and isolating the desired enantiomer in a stereochemical purity of from 60 to 100%, optionally from 70 to 100%, or optionally from 80 to 100%, in particular or optionally from 90 to 100%, based on the mixture of erythro or threo enantiomers present.

8. A herbicidal and/or plant growth-regulating composition, comprising one or more compounds of formula (I) and/or salt thereof as defined in claim 1 and one or more formulation auxiliaries customary in crop protection.

9. A method for controlling harmful plants and/or for regulating growth of a plant, comprising applying an effective amount of one or more compounds of formula (I) and/or salt thereof as defined in claim 1 is applied onto a plant, plant seed, soil in which and/or on which a plant grows and/or an area under cultivation.

10. A method according to claim 9, that wherein the compound of formula (I) and/or salt thereof is employed for selective control of a harmful plant and/or for regulating growth in a crop of a useful plant and/or ornamental plant.

11. A compound of formula (I) and/or salt thereof according to claim 1 capable of being used as a herbicide and/or plant growth regulator.

12. A herbicide and/or plant growth regulator comprising a compound of formula I and/or salt thereof as claimed in claim 1.

* * * * *

UNITED STATES PATENT AND TRADEMARK OFFICE
CERTIFICATE OF CORRECTION

PATENT NO. : 8,975,412 B2
APPLICATION NO. : 14/354795
DATED : March 10, 2015
INVENTOR(S) : Harald Jakobi et al.

Page 1 of 1

It is certified that error appears in the above-identified patent and that said Letters Patent is hereby corrected as shown below:

Title page, item [57] in the Abstract, formula (I) should appear as follows:

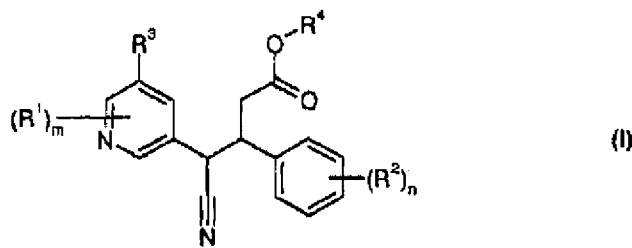

In the Specification

Column 2, lines 55-65, formula (I) should appear as follows:

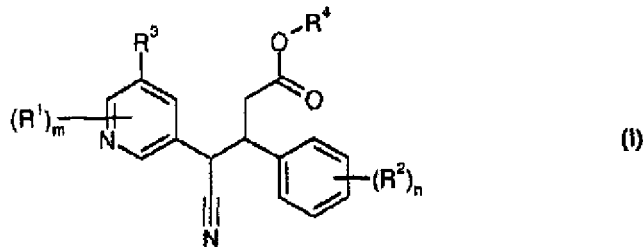

Signed and Sealed this
Thirtieth Day of June, 2015

Michelle K. Lee
*Director of the United States Patent and Trademark Office*